United States Patent [19]

Wexler

[11] Patent Number: 4,715,886

[45] Date of Patent: Dec. 29, 1987

[54] HERBICIDAL PYRAZOLE SULFONAMIDES

[75] Inventor: Barry A. Wexler, Wilmington, Del.

[73] Assignee: E. I. Du Pont de Nemours and Company, Wilmington, Del.

[21] Appl. No.: 26,416

[22] Filed: Mar. 16, 1987

Related U.S. Application Data

[62] Division of Ser. No. 726,386, Apr. 23, 1985, Pat. No. 4,671,817.

[51] Int. Cl.⁴ .................. C07D 513/04; A01N 47/36

[52] U.S. Cl. ...................................... 71/91; 544/48; 544/209; 544/212; 544/253; 544/278; 544/320; 544/324; 544/331; 548/212

[58] Field of Search ............... 71/91; 544/48, 209, 544/212, 253, 278, 320, 324, 331; 548/212

[56] References Cited

U.S. PATENT DOCUMENTS 4,622,062 11/1986 Wexler ................................ 71/90

Primary Examiner—Robert Gerstl

[57] ABSTRACT

Pyrazole sulfonamides are found to have utility as pre-emergent and/or postemergent herbicides or plant growth regulants.

24 Claims, No Drawings

HERBICIDAL PYRAZOLE SULFONAMIDES

This is a division of application Ser. No. 726,386, filed Apr. 23, 1985 now U.S. Pat. No. 4,671,817.

BACKGROUND OF THE INVENTION

This invention relates to novel pyrazole sulfonamides. The compounds of this invention and their agriculturally suitable salts, are useful as agricultural chemicals, e.g. plant growth regulants and herbicides. As herbicides, the compounds of this invention have both preemergent and/or postemergent utility. The invention is also intended to cover the use of these chemicals in the form of compositions.

Herbicidal sulfonylureas are claimed in U.S. Pat. Nos. 4,127,405 and 4,167,719.

EP-A-79,683 discloses herbicidal sulfonylureas including those of formula

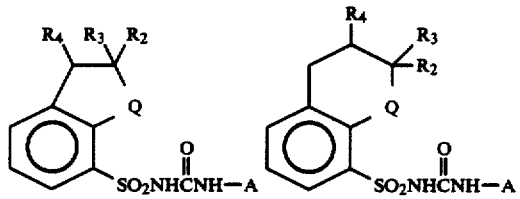

wherein
Q is O, S or $SO_2$;
$R_2$ is H or $C_1$-$C_3$ alkyl;
$R_3$ is H or $CH_3$; and
$R_4$ is H or $CH_3$.

EP-A-107,979 discloses, in part, herbicidal sulfonylureas of formula

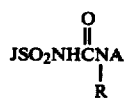

wherein
J is, among other values,

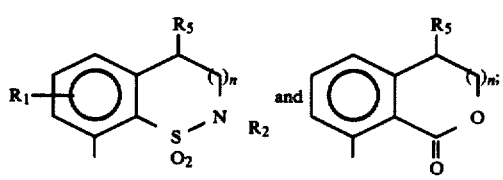

and
A is a heterocyclic pyrimidine, triazine, triazole or a derivative thereof.

South African Patent Application No. 83/5165 discloses herbicidal sulfonylureas of the formula

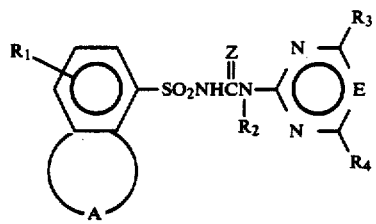

wherein A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group.

EP-A-87,780 (published 9/7/83) claims pyrazole sulfonylureas of formula

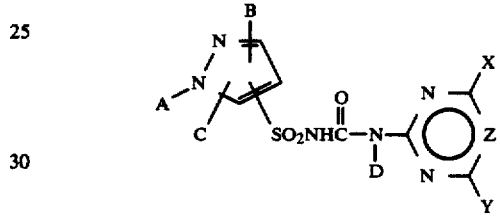

wherein
A is H, $C_1$-$C_8$ alkyl or optionally substituted phenyl;
B and C are independently H, halogen, $C_1$-$C_8$ alkyl, $CO_2R$, $SO_2NR_4R_5$, etc.
D is H or $C_1$-$C_8$ alkyl;
X and Y are independently H, halogen, $C_1$-$C_8$ alkyl, $C_1$-$C_8$ alkoxy, etc.; and
Z is C—$R_8$ or N.

The presence of undesired vegetation causes substantial damage to useful crops, especially agricultural products that satisfy man's basic food and fiber needs, such as cotton, rice, corn, wheat and the like. The current population explosion and concommitant world food and fiber shortage demand improvements in the efficiency of producing these crops. Preventing or minimizing loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need still exists however, for more effective herbicides.

SUMMARY OF THE INVENTION

This invention relates to novel compounds of Formula I, agriculturally suitable compositions containing them and their method-of-use as preemergent and/or postemergent herbicides or plant growth regulants.

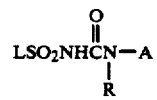

wherein
L is

[Structures L-1 and L-2 shown]

R is H or CH₃;
R₁ is H, C₁–C₃ alkyl, CH₂CH=CH₂, CH₂CH=CH, CH₂CF₃, CHF₂, C(O)CH₃, SO₂CH₃, SO₂N(CH₃)₂, CO₂CH₃, phenyl or phenyl substituted with NO₂, CH₃, OCH₃, Cl, Br or F;
R₂ is H or CH₃;
R₃ is R₄, SR₄, SO₂R₄, OR₄, C(O)R₄, C(O)OR₄, (C(O))₂OR₄, (CO)₂R₄, C(O)NR₅R₆, C(O)NRA, C(S)SR₄, NR₅R₆, OH, CN, P(O)R₇R₈, P(S)R₇R₈, Si(CH₃)₂R₉, J or C(O)J;
R₄ is C₁–C₁₀ alkyl, C₂–C₁₀ alkoxyalkyl, C₂–C₁₀ alkenyl, C₂–C₁₀ epoxyalkyl, C₂–C₁₀ alkynyl, C₃–C₆ cycloalkyl, C₄–C₇ cycloalkylalkyl or

[phenyl-R₁₀ structure]

when R₄ is C₃–C₆ cycloalkyl or C₄–C₇ cycloalkylalkyl it may optionally be substituted by C₁–C₄ alkyl, 1 to 3 atoms of Cl or F or 1 Br; when R₄ is C₁–C₁₀ alkyl, C₂–C₁₀ alkenyl or C₂–C₁₀ alkynyl it may optionally be substituted by one or more halogens and/or by (R₁₁)ₚ, provided that when p is 2, the values of R₁₁ may be identical or different;
p is 1 or 2;
R₅ is H or C₁–C₄ alkyl;
R₆ is H, C₁–C₁₀ alkyl, C₁–C₁₀ haloalkyl, C₂–C₁₀ alkenyl, C₂–C₁₀ alkynyl, C₃–C₆ cycloalkyl or

[phenyl-R₁₀ structure]

R₇ and R₈ are independently C₁–C₄ alkyl, C₁–C₄ alkoxy or C₁–C₄ alkylthio;
R₉ is C₁–C₁₀ alkyl, benzyl or

[phenyl-R₁₀ structure]

R₁₀ is H, F, Cl, Br, CH₃, OCH₃, NO₂, CN, SCH₃, SO₂CH₃ or CF₃;
R₁₁ is OR₆, OC(O)R₆, P⁺R₉R₁₃R₁₄, P⁺(C₆H₅)₃, OC(O)NR₅R₆, OSO₂R₆, OP(O)R₇R₈, P(O)R₇R₈, OP(S)R₇R₈, P(S)R₇R₈, OSi(CH₃)₂R₉, Si(CH₃)₂R₉, SR₆, SOR₆, SO₂R₆, SCN, CN, SP(O)R₇R₈, SP(S)R₇R₈, N⁺R₅R₆R₉, NR₅R₆, NR₅C(O)R₆, NR₅C(O)OR₆, NR₅C(O)NR₅R₆, NR₅SO₂R₆, NR₅P(O)R₇R₈, NR₅P(S)R₇R₈, NO₂, C(O)R₆, C(O)OR₆, C(O)NR₅R₆, SeR₆, naphthyl, J,

[structures with R₁₀, OCH₂, CH₃, O, R₁₂, R₅ etc.]

R₁₂ is H, F, Cl, Br, CH₃,

[phenyl-R₁₀ structures with O linkage]

R₁₃ and R₁₄ are independently C₁–C₃ alkyl;
J is a 5- or 6-membered aromatic heterocycle, a 5- or 6-membered dihydroaromatic heterocycle or a 5- or 6-membered tetrahydroaromatic heterocycle which contains 1–4 heteroatoms selected from 0–1 oxygen atoms, 0–1 sulfur atoms and/or 0–4 nitrogen atoms and these heterocycles may optionally be substituted by 1–4 CH₃, 1–2 OCH₃, SCH₃, Cl, N(CH₃)₂ or CN groups or J is a 5- or 6-membered lactone, lactam or cycloalkanone which may optionally be substituted by 1–4 CH₃ groups;
A is

[Structures A-1, A-2, A-3, A-4, A-5, A-6 shown]

X is H, C₁–C₄ alkyl, C₁–C₄ alkoxy, C₁–C₄ haloalkoxy, C₁–C₄ haloalkylthio, C₁–C₄ alkylthio, halogen, C₂–C₅ alkoxyalkyl, C₂–C₅ alkoxyalkoxy, amino, C₁–C₃ alkylamino, di(C₁–C₃ alkyl)amino or C₃–C₅ cycloalkyl;

Y is H, C₁–C₄ alkyl, C₁–C₄ alkoxy, C₁–C₄ haloalkoxy, C₁–C₄ haloalkylthio, C₁–C₄ alkylthio, halogen, C₂–C₅ alkoxyalkyl, C₂–C₅ alkoxyalkoxy, amino, C₁–C₃ alkylamino, di(C₁–C₃ alkyl)amino, C₃–C₄ alkenyloxy, C₃–C₄ alkynyloxy, C₂–C₅ alkylthioalkyl, C₂–C₅ alkylsulfinylalkyl, C₂–C₅ alkylsulfonylalkyl, C₁–C₄ haloalkyl, C₂–C₄ alkynyl, azido, cyano,

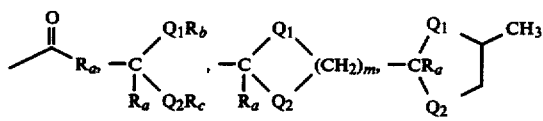

N(OCH$_3$)CH$_3$;

m is 2 or 3;

Q$_1$ and Q$_2$ are independently O or S;

R$_a$ is H or C$_1$-C$_3$ alkyl;

R$_b$ and R$_c$ are independently C$_1$-C$_3$ alkyl;

Z is CH, N, CCH$_3$, CC$_2$H$_5$, CCl or CBr;

Y$_1$ is O or CH$_2$;

X$_1$ is CH$_3$, OCH$_3$, OC$_2$H$_5$ or OCF$_2$H;

X$_2$ is CH$_3$, C$_2$H$_5$ or CH$_2$CF$_3$;

Y$_2$ is OCH$_3$, OC$_2$H$_5$, SCH$_3$, SC$_2$H$_5$, CH$_3$ or CH$_2$CH$_3$;

X$_3$ is CH$_3$ or OCH$_3$; and

Y$_3$ is H or CH$_3$;

provided that 1. when X is halogen, then Z is CH and Y is OCH$_3$, OC$_2$H$_5$, NH$_2$, NHCH$_3$, N(CH$_3$)$_2$ or OCF$_2$H;
2. when R$_3$ is R$_4$, then R$_4$ is other than C$_1$-C$_3$ alkyl or CF$_2$H;
3. the total number of carbon atoms in R$_3$ does not exceed 13;
4. when R$_6$ is H, then R$_{11}$ is other than SOR$_6$, SO$_2$R$_6$, OSO$_2$R$_6$ or NR$_5$CO$_2$R$_6$; and
5. when X or Y is OCF$_2$H, then Z is CH Preferred for reasons of their higher herbicidal acitivity, greater plant growth regulant activity or more favorable ease of synthesis are:

(1) Compounds of Formula I wherein
A is A-1;
X is CH$_3$, OCH$_3$, OCH$_2$CH$_3$, Cl, F, Br, OCF$_2$H, CH$_2$F, CF$_3$ or cyclopropyl;
Y is H, C$_1$-C$_3$ alkyl, OCH$_3$, OC$_2$H$_5$, CH$_2$OCH$_3$, NH$_2$, NHCH$_3$, N(OCH$_3$)CH$_3$, N(CH$_3$)$_2$, C$_2$H$_5$, CF$_3$, SCH$_3$, OCH$_2$CH=CH$_2$, OCH$_2$C≡CH, OCH$_2$CF$_3$, CN, N$_3$, OCH$_2$CH$_2$OCH$_3$, CH$_2$SCH$_3$,

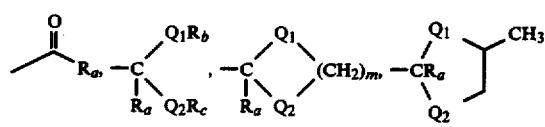

or QCF$_2$T;
Q is O or S; and
T is H, CHClF, CHBrF or CHFCF$_3$;

(2) Compounds of Preferred 1 wherein R$_3$ is C$_4$-C$_6$ alkyl, C$_1$-C$_6$ alkylcarbonyl, C$_1$-C$_6$ alkoxycarbonyl, C$_1$-C$_6$ alkyl substituted by 1-3 atoms of F, Cl or 1 Br, or by 1 or 2 groups selected from C$_1$-C$_2$ alkoxy, CN, C$_1$-C$_2$ alkoxycarbonyl, C$_1$-C$_2$ alkylcarbonyl, OH, C$_1$-C$_2$ alkylthio, C$_1$-C$_2$ alkylsulfonyl, C$_1$-C$_2$ alkylsulfonyloxy or C$_1$-C$_2$ alkylcarbonyloxy, C$_3$-C$_4$ alkenyl, C$_3$-C$_4$ haloalkenyl, C$_3$-C$_4$ alkynyl, C$_4$ alkynyl substituted by 1 atom of F or Cl, phenyl or phenyl substituted with Cl, CF$_3$, NO$_2$, CN or SO$_2$CH$_3$;

(3) Compounds of Preferred 2 wherein R$_1$ is H, C$_1$-C$_3$ alkyl, allyl, propargyl, CH$_2$CF$_3$ or CHF$_2$;

(4) Compounds of Preferred 3 wherein R is H, Y is CH$_3$, C$_2$H$_5$, OCH$_3$, CH$_2$OCH$_3$, OCF$_2$H or CH(OCH$_3$)$_2$, and Z is CH or N;

(5) Compounds of Preferred 4 wherein Z is CH; and R$_3$ is C$_4$ alkyl, C$_1$-C$_3$ haloalkyl substituted by 1-3 atoms of F or Cl or 1 Br, C$_1$-C$_3$ alkyl substituted with C$_1$-C$_2$ alkoxy, C$_1$-C$_2$ alkylthio, C$_1$-C$_2$ alkylsulfonyl or CN, C$_3$-C$_4$ alkenyl, C$_3$-C$_4$ haloalkenyl, C$_3$-C$_4$ alkynyl, C$_1$-C$_3$ alkoxycarbonyl or C$_1$-C$_3$ alkylcarbonyl; and (6) Compounds of Preferred 4 wherein Z is N; and R$_3$ is C$_1$-C$_3$ alkoxycarbonyl or C$_1$-C$_3$ alkylcarbonyl.

Specifically preferred for reasons of their expected highest herbicidal activity, greatest plant growth regulant activity or most favorable ease of synthesis are:

N-[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide;

5-butyl-N-[(4,6-dimethoxypyrimidin-2-yl)aminocarbonyl]-2,5,6,7-tetrahydro-2-methylpyrazolo[3,4-e][1,2]thiazine-3-sulfonamide, 4,4-dioxide; and 5-acetyl-2,5,6,7-tetrahydro-N-[(4-methoxy-6-methyl-1,3,5-triazin-2-yl)aminocarbonyl]-2-methyl-pyrazolo[3,4-e]thiazine-3-sulfonamide, 4,4-dioxide.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl, hexyl, heptyl, octyl, nonyl or decyl isomers.

Alkoxy denotes methoxy, ethoxy, n-propyloxy, isopropyloxy and the different butyl, pentyl, hexyl, heptyl, oxtyl or nonyl isomers.

Alkenyl denotes straight chain or branched alkenes, e.g. vinyl, 1-propenyl, 2-propenyl, isopropenyl and the different butenyl, pentenyl, hexenyl, heptenyl, octenyl, nonenyl or decenyl isomers.

Alkynyl denotes straight chain or branch alkynes, e.g. ethynyl, 1-propynyl, 2-propynyl and the different butynyl, pentynyl, hexynyl, heptynyl, octynyl, nonynyl and the decynyl isomers.

Alkylcarbonyl denotes e.g. acetyl, propionyl and isopropionyl.

Alkoxycarbonyl denotes, e.g., methoxycarbonyl and ethoxycarbonyl.

Alkylsulfonyl denotes, e.g., methylsulfonyl and ethylsulfonyl.

Alkylthio, alkylsulfinyl, alkylamino, alkylsulfamoyl, etc. are defined analogously to the above examples.

Cycloalkyl denotes cyclopropyl, cyclobutyl, cyclopentyl and cyclohexyl.

Cycloalkylalkyl denotes, for example, cyclopropylmethyl, 2-cyclopropylethyl and cyclohexylmethyl.

The term "halogen", either alone or in compound words such as "haloalkyl", denotes fluorine, chlorine, bromine or iodine. Further, when used in compound words such as "haloalkyl" said alkyl may be monohalogenated, substituted with more than one halogen, or fully substituted with halogen atoms. When more than one halogen is present said halogen may be the same or different. Examples of haloalkyl include CH$_2$CH$_2$F, CH$_2$CF$_3$ and CH$_2$CHFCl.

The total number of carbon atoms in a substituent group is indicated by the C$_i$-C$_j$ prefix where i and j are numbers from 1 to 10. For example, C$_1$-C$_3$ alkylsulfonyl would designate methylsulfonyl through propylsulfonyl, C$_2$ alkoxyalkoxy would designate OCH$_2$OCH$_3$, C$_2$ cyanoalkyl would designate CH$_2$CN and C$_3$ cyanoalkyl would designate CH$_2$CH$_2$CN and CH(CN)CH$_3$

DETAILED DESCRIPTION OF THE INVENTION

Synthesis

Compounds of the Invention

The sulfonylureas of Formula I may be prepared by a number of methods. These methods are described below, along with the appropriate references for greater detail.

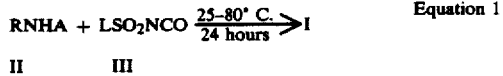

Equation 1

U.S. Pat. Nos. 4,127,405, 4,257,802 and 4,221,585 disclose these equations and are herein incorporated by reference.

Equation 2

This reaction is taught in EPO Publication No. 83,975 (published July 20, 1983).

Equation 3

The reaction is taught in EPO Publication No. 44,807 (published Jan. 27, 1982).

Intermediate Compounds

Heterocyclic sulfonyl isocyanates of Formula III may be prepared by procedures taught in U.S. Pat. No. 4,127,405.

Heterocyclic amines of FOrmula II may be prepared from procedures taught in U.S. Pat. No. 4,127,405 and U.S. Pat. No. 4,221,585.

Heterocyclic carbamates of Formula V are prepared by procedures taught in EPO Publication No. 83,975. The heterocyclic carbamates of Formula VI may be prepared by procedures taught in EPO No. 44,807 and references cited therein.

The preparation of the intermediate pyrazole sulfonamides such as VII and VIII where $R_1$, $R_2$ and $R_3$ are as previously described and n is 0, may be accomplished in one or more of the ways described below in Equations 4, 5 and 6.

Equation 4

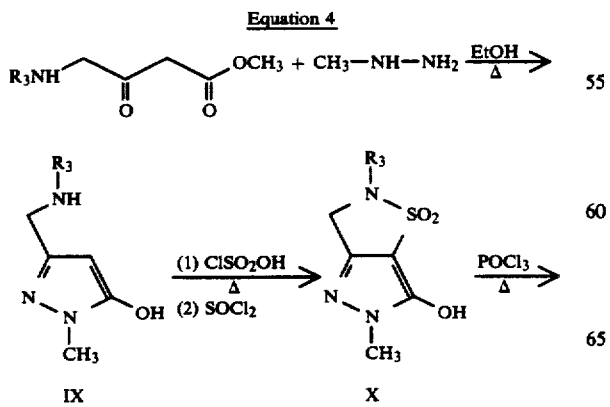

-continued
Equation 4

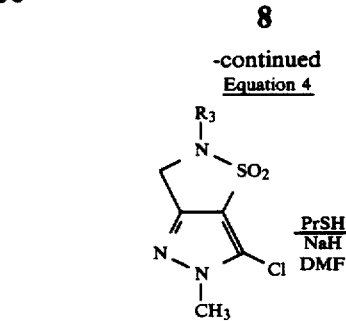

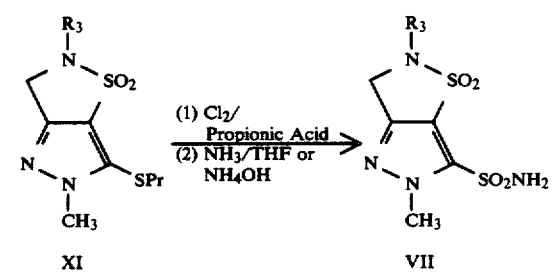

In Equation 4, condensation of a hydrazine with an amine derivative of a β-keto ester affords the pyrazole IX. Reaction of IX with chlorosulfonic acid and subsequent ring closure yields the cyclic sulfonamide X. Conversion to the chloride followed by displacement of the activated chloride would then afford the propylthio derivative XI. Standard oxidative chlorination in the appropriate solvent, followed by amination would then yield the desired 5-sulfonamide XII. The conditions for carrying out the transformation described in Equation 4 would be known to one skilled in the art. For example, the final transformation, a conversion of a thiol to a sulfonamide is taught by R. V. Robin and J. W. Clapp, J. Am. Chem. Soc., 72, 4890 (1950).

An alternate synthesis of sulfonamides VII and VIII is described in Equation 5. This route is the same as that taught in Equation 4 with hydrazine substituted for methylhydrazine.

Equation 5

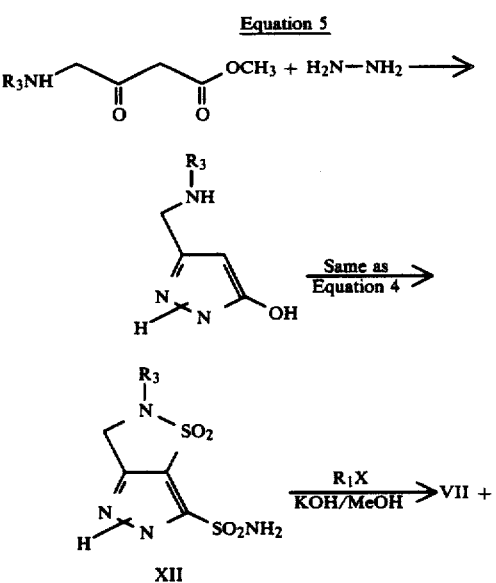

-continued
Equation 5

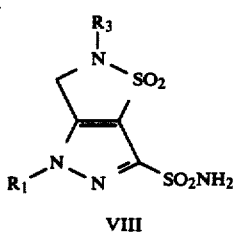

VIII

The resulting unsubstituted pyrazole XII may now be alkylated to afford the isomeric sulfonamides VII and VIII. Chromatographic separation of the two isomers then yields the individual sulfonamides. In other words, introduction of the N-substituent, $R_1$ at the end of the synthesis allows for the preparation of both sulfonamides VII and VIII.

Synthesis of sulfonamides XIII and XIV where $R_1$, $R_2$ and $R_3$ are as previously described and n is 1 is described in Equation 6.

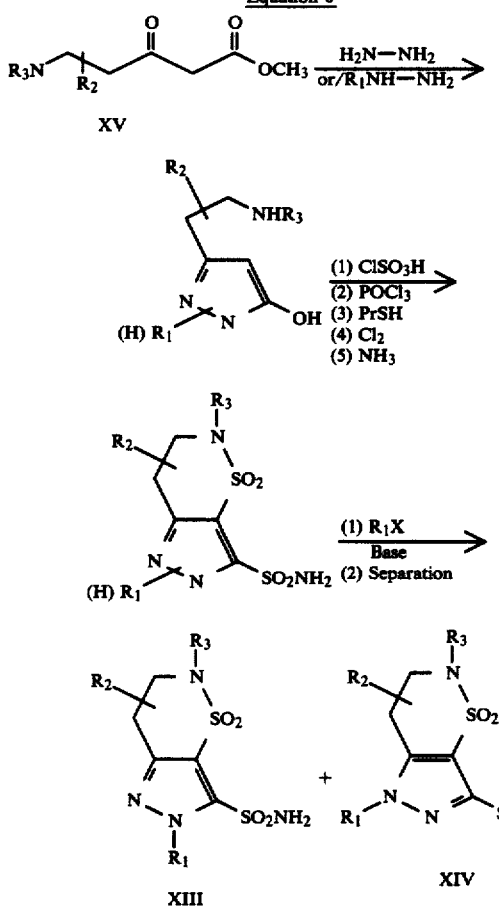

The transformations described in Equation 6, parallel those procedures described in Equations 4 and 5. Here, the homolog amino substituted keto ester XV is employed resulting in the [3.0.4] bicyclic pyrazoles XIII and XIV.

The prerequisite starting amino keto esters may be prepared using standard conditions well known to one skilled in the art. For example, alkylation of glycine with butyl bromide ($R_3$ = n-butyl) affords the acid XVI. Esterification followed by condensation with ethyl chloracetate yields the desired keto ester XVII. This sequence is described in Equation 7.

Equation 7

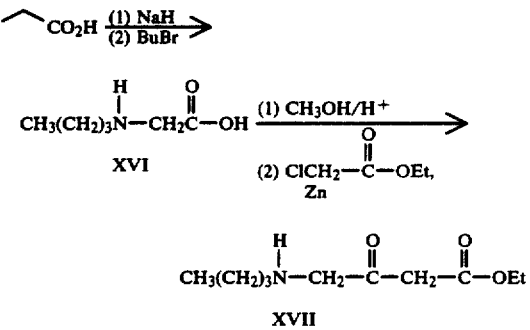

An alternate synthesis of sulfonamides VII and VIII is described in Equation 8. The benzylthio intermediate XIX is oxidatively chlorinated and aminated providing sulfonamides VII and VIII after chromatographic separation of the two isomers. The prerequisite heterocycle XVIII is prepared by the procedures taught in DT 2431734.

Equation 8

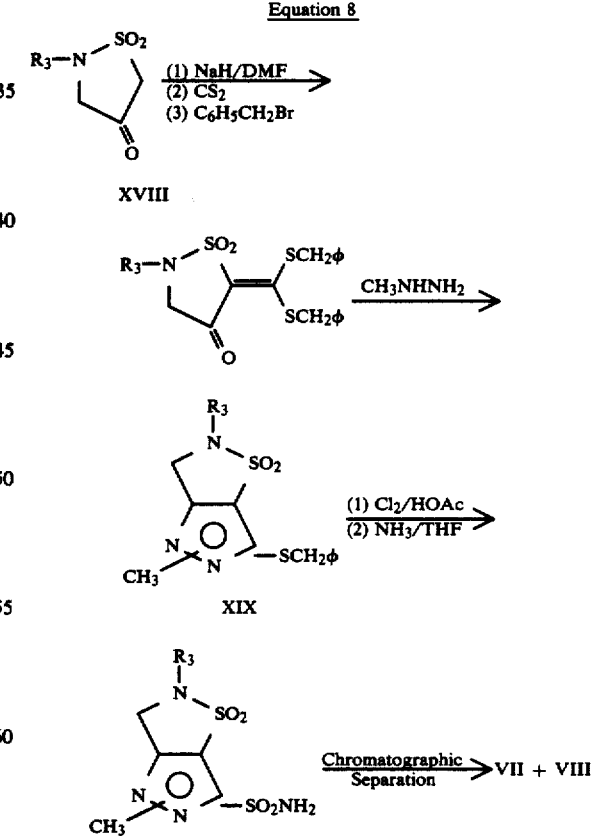

In the following examples, all parts are by weight and temperatures in degrees Centigrade unless otherwise stated.

EXAMPLE 1

Preparation of 5-Butyl-2,5,6,7-tetrahydro-2-methylpyrazole[3,4-e][1,2]thiazine-3-sulfonamide,4,4-dioxide Chlorine gas is bubbled through a stirring solution of 5-Butyl-2,5,6-tetrahydro-2-methyl-3-(propylthio)-pyrazole[3,4-c]-[1,2]thiazine-4-4-dioxide cooled to 5° C. in propionic acid and three equivalents of water. After 30 minutes the solids are filtered off and dried. The resulting solids are dissolved in tetrahydrofuran and added dropwise to a solution of ammonia in tetrahydrofuran. After stirring for 16 hours the solids are filtered and the filtrate is concentrated. The resulting solid is washed with ether and dried to afford the subject sulfonamide.

EXAMPLE 2

Preparation of 5-Butyl-N-[4,6-dimethyoxypyrimidin-2-yl)aminocarbonyl]-2,5,6,7-tetrahydro-2-methylpyrazolo[3,4-e][1,2]thiazine-3-sulfonamide,4-4-dioxide The sulfonamide from Example 1 is added to a flask containing one equivalent of the phenyl carbamate of 4,6-dimethoxy-2-aminopyrimidine in 10 ml of acetonitrile. One equivalent of diazobicycloundecane is added and the reaction is stirred for 1 hour. Five ml of 10% hydrochloric acid is added and the resulting solids are collected and dried to afford the desired compound.

| Table | | Structures for Tables Structure |
|---|---|---|
| I | n = 1 | |
| Ia | n = 0 | |
| II | n = 1 | |
| IIa | n = 0 | |
| III | n = 1 | |
| IIIa | n = 0 | |
| IV | n = 1 | |
| IVa | n = 0 | |

TABLE I

General Structure I

| R | $R_1$ | $R_2$ | $R_3$ | X | Y | Z | m.p. (°C.) |
|---|---|---|---|---|---|---|---|
| H | $CH_3$ | H | $CH_2F$ | $CH_3$ | $CH_3$ | CH | |
| H | $CH_3$ | H | $CH_2F$ | $CH_3$ | $OCH_3$ | CH | |
| H | $CH_3$ | H | $CH_2F$ | $OCH_3$ | $OCH_3$ | CH | |
| H | $CH_3$ | H | $CH_2F$ | $CH_3$ | $CH_3$ | N | |
| H | $CH_3$ | H | $CH_2F$ | $CH_3$ | $OCH_3$ | N | |
| H | $CH_3$ | H | $CH_2F$ | $OCH_3$ | $OCH_3$ | N | |
| H | $CH_3$ | H | $CH_2F$ | $OCH_3$ | Cl | CH | |
| H | $CH_3$ | H | $CH_2CH_2F$ | $CH_3$ | $CH_3$ | CH | |
| H | $CH_3$ | H | $CH_2CH_2F$ | $CH_3$ | $OCH_3$ | CH | |
| H | $CH_3$ | H | $CH_2CH_2F$ | $OCH_3$ | $OCH_3$ | CH | |
| H | $CH_3$ | H | $CH_2CH_2F$ | $CH_3$ | $CH_3$ | N | |
| H | $CH_3$ | H | $CH_2CH_2F$ | $CH_3$ | $OCH_3$ | N | |
| H | $CH_3$ | H | $CH_2CH_2F$ | $OCH_3$ | $OCH_3$ | N | |
| H | $CH_3$ | H | $CH_2CH_2F$ | $OCH_3$ | Cl | CH | |
| H | $CH_3$ | H | $CHFCH_2F$ | $CH_3$ | $CH_3$ | CH | |
| H | $CH_3$ | H | $CHFCH_2F$ | $CH_3$ | $OCH_3$ | CH | |
| H | $CH_3$ | H | $CHFCH_2F$ | $OCH_3$ | $OCH_3$ | CH | |
| H | $CH_3$ | H | $CHFCH_2F$ | $CH_3$ | $CH_3$ | N | |
| H | $CH_3$ | H | $CHFCH_2F$ | $OCH_3$ | $OCH_3$ | N | |
| H | $CH_3$ | H | $CHFCH_2F$ | $OCH_3$ | Cl | CH | |
| H | $CH_3$ | H | $CH_2CHF_2$ | $CH_3$ | $CH_3$ | CH | |
| H | $CH_3$ | H | $CH_2CHF_2$ | $CH_3$ | $OCH_3$ | CH | |
| H | $CH_3$ | H | $CH_2CHF_2$ | $OCH_3$ | $OCH_3$ | CH | |
| H | $CH_3$ | H | $CH_2CHF_2$ | $CH_3$ | $CH_3$ | N | |
| H | $CH_3$ | H | $CH_2CHF_2$ | $CH_3$ | $OCH_3$ | N | |
| H | $CH_3$ | H | $CH_2CHF_2$ | $OCH_3$ | $OCH_3$ | N | |
| H | $CH_3$ | H | $CH_2CHF_2$ | $OCH_3$ | Cl | CH | |
| H | $CH_3$ | H | $CH(CH_2F)_2$ | $CH_3$ | $CH_3$ | CH | |
| H | $CH_3$ | H | $CH(CH_2F)_2$ | $CH_3$ | $OCH_3$ | CH | |
| H | $CH_3$ | H | $CH(CH_2F)_2$ | $OCH_3$ | $OCH_3$ | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH₂CH₂F | CH₃ | CH₃ | N | |
| H | CH₃ | H | CH₂CH₂CH₂F | CH₃ | OCH₃ | N | |
| H | CH₃ | CH₃ | CH₂CH₂CH₂F | OCH₃ | OCH₃ | N | |
| H | CH₃ | H | CH₂CH₂CH₂F | OCH₃ | Cl | CH | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |
| H | CH₃ | H | CH₂(CH₂)₂CH₂F | OCH₃ | OCH₃ | CH | |
| H | CH₃ | H | CH(CH₃)CH₂F | CH₃ | CH₃ | N | |
| H | CH₃ | H | CH(CH₃)CH₂F | CH₃ | OCH₃ | N | |
| H | CH₃ | H | CH(CH₃)CH₂F | OCH₃ | OCH₃ | N | |
| H | CH₃ | H | CH(CH₃)CH₂F | OCH₃ | Cl | CH | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBrCH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBr—CH₃ | CH₃ | OCH₃ | N | |
| H | CH₃ | CH₃ | CH₂CHBr—CH₃ | OCH₃ | OCH₃ | N | |
| H | CH₃ | H | CH₂CHBr—CH₃ | OCH₃ | Cl | CH | |
| H | CH₃ | H | CH₂CHBr—CH₃ | CH₃ | CH₃ | CH | |
| H | CH₃ | H | CH₂CHBr—CH₃ | CH₃ | OCH₃ | CH | |
| H | CH₃ | H | CH₂CHBr—CH₃ | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |
| H | CH₃ | H | CH₂(CH₂)₂CH₂Cl | OCH₃ | OCH₃ | CH | |
| H | CH₃ | H | CH₂(CH₂)₂CH₂Cl | CH₃ | CH₃ | N | |
| H | CH₃ | H | CH₂(CH₂)₂CH₂Cl | CH₃ | OCH₃ | N | |
| H | CH₃ | H | CH₂(CH₂)₂CH₂Cl | OCH₃ | OCH₃ | N | |
| H | CH₃ | H | CH₂(CH₂)₂CH₂Cl | OCH₃ | Cl | CH | |
| H | CH₃ | H | CH₂(CH₂)₂CH₂Cl | CH₃ | CH₃ | CH | |
| CH₃ | CH₃ | H | CH(CH₃)CH₂Cl | CH₃ | OCH₃ | CH | |
| H | CH₃ | H | CH(CH₃)CH₂Cl | OCH₃ | OCH₃ | CH | |
| H | CH₃ | H | CH(CH₃)CH₂Cl | CH₃ | CH₃ | N | |
| H | CH₃ | H | CHClCHClCH₃ | CH₃ | OCH₃ | N | |
| H | CH₃ | H | CHClCHClCH₃ | OCH₃ | OCH₃ | N | |
| H | CH₃ | H | CHClCHClCH₃ | OCH₃ | Cl | CH | |
| H | CH₃ | H | CH₂I | CH₃ | CH₃ | CH | |
| H | CH₃ | H | CH₂I | CH₃ | OCH₃ | CH | |
| H | CH₃ | H | CH₂I | OCH₃ | OCH₃ | CH | |
| H | CH₃ | H | CH₂I | CH₃ | CH₃ | N | |
| H | CH₃ | H | CH₂I | CH₃ | OCH₃ | N | |
| H | CH₃ | H | CH₂I | OCH₃ | OCH₃ | N | |
| H | CH₃ | H | CH₂I | OCH₃ | Cl | CH | |
| H | CH₃ | H | CH₂CF₃ | CH₃ | CH₃ | CH | |
| H | CH₃ | H | CH₂CF₃ | CH₃ | OCH₃ | CH | |
| H | CH₃ | H | CH₂CF₃ | OCH₃ | OCH₃ | CH | |
| H | CH₃ | H | CH₂CF₃ | CH₃ | CH₃ | N | |
| H | CH₃ | H | CH₂CF₃ | CH₃ | OCH₃ | N | |
| H | CH₃ | H | CH₂CF₃ | OCH₃ | OCH₃ | N | |
| H | CH₃ | H | CH₂CF₃ | OCH₃ | Cl | CH | |
| H | CH₃ | H | CH₂CH₂CF₃ | CH₃ | CH₃ | CH | |
| H | CH₃ | H | CH₂CH₂CF₃ | CH₃ | OCH₃ | CH | |
| H | CH₃ | H | CH₂CH₂CF₃ | OCH₃ | OCH₃ | CH | |
| H | CH₃ | H | CH₂CH₂CF₃ | CH₃ | CH₃ | N | |
| H | CH₃ | H | CH₂CH₂CF₃ | OCH₃ | OCH₃ | N | |
| H | CH₃ | H | CH₂CH₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |
| H | CH₃ | H | CH₂(CH₂)₂CF₃ | CH₃ | OCH₃ | N | |
| H | CH₃ | H | CH₂(CH₂)₂CF₃ | OCH₃ | OCH₃ | N | |
| H | CH₃ | H | CH₂(CH₂)₃CF₃ | OCH₃ | Cl | CH | |
| H | CH₃ | H | CH₂(CH₂)₃CF₃ | CH₃ | CH₃ | CH | |
| H | CH₃ | H | CH₂(CH₂)₃CF₃ | CH₃ | OCH₃ | CH | |
| H | CH₃ | H | CH₂(CH₂)₃CF₃ | OCH₃ | OCH₃ | CH | |
| H | CH₃ | H | CH₂(CH₂)₃CF₃ | CH₃ | CH₃ | N | |
| H | CH₃ | H | CH₂(CH₂)₃CF₃ | CH₃ | OCH₃ | N | |
| H | CH₃ | CH₃ | CH₂(CH₂)₃CF₃ | OCH₃ | OCH₃ | N | |
| H | CH₃ | H | CH(CF₃)₂ | OCH₃ | Cl | CH | |
| H | CH₃ | H | CH(CF₃)₂ | CH₃ | CH₃ | CH | |
| H | CH₃ | H | CH(CF₃)₂ | CH₃ | OCH₃ | CH | |
| H | CH₃ | H | CH(CF₃)₂ | OCH₃ | OCH₃ | CH | |
| H | CH₃ | H | CH(CF₃)₂ | CH₃ | CH₃ | N | |
| H | CH₃ | H | CH(CF₃)₂ | CH₃ | OCH₃ | N | |
| H | CH₃ | H | CH(CF₃)₂ | OCH₃ | OCH₃ | N | |
| H | CH₃ | H | CH₂(CH₂)₄CF₃ | OCH₃ | Cl | CH | |
| H | CH₃ | H | CH₂(CH₂)₅CF₃ | CH₃ | CH₃ | CH | |
| CH₃ | CH₃ | H | CH₂(CH₂)₆CF₃ | CH₃ | OCH₃ | CH | |
| H | CH₃ | H | CH₂(CH₂)₇CF₃ | OCH₃ | OCH₃ | CH | |
| H | CH₃ | H | CH₂(CH₂)₈CF₃ | CH₃ | CH₃ | N | |
| H | CH₃ | H | CHF(CH₂)₈CF₃ | CH₃ | OCH₃ | N | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH(CHF)_8CF_3$ | $OCH_3$ | $OCH_3$ | N | |
| H | $CH_3$ | H | $CH(CHF)_8CF_3$ | $OCH_3$ | Cl | CH | |
| H | $CH_3$ | H | $CH_2OCH_3$ | $CH_3$ | $CH_3$ | CH | |
| H | $CH_3$ | H | $CH_2OCH_3$ | $CH_3$ | $OCH_3$ | CH | |
| H | $CH_3$ | H | $CH_2OCH_3$ | $OCH_3$ | $OCH_3$ | CH | |
| H | $CH_3$ | H | $CH_2OCH_3$ | $CH_3$ | $CH_3$ | N | |
| H | $CH_3$ | H | $CH_2OCH_3$ | $CH_3$ | $OCH_3$ | N | |
| H | $CH_3$ | H | $CH_2OCH_3$ | $OCH_3$ | $OCH_3$ | N | |
| H | $CH_3$ | H | $CH_2OCH_3$ | $OCH_3$ | Cl | CH | |
| H | $CH_3$ | H | $CH_2OCH_2CH_3$ | $CH_3$ | $CH_3$ | CH | |
| H | $CH_3$ | H | $CH_2OCH_2CH_3$ | $CH_3$ | $OCH_3$ | CH | |
| H | $CH_3$ | H | $CH_2OCH_2CH_3$ | $OCH_3$ | $OCH_3$ | CH | |
| H | $CH_3$ | H | $CH_2-OCH_2F$ | $CH_3$ | $CH_3$ | N | |
| H | $CH_3$ | H | $CH_2-OCH_2F$ | $CH_3$ | $OCH_3$ | N | |
| H | $CH_3$ | H | $CH_2-OCH_2F$ | $OCH_3$ | $OCH_3$ | N | |
| H | $CH_3$ | H | $CH_2-OCH_2F$ | $OCH_3$ | Cl | CH | |
| H | $CH_3$ | H | $CH_2-CH_2OCH_3$ | $CH_3$ | $CH_3$ | CH | |
| H | $CH_3$ | H | $CH_2-CH_2OCH_3$ | $CH_3$ | $OCH_3$ | CH | |
| H | $CH_3$ | H | $CH_2-CH_2OCH_3$ | $OCH_3$ | $OCH_3$ | CH | |
| H | $CH_3$ | H | $CH_2-CH_2OCH_3$ | $CH_3$ | $CH_3$ | N | |
| H | $CH_3$ | H | $CH(OCH_3)_2$ | $OCH_3$ | $OCH_3$ | N | |
| H | $CH_3$ | H | $CH(OCH_3)_2$ | $OCH_3$ | Cl | CH | |
| H | $CH_3$ | H | $CH_2(CH_2)_2OCH_3$ | $CH_3$ | $CH_3$ | CH | |
| H | $CH_3$ | H | $CH_2(CH_2)_2OCH_3$ | $CH_3$ | $OCH_3$ | CH | |
| H | $CH_3$ | H | $CH_2(CH_2)_2OCH_3$ | $OCH_3$ | $OCH_3$ | CH | |
| H | $CH_3$ | H | $CH_2(CH_2)_2OCH_3$ | $CH_3$ | $CH_3$ | N | |
| H | $CH_3$ | H | $CH_2(CH_2)_2OCH_3$ | $CH_3$ | $OCH_3$ | N | |
| H | $CH_3$ | H | $CH_2(CH_2)_3OCH_3$ | $OCH_3$ | $OCH_3$ | N | |
| H | $CH_3$ | H | $CH_2(CH_2)_3OCH_3$ | $OCH_3$ | Cl | CH | |
| H | $CH_3$ | H | $CH_2(CH_2)_3OCH_3$ | $CH_3$ | $CH_3$ | CH | |
| H | $CH_3$ | H | $CH_2(CH_2)_3OCH_3$ | $CH_3$ | $OCH_3$ | CH | |
| H | $CH_3$ | H | $CH_2(CH_2)_3OCH_3$ | $OCH_3$ | $OCH_3$ | CH | |
| H | $CH_3$ | H | $CH(OCH_3)CH_3$ | $CH_3$ | $CH_3$ | N | |
| H | $CH_3$ | H | $CH(OCH_3)CH_3$ | $CH_3$ | $OCH_3$ | N | |
| H | $CH_3$ | $CH_3$ | $CH(OCH_3)CH_3$ | $OCH_3$ | $OCH_3$ | N | |
| H | $CH_3$ | H | $CH_2OCH_2C≡CH_2$ | $OCH_3$ | Cl | CH | |
| H | $CH_3$ | H | $CH_2OCH_2C≡CH_2$ | $CH_3$ | $CH_3$ | CH | |
| H | $CH_3$ | H | $CH_2OCH_2C≡CH_2$ | $CH_3$ | $OCH_3$ | CH | |
| H | $CH_3$ | H | $CH_2OCH_2C≡CH_2$ | $OCH_3$ | $OCH_3$ | CH | |
| H | $CH_3$ | H | $CH_2OCH_2C≡CH_2$ | $CH_3$ | $CH_3$ | N | |
| H | $CH_3$ | H | $CH_2OCH_2C≡CH_2$ | $CH_3$ | $OCH_3$ | N | |
| H | $CH_3$ | H | $CH_2CH(OCH_3)_2$ | $OCH_3$ | $OCH_3$ | N | |
| H | $CH_3$ | H | $CH_2CH(OCH_3)_2$ | $OCH_3$ | Cl | CH | |
| H | $CH_3$ | H | $CH_2CH(OCH_3)_2$ | $CH_3$ | $CH_3$ | CH | |
| $CH_3$ | $CH_3$ | H | $CH_2CH(OCH_3)_2$ | $CH_3$ | $OCH_3$ | CH | |
| H | $CH_3$ | H | $CH_2C(OCH_3)_2CH_3$ | $OCH_3$ | $OCH_3$ | CH | |
| H | $CH_3$ | H | $CH_2C(OCH_3)_2CH_3$ | $CH_3$ | $CH_3$ | N | |
| H | $CH_3$ | H | $CH_2C(OCH_3)_2CH_3$ | $CH_3$ | $OCH_3$ | N | |
| H | $CH_3$ | H | $CH_2(CH_2)_6OCH_3$ | $OCH_3$ | $OCH_3$ | N | |
| H | $CH_3$ | H | $CH_2(CH_2)_6OCH_3$ | $OCH_3$ | Cl | CH | |
| H | $CH_3$ | H | $CH_2OC(O)CH_3$ | $CH_3$ | $CH_3$ | CH | |
| H | $CH_3$ | H | $CH_2OC(O)CH_3$ | $CH_3$ | $OCH_3$ | CH | |
| H | $CH_3$ | H | $CH_2OC(O)CH_3$ | $OCH_3$ | $OCH_3$ | CH | |
| H | $CH_3$ | H | $CH_2OC(O)CH_3$ | $CH_3$ | $CH_3$ | N | |
| H | $CH_3$ | H | $CH_2OC(O)CH_3$ | $CH_3$ | $OCH_3$ | N | |
| H | $CH_3$ | H | $CH_2OC(O)CH_3$ | $OCH_3$ | $OCH_3$ | N | |
| H | $CH_3$ | H | $CH_2OC(O)CH_3$ | $OCH_3$ | Cl | CH | |
| H | $CH_3$ | H | $CH_2CH_2OC(O)CH_3$ | $CH_3$ | $CH_3$ | CH | |
| H | $CH_3$ | H | $CH_2CH_2OC(O)CH_3$ | $CH_3$ | $OCH_3$ | CH | |
| H | $CH_3$ | H | $CH_2CH_2OC(O)CH_3$ | $OCH_3$ | $OCH_3$ | CH | |
| H | $CH_3$ | H | $CH_2CH_2OC(O)CH_3$ | $CH_3$ | $CH_3$ | N | |
| H | $CH_3$ | H | $CH_2CH_2OC(O)CH_3$ | $CH_3$ | $OCH_3$ | N | |
| H | $CH_3$ | H | $CH_2CH_2OC(O)CH_3$ | $OCH_3$ | $OCH_3$ | N | |
| H | $CH_3$ | H | $CH_2CH_2OC(O)CH_3$ | $OCH_3$ | Cl | CH | |
| H | $CH_3$ | H | $CH_2(CH_2)_2OC(O)CH_3$ | $CH_3$ | $CH_3$ | CH | |
| H | $CH_3$ | H | $CH_2(CH_2)_2OC(O)CH_3$ | $CH_3$ | $OCH_3$ | CH | |
| H | $CH_3$ | H | $CH_2(CH_2)_2OC(O)CH_3$ | $OCH_3$ | $OCH_3$ | CH | |
| H | $CH_3$ | H | $CH_2(CH_2)_3OC(O)CH_3$ | $CH_3$ | $CH_3$ | N | |
| H | $CH_3$ | H | $CH_2(CH_2)_3OC(O)CH_3$ | $OCH_3$ | $OCH_3$ | N | |
| H | $CH_3$ | H | $CH_2(CH_2)_3OC(O)CH_3$ | $OCH_3$ | Cl | CH | |
| H | $CH_3$ | H | $CH_2(CH_2)_3OC(O)CH_3$ | $CH_3$ | $CH_3$ | CH | |
| H | $CH_3$ | H | $CH_2P(CH_3)(Br)(CH_3)$ | $CH_3$ | $OCH_3$ | CH | |
| H | $CH_3$ | H | $CH_2P(C_6H_5)_3$ | $OCH_3$ | $OCH_3$ | CH | |
| H | $CH_3$ | H | $CH_2OC(O)N(CH_3)_2$ | $CH_3$ | $CH_3$ | N | |
| H | $CH_3$ | H | $CH_2OC(O)N(CH_3)_2$ | $CH_3$ | $OCH_3$ | N | |
| H | $CH_3$ | H | $CH_2OC(O)N(CH_3)_2$ | $OCH_3$ | $OCH_3$ | N | |
| H | $CH_3$ | H | $CH_2OC(O)N(CH_3)_2$ | $OCH_3$ | Cl | CH | |
| H | $CH_3$ | H | $CH_2OC(O)N(CH_3)_2$ | $CH_3$ | $CH_3$ | CH | |
| H | $CH_3$ | H | $CH_2OC(O)N(CH_3)_2$ | $CH_3$ | $OCH_3$ | CH | |
| H | $CH_3$ | H | $CH_2OC(O)N(CH_3)_2$ | $OCH_3$ | $OCH_3$ | CH | |

TABLE I-continued

General Structure I

| R | R₁ | R₂ | R₃ | X | Y | Z | m.p. (°C.) |
|---|----|----|----|---|---|---|------------|
| H | CH₃ | H | CH₂CH₂OC(O)N(CH₃)₂ | CH₃ | CH₃ | N | |
| H | CH₃ | H | CH₂CH₂OC(O)N(CH₃)₂ | CH₃ | OCH₃ | N | |
| H | CH₃ | CH₃ | CH₂CH₂OC(O)N(CH₃)₂ | OCH₃ | OCH₃ | N | |
| H | CH₃ | H | CH₂CH₂OC(O)N(CH₃)₂ | OCH₃ | Cl | CH | |
| H | CH₃ | H | CH₂CH₂OC(O)N(CH₃)₂ | CH₃ | CH₃ | CH | |
| H | CH₃ | H | CH₂CH₂OC(O)N(CH₃)₂ | CH₃ | OCH₃ | CH | |
| H | CH₃ | H | CH₂OSO₂CH₃ | OCH₃ | OCH₃ | CH | |
| H | CH₃ | H | CH₂OSO₂CH₃ | CH₃ | CH₃ | N | |
| H | CH₃ | H | CH₂OSO₂CH₃ | CH₃ | OCH₃ | N | |
| H | CH₃ | H | CH₂OSO₂CH₃ | OCH₃ | OCH₃ | N | |
| H | CH₃ | H | CH₂OSO₂CH₂CH₃ | OCH₃ | Cl | CH | |
| H | CH₃ | H | CH₂OSO₂CH₂CH₃ | CH₃ | CH₃ | CH | |
| CH₃ | CH₃ | H | CH₂OSO₂CH₂CH₃ | CH₃ | OCH₃ | CH | |
| H | CH₃ | H | CH₂(CH₂)₂OSO₂CH₃ | OCH₃ | OCH₃ | CH | |
| H | CH₃ | H | CH₂(CH₂)₂OSO₂CH₃ | CH₃ | CH₃ | N | |
| H | CH₃ | H | CH₂(CH₂)₂OSO₂CH₃ | CH₃ | OCH₃ | N | |
| H | CH₃ | H | CH₂(CH₂)₂OSO₂CH₃ | OCH₃ | OCH₃ | N | |
| H | CH₃ | H | CH₂(CH₂)₂OSO₂CH₃ | OCH₃ | Cl | CH | |
| H | CH₃ | H | CH₂OP(O)(CH₃)₂ | CH₃ | CH₃ | CH | |
| H | CH₃ | H | CH₂OP(O)(CH₃)₂ | CH₃ | OCH₃ | CH | |
| H | CH₃ | H | CH₂OP(O)(CH₃)₂ | OCH₃ | OCH₃ | CH | |
| H | CH₃ | H | CH₂OP(O)(CH₃)₂ | CH₃ | CH₃ | N | |
| H | CH₃ | H | CH₂OP(O)(CH₃)₂ | CH₃ | OCH₃ | N | |
| H | CH₃ | H | CH₂OP(O)(CH₃)₂ | OCH₃ | OCH₃ | N | |
| H | CH₃ | H | CH₂OP(O)(CH₃)₂ | OCH₃ | Cl | CH | |
| H | CH₃ | H | CH₂OP(O)(CH₃)Ph | CH₃ | CH₃ | CH | |
| H | CH₃ | H | CH₂OP(O)(CH₃)Ph | CH₃ | OCH₃ | CH | |
| H | CH₃ | H | CH₂OP(O)(CH₃)Ph | OCH₃ | OCH₃ | CH | |
| H | CH₃ | H | CH₂OP(O)(CH₃)Ph | CH₃ | CH₃ | N | |
| H | CH₃ | H | CH₂OP(O)(Ph)₂ | CH₃ | OCH₃ | N | |
| H | CH₃ | H | CH₂OP(O)(Ph)₂ | OCH₃ | OCH₃ | N | |
| H | CH₃ | H | CH₂OP(O)(Ph)₂ | OCH₃ | Cl | CH | |
| H | CH₃ | H | CH₂OP(O)(Ph)₂ | CH₃ | CH₃ | CH | |
| H | CH₃ | H | CH₂OP(O)(Ph)₂ | CH₃ | OCH₃ | CH | |
| H | CH₃ | H | CH₂OP(O)(Ph)₂ | OCH₃ | OCH₃ | CH | |
| H | CH₃ | H | CH₂CH₂OP(O)(CH₃)₂ | CH₃ | CH₃ | N | |
| H | CH₃ | H | CH₂CH₂OP(O)(CH₃)₂ | OCH₃ | OCH₃ | N | |
| H | CH₃ | H | CH₂CH₂OP(O)(CH₃)₂ | OCH₃ | Cl | CH | |
| H | CH₃ | H | CH₂CH₂OP(O)(CH₃)₂ | CH₃ | CH₃ | CH | |
| H | CH₃ | H | CH₂CH₂OP(O)(CH₃)₂ | CH₃ | OCH₃ | CH | |
| H | CH₃ | H | CH₂(CH₂)₂OP(O)(CH₃)₂ | OCH₃ | OCH₃ | CH | |
| H | CH₃ | H | CH₂(CH₂)₂OP(O)(CH₃)₂ | CH₃ | CH₃ | N | |
| H | CH₃ | H | CH₂(CH₂)₂OP(O)(CH₃)₂ | CH₃ | OCH₃ | N | |
| H | CH₃ | H | CH₂(CH₂)₂OP(O)(CH₃)₂ | OCH₃ | OCH₃ | N | |
| H | CH₃ | H | CH₂(CH₂)₂OP(O)(CH₃)₂ | OCH₃ | Cl | CH | |
| H | CH₃ | H | CH₂(CH₂)₂OP(O)(CH₃)₂ | CH₃ | CH₃ | CH | |
| H | CH₃ | H | CH₂P(O)(CH₃)₂ | CH₃ | OCH₃ | CH | |
| H | CH₃ | H | CH₂P(O)(CH₃)₂ | OCH₃ | OCH₃ | CH | |
| H | CH₃ | H | CH₂P(O)(CH₃)₂ | CH₃ | CH₃ | N | |
| H | CH₃ | H | CH₂P(O)(CH₃)₂ | CH₃ | OCH₃ | N | |
| H | CH₃ | CH₃ | CH₂P(O)(CH₃)₂ | OCH₃ | OCH₃ | N | |
| H | CH₃ | H | CH₂P(O)(CH₃)₂ | OCH₃ | Cl | CH | |
| H | CH₃ | H | CH₂P(O)(CH₃)₂ | CH₃ | CH₃ | CH | |
| H | CH₃ | H | CH₂P(O)(OCH₃)₂ | CH₃ | OCH₃ | CH | |
| H | CH₃ | H | CH₂P(O)(OCH₃)₂ | OCH₃ | OCH₃ | CH | |
| H | CH₃ | H | CH₂P(O)(OCH₃)₂ | CH₃ | CH₃ | N | |
| H | CH₃ | H | CH₂P(O)(OCH₃)₂ | CH₃ | OCH₃ | N | |
| H | CH₃ | H | CH₂P(O)(OCH₃)₂ | OCH₃ | OCH₃ | N | |
| H | CH₃ | H | CH₂P(O)(OCH₃)₂ | OCH₃ | Cl | CH | |
| H | CH₃ | H | CH₂P(O)(OCH₃)₂ | CH₃ | CH₃ | CH | |
| CH₃ | CH₃ | H | CH₂CH₂P(O)(OCH₂CH₃)₂ | CH₃ | OCH₃ | CH | |
| H | CH₃ | H | CH₂CH₂P(O)(OCH₂CH₃)₂ | OCH₃ | OCH₃ | CH | |
| H | CH₃ | H | CH₂(CH₂)₃P(O)(OCH₃)₂ | CH₃ | CH₃ | N | |
| H | CH₃ | H | CH₂(CH₂)₃P(O)(OCH₃)₂ | CH₃ | OCH₃ | N | |
| H | CH₃ | H | CH₂(CH₂)₃P(O)(OCH₃)₂ | OCH₃ | OCH₃ | N | |
| H | CH₃ | H | CH₂(CH₂)₃P(O)(OCH₃)₂ | OCH₃ | Cl | CH | |
| H | CH₃ | H | CH₂OP(S)(CH₃)₂ | CH₃ | CH₃ | CH | |
| H | CH₃ | H | CH₂OP(S)(CH₃)₂ | CH₃ | OCH₃ | CH | |
| H | CH₃ | H | CH₂OP(S)(CH₃)₂ | OCH₃ | OCH₃ | CH | |
| H | CH₃ | H | CH₂OP(S)(CH₃)₂ | CH₃ | CH₃ | N | |
| H | CH₃ | H | CH₂OP(S)(CH₃)₂ | CH₃ | OCH₃ | N | |
| H | CH₃ | H | CH₂OP(S)(CH₃)₂ | OCH₃ | OCH₃ | N | |
| H | CH₃ | H | CH₂OP(S)(CH₃)₂ | OCH₃ | Cl | CH | |
| H | CH₃ | H | CH₂OP(S)(OCH₃)₂ | CH₃ | CH₃ | CH | |
| H | CH₃ | H | CH₂OP(S)(OCH₃)₂ | CH₃ | OCH₃ | CH | |
| H | CH₃ | H | CH₂OP(S)(OCH₃)₂ | OCH₃ | OCH₃ | CH | |
| H | CH₃ | H | CH₂OP(S)(OCH₃)₂ | CH₃ | CH₃ | N | |
| H | CH₃ | H | CH₂OP(S)(OCH₃)₂ | CH₃ | OCH₃ | N | |
| H | CH₃ | H | CH₂OP(S)(OCH₃)₂ | OCH₃ | OCH₃ | N | |
| H | CH₃ | H | CH₂OP(S)(OCH₃)₂ | OCH₃ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂P(S)(CH₃)₂ | OCH₃ | OCH₃ | CH | |
| H | CH₃ | H | CH₂P(S)(CH₃)₂ | CH₃ | CH₃ | N | |
| H | CH₃ | H | CH₂P(S)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(OCH₃)₂ | CH₃ | CH₃ | CH | |
| H | CH₃ | H | CH₂P(S)(OCH₃)₂ | CH₃ | OCH₃ | CH | |
| H | CH₃ | H | CH₂P(S)(OCH₃)₂ | OCH₃ | OCH₃ | CH | |
| H | CH₃ | H | CH₂P(S)(OCH₃)₂ | CH₃ | CH₃ | N | |
| H | CH₃ | H | CH₂P(S)(OCH₃)₂ | CH₃ | OCH₃ | N | |
| H | CH₃ | H | CH₂P(S)(OCH₃)₂ | OCH₃ | OCH₃ | N | |
| H | CH₃ | H | CH₂P(S)(OCH₃)₂ | OCH₃ | Cl | CH | |
| H | CH₃ | H | CH₂CH₂OP(S)(CH₃)₂ | CH₃ | CH₃ | CH | |
| H | CH₃ | H | CH₂CH₂OP(S)(CH₃)₂ | CH₃ | OCH₃ | CH | |
| H | CH₃ | H | CH₂CH₂OP(S)(CH₃)₂ | OCH₃ | OCH₃ | CH | |
| H | CH₃ | H | CH₂CH₂OP(S)(CH₃)₂ | CH₃ | CH₃ | N | |
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | CH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |

TABLE I-continued

General Structure I

| R | R₁ | R₂ | R₃ | X | Y | Z | m.p. (°C.) |
|---|----|----|----|---|---|---|------------|
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂(CH₂)₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₃SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |
| H | CH₃ | CH₃ | CH₂CH₂SO₂CH₃ | OCH₃ | OCH₃ | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | H | CH₂(CH₂)₃SO₂CH₃ | CH₃ | OCH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | CH₃ | OCH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | OCH₃ | CH | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CH | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |
| H | CH₃ | H | CH₂CH₂CN | OCH₃ | Cl | CH | |
| CH₃ | CH₃ | H | CH₂CH₂CN | CH₃ | CH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2P(S)(CH_3)_2$ | $CH_3$ | $CH_3$ | CH | |
| H | $CH_3$ | H | $CH_2P(S)(CH_3)_2$ | $CH_3$ | $OCH_3$ | CH | |
| H | $CH_3$ | H | $CH_2-CH_2P(S)(CH_3)_2$ | $OCH_3$ | $OCH_3$ | CH | |
| H | $CH_3$ | H | $CH_2-CH_2P(S)(CH_3)_2$ | $CH_3$ | $CH_3$ | N | |
| H | $CH_3$ | H | $CH_2-CH_2P(S)(CH_3)_2$ | $OCH_3$ | $OCH_3$ | N | |
| H | $CH_3$ | H | $CH_2-CH_2P(S)(CH_3)_2$ | $OCH_3$ | Cl | CH | |
| H | $CH_3$ | H | $CH_2-CH_2P(S)(CH_3)_2$ | $CH_3$ | $CH_3$ | CH | |
| H | $CH_3$ | H | $CH_2N(CH_3)_2$ | $CH_3$ | $OCH_3$ | CH | |
| H | $CH_3$ | H | $CH_2N(CH_3)_2$ | $OCH_3$ | $OCH_3$ | CH | |
| H | $CH_3$ | H | $CH_2N(CH_3)_2$ | $CH_3$ | $CH_3$ | N | |
| H | $CH_3$ | H | $CH_2N(CH_3)_2$ | $CH_3$ | $OCH_3$ | N | |
| H | $CH_3$ | H | $CH_2N(CH_3)_2$ | $OCH_3$ | $OCH_3$ | N | |
| H | $CH_3$ | H | $CH_2N(CH_3)_2$ | $OCH_3$ | Cl | CH | |
| H | $CH_3$ | H | $CH_2N(CH_3)_2$ | $CH_3$ | $CH_3$ | CH | |
| H | $CH_3$ | H | $CH_2(CH_2)_3N(CH_3)_2$ | $CH_3$ | $OCH_3$ | CH | |
| H | $CH_3$ | H | $CH_2(CH_2)_3N(CH_3)_2$ | $OCH_3$ | $OCH_3$ | CH | |
| H | $CH_3$ | H | $CH_2(CH_2)_3N(CH_3)_2$ | $CH_3$ | $CH_3$ | N | |
| H | $CH_3$ | H | $CH_2(CH_2)_3N(CH_3)_2$ | $CH_3$ | $OCH_3$ | N | |
| H | $CH_3$ | $CH_3$ | $CH_2(CH_2)_3N(CH_3)_2$ | $OCH_3$ | $OCH_3$ | N | |
| H | $CH_3$ | H | $CH_2(CH_2)_3N(CH_3)_2$ | $OCH_3$ | Cl | CH | |
| H | $CH_3$ | H | $CH_2(CH_2)_3N(CH_3)_2$ | $CH_3$ | $CH_3$ | CH | |
| H | $CH_3$ | H | $CH_2N(CH_3)_2Ph$ | $CH_3$ | $OCH_3$ | CH | |
| H | $CH_3$ | H | $CH_2N(CH_3)_2Ph$ | $OCH_3$ | $OCH_3$ | CH | |
| H | $CH_3$ | H | $CH_2N(CH_3)_2Ph$ | $CH_3$ | $CH_3$ | N | |
| H | $CH_3$ | H | $CH_2N(CH_3)_2Ph$ | $CH_3$ | $OCH_3$ | N | |
| H | $CH_3$ | H | $CH_2-CH(CH_3)N(CH_3)_2$ | $OCH_3$ | $OCH_3$ | N | |
| H | $CH_3$ | H | $CH_2-CH(CH_3)N(CH_3)_2$ | $OCH_3$ | Cl | CH | |
| H | $CH_3$ | H | $CH_2-CH(CH_3)N(CH_3)_2$ | $CH_3$ | $CH_3$ | CH | |
| $CH_3$ | $CH_3$ | H | $CH_2-CH(CH_3)N(CH_3)_2$ | $CH_3$ | $OCH_3$ | CH | |
| H | $CH_3$ | H | $CH_2-CH(CH_3)N(CH_3)_2$ | $OCH_3$ | $OCH_3$ | CH | |
| H | $CH_3$ | H | $CH_2CH_2CH(CH_3)_2$ | $CH_3$ | $CH_3$ | N | |
| H | $CH_3$ | H | $CH_2CH_2CH(CH_3)_2$ | $CH_3$ | $OCH_3$ | N | |
| H | $CH_3$ | H | $CH_2CH_2CH(CH_3)_2$ | $OCH_3$ | $OCH_3$ | N | |
| H | $CH_3$ | H | $CH_2CH_2CH(CH_3)_2$ | $OCH_3$ | Cl | CH | |
| H | $CH_3$ | H | $CH_2NHC(O)CH_3$ | $CH_3$ | $CH_3$ | CH | |
| H | $CH_3$ | H | $CH_2NHC(O)CH_3$ | $CH_3$ | $OCH_3$ | CH | |
| H | $CH_3$ | H | $CH_2NHC(O)CH_3$ | $OCH_3$ | $OCH_3$ | CH | |
| H | $CH_3$ | H | $CH_2NHC(O)CH_3$ | $CH_3$ | $CH_3$ | N | |
| H | $CH_3$ | H | $CH_2NHC(O)CH_3$ | $CH_3$ | $OCH_3$ | N | |
| H | $CH_3$ | H | $CH_2NHC(O)CH_3$ | $OCH_3$ | $OCH_3$ | N | |
| H | $CH_3$ | H | $CH_2NHC(O)CH_3$ | $OCH_3$ | Cl | CH | |
| H | $CH_3$ | H | $CH_2CH_2N(CH_3)C(O)CH_3$ | $CH_3$ | $CH_3$ | CH | |
| H | $CH_3$ | H | $CH_2CH_2N(CH_3)C(O)CH_3$ | $CH_3$ | $OCH_3$ | CH | |
| H | $CH_3$ | H | $CH_2CH_2N(CH_3)C(O)CH_3$ | $OCH_3$ | $OCH_3$ | CH | |
| H | $CH_3$ | H | $CH_2CH_2N(CH_3)C(O)CH_3$ | $CH_3$ | $CH_3$ | N | |
| H | $CH_3$ | H | $CH_2(CH_2)_3NHC(O)CH_3$ | $CH_3$ | $OCH_3$ | N | |
| H | $CH_3$ | H | $CH_2(CH_2)_3NHC(O)CH_3$ | $OCH_3$ | $OCH_3$ | N | |
| H | $CH_3$ | H | $CH_2N(CH_3)C(O)OCH_3$ | $OCH_3$ | Cl | CH | |
| H | $CH_3$ | H | $CH_2N(CH_3)C(O)OCH_3$ | $CH_3$ | $CH_3$ | CH | |
| H | $CH_3$ | H | $CH_2NHC(O)OCH_3$ | $CH_3$ | $OCH_3$ | CH | |
| H | $CH_3$ | H | $CH_2NHC(O)OCH_3$ | $OCH_3$ | $OCH_3$ | CH | |
| H | $CH_3$ | H | $CH_2NHC(O)OCH_3$ | $CH_3$ | $CH_3$ | N | |
| H | $CH_3$ | H | $CH_2NHC(O)OCH_3$ | $OCH_3$ | $OCH_3$ | N | |
| H | $CH_3$ | H | $CH_2NHC(O)OCH_3$ | $OCH_3$ | Cl | CH | |
| H | $CH_3$ | H | $CH_2NHC(O)OCH_3$ | $CH_3$ | $CH_3$ | CH | |
| H | $CH_3$ | H | $CH_2(CH_2)_3NHC(O)OCH_3$ | $CH_3$ | $OCH_3$ | CH | |
| H | $CH_3$ | H | $CH_2(CH_2)_3NHC(O)OCH_3$ | $OCH_3$ | $OCH_3$ | CH | |
| H | $CH_3$ | H | $CH_2(CH_2)_3NHC(O)OCH_3$ | $CH_3$ | $CH_3$ | N | |
| H | $CH_3$ | H | $CH_2N(CH_3)C(O)OCH_2CH_3$ | $CH_3$ | $OCH_3$ | N | |
| H | $CH_3$ | H | $CH(CH_3)NHC(O)OCH_3$ | $OCH_3$ | $OCH_3$ | N | |
| H | $CH_3$ | H | $CH(CH_3)NHC(O)OCH_3$ | $OCH_3$ | Cl | CH | |
| H | $CH_3$ | H | $CH(CH_3)NHC(O)OCH_3$ | $CH_3$ | $CH_3$ | CH | |
| H | $CH_3$ | H | $CH_2NHSO_2CH_3$ | $CH_3$ | $OCH_3$ | CH | |
| H | $CH_3$ | H | $CH_2NHSO_2CH_3$ | $OCH_3$ | $OCH_3$ | CH | |
| H | $CH_3$ | H | $CH_2NHSO_2CH_3$ | $CH_3$ | $CH_3$ | N | |
| H | $CH_3$ | H | $CH_2NHSO_2CH_3$ | $CH_3$ | $OCH_3$ | N | |
| H | $CH_3$ | $CH_3$ | $CH_2NHSO_2CH_3$ | $OCH_3$ | $OCH_3$ | N | |
| H | $CH_3$ | H | $CH_2CH_2NHSO_2CH_3$ | $OCH_3$ | Cl | CH | |
| H | $CH_3$ | H | $CH_2CH_2NHSO_2CH_3$ | $CH_3$ | $CH_3$ | CH | |
| H | $CH_3$ | H | $CH_2CH_2NHSO_2CH_3$ | $CH_3$ | $OCH_3$ | CH | |
| H | $CH_3$ | H | $CH_2CH_2NHSO_2CH_3$ | $OCH_3$ | $OCH_3$ | CH | |
| H | $CH_3$ | H | $CH_2CH_2NHSO_2CH_3$ | $CH_3$ | $CH_3$ | N | |
| H | $CH_3$ | H | $CH_2CH_2NHSO_2CH_3$ | $CH_3$ | $OCH_3$ | N | |
| H | $CH_3$ | H | $CH_2(CH_2)_3NHSO_2CH_3$ | $OCH_3$ | $OCH_3$ | N | |
| H | $CH_3$ | H | $CH_2(CH_2)_3NHSO_2CH_3$ | $OCH_3$ | Cl | CH | |
| H | $CH_3$ | H | $CH_2(CH_2)_3NHSO_2CH_3$ | $CH_3$ | $CH_3$ | CH | |
| $CH_3$ | $CH_3$ | H | $CH_2NHP(O)(CH_3)_2$ | $CH_3$ | $OCH_3$ | CH | |
| H | $CH_3$ | H | $CH_2NHP(O)(CH_3)_2$ | $OCH_3$ | $OCH_3$ | CH | |
| H | $CH_3$ | H | $CH_2NHP(O)(CH_3)_2$ | $CH_3$ | $CH_3$ | N | |
| H | $CH_3$ | H | $CH_2NHP(O)(OCH_3)_2$ | $CH_3$ | $OCH_3$ | N | |

4,715,886

TABLE I-continued

General Structure I

| R | R₁ | R₂ | R₃ | X | Y | Z | m.p. (°C.) |
|---|---|---|---|---|---|---|---|
| H | CH₃ | H | CH₂NHP(O)(OCH₃)₂ | OCH₃ | OCH₃ | N | |
| H | CH₃ | H | CH₂NHP(O)(OCH₃)₂ | OCH₃ | Cl | CH | |
| H | CH₃ | H | CH=CH₂ | CH₃ | CH₃ | CH | |
| H | CH₃ | H | CH=CH₂ | CH₃ | OCH₃ | CH | |
| H | CH₃ | H | CH₂NO₂ | CH₃ | CH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |
| H | CH₃ | H | CH₂C(O)CH₃ | CH₃ | CH₃ | N | |
| H | CH₃ | H | CH₂C(O)CH₃ | OCH₃ | OCH₃ | N | |
| H | CH₃ | H | CH₂C(O)CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH₂CH₃ | CH₃ | CH₃ | N | |
| H | CH₃ | H | CH₂C(O)CH₂CH₃ | CH₃ | OCH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂(CH₂)₃C(O)CH₃ | CH₃ | CH₃ | CH | |
| H | CH₃ | H | CH₂(CH₂)₃C(O)CH₃ | CH₃ | OCH₃ | CH | |
| H | CH₃ | H | CH₂(CH₂)₃C(O)CH₃ | OCH₃ | OCH₃ | CH | |
| H | CH₃ | H | CH₂(CH₂)₃C(O)CH₃ | CH₃ | CH₃ | N | |
| H | CH₃ | H | CH₂(CH₂)₃C(O)CH₃ | CH₃ | OCH₃ | N | |
| H | CH₃ | CH₃ | CH₂(CH₂)₃C(O)CH₃ | OCH₃ | OCH₃ | N | |
| H | CH₃ | H | CH₂(CH₂)₃C(O)CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | CH | |
| H | CH₃ | H | CH₂CH₂C(O)CH₃ | CH₃ | CH₃ | N | |
| H | CH₃ | H | CH₂—CH(CH₃)C(O)CH₃ | CH₃ | OCH₃ | N | |
| H | CH₃ | CH₃ | CH₂—CH(CH₂)C(O)CH₃ | OCH₃ | OCH₃ | N | |
| H | CH₃ | H | CH₂—CH(CH₂)C(O)CH₃ | OCH₃ | Cl | CH | |
| H | CH₃ | H | CH₂—CH(CH₃)C(O)CH₃ | CH₃ | CH₃ | CH | |
| CH₃ | CH₃ | CH₃ | CH₂—CH(CH₂)C(O)CH₃ | CH₃ | OCH₃ | CH | |
| H | CH₃ | H | CH₂(CH₂)₆C(O)CH₂CH₃ | OCH₃ | OCH₃ | CH | |
| H | CH₃ | H | CH₂(CH₂)₆C(O)CH₂CH₃ | CH₃ | CH₃ | N | |
| H | CH₃ | H | CH₂(CH₂)₆C(O)CH₂CH₃ | CH₃ | OCH₃ | N | |
| H | CH₃ | H | CH₂(CH₂)₆C(O)CH₂CH₃ | OCH₃ | OCH₃ | N | |
| H | CH₃ | H | CH₂(CH₂)₆C(O)CH₂CH₃ | OCH₃ | Cl | CH | |
| H | CH₃ | H | CH₂C(O)OCH₃ | CH₃ | CH₃ | CH | |
| H | CH₃ | H | CH₂C(O)OCH₃ | CH₃ | OCH₃ | CH | |
| H | CH₃ | H | CH₂C(O)OCH₃ | OCH₃ | OCH₃ | CH | |
| H | CH₃ | H | CH₂C(O)OCH₃ | CH₃ | CH₃ | N | |
| H | CH₃ | H | CH₂C(O)OCH₃ | CH₃ | OCH₃ | N | |
| H | CH₃ | H | CH₂C(O)OCH₃ | OCH₃ | OCH₃ | N | |
| H | CH₃ | H | CH₂C(O)OCH₃ | OCH₃ | Cl | CH | |
| H | CH₃ | H | CH₂C(O)OCH₂CH₃ | CH₃ | CH₃ | CH | |
| H | CH₃ | H | CH₂C(O)OCH₂CH₃ | CH₃ | OCH₃ | CH | |
| H | CH₃ | H | CH₂C(O)OCH₂CH₃ | OCH₃ | OCH₃ | CH | |
| H | CH₃ | H | CH₂C(O)OCH₂CH₃ | CH₃ | CH₃ | N | |
| H | CH₃ | H | CH₂C(O)OCH₂CH₃ | CH₃ | OCH₃ | N | |
| H | CH₃ | H | CH₂C(O)OCH₂CH₃ | OCH₃ | OCH₃ | N | |
| H | CH₃ | H | CH₂C(O)OCH₂CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | N | |
| H | CH₃ | H | CH₂CH₂C(O)CH₃ | CH₃ | CH₃ | N | |
| H | CH₃ | H | CH₂CH₂C(O)CH₃ | CH₃ | OCH₃ | N | |
| H | CH₃ | H | CH₂CH₂C(O)CH₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | CH₂CH₂C(O)N(CH₃)₂ | CH₃ | CH₃ | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH₂C(O)N(CH₃)₂ | CH₃ | OCH₃ | CH | |
| H | CH₃ | H | CH₂CH₂C(O)N(CH₃)₂ | OCH₃ | OCH₃ | CH | |
| H | CH₃ | H | CH₂CH₂C(O)N(CH₃)₂ | CH₃ | CH₃ | N | |
| H | CH₃ | H | CH₂CH₂C(O)N(CH₃)₂ | CH₃ | OCH₃ | N | |
| H | CH₃ | CH₃ | CH₂CH₂C(O)N(CH₃)₂ | OCH₃ | OCH₃ | N | |
| H | CH₃ | H | CH₂CH₂C(O)N(CH₃)₂ | OCH₃ | Cl | CH | |
| H | CH₃ | H | CH₂C(O)N(CH₃)CH₂CH₃ | CH₃ | CH₃ | CH | |
| H | CH₃ | H | CH₂C(O)N(CH₃)CH₂CH₃ | CH₃ | OCH₃ | CH | |
| H | CH₃ | H | CH₂C(O)N(CH₃)CH₂CH₃ | OCH₃ | OCH₃ | CH | |
| H | CH₃ | H | CH₂C(O)N(CH₃)CH₂CH₃ | CH₃ | CH₃ | N | |
| H | CH₃ | H | CH₂C(O)N(CH₃)CH₂OCH₃ | CH₃ | OCH₃ | N | |
| H | CH₃ | H | CH₂C(O)N(CH₃)CH₂OCH₃ | OCH₃ | OCH₃ | N | |
| H | CH₃ | H | CH₂C(O)N(CH₃)CH₂OCH₃ | OCH₃ | Cl | CH | |
| H | CH₃ | H | CH₂SeCH₃ | CH₃ | CH₃ | CH | |
| CH₃ | CH₃ | H | CH₂SeCH₃ | CH₃ | OCH₃ | CH | |
| H | CH₃ | H | CH₂SeCH₃ | OCH₃ | OCH₃ | CH | |
| H | CH₃ | H | CH₂SePh | CH₃ | CH₃ | N | |
| H | CH₃ | H | CH₂SePh | CH₃ | OCH₃ | N | |
| H | CH₃ | H | CH₂—CH₂SeCH₃ | OCH₃ | OCH₃ | N | |
| H | CH₃ | H | CH₂—CH₂SeCH₃ | OCH₃ | Cl | CH | |
| H | CH₃ | H | CH=CH₂ | OCH₃ | OCH₃ | CH | |
| H | CH₃ | H | CH=CH₂ | CH₃ | CH₃ | N | |
| H | CH₃ | H | CH=CH₂ | CH₃ | OCH₃ | N | |
| H | CH₃ | H | CH=CH₂ | OCH₃ | OCH₃ | N | |
| H | CH₃ | H | CH=CH₂ | OCH₃ | Cl | CH | |
| H | CH₃ | H | CH=CH—CH₃ | CH₃ | CH₃ | CH | |
| H | CH₃ | H | CH=CH—CH₃ | CH₃ | OCH₃ | CH | |
| H | CH₃ | H | CH=CH—CH₃ | OCH₃ | OCH₃ | CH | |
| H | CH₃ | H | CH=CH—CH₃ | CH₃ | CH₃ | N | |
| H | CH₃ | H | CH=CH—CH₃ | CH₃ | OCH₃ | N | |
| H | CH₃ | H | CH=CH—CH₃ | OCH₃ | OCH₃ | N | |
| H | CH₃ | H | CH=CH—CH₃ | OCH₃ | Cl | CH | |
| H | CH₃ | H | CH=CH—CH₂—CH₃ | CH₃ | CH₃ | CH | |
| H | CH₃ | H | CH=CH—CH₂—CH₃ | CH₃ | OCH₃ | CH | |
| H | CH₃ | H | CH=CH—CH₂—CH₃ | OCH₃ | OCH₃ | CH | |
| H | CH₃ | H | CH=CH—CH₂—CH₃ | CH₃ | CH₃ | N | |
| H | CH₃ | H | CH=CH—CH₂—CH₃ | OCH₃ | OCH₃ | N | |
| H | CH₃ | H | CH=CH—CH₂—CH₃ | OCH₃ | Cl | CH | |
| H | CH₃ | H | CH=C(CH₃)₂ | CH₃ | CH₃ | CH | |
| H | CH₃ | H | CH=C(CH₃)₂ | CH₃ | OCH₃ | CH | |
| H | CH₃ | H | CH=C(CH₃)₂ | OCH₃ | OCH₃ | CH | |
| H | CH₃ | H | CH=C(CH₃)₂ | CH₃ | CH₃ | N | |
| H | CH₃ | H | CH=C(CH₃)₂ | CH₃ | OCH₃ | N | |
| H | CH₃ | H | CH=C(CH₃)₂ | OCH₃ | OCH₃ | N | |
| H | CH₃ | H | CH=C(CH₃)₂ | OCH₃ | Cl | CH | |
| H | CH₃ | H | CH=CH(CH₂)₃CH₃ | CH₃ | CH₃ | CH | |
| H | CH₃ | H | CH=CH(CH₂)₃CH₃ | CH₃ | OCH₃ | CH | |
| H | CH₃ | H | CH=CH(CH₂)₃CH₃ | OCH₃ | OCH₃ | CH | |
| H | CH₃ | H | CH=CH(CH₂)₃CH₃ | CH₃ | CH₃ | N | |
| H | CH₃ | H | CH=CH(CH₂)₃CH₃ | CH₃ | OCH₃ | N | |
| H | CH₃ | CH₃ | CH=CH(CH₂)₃CH₃ | OCH₃ | OCH₃ | N | |
| H | CH₃ | H | CH=CH(CH₂)₃CH₃ | OCH₃ | Cl | CH | |
| H | CH₃ | H | CH=C(CH₃)CH₂CH₃ | CH₃ | CH₃ | CH | |
| H | CH₃ | H | CH=C(CH₃)CH₂CH₃ | CH₃ | OCH₃ | CH | |
| H | CH₃ | H | CH=C(CH₃)CH₂CH₃ | OCH₃ | OCH₃ | CH | |
| H | CH₃ | H | CH=CH—CH(CH₃)₂ | CH₃ | CH₃ | N | |
| H | CH₃ | H | CH=CH—CH(CH₃)₂ | CH₃ | OCH₃ | N | |
| H | CH₃ | H | CH=CH—CH(CH₃)₂ | OCH₃ | OCH₃ | N | |
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | $CH_2(CH_2)_7C\equiv CH$ | $OCH_3$ | $OCH_3$ | N | |
| H | $CH_3$ | H | $CH_2(CH_2)_7C\equiv CH$ | $OCH_3$ | Cl | CH | |
| H | $CH_3$ | H | 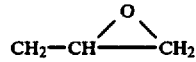 | $CH_3$ | $CH_3$ | CH | |
| H | $CH_3$ | H | 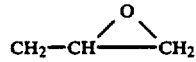 | $CH_3$ | $OCH_3$ | CH | |
| H | $CH_3$ | H | 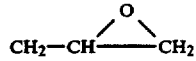 | $OCH_3$ | $OCH_3$ | CH | |
| H | $CH_3$ | H | 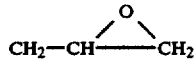 | $CH_3$ | $CH_3$ | N | |
| H | $CH_3$ | H | 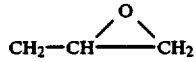 | $CH_3$ | $OCH_3$ | N | |
| H | $CH_3$ | H | 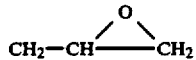 | $OCH_3$ | $OCH_3$ | N | |
| H | $CH_3$ | H | 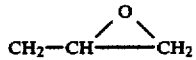 | $OCH_3$ | Cl | CH | |
| H | $CH_3$ | H | 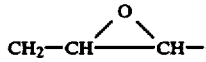 | $CH_3$ | $CH_3$ | CH | |
| H | $CH_3$ | H | 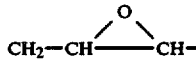 | $CH_3$ | $OCH_3$ | CH | |
| H | $CH_3$ | H | 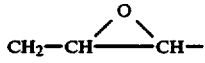 | $OCH_3$ | $OCH_3$ | CH | |
| H | $CH_3$ | H | 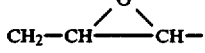 | $CH_3$ | $CH_3$ | N | |
| H | $CH_3$ | H | 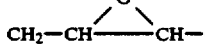 | $CH_3$ | $OCH_3$ | N | |
| H | $CH_3$ | H | 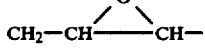 | $OCH_3$ | $OCH_3$ | N | |
| H | $CH_3$ | H | 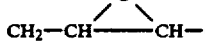 | $OCH_3$ | Cl | CH | |
| H | $CH_3$ | H | 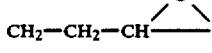 | $CH_3$ | $CH_3$ | CH | |
| H | $CH_3$ | H | 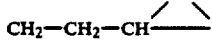 | $CH_3$ | $OCH_3$ | CH | |
| H | $CH_3$ | H | 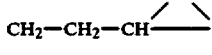 | $OCH_3$ | $OCH_3$ | CH | |
| H | $CH_3$ | H | 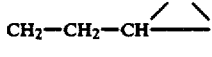 | $CH_3$ | $CH_3$ | N | |
| H | $CH_3$ | H | 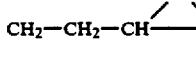 | $OCH_3$ | $OCH_3$ | N | |

TABLE I-continued

General Structure I

| R | R₁ | R₂ | R₃ | X | Y | Z | m.p. (°C.) |
|---|----|----|----|----|----|----|----|
| H | CH₃ | H | CH₂—CH₂—CH(—O—)CH₂ (epoxide) | OCH₃ | Cl | CH | |
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |
| H | CH₃ | CH₃ | cyclopentyl | OCH₃ | OCH₃ | N | |
| H | CH₃ | H | cyclopentyl | OCH₃ | Cl | CH | |
| H | CH₃ | H | cyclohexyl | CH₃ | CH₃ | CH | |
| H | CH₃ | H | cyclohexyl | CH₃ | OCH₃ | CH | |
| H | CH₃ | H | cyclohexyl | OCH₃ | OCH₃ | CH | |
| H | CH₃ | H | cyclohexyl | CH₃ | CH₃ | N | |
| H | CH₃ | H | cyclohexyl | CH₃ | OCH₃ | N | |
| H | CH₃ | CH₃ | cyclohexyl | OCH₃ | OCH₃ | N | |
| H | CH₃ | H | cyclohexyl | OCH₃ | Cl | CH | |
| H | CH₃ | H | cyclopropyl | CH₃ | CH₃ | CH | |
| CH₃ | CH₃ | H | cyclopropyl | OCH₃ | OCH₃ | CH | |
| H | CH₃ | H | cyclopropyl | OCH₃ | OCH₃ | CH | |
| H | CH₃ | H | cyclopropyl | CH₃ | CH₃ | N | |
| H | CH₃ | H | cyclopropyl | CH₃ | OCH₃ | N | |
| H | CH₃ | H | cyclopropyl | OCH₃ | OCH₃ | N | |
| H | CH₃ | H | cyclopropyl | OCH₃ | Cl | CH | |
| H | CH₃ | H | CH₂—cyclopropyl | CH₃ | CH₃ | CH | |
| H | CH₃ | H | CH₂—cyclopropyl | CH₃ | OCH₃ | CH | |
| H | CH₃ | H | CH₂—cyclopropyl | OCH₃ | OCH₃ | CH | |
| H | CH₃ | H | CH₂—cyclopropyl | CH₃ | CH₃ | N | |
| H | CH₃ | H | CH₂—cyclopropyl | CH₃ | OCH₃ | N | |
| H | CH₃ | H | CH₂—cyclopropyl | OCH₃ | OCH₃ | N | |
| H | CH₃ | H | CH₂—cyclopropyl | OCH₃ | Cl | CH | |
| H | CH₃ | H | CH₂—cyclopentyl | CH₃ | CH₃ | CH | |
| H | CH₃ | H | CH₂—cyclopentyl | CH₃ | OCH₃ | CH | |
| H | CH₃ | H | CH₂—cyclopentyl | OCH₃ | OCH₃ | CH | |
| H | CH₃ | H | CH₂—cyclopentyl | CH₃ | CH₃ | N | |
| H | CH₃ | H | CH₂—cyclopentyl | CH₃ | OCH₃ | N | |
| H | CH₃ | H | CH₂—cyclopentyl | OCH₃ | OCH₃ | N | |
| H | CH₃ | H | CH₂—cyclopentyl | OCH₃ | Cl | CH | |
| H | CH₃ | H | C₆H₅ | CH₃ | CH₃ | CH | |
| H | CH₃ | H | C₆H₅ | CH₃ | OCH₃ | CH | |
| H | CH₃ | H | C₆H₅ | OCH₃ | OCH₃ | CH | |
| H | CH₃ | H | C₆H₅ | CH₃ | CH₃ | N | |
| H | CH₃ | H | C₆H₅ | CH₃ | OCH₃ | N | |
| H | CH₃ | H | C₆H₅ | OCH₃ | Cl | CH | |
| H | CH₃ | H | CH=CH—CF₃ | CH₃ | CH₃ | CH | |
| H | CH₃ | H | CH=CH—CF₃ | CH₃ | OCH₃ | CH | |
| H | CH₃ | H | CH=CH—CF₃ | OCH₃ | OCH₃ | CH | |
| H | CH₃ | H | CH=CH—CF₃ | CH₃ | CH₃ | N | |
| H | CH₃ | H | CH=CH—CF₃ | CH₃ | OCH₃ | N | |
| H | CH₃ | H | CH=CH—CF₃ | OCH₃ | OCH₃ | N | |
| H | CH₃ | H | CH=CH—CF₃ | OCH₃ | Cl | CH | |
| H | CH₃ | H | CH₂—C≡C—CF₃ | CH₃ | CH₃ | CH | |
| H | CH₃ | H | CH₂—C≡C—CF₃ | CH₃ | OCH₃ | CH | |
| H | CH₃ | H | CH₂—C≡C—CF₃ | OCH₃ | OCH₃ | CH | |
| H | CH₃ | H | CH₂—C≡C—CF₃ | CH₃ | CH₃ | N | |
| H | CH₃ | H | CH₂—C≡C—CF₃ | CH₃ | OCH₃ | N | |
| H | CH₃ | CH₃ | CH₂—C≡C—CF₃ | OCH₃ | OCH₃ | N | |
| H | CH₃ | H | CH₂—CH=CF₂ | OCH₃ | Cl | CH | |
| H | CH₃ | H | CH=CH—CH₂Cl | CH₃ | CH₃ | CH | |
| H | CH₃ | H | CH=CH—CH₂Cl | CH₃ | OCH₃ | CH | |
| H | CH₃ | H | CH=CH—CH₂Cl | OCH₃ | OCH₃ | CH | |
| H | CH₃ | H | CH=CH—CH₂Cl | CH₃ | CH₃ | N | |
| H | CH₃ | H | CH=CH—CH₂Cl | CH₃ | OCH₃ | N | |
| H | CH₃ | H | CH=CH—CH₂Cl | OCH₃ | OCH₃ | N | |
| H | CH₃ | H | CH₂—C(CHF)(CH₂) (fluorocyclopropyl) | OCH₃ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | CH₂—C(CHF)(CH₂) cyclopropyl | CH₃ | CH₃ | CH | |
| CH₃ | CH₃ | H | CH₂—C(CHF)(CH₂) cyclopropyl | CH₃ | OCH₃ | CH | |
| H | CH₃ | H | CH₂—C(CHF)(CH₂) cyclopropyl | OCH₃ | OCH₃ | CH | |
| H | CH₃ | H | CH₂—C(CHF)(CH₂) cyclopropyl | CH₃ | CH₃ | N | |
| H | CH₃ | H | CH₂—C(CHF)(CH₂) cyclopropyl | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡C—OCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | OCH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | CH₃ | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—C≡C—CH₂OCH₃ | OCH₃ | OCH₃ | CH | |
| H | CH₃ | H | CH₂—CH=CH—CH₂SCH₃ | CH₃ | CH₃ | N | |
| H | CH₃ | H | CH₂—CH=CH—CH₂SCH₃ | CH₃ | OCH₃ | N | |
| H | CH₃ | H | CH₂—CH=CH—CH₂SCH₃ | OCH₃ | OCH₃ | N | |
| H | CH₃ | H | CH₂—CH=CH—CH₂SCH₃ | OCH₃ | Cl | CH | |
| H | CH₃ | H | CH=CH—CH₂N(CH₃)₂ | CH₃ | CH₃ | CH | |
| CH₃ | CH₃ | H | CH=CH—CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | CH₃ | OCH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |

TABLE I-continued

General Structure I

| R | R₁ | R₂ | R₃ | X | Y | Z | m.p. (°C.) |
|---|---|---|---|---|---|---|---|
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |
| H | CH₃ | H | SCH₃ | OCH₃ | OCH₃ | N | |
| H | CH₃ | H | SCH₃ | OCH₃ | Cl | CH | |
| H | CH₃ | H | SCH₂CF₃ | CH₃ | CH₃ | CH | |
| H | CH₃ | H | SCH₂CH₃ | CH₃ | OCH₃ | CH | |
| H | CH₃ | H | SCH₂CH₃ | OCH₃ | OCH₃ | CH | |
| H | CH₃ | H | SCH₂CH₃ | CH₃ | CH₃ | N | |
| H | CH₃ | H | SCH₂CH₃ | CH₃ | OCH₃ | N | |
| H | CH₃ | H | SCH₂CH₃ | OCH₃ | OCH₃ | N | |
| H | CH₃ | H | SCH₂CH₃ | OCH₃ | Cl | CH | |
| H | CH₃ | H | SO₂CH₃ | CH₃ | CH₃ | CH | |
| H | CH₃ | H | SO₂CH₃ | CH₃ | OCH₃ | CH | |
| H | CH₃ | H | SO₂CH₃ | OCH₃ | OCH₃ | CH | |
| H | CH₃ | H | SO₂CH₃ | CH₃ | CH₃ | N | |
| H | CH₃ | H | SO₂CH₃ | OCH₃ | OCH₃ | N | |
| H | CH₃ | H | SO₂CH₃ | OCH₃ | Cl | CH | |
| H | CH₃ | H | SO₂CH₂CH₃ | CH₃ | CH₃ | CH | |
| H | CH₃ | H | SO₂CH₂CH₃ | CH₃ | OCH₃ | CH | |
| H | CH₃ | H | SO₂CH₂CH₃ | OCH₃ | OCH₃ | CH | |
| H | CH₃ | H | SO₂CH₂CH₃ | CH₃ | CH₃ | N | |
| H | CH₃ | H | SO₂CH₂CH₃ | CH₃ | OCH₃ | N | |
| H | CH₃ | H | SO₂CH₂CH₃ | OCH₃ | OCH₃ | N | |
| H | CH₃ | H | SO₂CH₂CH₃ | OCH₃ | Cl | CH | |
| H | CH₃ | H | OCH₃ | CH₃ | CH₃ | CH | |
| H | CH₃ | H | OCH₃ | CH₃ | OCH₃ | CH | |
| H | CH₃ | H | OCH₃ | OCH₃ | OCH₃ | CH | |
| H | CH₃ | H | OCH₃ | CH₃ | CH₃ | N | |
| H | CH₃ | H | OCH₃ | CH₃ | OCH₃ | N | |
| H | CH₃ | CH₃ | OCH₃ | OCH₃ | OCH₃ | N | |
| H | CH₃ | H | OCH₃ | OCH₃ | Cl | CH | |
| H | CH₃ | H | OCH₂CH₃ | CH₃ | CH₃ | CH | |
| H | CH₃ | H | OCH₂CH₃ | CH₃ | OCH₃ | CH | |
| H | CH₃ | H | OCH₂CH₃ | OCH₃ | OCH₃ | CH | |
| H | CH₃ | H | OCH₂CH₃ | CH₃ | CH₃ | N | |
| H | CH₃ | H | OCH₂CH₃ | CH₃ | OCH₃ | N | |
| H | CH₃ | H | OCH₂CH₃ | OCH₃ | OCH₃ | N | |
| H | CH₃ | H | OCH₂CH₃ | OCH₃ | Cl | CH | |
| H | CH₃ | H | OCH(CH₃)₂ | CH₃ | CH₃ | CH | |
| CH₃ | CH₃ | H | OCH(CH₃)₂ | CH₃ | OCH₃ | CH | |
| H | CH₃ | H | OCH(CH₃)₂ | OCH₃ | OCH₃ | CH | |
| H | CH₃ | H | OCH(CH₃)₂ | CH₃ | CH₃ | N | |
| H | CH₃ | H | OCH(CH₃)₂ | CH₃ | OCH₃ | N | |
| H | CH₃ | H | OCH(CH₃)₂ | OCH₃ | OCH₃ | N | |
| H | CH₃ | H | OCH(CH₃)₂ | OCH₃ | Cl | CH | |
| H | CH₃ | H | C(O)CH₃ | CH₃ | CH₃ | CH | |
| H | CH₃ | H | C(O)CH₃ | CH₃ | OCH₃ | CH | |
| H | CH₃ | H | C(O)CH₃ | OCH₃ | OCH₃ | CH | |
| H | CH₃ | H | C(O)CH₃ | CH₃ | CH₃ | N | |
| H | CH₃ | H | C(O)CH₃ | CH₃ | OCH₃ | N | |
| H | CH₃ | H | C(O)CH₃ | OCH₃ | OCH₃ | N | |
| H | CH₃ | H | C(O)CH₃ | OCH₃ | Cl | CH | |
| H | CH₃ | H | C(O)CH₂CH₃ | CH₃ | CH₃ | CH | |
| H | CH₃ | H | C(O)CH₂CH₃ | CH₃ | OCH₃ | CH | |
| H | CH₃ | H | C(O)CH₂CH₃ | OCH₃ | OCH₃ | CH | |
| H | CH₃ | H | C(O)CH₂CH₃ | CH₃ | CH₃ | N | |
| H | CH₃ | H | C(O)CH₂CH₃ | CH₃ | OCH₃ | N | |
| H | CH₃ | H | C(O)CH₂CH₃ | OCH₃ | OCH₃ | N | |
| H | CH₃ | H | C(O)CH₂CH₃ | OCH₃ | Cl | CH | |
| H | CH₃ | H | C(O)CH(CH₃)₂ | CH₃ | CH₃ | CH | |
| H | CH₃ | H | C(O)CH(CH₃)₂ | CH₃ | OCH₃ | CH | |
| H | CH₃ | H | C(O)CH(CH₃)₂ | OCH₃ | OCH₃ | CH | |
| H | CH₃ | H | C(O)CH(CH₃)₂ | CH₃ | CH₃ | N | |
| H | CH₃ | H | C(O)CH(CH₃)₂ | OCH₃ | OCH₃ | N | |
| H | CH₃ | H | C(O)CH(CH₃)₂ | OCH₃ | Cl | CH | |
| H | CH₃ | H | C(O)CHF₂ | CH₃ | CH₃ | CH | |
| H | CH₃ | H | C(O)CHF₂ | CH₃ | OCH₃ | CH | |
| H | CH₃ | H | C(O)CHF₂ | OCH₃ | OCH₃ | CH | |
| H | CH₃ | H | C(O)CF₃ | CH₃ | CH₃ | N | |
| H | CH₃ | H | C(O)CF₃ | CH₃ | OCH₃ | N | |
| H | CH₃ | H | C(O)CF₃ | OCH₃ | OCH₃ | N | |
| H | CH₃ | H | C(O)CF₃ | OCH₃ | Cl | CH | |
| H | CH₃ | H | C(O)CH₂CH₂CH₃ | CH₃ | CH₃ | CH | |
| H | CH₃ | H | C(O)CH₂CH₂CH₃ | CH₃ | OCH₃ | CH | |
| H | CH₃ | H | C(O)CH₂CH₂CH₃ | OCH₃ | OCH₃ | CH | |
| H | CH₃ | H | C(O)CH₂CH₂CH₃ | CH₃ | CH₃ | N | |
| H | CH₃ | H | C(O)CH₂CH₂CH₃ | CH₃ | OCH₃ | N | |

TABLE I-continued

General Structure I

| R | R₁ | R₂ | R₃ | X | Y | Z | m.p. (°C.) |
|---|---|---|---|---|---|---|---|
| H | CH₃ | CH₃ | C(O)CH₂CH₂CH₃ | OCH₃ | OCH₃ | N | |
| H | CH₃ | H | C(O)CH₂CH₂CH₃ | OCH₃ | Cl | CH | |
| H | CH₃ | H | C(O)CH₂OCH₃ | CH₃ | CH₃ | CH | |
| H | CH₃ | H | C(O)CH₂OCH₃ | CH₃ | OCH₃ | CH | |
| H | CH₃ | H | C(O)CH₂OCH₃ | OCH₃ | OCH₃ | CH | |
| H | CH₃ | H | C(O)CH₂OCH₃ | CH₃ | CH₃ | N | |
| H | CH₃ | H | C(O)CH₂Cl | CH₃ | OCH₃ | N | |
| H | CH₃ | H | C(O)CH₂Cl | OCH₃ | OCH₃ | N | |
| H | CH₃ | H | C(O)CH₂Cl | OCH₃ | Cl | CH | |
| H | CH₃ | H | C(O)CH₂CH(CH₃)CN | CH₃ | CH₃ | CH | |
| CH₃ | CH₃ | H | C(O)CH₂CH(CH₃)CN | CH₃ | OCH₃ | CH | |
| H | CH₃ | H | C(O)CH₂N(CH₃)₂ | OCH₃ | OCH₃ | CH | |
| H | CH₃ | H | C(O)CH₂N(CH₃)₂ | CH₃ | CH₃ | N | |
| H | CH₃ | H | C(O)CH₂CH=CH₂ | CH₃ | OCH₃ | N | |
| H | CH₃ | H | C(O)CH₂CH=CH₂ | OCH₃ | OCH₃ | N | |
| H | CH₃ | H | C(O)CH₂C≡CH | OCH₃ | Cl | CH | |
| H | CH₃ | H | CO₂CH₃ | CH₃ | CH₃ | CH | |
| H | CH₃ | H | CO₂CH₃ | CH₃ | OCH₃ | CH | |
| H | CH₃ | H | CO₂CH₃ | OCH₃ | OCH₃ | CH | |
| H | CH₃ | H | CO₂CH₃ | CH₃ | CH₃ | N | |
| H | CH₃ | H | CO₂CH₃ | CH₃ | OCH₃ | N | |
| H | CH₃ | H | CO₂CH₃ | OCH₃ | OCH₃ | N | |
| H | CH₃ | H | CO₂CH₃ | OCH₃ | Cl | CH | |
| H | CH₃ | H | CO₂CH₂CH₃ | CH₃ | CH₃ | CH | |
| H | CH₃ | H | CO₂CH₂CH₃ | CH₃ | OCH₃ | CH | |
| H | CH₃ | H | CO₂CH₂CH₃ | OCH₃ | OCH₃ | CH | |
| H | CH₃ | H | CO₂CH₂CH₃ | CH₃ | CH₃ | N | |
| H | CH₃ | H | CO₂CH₂CH₃ | CH₃ | OCH₃ | N | |
| H | CH₃ | H | CO₂CH₂CH₃ | OCH₃ | OCH₃ | N | |
| H | CH₃ | H | CO₂CH₂CH₃ | OCH₃ | Cl | CH | |
| H | CH₃ | H | CO₂CH₂CF₃ | CH₃ | CH₃ | CH | |
| H | CH₃ | H | CO₂CH₂CF₃ | CH₃ | OCH₃ | CH | |
| H | CH₃ | H | CO₂CH₂CF₃ | OCH₃ | OCH₃ | CH | |
| H | CH₃ | H | CO₂CH₂CF₃ | CH₃ | CH₃ | N | |
| H | CH₃ | H | CO₂CF₃ | OCH₃ | OCH₃ | N | |
| H | CH₃ | H | CO₂CF₃ | OCH₃ | Cl | CH | |
| H | CH₃ | H | CO₂CF₃ | CH₃ | CH₃ | CH | |
| H | CH₃ | H | CO₂CH₂C≡CH | CH₃ | OCH₃ | CH | |
| H | CH₃ | H | CO₂CH₂C≡CH | OCH₃ | OCH₃ | CH | |
| H | CH₃ | H | CO₂CH₂C≡CH | CH₃ | CH₃ | N | |
| H | CH₃ | H | CO₂CH₂C≡CH | CH₃ | OCH₃ | N | |
| H | CH₃ | H | CO₂CH₂C≡CH | OCH₃ | OCH₃ | N | |
| H | CH₃ | H | CO₂CH₂CH=CH₂ | OCH₃ | Cl | CH | |
| H | CH₃ | H | CO₂CH₂CH=CH₂ | CH₃ | CH₃ | CH | |
| H | CH₃ | H | CO₂CH₂CH=CH₂ | CH₃ | OCH₃ | CH | |
| H | CH₃ | H | CO₂CH₂CH=CH₂ | OCH₃ | OCH₃ | CH | |
| H | CH₃ | H | CO₂CH₂CH=CH₂ | CH₃ | CH₃ | N | |
| H | CH₃ | H | CO₂CH₂CH=CH₂ | CH₃ | OCH₃ | N | |
| H | CH₃ | CH₃ | CO₂CH₃ | OCH₃ | OCH₃ | N | |
| H | CH₃ | H | CO₂CF₃ | OCH₃ | Cl | CH | |
| H | CH₃ | H | CO₂CF₃ | CH₃ | CH₃ | CH | |
| H | CH₃ | H | CO₂CF₃ | CH₃ | OCH₃ | CH | |
| H | CH₃ | H | CO₂CF₃ | OCH₃ | OCH₃ | CH | |
| H | CH₃ | H | CO₂CH₂CH₂Cl | CH₃ | CH₃ | N | |
| H | CH₃ | H | CO₂CH₂CH₂Cl | CH₃ | OCH₃ | N | |
| H | CH₃ | H | CO₂CH₂CH₂Cl | OCH₃ | OCH₃ | N | |
| H | CH₃ | H | CO₂CH₂CH₂P(O)(CH₃)₂ | OCH₃ | Cl | CH | |
| H | CH₃ | H | CO₂CH₂CH₂P(O)(CH₃)₂ | CH₃ | CH₃ | CH | |
| CH₃ | CH₃ | H | CO₂C(CH₃)₃ | CH₃ | OCH₃ | CH | |
| H | CH₃ | H | CO₂C(CH₃)₃ | OCH₃ | OCH₃ | CH | |
| H | CH₃ | H | CO₂CH₂(CH₂)₄CH₃ | CH₃ | CH₃ | N | |
| H | CH₃ | H | CO₂CH₂(CH₂)₄CH₃ | CH₃ | OCH₃ | N | |
| H | CH₃ | H | CO₂CH₂OCH₃ | OCH₃ | OCH₃ | N | |
| H | CH₃ | H | CO₂CH₂OCH₃ | OCH₃ | Cl | CH | |
| H | CH₃ | H | (C(O))₂OCH₃ | CH₃ | CH₃ | CH | |
| H | CH₃ | H | (C(O))₂OCH₃ | CH₃ | OCH₃ | CH | |
| H | CH₃ | H | (C(O))₂OCH₃ | OCH₃ | OCH₃ | CH | |
| H | CH₃ | H | (C(O))₂OCH₃ | CH₃ | CH₃ | N | |
| H | CH₃ | H | (C(O))₂OCH₃ | CH₃ | OCH₃ | N | |
| H | CH₃ | H | (C(O))₂OCH₃ | OCH₃ | OCH₃ | N | |
| H | CH₃ | H | (C(O))₂OCH₃ | OCH₃ | Cl | CH | |
| H | CH₃ | H | (CO)₂CH₃ | CH₃ | CH₃ | CH | |
| H | CH₃ | H | (CO)₂CH₃ | CH₃ | OCH₃ | CH | |
| H | CH₃ | H | (CO)₂CH₃ | OCH₃ | OCH₃ | CH | |
| H | CH₃ | H | (CO)₂CH₃ | CH₃ | CH₃ | N | |
| H | CH₃ | H | (CO)₂CH₃ | CH₃ | OCH₃ | N | |
| H | CH₃ | H | (CO)₂CH₃ | OCH₃ | OCH₃ | N | |
| H | CH₃ | H | (CO)₂CH₃ | OCH₃ | Cl | CH | |
| H | CH₃ | H | C(O)N(CH₃)₂ | CH₃ | CH₃ | CH | |
| H | CH₃ | H | (CO)N(CH₃)₂ | CH₃ | OCH₃ | CH | |

TABLE I-continued

General Structure I

| R | R₁ | R₂ | R₃ | X | Y | Z | m.p. (°C.) |
|---|---|---|---|---|---|---|---|
| H | CH₃ | H | C(O)N(CH₃)₂ | OCH₃ | OCH₃ | CH | |
| H | CH₃ | H | C(O)N(CH₃)₂ | CH₃ | CH₃ | N | |
| H | CH₃ | H | C(O)N(CH₃)₂ | OCH₃ | OCH₃ | N | |
| H | CH₃ | H | C(O)N(CH₃)₂ | OCH₃ | Cl | CH | |
| H | CH₃ | H | C(O)N(CH₂CH₃)₂ | CH₃ | CH₃ | CH | |
| H | CH₃ | H | C(O)N(CH₂CH₃)₂ | CH₃ | OCH₃ | CH | |
| H | CH₃ | H | C(O)N(CH₂CH₃)₂ | OCH₃ | OCH₃ | CH | |
| H | CH₃ | H | C(O)N(CH₂CH₃)₂ | CH₃ | CH₃ | N | |
| H | CH₃ | H | C(O)N(CH₂CH₃)₂ | CH₃ | OCH₃ | N | |
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |

TABLE I-continued

General Structure I

| R | $R_1$ | $R_2$ | $R_3$ | X | Y | Z | m.p. (°C.) |
|---|---|---|---|---|---|---|---|
| H | $CH_3$ | H | OH | $OCH_3$ | $OCH_3$ | N | |
| H | $CH_3$ | H | OH | $OCH_3$ | Cl | CH | |
| H | $CH_3$ | H | CN | $CH_3$ | $CH_3$ | CH | |
| H | $CH_3$ | H | CN | $CH_3$ | $OCH_3$ | CH | |
| H | $CH_3$ | H | CN | $OCH_3$ | $OCH_3$ | CH | |
| H | $CH_3$ | H | CN | $CH_3$ | $CH_3$ | N | |
| H | $CH_3$ | H | CN | $CH_3$ | $OCH_3$ | N | |
| H | $CH_3$ | H | CN | $OCH_3$ | $OCH_3$ | N | |
| H | $CH_3$ | H | CN | $OCH_3$ | Cl | CH | |
| H | $CH_3$ | H | $P(O)(CH_3)_2$ | $CH_3$ | $CH_3$ | CH | |
| H | $CH_3$ | H | $P(O)(CH_3)_2$ | $CH_3$ | $OCH_3$ | CH | |
| H | $CH_3$ | H | $P(O)(CH_3)_2$ | $OCH_3$ | $OCH_3$ | CH | |
| H | $CH_3$ | H | $P(O)(CH_3)_2$ | $CH_3$ | $CH_3$ | N | |
| H | $CH_3$ | H | $P(O)(CH_3)_2$ | $OCH_3$ | $OCH_3$ | N | |
| H | $CH_3$ | H | $P(O)(OCH_3)_2$ | $OCH_3$ | Cl | CH | |
| H | $CH_3$ | H | $P(O)(OCH_3)_2$ | $CH_3$ | $CH_3$ | CH | |
| H | $CH_3$ | H | $P(O)(OCH_3)_2$ | $CH_3$ | $OCH_3$ | CH | |
| H | $CH_3$ | H | $P(O)(OCH_3)_2$ | $OCH_3$ | $OCH_3$ | CH | |
| H | $CH_3$ | H | $P(O)(OCH_3)SCH_3$ | $CH_3$ | $CH_3$ | N | |
| H | $CH_3$ | H | $P(O)(OCH_3)SCH_3$ | $CH_3$ | $OCH_3$ | N | |
| H | $CH_3$ | H | $P(O)(OCH_3)SCH_3$ | $OCH_3$ | $OCH_3$ | N | |
| H | $CH_3$ | H | $P(O)(OCH_3)SCH_3$ | $OCH_3$ | Cl | CH | |
| H | $CH_3$ | H | $P(O)(OCH_3)SCH_2CH_2CH_3$ | $CH_3$ | $CH_3$ | CH | |
| H | $CH_3$ | H | $P(O)(OCH_3)SCH_2CH_2CH_3$ | $CH_3$ | $OCH_3$ | CH | |
| H | $CH_3$ | H | $P(O)(OCH_3)SCH_2CH_2CH_3$ | $OCH_3$ | $OCH_3$ | CH | |
| H | $CH_3$ | H | $P(O)(OCH_3)SCH_2CH_2CH_3$ | $CH_3$ | $CH_3$ | N | |
| H | $CH_3$ | H | $P(O)(OCH_3)SCH_2CH_2CH_3$ | $CH_3$ | $OCH_3$ | N | |
| H | $CH_3$ | $CH_3$ | OH | $OCH_3$ | $OCH_3$ | N | |
| H | $CH_3$ | H | $P(S)(CH_3)_2$ | $OCH_3$ | Cl | CH | |
| H | $CH_3$ | H | $P(S)(CH_3)_2$ | $CH_3$ | $CH_3$ | CH | |
| H | $CH_3$ | H | $P(S)(CH_3)_2$ | $CH_3$ | $OCH_3$ | CH | |
| H | $CH_3$ | H | $P(S)(CH_3)_2$ | $OCH_3$ | $OCH_3$ | CH | |
| H | $CH_3$ | H | $P(S)(CH_3)_2$ | $CH_3$ | $CH_3$ | N | |
| H | $CH_3$ | H | $P(S)(CH_3)_2$ | $CH_3$ | $OCH_3$ | N | |
| H | $CH_3$ | H | $P(S)(CH_3)_2$ | $OCH_3$ | $OCH_3$ | N | |
| H | $CH_3$ | H | $P(S)(OCH_3)_2$ | $OCH_3$ | Cl | CH | |
| H | $CH_3$ | H | $P(S)(OCH_3)_2$ | $CH_3$ | $CH_3$ | CH | |
| $CH_3$ | $CH_3$ | H | $P(S)(OCH_3)_2$ | $CH_3$ | $OCH_3$ | CH | |
| H | $CH_3$ | H | $P(S)(OCH_3)_2$ | $OCH_3$ | $OCH_3$ | CH | |
| H | $CH_3$ | H | $P(S)(OCH_3)_2$ | $CH_3$ | $CH_3$ | N | |
| H | $CH_3$ | H | $P(S)(OCH_3)_2$ | $CH_3$ | $OCH_3$ | N | |
| H | $CH_3$ | H | $P(S)(OCH_3)SCH_3$ | $OCH_3$ | $OCH_3$ | N | |
| H | $CH_3$ | H | $P(S)(OCH_3)SCH_3$ | $OCH_3$ | Cl | CH | |
| H | $CH_3$ | H | $NO_2$ | $CH_3$ | $CH_3$ | CH | |
| H | $CH_3$ | H | $NO_2$ | $CH_3$ | $OCH_3$ | CH | |
| H | $CH_3$ | H | $NO_2$ | $OCH_3$ | $OCH_3$ | CH | |
| H | $CH_3$ | H | $NO_2$ | $CH_3$ | $CH_3$ | N | |
| H | $CH_3$ | H | $NO_2$ | $CH_3$ | $OCH_3$ | N | |
| H | $CH_3$ | H | $NO_2$ | $OCH_3$ | $OCH_3$ | N | |
| H | $CH_3$ | H | $CH_2C(O)CH(\text{-}CH_2\text{-}CH_2\text{-})$ (cyclopropyl) | $CH_3$ | $CH_3$ | N | |
| H | $CH_3$ | H | $CH_2C(O)CH(\text{-}CH_2\text{-}CH_2\text{-})$ (cyclopropyl) | $CH_3$ | $OCH_3$ | N | |
| H | $CH_3$ | H | $CH_2C(O)CH(\text{-}CH_2\text{-}CH_2\text{-})$ (cyclopropyl) | $OCH_3$ | $OCH_3$ | N | |
| H | $CH_3$ | H | $CH_2C(O)CH(\text{-}CH_2\text{-}CH_2\text{-})$ (cyclopropyl) | $OCH_3$ | Cl | CH | |
| H | $CH_3$ | H | $CH_2C(O)CH(\text{-}CH_2\text{-}CH_2\text{-})$ (cyclopropyl) | $CH_3$ | $CH_3$ | CH | |

TABLE I-continued

| | | | General Structure I | | | | |
|---|---|---|---|---|---|---|---|
| R | $R_1$ | $R_2$ | $R_3$ | X | Y | Z | m.p. (°C.) |
| H | $CH_3$ | H | $CH_2C(O)CH\begin{smallmatrix}CH_2\\|\\CH_2\end{smallmatrix}$ | $CH_3$ | $OCH_3$ | CH | |
| H | $CH_3$ | H | $CH_2C(O)Ph$ | $OCH_3$ | $OCH_3$ | CH | |
| H | $CH_3$ | H | $CH_2C(O)Ph$ | $CH_3$ | $CH_3$ | N | |
| H | $CH_3$ | H | $CH_2C(O)Ph$ | $CH_3$ | $OCH_3$ | N | |
| H | $CH_3$ | $CH_3$ | $CH_2C(O)Ph$ | $OCH_3$ | $OCH_3$ | N | |
| H | $CH_3$ | H | $CH_2C(O)Ph$ | $OCH_3$ | Cl | CH | |
| H | $CH_3$ | H | $CH_2C(O)Ph$ | $CH_3$ | $CH_3$ | CH | |
| H | $CH_3$ | H | $CH_2C(O)Ph$ | $CH_3$ | $OCH_3$ | CH | |
| H | $CH_3$ | H | $CH(CH)_3C(O)CH_3$ | $OCH_3$ | $OCH_3$ | CH | |
| H | $CH_3$ | H | $CH(CH)_3C(O)CH_3$ | $CH_3$ | $CH_3$ | N | |
| H | $CH_3$ | H | $CH(CH)_3C(O)CH_3$ | $CH_3$ | $OCH_3$ | N | |
| H | $CH_3$ | H | $CH(CH)_3C(O)CH_3$ | $OCH_3$ | $OCH_3$ | N | |
| H | $CH_3$ | H | $CH_2CF_2-C(O)CH_3$ | $OCH_3$ | Cl | CH | |
| H | $CH_3$ | H | $CH_2CF_2-C(O)CH_3$ | $CH_3$ | $CH_3$ | CH | |
| $CH_3$ | $CH_3$ | H | $CH_2CF_2-C(O)CH_3$ | $CH_3$ | $OCH_3$ | CH | |
| H | $CH_3$ | H | $CH_2CF_2-C(O)CH_3$ | $OCH_3$ | $OCH_3$ | CH | |
| H | $CH_3$ | H | $CH_2C(O)CH_2OCH_3$ | $CH_3$ | $CH_3$ | N | |
| H | $CH_3$ | H | $CH_2C(O)CH_2OCH_3$ | $CH_3$ | $OCH_3$ | N | |
| H | $CH_3$ | H | $CH_2C(O)CH_2OCH_3$ | $OCH_3$ | $OCH_3$ | N | |
| H | $CH_3$ | H | $CH_2C(O)CH_2OCH_3$ | $OCH_3$ | Cl | CH | |
| H | $CH_3$ | H | $CH_2CO_2CH_3$ | $CH_3$ | $CH_3$ | CH | |
| H | $CH_3$ | H | $CH_2CO_2CH_3$ | $CH_3$ | $OCH_3$ | CH | |
| H | $CH_3$ | H | $CH_2CO_2CH_3$ | $OCH_3$ | $OCH_3$ | CH | |
| H | $CH_3$ | H | $CH_2CO_2CH_3$ | $CH_3$ | $CH_3$ | N | |
| H | $CH_3$ | H | $CH_2CO_2CH_3$ | $CH_3$ | $OCH_3$ | N | |
| H | $CH_3$ | H | $CH_2CO_2CH_3$ | $OCH_3$ | $OCH_3$ | N | |
| H | $CH_3$ | H | $CH_2CO_2CH_3$ | $OCH_3$ | Cl | CH | |
| H | $CH_3$ | H | $CH_2CO_2CH_2CH_3$ | $CH_3$ | $CH_3$ | CH | |
| H | $CH_3$ | H | $CH_2CO_2CH_2CH_3$ | $CH_3$ | $OCH_3$ | CH | |
| H | $CH_3$ | H | $CH_2CO_2CH_2CH_3$ | $OCH_3$ | $OCH_3$ | CH | |
| H | $CH_3$ | H | $CH_2CO_2CH_2CH_3$ | $CH_3$ | $CH_3$ | N | |
| H | $CH_3$ | H | $CH_2CO_2CH_2CH_3$ | $CH_3$ | $OCH_3$ | N | |
| H | $CH_3$ | H | $CH_2CO_2CH_2CH_3$ | $OCH_3$ | $OCH_3$ | N | |
| H | $CH_3$ | H | $CH_2CO_2CH_2CH_3$ | $OCH_3$ | Cl | CH | |
| H | $CH_3$ | H | $CH_2CH_2CO_2CH_3$ | $CH_3$ | $CH_3$ | CH | |
| H | $CH_3$ | H | $CH_2CH_2CO_2CH_3$ | $CH_3$ | $OCH_3$ | CH | |
| H | $CH_3$ | H | $CH_2CH_2CO_2CH_3$ | $OCH_3$ | $OCH_3$ | CH | |
| H | $CH_3$ | H | $CH_2CH_2CO_2CH_3$ | $CH_3$ | $CH_3$ | N | |
| H | $CH_3$ | H | $CH_2CH_2CO_2CH_3$ | $CH_3$ | $OCH_3$ | N | |
| H | $CH_3$ | H | $CH_2CH_2CO_2CH_3$ | $OCH_3$ | Cl | CH | |
| H | $CH_3$ | H | $CH_2-CO_2CH_2CH=CH_2$ | $CH_3$ | $CH_3$ | CH | |
| H | $CH_3$ | H | $CH_2-CO_2CH_2CH=CH_2$ | $CH_3$ | $OCH_3$ | CH | |
| H | $CH_3$ | H | $CH_2-CO_2CH_2CH=CH_2$ | $OCH_3$ | $OCH_3$ | CH | |
| H | $CH_3$ | H | $CH_2-CO_2CH_2CH=CH_2$ | $CH_3$ | $CH_3$ | N | |
| H | $CH_3$ | H | $CH_2-CO_2CH_2CH=CH_2$ | $CH_3$ | $OCH_3$ | N | |
| H | $CH_3$ | H | $CH_2-CO_2CH_2CH=CH_2$ | $OCH_3$ | $OCH_3$ | N | |
| H | $CH_3$ | H | $CH_2-CO_2CH_2CH=CH_2$ | $OCH_3$ | Cl | CH | |
| H | $CH_3$ | H | $CH_2(CH_2)_4CO_2CH_3$ | $CH_3$ | $CH_3$ | CH | |
| H | $CH_3$ | H | $CH_2(CH_2)_4CO_2CH_3$ | $CH_3$ | $OCH_3$ | CH | |
| H | $CH_3$ | H | $CH_2(CH_2)_4CO_2CH_3$ | $OCH_3$ | $OCH_3$ | CH | |
| H | $CH_3$ | H | $CH_2(CH_2)_4CO_2CH_3$ | $CH_3$ | $CH_3$ | N | |
| H | $CH_3$ | H | $CH_2(CH_2)_4CO_2CH_3$ | $CH_3$ | $OCH_3$ | N | |
| H | $CH_3$ | $CH_3$ | $CH_2(CH_2)_4CO_2CH_3$ | $OCH_3$ | $OCH_3$ | N | |
| H | $CH_3$ | H | $CH_2(CH_2)_4CO_2CH_3$ | $OCH_3$ | Cl | CH | |
| H | $CH_3$ | H | $CH_2CO_2CH_2C\equiv CH$ | $CH_3$ | $CH_3$ | CH | |
| H | $CH_3$ | H | $CH_2CO_2CH_2C\equiv CH$ | $CH_3$ | $OCH_3$ | CH | |
| H | $CH_3$ | H | $CH_2CO_2CH_2C\equiv CH$ | $OCH_3$ | $OCH_3$ | CH | |
| H | $CH_3$ | H | $CH_2CO_2CH_2C\equiv CH$ | $CH_3$ | $CH_3$ | N | |
| H | $CH_3$ | H | $CH_2CO_2CH_2C\equiv CH$ | $CH_3$ | $OCH_3$ | N | |
| H | $CH_3$ | H | $CH_2CO_2CH_2C\equiv CH$ | $OCH_3$ | $OCH_3$ | N | |
| H | $CH_3$ | H | $CH_2CO_2CH_2C\equiv CH$ | $OCH_3$ | Cl | CH | |
| H | $CH_3$ | H | $CH_2CO_2CF_3$ | $CH_3$ | $CH_3$ | CH | |
| $CH_3$ | $CH_3$ | H | $CH_2CO_2CF_3$ | $CH_3$ | $OCH_3$ | CH | |
| H | $CH_3$ | H | $CH_2CO_2CF_3$ | $OCH_3$ | $OCH_3$ | CH | |
| H | $CH_3$ | H | $CH_2CO_2CF_3$ | $CH_3$ | $CH_3$ | N | |
| H | $CH_3$ | H | $CH_2CO_2CF_3$ | $CH_3$ | $OCH_3$ | N | |
| H | $CH_3$ | H | $CH_2CO_2CF_3$ | $OCH_3$ | $OCH_3$ | N | |
| H | $CH_3$ | H | $CH_2CO_2CF_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |

TABLE I-continued

General Structure I

| R | R₁ | R₂ | R₃ | X | Y | Z | m.p. (°C.) |
|---|----|----|----|----|----|---|---|
| H | CH₃ | H | SeCH₃ | CH₃ | CH₃ | CH | |
| H | CH₃ | H | SeCH₃ | CH₃ | OCH₃ | CH | |
| H | CH₃ | H | SeCH₃ | OCH₃ | OCH₃ | CH | |
| H | CH₃ | H | SeCH₃ | CH₃ | CH₃ | N | |
| H | CH₃ | H | SeCH₃ | CH₃ | OCH₃ | N | |
| H | CH₃ | H | SeCH₃ | OCH₃ | OCH₃ | N | |
| H | CH₃ | H | SeCH₃ | OCH₃ | Cl | CH | |
| H | CH₃ | H | CH₂Ph | CH₃ | CH₃ | CH | |
| H | CH₃ | H | CH₂Ph | CH₃ | OCH₃ | CH | |
| H | CH₃ | H | CH₂Ph | OCH₃ | OCH₃ | CH | |
| H | CH₃ | H | CH₂Ph | CH₃ | CH₃ | N | |
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A—HET | CH₃ | CH₃ | CH | |
| H | CH₃ | H | A—HET | CH₃ | OCH₃ | CH | |
| H | CH₃ | H | A—HET | OCH₃ | OCH₃ | CH | |
| H | CH₃ | H | A—HET | CH₃ | CH₃ | N | |
| H | CH₃ | H | A—HET | CH₃ | OCH₃ | N | |
| H | CH₃ | H | A—HET | OCH₃ | OCH₃ | N | |
| H | CH₃ | H | A—HET | OCH₃ | Cl | CH | |
| H | CH₃ | H | B—HET | CH₃ | CH₃ | CH | |
| H | CH₃ | H | B—HET | CH₃ | OCH₃ | CH | |
| H | CH₃ | H | B—HET | OCH₃ | OCH₃ | CH | |
| H | CH₃ | H | B—HET | CH₃ | CH₃ | N | |
| H | CH₃ | H | B—HET | CH₃ | OCH₃ | N | |
| H | CH₃ | CH₃ | B—HET | OCH₃ | OCH₃ | N | |
| H | CH₃ | H | B—HET | OCH₃ | Cl | CH | |
| H | CH₃ | H | C—HET | CH₃ | CH₃ | CH | |
| H | CH₃ | H | C—HET | CH₃ | OCH₃ | CH | |
| H | CH₃ | H | C—HET | OCH₃ | OCH₃ | CH | |
| H | CH₃ | H | C—HET | CH₃ | CH₃ | N | |
| H | CH₃ | H | C—HET | CH₃ | OCH₃ | N | |
| H | CH₃ | H | C—HET | OCH₃ | OCH₃ | N | |
| H | CH₃ | H | C—HET | OCH₃ | Cl | CH | |
| H | CH₃ | H | D—HET | CH₃ | CH₃ | CH | |
| CH₃ | CH₃ | H | D—HET | CH₃ | OCH₃ | CH | |
| H | CH₃ | H | D—HET | OCH₃ | OCH₃ | CH | |
| H | CH₃ | H | D—HET | CH₃ | CH₃ | N | |
| H | CH₃ | H | D—HET | CH₃ | OCH₃ | N | |
| H | CH₃ | H | D—HET | OCH₃ | OCH₃ | N | |
| H | CH₃ | H | D—HET | OCH₃ | Cl | CH | |
| H | CH₃ | H | C(O)A—HET | CH₃ | CH₃ | CH | |
| H | CH₃ | H | C(O)A—HET | CH₃ | OCH₃ | CH | |
| H | CH₃ | H | C(O)A—HET | OCH₃ | OCH₃ | CH | |
| H | CH₃ | H | C(O)A—HET | CH₃ | CH₃ | N | |
| H | CH₃ | H | C(O)A—HET | CH₃ | OCH₃ | N | |
| H | CH₃ | H | C(O)A—HET | OCH₃ | OCH₃ | N | |

TABLE I-continued

General Structure I

| R | R₁ | R₂ | R₃ | X | Y | Z | m.p. (°C.) |
|---|----|----|----|---|---|---|------------|
| H | CH₃ | H | C(O)A—HET | OCH₃ | Cl | CH | |
| H | CH₃ | H | C(O)B—HET | CH₃ | CH₃ | CH | |
| H | CH₃ | H | C(O)B—HET | CH₃ | OCH₃ | CH | |
| H | CH₃ | H | C(O)B—HET | OCH₃ | OCH₃ | CH | |
| H | CH₃ | H | C(O)B—HET | CH₃ | CH₃ | N | |
| H | CH₃ | H | C(O)B—HET | CH₃ | OCH₃ | N | |
| H | CH₃ | H | C(O)B—HET | OCH₃ | OCH₃ | N | |
| H | CH₃ | H | C(O)B—HET | OCH₃ | Cl | CH | |
| H | CH₃ | H | C(O)C—HET | CH₃ | CH₃ | CH | |
| H | CH₃ | H | C(O)C—HET | CH₃ | OCH₃ | CH | |
| H | CH₃ | H | C(O)C—HET | OCH₃ | OCH₃ | CH | |
| H | CH₃ | H | C(O)C—HET | CH₃ | CH₃ | N | |
| H | CH₃ | H | C(O)C—HET | OCH₃ | OCH₃ | N | |
| H | CH₃ | H | C(O)C—HET | OCH₃ | Cl | CH | |
| H | CH₃ | H | C(O)D—HET | CH₃ | CH₃ | CH | |
| H | CH₃ | H | C(O)D—HET | CH₃ | OCH₃ | CH | |
| H | CH₃ | H | C(O)D—HET | OCH₃ | OCH₃ | CH | |
| H | CH₃ | H | C(O)D—HET | CH₃ | CH₃ | N | |
| H | CH₃ | H | C(O)D—HET | CH₃ | OCH₃ | N | |
| H | CH₃ | H | C(O)D—HET | OCH₃ | OCH₃ | N | |
| H | CH₃ | H | C(O)D—HET | OCH₃ | Cl | CH | | wherein

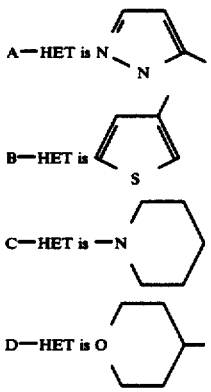

A—HET is pyrazolyl

B—HET is thienyl (methyl-substituted)

C—HET is piperidinyl

D—HET is tetrahydropyranyl (O-containing)

TABLE Ia

General Structure Ia

| R | R₁ | R₂ | R₃ | X | Y | Z | m.p. (°C.) |
|---|----|----|----|---|---|---|------------|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |
| H | CH₃ | H | CH₂CHF₂ | CH₃ | CH₃ | CH | |
| H | CH₃ | H | CH₂CHF₂ | CH₃ | OCH₃ | CH | |
| H | CH₃ | H | CH₂CHF₂ | OCH₃ | OCH₃ | CH | |
| H | CH₃ | H | CH₂CHF₂ | CH₃ | CH₃ | N | |
| H | CH₃ | H | CH₂CHF₂ | CH₃ | OCH₃ | N | |
| H | CH₃ | H | CH₂CHF₂ | OCH₃ | OCH₃ | N | |
| H | CH₃ | H | CH₂CHF₂ | OCH₃ | Cl | CH | |
| H | CH₃ | H | CH(CH₂F)₂ | CH₃ | CH₃ | CH | |
| H | CH₃ | H | CH(CH₂F)₂ | CH₃ | OCH₃ | CH | |
| H | CH₃ | H | CH(CH₂F)₂ | OCH₃ | OCH₃ | CH | |
| H | CH₃ | H | CH₂CH₂CH₂F | CH₃ | CH₃ | N | |
| H | CH₃ | H | CH₂CH₂CH₂F | CH₃ | OCH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | CH₃ | CH₂CH₂CH₂F | OCH₃ | OCH₃ | N | |
| H | CH₃ | H | CH₂CH₂CH₂F | OCH₃ | Cl | CH | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |
| H | CH₃ | H | CH₂(CH₂)₂CH₂F | OCH₃ | OCH₃ | CH | |
| H | CH₃ | H | CH(CH₃)CH₂F | CH₃ | CH₃ | N | |
| H | CH₃ | H | CH(CH₃)CH₂F | CH₃ | OCH₃ | N | |
| H | CH₃ | H | CH(CH₃)CH₂F | OCH₃ | OCH₃ | N | |
| H | CH₃ | H | CH(CH₃)CH₂F | OCH₃ | Cl | CH | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBrCH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBrCH₃ | CH₃ | OCH₃ | N | |
| H | CH₃ | CH₃ | CH₂CHBrCH₃ | OCH₃ | OCH₃ | N | |
| H | CH₃ | H | CH₂CHBrCH₃ | OCH₃ | Cl | CH | |
| H | CH₃ | H | CH₂CHBrCH₃ | CH₃ | CH₃ | CH | |
| H | CH₃ | H | CH₂CHBrCH₃ | CH₃ | OCH₃ | CH | |
| H | CH₃ | H | CH₂(CH₂)₂CH₂Br | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |
| H | CH₃ | H | CH₂(CH₂)₂CH₂Cl | OCH₃ | OCH₃ | CH | |
| H | CH₃ | H | CH₂(CH₂)₂CH₂Cl | CH₃ | CH₃ | N | |
| H | CH₃ | H | CH₂(CH₂)₂CH₂Cl | CH₃ | OCH₃ | N | |
| H | CH₃ | H | CH₂(CH₂)₂CH₂Cl | OCH₃ | OCH₃ | N | |
| H | CH₃ | H | CH₂(CH₂)₂CH₂Cl | OCH₃ | Cl | CH | |
| H | CH₃ | H | CH₂(CH₂)₂CH₂Cl | CH₃ | CH₃ | CH | |
| CH₃ | CH₃ | H | CH(CH₃)CH₂Cl | CH₃ | OCH₃ | CH | |
| H | CH₃ | H | CH(CH₃)CH₂Cl | OCH₃ | OCH₃ | CH | |
| H | CH₃ | H | CH(CH₃)CH₂Cl | CH₃ | CH₃ | N | |
| H | CH₃ | H | CHClCHClCH₃ | CH₃ | OCH₃ | N | |
| H | CH₃ | H | CHClCHClCH₃ | OCH₃ | OCH₃ | N | |
| H | CH₃ | H | CHClCHClCH₃ | OCH₃ | Cl | CH | |
| H | CH₃ | H | CH₂I | CH₃ | CH₃ | CH | |
| H | CH₃ | H | CH₂I | CH₃ | OCH₃ | CH | |
| H | CH₃ | H | CH₂I | OCH₃ | OCH₃ | CH | |
| H | CH₃ | H | CH₂I | CH₃ | CH₃ | N | |
| H | CH₃ | H | CH₂I | CH₃ | OCH₃ | N | |
| H | CH₃ | H | CH₂I | OCH₃ | OCH₃ | N | |
| H | CH₃ | H | CH₂I | OCH₃ | Cl | CH | |
| H | CH₃ | H | CH₂CF₃ | CH₃ | CH₃ | CH | |
| H | CH₃ | H | CH₂CF₃ | CH₃ | OCH₃ | CH | |
| H | CH₃ | H | CH₂CF₃ | OCH₃ | OCH₃ | CH | |
| H | CH₃ | H | CH₂CF₃ | CH₃ | CH₃ | N | |
| H | CH₃ | H | CH₂CF₃ | CH₃ | OCH₃ | N | |
| H | CH₃ | H | CH₂CF₃ | OCH₃ | OCH₃ | N | |
| H | CH₃ | H | CH₂CF₃ | OCH₃ | Cl | CH | |
| H | CH₃ | H | CH₂CH₂CF₃ | CH₃ | CH₃ | CH | |
| H | CH₃ | H | CH₂CH₂CF₃ | CH₃ | OCH₃ | CH | |
| H | CH₃ | H | CH₂CH₂CF₃ | OCH₃ | OCH₃ | CH | |
| H | CH₃ | H | CH₂CH₂CF₃ | CH₃ | CH₃ | N | |
| H | CH₃ | H | CH₂CH₂CF₃ | OCH₃ | OCH₃ | N | |
| H | CH₃ | H | CH₂CH₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |
| H | CH₃ | H | CH₂(CH₂)₂CF₃ | CH₃ | OCH₃ | N | |
| H | CH₃ | H | CH₂(CH₂)₂CF₃ | OCH₃ | OCH₃ | N | |
| H | CH₃ | H | CH₂(CH₂)₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |
| H | CH₃ | H | CH₂(CH₂)₂CF₃ | CH₃ | OCH₃ | N | |
| H | CH₃ | CH₃ | CH₂(CH₂)₂CF₃ | OCH₃ | OCH₃ | N | |
| H | CH₃ | H | CH(CF₃)₂ | OCH₃ | Cl | CH | |
| H | CH₃ | H | CH(CF₃)₂ | CH₃ | CH₃ | CH | |
| H | CH₃ | H | CH(CF₃)₂ | CH₃ | OCH₃ | CH | |
| H | CH₃ | H | CH(CF₃)₂ | OCH₃ | OCH₃ | CH | |
| H | CH₃ | H | CH(CF₃)₂ | CH₃ | CH₃ | N | |
| H | CH₃ | H | CH(CF₃)₂ | CH₃ | OCH₃ | N | |
| H | CH₃ | H | CH(CF₃)₂ | OCH₃ | OCH₃ | N | |
| H | CH₃ | H | CH₂(CH₂)₄CF₃ | OCH₃ | Cl | CH | |
| H | CH₃ | H | CH₂(CH₂)₅CF₃ | CH₃ | CH₃ | CH | |
| CH₃ | CH₃ | H | CH₂(CH₂)₆CF₃ | CH₃ | OCH₃ | CH | |
| H | CH₃ | H | CH₂(CH₂)₇CF₃ | OCH₃ | OCH₃ | CH | |
| H | CH₃ | H | CH₂(CH₂)₈CF₃ | CH₃ | CH₃ | N | |
| H | CH₃ | H | CHF(CH₂)₈CF₃ | CH₃ | OCH₃ | N | |
| H | CH₃ | H | CH(CHF)₈CF₃ | OCH₃ | OCH₃ | N | |
| H | CH₃ | H | CH(CHF)₈CF₃ | OCH₃ | Cl | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂OCH₃ | CH₃ | CH₃ | CH | |
| H | CH₃ | H | CH₂OCH₃ | CH₃ | OCH₃ | CH | |
| H | CH₃ | H | CH₂OCH₃ | OCH₃ | OCH₃ | CH | |
| H | CH₃ | H | CH₂OCH₃ | CH₃ | CH₃ | N | |
| H | CH₃ | H | CH₂OCH₃ | CH₃ | OCH₃ | N | |
| H | CH₃ | H | CH₂OCH₃ | OCH₃ | OCH₃ | N | |
| H | CH₃ | H | CH₂OCH₃ | OCH₃ | Cl | CH | |
| H | CH₃ | H | CH₂OCH₂CH₃ | CH₃ | CH₃ | CH | |
| H | CH₃ | H | CH₂OCH₂CH₃ | CH₃ | OCH₃ | CH | |
| H | CH₃ | H | CH₂OCH₂CH₃ | OCH₃ | OCH₃ | CH | |
| H | CH₃ | H | CH₂—OCH₂F | CH₃ | CH₃ | N | |
| H | CH₃ | H | CH₂—OCH₂F | CH₃ | OCH₃ | N | |
| H | CH₃ | H | CH₂—OCH₂F | OCH₃ | OCH₃ | N | |
| H | CH₃ | H | CH₂—OCH₂F | OCH₃ | Cl | CH | |
| H | CH₃ | H | CH₂—CH₂OCH₃ | CH₃ | CH₃ | CH | |
| H | CH₃ | H | CH₂—CH₂OCH₃ | CH₃ | OCH₃ | CH | |
| H | CH₃ | H | CH₂—CH₂OCH₃ | OCH₃ | OCH₃ | CH | |
| H | CH₃ | H | CH₂—CH₂OCH₃ | CH₃ | CH₃ | N | |
| H | CH₃ | H | CH(OCH₃)₂ | OCH₃ | OCH₃ | N | |
| H | CH₃ | H | CH(OCH₃)₂ | OCH₃ | Cl | CH | |
| H | CH₃ | H | CH₂(CH₂)₂OCH₃ | CH₃ | CH₃ | CH | |
| H | CH₃ | H | CH₂(CH₂)₂OCH₃ | CH₃ | OCH₃ | CH | |
| H | CH₃ | H | CH₂(CH₂)₂OCH₃ | OCH₃ | OCH₃ | CH | |
| H | CH₃ | H | CH₂(CH₂)₂OCH₃ | CH₃ | CH₃ | N | |
| H | CH₃ | H | CH₂(CH₂)₂OCH₃ | CH₃ | OCH₃ | N | |
| H | CH₃ | H | CH₂(CH₂)₃OCH₃ | OCH₃ | OCH₃ | N | |
| H | CH₃ | H | CH₂(CH₂)₃OCH₃ | OCH₃ | Cl | CH | |
| H | CH₃ | H | CH₂(CH₂)₃OCH₃ | CH₃ | CH₃ | CH | |
| H | CH₃ | H | CH₂(CH₂)₃OCH₃ | CH₃ | OCH₃ | CH | |
| H | CH₃ | H | CH₂(CH₂)₃OCH₃ | OCH₃ | OCH₃ | CH | |
| H | CH₃ | H | CH(OCH₃)CH₃ | CH₃ | CH₃ | N | |
| H | CH₃ | H | CH(OCH₃)CH₃ | CH₃ | OCH₃ | N | |
| H | CH₃ | CH₃ | CH(OCH₃)CH₃ | OCH₃ | OCH₃ | N | |
| H | CH₃ | H | CH₂OCH₂C≡CH₂ | OCH₃ | Cl | CH | |
| H | CH₃ | H | CH₂OCH₂C≡CH₂ | CH₃ | CH₃ | CH | |
| H | CH₃ | H | CH₂OCH₂C≡CH₂ | CH₃ | OCH₃ | CH | |
| H | CH₃ | H | CH₂OCH₂C≡CH₂ | OCH₃ | OCH₃ | CH | |
| H | CH₃ | H | CH₂OCH₂C≡CH₂ | CH₃ | CH₃ | N | |
| H | CH₃ | H | CH₂OCH₂C≡CH₂ | CH₃ | OCH₃ | N | |
| H | CH₃ | H | CH₂CH(OCH₃)₂ | OCH₃ | OCH₃ | N | |
| H | CH₃ | H | CH₂CH(OCH₃)₂ | OCH₃ | Cl | CH | |
| H | CH₃ | H | CH₂CH(OCH₃)₂ | CH₃ | CH₃ | CH | |
| CH₃ | CH₃ | H | CH₂CH(OCH₃)₂ | CH₃ | OCH₃ | CH | |
| H | CH₃ | H | CH₂C(OCH₃)₂CH₃ | OCH₃ | OCH₃ | CH | |
| H | CH₃ | H | CH₂C(OCH₃)₂CH₃ | CH₃ | CH₃ | N | |
| H | CH₃ | H | CH₂C(OCH₃)₂CH₃ | CH₃ | OCH₃ | N | |
| H | CH₃ | H | CH₂(CH₂)₆OCH₃ | OCH₃ | OCH₃ | N | |
| H | CH₃ | H | CH₂(CH₂)₆OCH₃ | OCH₃ | Cl | CH | |
| H | CH₃ | H | CH₂OC(O)CH₃ | CH₃ | CH₃ | CH | |
| H | CH₃ | H | CH₂OC(O)CH₃ | CH₃ | OCH₃ | CH | |
| H | CH₃ | H | CH₂OC(O)CH₃ | OCH₃ | OCH₃ | CH | |
| H | CH₃ | H | CH₂OC(O)CH₃ | CH₃ | CH₃ | N | |
| H | CH₃ | H | CH₂OC(O)CH₃ | CH₃ | OCH₃ | N | |
| H | CH₃ | H | CH₂OC(O)CH₃ | OCH₃ | OCH₃ | N | |
| H | CH₃ | H | CH₂OC(O)CH₃ | OCH₃ | Cl | CH | |
| H | CH₃ | H | CH₂CH₂OC(O)CH₃ | CH₃ | CH₃ | CH | |
| H | CH₃ | H | CH₂CH₂OC(O)CH₃ | CH₃ | OCH₃ | CH | |
| H | CH₃ | H | CH₂CH₂OC(O)CH₃ | OCH₃ | OCH₃ | CH | |
| H | CH₃ | H | CH₂CH₂OC(O)CH₃ | CH₃ | CH₃ | N | |
| H | CH₃ | H | CH₂CH₂OC(O)CH₃ | CH₃ | OCH₃ | N | |
| H | CH₃ | H | CH₂CH₂OC(O)CH₃ | OCH₃ | OCH₃ | N | |
| H | CH₃ | H | CH₂CH₂OC(O)CH₃ | OCH₃ | Cl | CH | |
| H | CH₃ | H | CH₂(CH₂)₂OC(O)CH₃ | CH₃ | CH₃ | CH | |
| H | CH₃ | H | CH₂(CH₂)₂OC(O)CH₃ | CH₃ | OCH₃ | CH | |
| H | CH₃ | H | CH₂(CH₂)₂OC(O)CH₃ | OCH₃ | OCH₃ | CH | |
| H | CH₃ | H | CH₂(CH₂)₃OC(O)CH₃ | CH₃ | CH₃ | N | |
| H | CH₃ | H | CH₂(CH₂)₃OC(O)CH₃ | OCH₃ | OCH₃ | N | |
| H | CH₃ | H | CH₂(CH₂)₃OC(O)CH₃ | OCH₃ | Cl | CH | |
| H | CH₃ | H | CH₂(CH₂)₃OC(O)CH₃ | CH₃ | CH₃ | CH | |
| H | CH₃ | H | CH₂P(CH₃)(Br)(CH₃) | CH₃ | OCH₃ | CH | |
| H | CH₃ | H | CH₂P(C₆H₅)₃ | OCH₃ | OCH₃ | CH | |
| H | CH₃ | H | CH₂OC(O)N(CH₃)₂ | CH₃ | CH₃ | N | |
| H | CH₃ | H | CH₂OC(O)N(CH₃)₂ | CH₃ | OCH₃ | N | |
| H | CH₃ | H | CH₂OC(O)N(CH₃)₂ | OCH₃ | OCH₃ | N | |
| H | CH₃ | H | CH₂OC(O)N(CH₃)₂ | OCH₃ | Cl | CH | |
| H | CH₃ | H | CH₂OC(O)N(CH₃)₂ | CH₃ | CH₃ | CH | |
| H | CH₃ | H | CH₂OC(O)N(CH₃)₂ | CH₃ | OCH₃ | CH | |
| H | CH₃ | H | CH₂OC(O)N(CH₃)₂ | OCH₃ | OCH₃ | CH | |
| H | CH₃ | H | CH₂CH₂OC(O)N(CH₃)₂ | CH₃ | CH₃ | N | |
| H | CH₃ | H | CH₂CH₂OC(O)N(CH₃)₂ | CH₃ | OCH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | CH₃ | CH₂CH₂OC(O)N(CH₃)₂ | OCH₃ | OCH₃ | N | |
| H | CH₃ | H | CH₂CH₂OC(O)N(CH₃)₂ | OCH₃ | Cl | CH | |
| H | CH₃ | H | CH₂CH₂OC(O)N(CH₃)₂ | CH₃ | CH₃ | CH | |
| H | CH₃ | H | CH₂CH₂OC(O)N(CH₃)₂ | CH₃ | OCH₃ | CH | |
| H | CH₃ | H | CH₂OSO₂CH₃ | OCH₃ | OCH₃ | CH | |
| H | CH₃ | H | CH₂OSO₂CH₃ | CH₃ | CH₃ | N | |
| H | CH₃ | H | CH₂OSO₂CH₃ | CH₃ | OCH₃ | N | |
| H | CH₃ | H | CH₂OSO₂CH₃ | OCH₃ | OCH₃ | N | |
| H | CH₃ | H | CH₂OSO₂CH₂CH₃ | OCH₃ | Cl | CH | |
| H | CH₃ | H | CH₂OSO₂CH₂CH₃ | CH₃ | CH₃ | CH | |
| CH₃ | CH₃ | H | CH₂OSO₂CH₂CH₃ | CH₃ | OCH₃ | CH | |
| H | CH₃ | H | CH₂(CH₂)₂OSO₂CH₃ | OCH₃ | OCH₃ | CH | |
| H | CH₃ | H | CH₂(CH₂)₂OSO₂CH₃ | CH₃ | CH₃ | N | |
| H | CH₃ | H | CH₂(CH₂)₂OSO₂CH₃ | CH₃ | OCH₃ | N | |
| H | CH₃ | H | CH₂(CH₂)₂OSO₂CH₃ | OCH₃ | OCH₃ | N | |
| H | CH₃ | H | CH₂(CH₂)₂OSO₂CH₃ | OCH₃ | Cl | CH | |
| H | CH₃ | H | CH₂OP(O)(CH₃)₂ | CH₃ | CH₃ | CH | |
| H | CH₃ | H | CH₂OP(O)(CH₃)₂ | CH₃ | OCH₃ | CH | |
| H | CH₃ | H | CH₂OP(O)(CH₃)₂ | OCH₃ | OCH₃ | CH | |
| H | CH₃ | H | CH₂OP(O)(CH₃)₂ | CH₃ | CH₃ | N | |
| H | CH₃ | H | CH₂OP(O)(CH₃)₂ | CH₃ | OCH₃ | N | |
| H | CH₃ | H | CH₂OP(O)(CH₃)₂ | OCH₃ | OCH₃ | N | |
| H | CH₃ | H | CH₂OP(O)(CH₃)₂ | OCH₃ | Cl | CH | |
| H | CH₃ | H | CH₂OP(O)(CH₃)Ph | CH₃ | CH₃ | CH | |
| H | CH₃ | H | CH₂OP(O)(CH₃)Ph | CH₃ | OCH₃ | CH | |
| H | CH₃ | H | CH₂OP(O)(CH₃)Ph | OCH₃ | OCH₃ | CH | |
| H | CH₃ | H | CH₂OP(O)(CH₃)Ph | CH₃ | CH₃ | N | |
| H | CH₃ | H | CH₂OP(O)(Ph)₂ | CH₃ | OCH₃ | N | |
| H | CH₃ | H | CH₂OP(O)(Ph)₂ | OCH₃ | OCH₃ | N | |
| H | CH₃ | H | CH₂OP(O)(Ph)₂ | OCH₃ | Cl | CH | |
| H | CH₃ | H | CH₂OP(O)(Ph)₂ | CH₃ | CH₃ | CH | |
| H | CH₃ | H | CH₂OP(O)(Ph)₂ | CH₃ | OCH₃ | CH | |
| H | CH₃ | H | CH₂OP(O)(Ph)₂ | OCH₃ | OCH₃ | CH | |
| H | CH₃ | H | CH₂CH₂OP(O)(CH₃)₂ | CH₃ | CH₃ | N | |
| H | CH₃ | H | CH₂CH₂OP(O)(CH₃)₂ | OCH₃ | OCH₃ | N | |
| H | CH₃ | H | CH₂CH₂OP(O)(CH₃)₂ | OCH₃ | Cl | CH | |
| H | CH₃ | H | CH₂CH₂OP(O)(CH₃)₂ | CH₃ | CH₃ | CH | |
| H | CH₃ | H | CH₂CH₂OP(O)(CH₃)₂ | CH₃ | OCH₃ | CH | |
| H | CH₃ | H | CH₂(CH₂)₂OP(O)(CH₃)₂ | OCH₃ | OCH₃ | CH | |
| H | CH₃ | H | CH₂(CH₂)₂OP(O)(CH₃)₂ | CH₃ | CH₃ | N | |
| H | CH₃ | H | CH₂(CH₂)₂OP(O)(CH₃)₂ | CH₃ | OCH₃ | N | |
| H | CH₃ | H | CH₂(CH₂)₂OP(O)(CH₃)₂ | OCH₃ | OCH₃ | N | |
| H | CH₃ | H | CH₂(CH₂)₂OP(O)(CH₃)₂ | OCH₃ | Cl | CH | |
| H | CH₃ | H | CH₂(CH₂)₂OP(O)(CH₃)₂ | CH₃ | CH₃ | CH | |
| H | CH₃ | H | CH₂P(O)(CH₃)₂ | CH₃ | OCH₃ | CH | |
| H | CH₃ | H | CH₂P(O)(CH₃)₂ | OCH₃ | OCH₃ | CH | |
| H | CH₃ | H | CH₂P(O)(CH₃)₂ | CH₃ | CH₃ | N | |
| H | CH₃ | H | CH₂P(O)(CH₃)₂ | CH₃ | OCH₃ | N | |
| H | CH₃ | H | CH₂P(O)(CH₃)₂ | OCH₃ | OCH₃ | N | |
| H | CH₃ | H | CH₂P(O)(CH₃)₂ | OCH₃ | Cl | CH | |
| H | CH₃ | H | CH₂P(O)(OCH₃)₂ | CH₃ | CH₃ | CH | |
| H | CH₃ | H | CH₂P(O)(OCH₃)₂ | CH₃ | OCH₃ | CH | |
| H | CH₃ | H | CH₂P(O)(OCH₃)₂ | OCH₃ | OCH₃ | CH | |
| H | CH₃ | H | CH₂P(O)(OCH₃)₂ | CH₃ | CH₃ | N | |
| H | CH₃ | H | CH₂P(O)(OCH₃)₂ | CH₃ | OCH₃ | N | |
| H | CH₃ | H | CH₂P(O)(OCH₃)₂ | OCH₃ | OCH₃ | N | |
| H | CH₃ | H | CH₂P(O)(OCH₃)₂ | OCH₃ | Cl | CH | |
| H | CH₃ | H | CH₂P(O)(OCH₃)₂ | CH₃ | CH₃ | CH | |
| CH₃ | CH₃ | H | CH₂CH₂P(O)(OCH₂CH₃)₂ | CH₃ | OCH₃ | CH | |
| H | CH₃ | H | CH₂CH₂P(O)(OCH₂CH₃)₂ | OCH₃ | OCH₃ | CH | |
| H | CH₃ | H | CH₂(CH₂)₃P(O)(OCH₃)₂ | CH₃ | CH₃ | N | |
| H | CH₃ | H | CH₂(CH₂)₃P(O)(OCH₃)₂ | CH₃ | OCH₃ | N | |
| H | CH₃ | H | CH₂(CH₂)₃P(O)(OCH₃)₂ | OCH₃ | OCH₃ | N | |
| H | CH₃ | H | CH₂(CH₂)₃P(O)(OCH₃)₂ | OCH₃ | Cl | CH | |
| H | CH₃ | H | CH₂OP(S)(CH₃)₂ | CH₃ | CH₃ | CH | |
| H | CH₃ | H | CH₂OP(S)(CH₃)₂ | CH₃ | OCH₃ | CH | |
| H | CH₃ | H | CH₂OP(S)(CH₃)₂ | OCH₃ | OCH₃ | CH | |
| H | CH₃ | H | CH₂OP(S)(CH₃)₂ | CH₃ | CH₃ | N | |
| H | CH₃ | H | CH₂OP(S)(CH₃)₂ | CH₃ | OCH₃ | N | |
| H | CH₃ | H | CH₂OP(S)(CH₃)₂ | OCH₃ | OCH₃ | N | |
| H | CH₃ | H | CH₂OP(S)(CH₃)₂ | OCH₃ | Cl | CH | |
| H | CH₃ | H | CH₂OP(S)(OCH₃)₂ | CH₃ | CH₃ | CH | |
| H | CH₃ | H | CH₂OP(S)(OCH₃)₂ | CH₃ | OCH₃ | CH | |
| H | CH₃ | H | CH₂OP(S)(OCH₃)₂ | OCH₃ | OCH₃ | CH | |
| H | CH₃ | H | CH₂OP(S)(OCH₃)₂ | CH₃ | CH₃ | N | |
| H | CH₃ | H | CH₂OP(S)(OCH₃)₂ | CH₃ | OCH₃ | N | |
| H | CH₃ | H | CH₂OP(S)(OCH₃)₂ | OCH₃ | OCH₃ | N | |
| H | CH₃ | H | CH₂OP(S)(OCH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |

TABLE Ia-continued

General Structure Ia

| R | R₁ | R₂ | R₃ | X | Y | Z | m.p. (°C.) |
|---|----|----|----|---|---|---|------------|
| H | CH₃ | H | CH₂P(S)(CH₃)₂ | OCH₃ | OCH₃ | CH | |
| H | CH₃ | H | CH₂P(S)(CH₃)₂ | CH₃ | CH₃ | N | |
| H | CH₃ | H | CH₂P(S)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(OCH₃)₂ | CH₃ | CH₃ | CH | |
| H | CH₃ | H | CH₂P(S)(OCH₃)₂ | CH₃ | OCH₃ | CH | |
| H | CH₃ | H | CH₂P(S)(OCH₃)₂ | OCH₃ | OCH₃ | CH | |
| H | CH₃ | H | CH₂P(S)(OCH₃)₂ | CH₃ | CH₃ | N | |
| H | CH₃ | H | CH₂P(S)(OCH₃)₂ | CH₃ | OCH₃ | N | |
| H | CH₃ | H | CH₂P(S)(OCH₃)₂ | OCH₃ | OCH₃ | N | |
| H | CH₃ | H | CH₂P(S)(OCH₃)₂ | OCH₃ | Cl | CH | |
| H | CH₃ | H | CH₂CH₂OP(S)(CH₃)₂ | CH₃ | CH₃ | CH | |
| H | CH₃ | H | CH₂CH₂OP(S)(CH₃)₂ | CH₃ | OCH₃ | CH | |
| H | CH₃ | H | CH₂CH₂OP(S)(CH₃)₂ | OCH₃ | OCH₃ | CH | |
| H | CH₃ | H | CH₂CH₂OP(S)(CH₃)₂ | CH₃ | CH₃ | N | |
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂(CH₂)₂SCH₃ | CH₃ | CH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₃SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | CH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | CH₃ | CH₂CH₂SO₂CH₃ | OCH₃ | OCH₃ | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | H | CH₂(CH₂)₃SO₂CH₃ | CH₃ | OCH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | CH₃ | OCH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | OCH₃ | CH | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CH | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |
| H | CH₃ | H | CH₂CH₂CN | OCH₃ | Cl | CH | |
| H | CH₃ | H | CH₂CH₂CN | CH₃ | CH₃ | CH | |
| CH₃ | CH₃ | H | CH₂CH₂CN | CH₃ | OCH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂—CH₂P(S)(CH₃)₂ | OCH₃ | OCH₃ | CH | |
| H | CH₃ | H | CH₂—CH₂P(S)(CH₃)₂ | CH₃ | CH₃ | N | |
| H | CH₃ | H | CH₂—CH₂P(S)(CH₃)₂ | OCH₃ | OCH₃ | N | |
| H | CH₃ | H | CH₂—CH₂P(S)(CH₃)₂ | OCH₃ | Cl | CH | |
| H | CH₃ | H | CH₂—CH₂P(S)(CH₃)₂ | CH₃ | CH₃ | CH | |
| H | CH₃ | H | CH₂N(CH₃)₂ | CH₃ | OCH₃ | CH | |
| H | CH₃ | H | CH₂N(CH₃)₂ | OCH₃ | OCH₃ | CH | |
| H | CH₃ | H | CH₂N(CH₃)₂ | CH₃ | CH₃ | N | |
| H | CH₃ | H | CH₂N(CH₃)₂ | OCH₃ | OCH₃ | N | |
| H | CH₃ | H | CH₂N(CH₃)₂ | OCH₃ | Cl | CH | |
| H | CH₃ | H | CH₂N(CH₃)₂ | CH₃ | CH₃ | CH | |
| H | CH₃ | H | CH₂(CH₂)₃N(CH₃)₂ | CH₃ | OCH₃ | CH | |
| H | CH₃ | H | CH₂(CH₂)₃N(CH₃)₂ | OCH₃ | OCH₃ | CH | |
| H | CH₃ | H | CH₂(CH₂)₃N(CH₃)₂ | CH₃ | CH₃ | N | |
| H | CH₃ | H | CH₂(CH₂)₃N(CH₃)₂ | CH₃ | OCH₃ | N | |
| H | CH₃ | CH₃ | CH₂(CH₂)₃N(CH₃)₂ | OCH₃ | OCH₃ | N | |
| H | CH₃ | H | CH₂(CH₂)₃N(CH₃)₂ | OCH₃ | Cl | CH | |
| H | CH₃ | H | CH₂(CH₂)₃N(CH₃)₂ | CH₃ | CH₃ | CH | |
| H | CH₃ | H | CH₂N(CH₃)₂Ph | CH₃ | OCH₃ | CH | |
| H | CH₃ | H | CH₂N(CH₃)₂Ph | OCH₃ | OCH₃ | CH | |
| H | CH₃ | H | CH₂N(CH₃)₂Ph | CH₃ | CH₃ | N | |
| H | CH₃ | H | CH₂N(CH₃)₂Ph | CH₃ | OCH₃ | N | |
| H | CH₃ | H | CH₂—CH(CH₃)N(CH₃)₂ | OCH₃ | OCH₃ | N | |
| H | CH₃ | H | CH₂—CH(CH₃)N(CH₃)₂ | OCH₃ | Cl | CH | |
| H | CH₃ | H | CH₂—CH(CH₃)N(CH₃)₂ | CH₃ | CH₃ | CH | |
| CH₃ | CH₃ | H | CH₂—CH(CH₃)N(CH₃)₂ | CH₃ | OCH₃ | CH | |
| H | CH₃ | H | CH₂—CH(CH₃)N(CH₃)₂ | OCH₃ | OCH₃ | CH | |
| H | CH₃ | H | CH₂CH₂CH(CH₃)₂ | CH₃ | CH₃ | N | |
| H | CH₃ | H | CH₂CH₂CH(CH₃)₂ | CH₃ | OCH₃ | N | |
| H | CH₃ | H | CH₂CH₂CH(CH₃)₂ | OCH₃ | OCH₃ | N | |
| H | CH₃ | H | CH₂CH₂CH(CH₃)₂ | OCH₃ | Cl | CH | |
| H | CH₃ | H | CH₂NHC(O)CH₃ | CH₃ | CH₃ | CH | |
| H | CH₃ | H | CH₂NHC(O)CH₃ | CH₃ | OCH₃ | CH | |
| H | CH₃ | H | CH₂NHC(O)CH₃ | OCH₃ | OCH₃ | CH | |
| H | CH₃ | H | CH₂NHC(O)CH₃ | CH₃ | CH₃ | N | |
| H | CH₃ | H | CH₂NHC(O)CH₃ | CH₃ | OCH₃ | N | |
| H | CH₃ | H | CH₂NHC(O)CH₃ | OCH₃ | OCH₃ | N | |
| H | CH₃ | H | CH₂NHC(O)CH₃ | OCH₃ | Cl | CH | |
| H | CH₃ | H | CH₂CH₂N(CH₃)C(O)CH₃ | CH₃ | CH₃ | CH | |
| H | CH₃ | H | CH₂CH₂N(CH₃)C(O)CH₃ | CH₃ | OCH₃ | CH | |
| H | CH₃ | H | CH₂CH₂N(CH₃)C(O)CH₃ | OCH₃ | OCH₃ | CH | |
| H | CH₃ | H | CH₂CH₂N(CH₃)C(O)CH₃ | CH₃ | CH₃ | N | |
| H | CH₃ | H | CH₂(CH₂)₃NHC(O)CH₃ | CH₃ | OCH₃ | N | |
| H | CH₃ | H | CH₂(CH₂)₃NHC(O)CH₃ | OCH₃ | OCH₃ | N | |
| H | CH₃ | H | CH₂N(CH₃)C(O)OCH₃ | OCH₃ | Cl | CH | |
| H | CH₃ | H | CH₂N(CH₃)C(O)OCH₃ | CH₃ | CH₃ | CH | |
| H | CH₃ | H | CH₂NHC(O)OCH₃ | CH₃ | OCH₃ | CH | |
| H | CH₃ | H | CH₂NHC(O)OCH₃ | OCH₃ | OCH₃ | CH | |
| H | CH₃ | H | CH₂NHC(O)OCH₃ | CH₃ | CH₃ | N | |
| H | CH₃ | H | CH₂NHC(O)OCH₃ | OCH₃ | OCH₃ | N | |
| H | CH₃ | H | CH₂NHC(O)OCH₃ | OCH₃ | Cl | CH | |
| H | CH₃ | H | CH₂NHC(O)OCH₃ | CH₃ | CH₃ | CH | |
| H | CH₃ | H | CH₂(CH₂)₃NHC(O)OCH₃ | CH₃ | OCH₃ | CH | |
| H | CH₃ | H | CH₂(CH₂)₃NHC(O)OCH₃ | OCH₃ | OCH₃ | CH | |
| H | CH₃ | H | CH₂(CH₂)₃NHC(O)OCH₃ | CH₃ | CH₃ | N | |
| H | CH₃ | H | CH₂N(CH₃)C(O)OCH₂CH₃ | CH₃ | OCH₃ | N | |
| H | CH₃ | H | CH(CH₃)NHC(O)OCH₃ | OCH₃ | OCH₃ | N | |
| H | CH₃ | H | CH(CH₃)NHC(O)OCH₃ | OCH₃ | Cl | CH | |
| H | CH₃ | H | CH(CH₃)NHC(O)OCH₃ | CH₃ | CH₃ | CH | |
| H | CH₃ | H | CH₂NHSO₂CH₃ | CH₃ | OCH₃ | CH | |
| H | CH₃ | H | CH₂NHSO₂CH₃ | OCH₃ | OCH₃ | CH | |
| H | CH₃ | H | CH₂NHSO₂CH₃ | CH₃ | CH₃ | N | |
| H | CH₃ | H | CH₂NHSO₂CH₃ | CH₃ | OCH₃ | N | |
| H | CH₃ | CH₃ | CH₂NHSO₂CH₃ | OCH₃ | OCH₃ | N | |
| H | CH₃ | H | CH₂CH₂NHSO₂CH₃ | OCH₃ | Cl | CH | |
| H | CH₃ | H | CH₂CH₂NHSO₂CH₃ | CH₃ | CH₃ | CH | |
| H | CH₃ | H | CH₂CH₂NHSO₂CH₃ | CH₃ | OCH₃ | CH | |
| H | CH₃ | H | CH₂CH₂NHSO₂CH₃ | OCH₃ | OCH₃ | CH | |
| H | CH₃ | H | CH₂CH₂NHSO₂CH₃ | CH₃ | CH₃ | N | |
| H | CH₃ | H | CH₂CH₂NHSO₂CH₃ | CH₃ | OCH₃ | N | |
| H | CH₃ | H | CH₂(CH₂)₃NHSO₂CH₃ | OCH₃ | OCH₃ | N | |
| H | CH₃ | H | CH₂(CH₂)₃NHSO₂CH₃ | OCH₃ | Cl | CH | |
| H | CH₃ | H | CH₂(CH₂)₃NHSO₂CH₃ | CH₃ | CH₃ | CH | |
| CH₃ | CH₃ | H | CH₂NHP(O)(CH₃)₂ | CH₃ | OCH₃ | CH | |
| H | CH₃ | H | CH₂NHP(O)(CH₃)₂ | OCH₃ | OCH₃ | CH | |
| H | CH₃ | H | CH₂NHP(O)(CH₃)₂ | CH₃ | CH₃ | N | |
| H | CH₃ | H | CH₂NHP(O)(OCH₃)₂ | CH₃ | OCH₃ | N | |
| H | CH₃ | H | CH₂NHP(O)(CH₃)₂ | OCH₃ | OCH₃ | N | |
| H | CH₃ | H | CH₂NHP(O)(CH₃)₂ | OCH₃ | Cl | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂=CH₂ | CH₃ | CH₃ | CH | |
| H | CH₃ | H | CH₂=CH₂ | CH₃ | OCH₃ | CH | |
| H | CH₃ | H | CH₂NO₂ | CH₃ | CH₃ | CH | |
| H | CH₃ | H | CH₂NO₂ | CH₃ | OCH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |
| H | CH₃ | H | CH₂C(O)CH₃ | CH₃ | CH₃ | N | |
| H | CH₃ | H | CH₂C(O)CH₃ | OCH₃ | OCH₃ | N | |
| H | CH₃ | H | CH₂C(O)CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH₂CH₃ | CH₃ | CH₃ | N | |
| H | CH₃ | H | CH₂C(O)CH₂CH₃ | CH₃ | OCH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂(CH₂)₃C(O)CH₃ | CH₃ | CH₃ | CH | |
| H | CH₃ | H | CH₂(CH₂)₃C(O)CH₃ | CH₃ | OCH₃ | CH | |
| H | CH₃ | H | CH₂(CH₂)₃C(O)CH₃ | OCH₃ | OCH₃ | CH | |
| H | CH₃ | H | CH₂(CH₂)₃C(O)CH₃ | CH₃ | CH₃ | N | |
| H | CH₃ | H | CH₂(CH₂)₃C(O)CH₃ | CH₃ | OCH₃ | N | |
| H | CH₃ | CH₃ | CH₂(CH₂)₃C(O)CH₃ | OCH₃ | OCH₃ | N | |
| H | CH₃ | H | CH₂(CH₂)₃C(O)CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | OCH₃ | OCH₃ | CH | |
| H | CH₃ | H | CH₂CH₂C(O)CH₃ | CH₃ | CH₃ | N | |
| H | CH₃ | H | CH₂—CH(CH₃)C(O)CH₃ | CH₃ | OCH₃ | N | |
| H | CH₃ | CH₃ | CH₂—CH(CH₂)C(O)CH₃ | OCH₃ | OCH₃ | N | |
| H | CH₃ | H | CH₂—CH(CH₂)C(O)CH₃ | OCH₃ | Cl | CH | |
| H | CH₃ | H | CH₂—CH(CH₃)C(O)CH₃ | CH₃ | CH₃ | CH | |
| CH₃ | CH₃ | CH₃ | CH₂—CH(CH₃)C(O)CH₃ | CH₃ | OCH₃ | CH | |
| H | CH₃ | H | CH₂(CH₂)₆C(O)CH₂CH₃ | OCH₃ | OCH₃ | CH | |
| H | CH₃ | H | CH₂(CH₂)₆C(O)CH₂CH₃ | CH₃ | CH₃ | N | |
| H | CH₃ | H | CH₂(CH₂)₆C(O)CH₂CH₃ | CH₃ | OCH₃ | N | |
| H | CH₃ | H | CH₂(CH₂)₆C(O)CH₂CH₃ | OCH₃ | OCH₃ | N | |
| H | CH₃ | H | CH₂(CH₂)₆C(O)CH₂CH₃ | OCH₃ | Cl | CH | |
| H | CH₃ | H | CH₂C(O)OCH₃ | CH₃ | CH₃ | CH | |
| H | CH₃ | H | CH₂C(O)OCH₃ | CH₃ | OCH₃ | CH | |
| H | CH₃ | H | CH₂C(O)OCH₃ | OCH₃ | OCH₃ | CH | |
| H | CH₃ | H | CH₂C(O)OCH₃ | CH₃ | CH₃ | N | |
| H | CH₃ | H | CH₂C(O)OCH₃ | CH₃ | OCH₃ | N | |
| H | CH₃ | H | CH₂C(O)OCH₃ | OCH₃ | OCH₃ | N | |
| H | CH₃ | H | CH₂C(O)OCH₃ | OCH₃ | Cl | CH | |
| H | CH₃ | H | CH₂C(O)OCH₂CH₃ | CH₃ | CH₃ | CH | |
| H | CH₃ | H | CH₂C(O)OCH₂CH₃ | CH₃ | OCH₃ | CH | |
| H | CH₃ | H | CH₂C(O)OCH₂CH₃ | OCH₃ | OCH₃ | CH | |
| H | CH₃ | H | CH₂C(O)OCH₂CH₃ | CH₃ | CH₃ | N | |
| H | CH₃ | H | CH₂C(O)OCH₂CH₃ | CH₃ | OCH₃ | N | |
| H | CH₃ | H | CH₂C(O)OCH₂CH₃ | OCH₃ | OCH₃ | N | |
| H | CH₃ | H | CH₂C(O)OCH₂CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | N | |
| H | CH₃ | H | CH₂CH₂C(O)CH₃ | CH₃ | CH₃ | N | |
| H | CH₃ | H | CH₂CH₂C(O)CH₃ | OCH₃ | OCH₃ | N | |
| H | CH₃ | H | CH₂CH₂C(O)CH₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | CH₂CH₂C(O)N(CH₃)₂ | CH₃ | CH₃ | CH | |
| H | CH₃ | H | CH₂CH₂C(O)N(CH₃)₂ | CH₃ | OCH₃ | CH | |
| H | CH₃ | H | CH₂CH₂C(O)N(CH₃)₂ | OCH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂CH₂C(O)N(CH₃)₂ | CH₃ | CH₃ | N | |
| H | CH₃ | H | CH₂CH₂C(O)N(CH₃)₂ | CH₃ | OCH₃ | N | |
| H | CH₃ | CH₃ | CH₂CH₂C(O)N(CH₃)₂ | OCH₃ | OCH₃ | N | |
| H | CH₃ | H | CH₂CH₂C(O)N(CH₃)₂ | OCH₃ | Cl | CH | |
| H | CH₃ | H | CH₂C(O)N(CH₃)CH₂CH₃ | CH₃ | CH₃ | CH | |
| H | CH₃ | H | CH₂C(O)N(CH₃)CH₂CH₃ | CH₃ | OCH₃ | CH | |
| H | CH₃ | H | CH₂C(O)N(CH₃)CH₂CH₃ | OCH₃ | OCH₃ | CH | |
| H | CH₃ | H | CH₂C(O)N(CH₃)CH₂CH₃ | CH₃ | CH₃ | N | |
| H | CH₃ | H | CH₂C(O)N(CH₃)CH₂OCH₃ | CH₃ | OCH₃ | N | |
| H | CH₃ | H | CH₂C(O)N(CH₃)CH₂OCH₃ | OCH₃ | OCH₃ | N | |
| H | CH₃ | H | CH₂C(O)N(CH₃)CH₂OCH₃ | OCH₃ | Cl | CH | |
| H | CH₃ | H | CH₂SeCH₃ | CH₃ | CH₃ | CH | |
| CH₃ | CH₃ | H | CH₂SeCH₃ | CH₃ | OCH₃ | CH | |
| H | CH₃ | H | CH₂SeCH₃ | OCH₃ | OCH₃ | CH | |
| H | CH₃ | H | CH₂SePh | CH₃ | CH₃ | N | |
| H | CH₃ | H | CH₂SePh | CH₃ | OCH₃ | N | |
| H | CH₃ | H | CH₂—CH₂SeCH₃ | OCH₃ | OCH₃ | N | |
| H | CH₃ | H | CH₂—CH₂SeCH₃ | OCH₃ | Cl | CH | |
| H | CH₃ | H | CH=CH₂ | OCH₃ | OCH₃ | CH | |
| H | CH₃ | H | CH=CH₂ | CH₃ | CH₃ | N | |
| H | CH₃ | H | CH=CH₂ | OCH₃ | OCH₃ | N | |
| H | CH₃ | H | CH=CH₂ | CH₃ | OCH₃ | N | |
| H | CH₃ | H | CH=CH₂ | OCH₃ | Cl | CH | |
| H | CH₃ | H | CH=CH—CH₃ | CH₃ | CH₃ | CH | |
| H | CH₃ | H | CH=CH—CH₃ | CH₃ | OCH₃ | CH | |
| H | CH₃ | H | CH=CH—CH₃ | OCH₃ | OCH₃ | CH | |
| H | CH₃ | H | CH=CH—CH₃ | CH₃ | CH₃ | N | |
| H | CH₃ | H | CH=CH—CH₃ | CH₃ | OCH₃ | N | |
| H | CH₃ | H | CH=CH—CH₃ | OCH₃ | OCH₃ | N | |
| H | CH₃ | H | CH=CH—CH₃ | OCH₃ | Cl | CH | |
| H | CH₃ | H | CH=CH—CH₂—CH₃ | CH₃ | CH₃ | CH | |
| H | CH₃ | H | CH=CH—CH₂—CH₃ | CH₃ | OCH₃ | CH | |
| H | CH₃ | H | CH=CH—CH₂—CH₃ | OCH₃ | OCH₃ | CH | |
| H | CH₃ | H | CH=CH—CH₂—CH₃ | CH₃ | CH₃ | N | |
| H | CH₃ | H | CH=CH—CH₂—CH₃ | OCH₃ | OCH₃ | N | |
| H | CH₃ | H | CH=CH—CH₂—CH₃ | OCH₃ | Cl | CH | |
| H | CH₃ | H | CH=C(CH₃)₂ | CH₃ | CH₃ | CH | |
| H | CH₃ | H | CH=C(CH₃)₂ | CH₃ | OCH₃ | CH | |
| H | CH₃ | H | CH=C(CH₃)₂ | OCH₃ | OCH₃ | CH | |
| H | CH₃ | H | CH=C(CH₃)₂ | CH₃ | CH₃ | N | |
| H | CH₃ | H | CH=C(CH₃)₂ | CH₃ | OCH₃ | N | |
| H | CH₃ | H | CH=C(CH₃)₂ | OCH₃ | OCH₃ | N | |
| H | CH₃ | H | CH=C(CH₃)₂ | OCH₃ | Cl | CH | |
| H | CH₃ | H | CH=CH(CH₂)₃CH₃ | CH₃ | CH₃ | CH | |
| H | CH₃ | H | CH=CH(CH₂)₃CH₃ | CH₃ | OCH₃ | CH | |
| H | CH₃ | H | CH=CH(CH₂)₃CH₃ | OCH₃ | OCH₃ | CH | |
| H | CH₃ | H | CH=CH(CH₂)₃CH₃ | CH₃ | CH₃ | N | |
| H | CH₃ | H | CH=CH(CH₂)₃CH₃ | CH₃ | OCH₃ | N | |
| H | CH₃ | CH₃ | CH=CH(CH₂)₃CH₃ | OCH₃ | OCH₃ | N | |
| H | CH₃ | H | CH=CH(CH₂)₃CH₃ | OCH₃ | Cl | CH | |
| H | CH₃ | H | CH=C(CH₃)CH₂CH₃ | CH₃ | CH₃ | CH | |
| H | CH₃ | H | CH=C(CH₃)CH₂CH₃ | CH₃ | OCH₃ | CH | |
| H | CH₃ | H | CH=C(CH₃)CH₂CH₃ | OCH₃ | OCH₃ | CH | |
| H | CH₃ | H | CH=CH—CH(CH₃)₂ | CH₃ | CH₃ | N | |
| H | CH₃ | H | CH=CH—CH(CH₃)₂ | CH₃ | OCH₃ | N | |
| H | CH₃ | H | CH=CH—CH(CH₃)₂ | OCH₃ | OCH₃ | N | |
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | CH₂—CH(—O—)CH₂ | CH₃ | CH₃ | CH | |
| H | CH₃ | H | CH₂—CH(—O—)CH₂ | CH₃ | OCH₃ | CH | |
| H | CH₃ | H | CH₂—CH(—O—)CH₂ | OCH₃ | OCH₃ | CH | |
| H | CH₃ | H | CH₂—CH(—O—)CH₂ | CH₃ | CH₃ | N | |
| H | CH₃ | H | CH₂—CH(—O—)CH₂ | CH₃ | OCH₃ | N | |
| H | CH₃ | H | CH₂—CH(—O—)CH₂ | OCH₃ | OCH₃ | N | |
| H | CH₃ | H | CH₂—CH(—O—)CH₂ | OCH₃ | Cl | CH | |
| H | CH₃ | H | CH₂—CH(—O—)CH—CH₃ | CH₃ | CH₃ | CH | |
| H | CH₃ | H | CH₂—CH(—O—)CH—CH₃ | CH₃ | OCH₃ | CH | |
| H | CH₃ | H | CH₂—CH(—O—)CH—CH₃ | OCH₃ | OCH₃ | CH | |
| H | CH₃ | H | CH₂—CH(—O—)CH—CH₃ | CH₃ | CH₃ | N | |
| H | CH₃ | H | CH₂—CH(—O—)CH—CH₃ | CH₃ | OCH₃ | N | |
| H | CH₃ | H | CH₂—CH(—O—)CH—CH₃ | OCH₃ | OCH₃ | N | |
| H | CH₃ | H | CH₂—CH(—O—)CH—CH₃ | OCH₃ | Cl | CH | |
| H | CH₃ | H | CH₂—CH₂—CH(—O—)CH₂ | CH₃ | CH₃ | CH | |
| H | CH₃ | H | CH₂—CH₂—CH(—O—)CH₂ | CH₃ | OCH₃ | CH | |
| H | CH₃ | H | CH₂—CH₂—CH(—O—)CH₂ | OCH₃ | OCH₃ | CH | |
| H | CH₃ | H | CH₂—CH₂—CH(—O—)CH₂ | CH₃ | CH₃ | N | |
| H | CH₃ | H | CH₂—CH₂—CH(—O—)CH₂ | OCH₃ | OCH₃ | N | |
| H | CH₃ | H | CH₂—CH₂—CH(—O—)CH₂ | OCH₃ | Cl | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |
| H | CH₃ | CH₃ | cyclopentyl | OCH₃ | OCH₃ | N | |
| H | CH₃ | H | cyclopentyl | OCH₃ | Cl | CH | |
| H | CH₃ | H | cyclohexyl | CH₃ | CH₃ | CH | |
| H | CH₃ | H | cyclohexyl | CH₃ | OCH₃ | CH | |
| H | CH₃ | H | cyclohexyl | OCH₃ | OCH₃ | CH | |
| H | CH₃ | H | cyclohexyl | CH₃ | CH₃ | N | |
| H | CH₃ | H | cyclohexyl | CH₃ | OCH₃ | N | |
| H | CH₃ | CH₃ | cyclohexyl | OCH₃ | OCH₃ | N | |
| H | CH₃ | H | cyclohexyl | OCH₃ | Cl | CH | |
| H | CH₃ | H | cyclopropyl | CH₃ | CH₃ | CH | |
| CH₃ | CH₃ | H | cyclopropyl | CH₃ | OCH₃ | CH | |
| H | CH₃ | H | cyclopropyl | OCH₃ | OCH₃ | CH | |
| H | CH₃ | H | cyclopropyl | CH₃ | CH₃ | N | |
| H | CH₃ | H | cyclopropyl | CH₃ | OCH₃ | N | |
| H | CH₃ | H | cyclopropyl | OCH₃ | OCH₃ | N | |
| H | CH₃ | H | cyclopropyl | OCH₃ | Cl | CH | |
| H | CH₃ | H | CH₂—cyclopropyl | CH₃ | CH₃ | CH | |
| H | CH₃ | H | CH₂—cyclopropyl | OCH₃ | OCH₃ | CH | |
| H | CH₃ | H | CH₂—cyclopropyl | CH₃ | CH₃ | N | |
| H | CH₃ | H | CH₂—cyclopropyl | CH₃ | OCH₃ | N | |
| H | CH₃ | H | CH₂—cyclopropyl | OCH₃ | OCH₃ | N | |
| H | CH₃ | H | CH₂—cyclopropyl | OCH₃ | Cl | CH | |
| H | CH₃ | H | CH₂—cyclopentyl | CH₃ | CH₃ | CH | |
| H | CH₃ | H | CH₂—cyclopentyl | CH₃ | OCH₃ | CH | |
| H | CH₃ | H | CH₂—cyclopentyl | OCH₃ | OCH₃ | CH | |
| H | CH₃ | H | CH₂—cyclopentyl | CH₃ | CH₃ | N | |
| H | CH₃ | H | CH₂—cyclopentyl | CH₃ | OCH₃ | N | |
| H | CH₃ | H | CH₂—cyclopentyl | OCH₃ | OCH₃ | N | |
| H | CH₃ | H | CH₂—cyclopentyl | OCH₃ | Cl | CH | |
| H | CH₃ | H | C₆H₅ | CH₃ | CH₃ | CH | |
| H | CH₃ | H | C₆H₅ | CH₃ | OCH₃ | CH | |
| H | CH₃ | H | C₆H₅ | OCH₃ | OCH₃ | CH | |
| H | CH₃ | H | C₆H₅ | CH₃ | CH₃ | N | |
| H | CH₃ | H | C₆H₅ | CH₃ | OCH₃ | N | |
| H | CH₃ | H | C₆H₅ | OCH₃ | OCH₃ | N | |
| H | CH₃ | H | C₆H₅ | OCH₃ | Cl | CH | |
| H | CH₃ | H | CH=CH—CF₃ | CH₃ | CH₃ | CH | |
| H | CH₃ | H | CH=CH—CF₃ | CH₃ | OCH₃ | CH | |
| H | CH₃ | H | CH=CH—CF₃ | OCH₃ | OCH₃ | CH | |
| H | CH₃ | H | CH=CH—CF₃ | CH₃ | CH₃ | N | |
| H | CH₃ | H | CH=CH—CF₃ | CH₃ | OCH₃ | N | |
| H | CH₃ | H | CH=CH—CF₃ | OCH₃ | OCH₃ | N | |
| H | CH₃ | H | CH=CH—CF₃ | OCH₃ | Cl | CH | |
| H | CH₃ | H | CH₂—C≡C—CF₃ | CH₃ | CH₃ | CH | |
| H | CH₃ | H | CH₂—C≡C—CF₃ | CH₃ | OCH₃ | CH | |
| H | CH₃ | H | CH₂—C≡C—CF₃ | OCH₃ | OCH₃ | CH | |
| H | CH₃ | H | CH₂—C≡C—CF₃ | CH₃ | CH₃ | N | |
| H | CH₃ | H | CH₂—C≡C—CF₃ | CH₃ | OCH₃ | N | |
| H | CH₃ | CH₃ | CH₂—C≡C—CF₃ | OCH₃ | OCH₃ | N | |
| H | CH₃ | H | CH₂—CH=CF₂ | OCH₃ | Cl | CH | |
| H | CH₃ | H | CH=CH—CH₂Cl | CH₃ | CH₃ | CH | |
| H | CH₃ | H | CH=CH—CH₂Cl | OCH₃ | OCH₃ | CH | |
| H | CH₃ | H | CH=CH—CH₂Cl | CH₃ | CH₃ | N | |
| H | CH₃ | H | CH=CH—CH₂Cl | CH₃ | OCH₃ | N | |
| H | CH₃ | H | CH=CH—CH₂Cl | OCH₃ | OCH₃ | N | |
| H | CH₃ | H | CH₂—C⟨CHF / CH₂⟩ (cyclopropyl with CHF) | OCH₃ | Cl | CH | |
| H | CH₃ | H | CH₂—C⟨CHF / CH₂⟩ (cyclopropyl with CHF) | CH₃ | CH₃ | CH | |

TABLE Ia-continued

General Structure Ia

| R | R₁ | R₂ | R₃ | X | Y | Z | m.p. (°C.) |
|---|---|---|---|---|---|---|---|
| CH₃ | CH₃ | H | 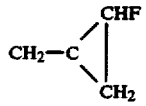 | CH₃ | OCH₃ | CH | |
| H | CH₃ | H | 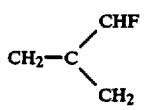 | OCH₃ | OCH₃ | CH | |
| H | CH₃ | H | 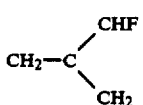 | CH₃ | CH₃ | N | |
| H | CH₃ | H | 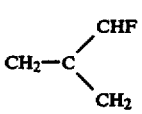 | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡CHOCH₃ | CH₃ | OCH₃ | N | |
| H | CH₃ | H | CH₂—C≡CHOCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | OCH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | H | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—C≡C—CH₂OCH₃ | OCH₃ | OCH₃ | CH | |
| H | CH₃ | H | CH₂—CH=CH—CH₂SCH₃ | CH | CH₃ | N | |
| H | CH₃ | H | CH₂—CH=CH—CH₂SCH₃ | CH | OCH₃ | N | |
| H | CH₃ | H | CH₂—CH=CH—CH₂SCH₃ | OCH | OCH₃ | N | |
| H | CH₃ | H | CH₂—CH=CH—CH₂SCH₃ | OCH | Cl | CH | |
| H | CH₃ | H | CH=CH—CH₂N(CH₃)₂ | CH₃ | CH₃ | CH | |
| CH₃ | CH₃ | H | CH=CH—CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | CH₃ | OCH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |

TABLE Ia-continued

General Structure Ia

| R | $R_1$ | $R_2$ | $R_3$ | X | Y | Z | m.p. (°C) |
|---|---|---|---|---|---|---|---|
| H | $CH_3$ | H | $SCH_3$ | $OCH_3$ | $OCH_3$ | N | |
| H | $CH_3$ | H | $SCH_3$ | $OCH_3$ | Cl | CH | |
| H | $CH_3$ | H | $SCH_2CF_3$ | $CH_3$ | $CH_3$ | CH | |
| H | $CH_3$ | H | $SCH_2CH_3$ | $CH_3$ | $OCH_3$ | CH | |
| H | $CH_3$ | H | $SCH_2CH_3$ | $OCH_3$ | $OCH_3$ | CH | |
| H | $CH_3$ | H | $SCH_2CH_3$ | $CH_3$ | $CH_3$ | N | |
| H | $CH_3$ | H | $SCH_2CH_3$ | $CH_3$ | $OCH_3$ | N | |
| H | $CH_3$ | H | $SCH_2CH_3$ | $OCH_3$ | $OCH_3$ | N | |
| H | $CH_3$ | H | $SCH_2CH_3$ | $OCH_3$ | Cl | CH | |
| H | $CH_3$ | H | $SO_2CH_3$ | $CH_3$ | $CH_3$ | CH | |
| H | $CH_3$ | H | $SO_2CH_3$ | $CH_3$ | $OCH_3$ | CH | |
| H | $CH_3$ | H | $SO_2CH_3$ | $OCH_3$ | $OCH_3$ | CH | |
| H | $CH_3$ | H | $SO_2CH_3$ | $CH_3$ | $CH_3$ | N | |
| H | $CH_3$ | H | $SO_2CH_3$ | $OCH_3$ | $OCH_3$ | N | |
| H | $CH_3$ | H | $SO_2CH_3$ | $OCH_3$ | Cl | CH | |
| H | $CH_3$ | H | $SO_2CH_2CH_3$ | $CH_3$ | $CH_3$ | CH | |
| H | $CH_3$ | H | $SO_2CH_2CH_3$ | $CH_3$ | $OCH_3$ | CH | |
| H | $CH_3$ | H | $SO_2CH_2CH_3$ | $OCH_3$ | $OCH_3$ | CH | |
| H | $CH_3$ | H | $SO_2CH_2CH_3$ | $CH_3$ | $CH_3$ | N | |
| H | $CH_3$ | H | $SO_2CH_2CH_3$ | $CH_3$ | $OCH_3$ | N | |
| H | $CH_3$ | H | $SO_2CH_2CH_3$ | $OCH_3$ | $OCH_3$ | N | |
| H | $CH_3$ | H | $SO_2CH_2CH_3$ | $OCH_3$ | Cl | CH | |
| H | $CH_3$ | H | $OCH_3$ | $CH_3$ | $CH_3$ | CH | |
| H | $CH_3$ | H | $OCH_3$ | $CH_3$ | $OCH_3$ | CH | |
| H | $CH_3$ | H | $OCH_3$ | $OCH_3$ | $OCH_3$ | CH | |
| H | $CH_3$ | H | $OCH_3$ | $CH_3$ | $CH_3$ | N | |
| H | $CH_3$ | H | $OCH_3$ | $CH_3$ | $OCH_3$ | N | |
| H | $CH_3$ | $CH_3$ | $OCH_3$ | $OCH_3$ | $OCH_3$ | N | |
| H | $CH_3$ | H | $OCH_3$ | $OCH_3$ | Cl | CH | |
| H | $CH_3$ | H | $OCH_2CH_3$ | $CH_3$ | $CH_3$ | CH | |
| H | $CH_3$ | H | $OCH_2CH_3$ | $CH_3$ | $OCH_3$ | CH | |
| H | $CH_3$ | H | $OCH_2CH_3$ | $OCH_3$ | $OCH_3$ | CH | |
| H | $CH_3$ | H | $OCH_2CH_3$ | $CH_3$ | $CH_3$ | N | |
| H | $CH_3$ | H | $OCH_2CH_3$ | $CH_3$ | $OCH_3$ | N | |
| H | $CH_3$ | H | $OCH_2CH_3$ | $OCH_3$ | $OCH_3$ | N | |
| H | $CH_3$ | H | $OCH_2CH_3$ | $OCH_3$ | Cl | CH | |
| H | $CH_3$ | H | $OCH(CH_3)_2$ | $CH_3$ | $CH_3$ | CH | |
| $CH_3$ | $CH_3$ | H | $OCH(CH_3)_2$ | $CH_3$ | $OCH_3$ | CH | |
| H | $CH_3$ | H | $OCH(CH_3)_2$ | $OCH_3$ | $OCH_3$ | CH | |
| H | $CH_3$ | H | $OCH(CH_3)_2$ | $CH_3$ | $CH_3$ | N | |
| H | $CH_3$ | H | $OCH(CH_3)_2$ | $CH_3$ | $OCH_3$ | N | |
| H | $CH_3$ | H | $OCH(CH_3)_2$ | $OCH_3$ | $OCH_3$ | N | |
| H | $CH_3$ | H | $OCH(CH_3)_2$ | $OCH_3$ | Cl | CH | |
| H | $CH_3$ | H | $C(O)CH_3$ | $CH_3$ | $CH_3$ | CH | |
| H | $CH_3$ | H | $C(O)CH_3$ | $CH_3$ | $OCH_3$ | CH | |
| H | $CH_3$ | H | $C(O)CH_3$ | $OCH_3$ | $OCH_3$ | CH | |
| H | $CH_3$ | H | $C(O)CH_3$ | $CH_3$ | $CH_3$ | N | |
| H | $CH_3$ | H | $C(O)CH_3$ | $CH_3$ | $OCH_3$ | N | |
| H | $CH_3$ | H | $C(O)CH_3$ | $OCH_3$ | $OCH_3$ | N | |
| H | $CH_3$ | H | $C(O)CH_3$ | $OCH_3$ | Cl | CH | |
| H | $CH_3$ | H | $C(O)CH_2CH_3$ | $CH_3$ | $CH_3$ | CH | |
| H | $CH_3$ | H | $C(O)CH_2CH_3$ | $CH_3$ | $OCH_3$ | CH | |
| H | $CH_3$ | H | $C(O)CH_2CH_3$ | $OCH_3$ | $OCH_3$ | CH | |
| H | $CH_3$ | H | $C(O)CH_2CH_3$ | $CH_3$ | $CH_3$ | N | |
| H | $CH_3$ | H | $C(O)CH_2CH_3$ | $CH_3$ | $OCH_3$ | N | |
| H | $CH_3$ | H | $C(O)CH_2CH_3$ | $OCH_3$ | $OCH_3$ | N | |
| H | $CH_3$ | H | $C(O)CH_2CH_3$ | $OCH_3$ | Cl | CH | |
| H | $CH_3$ | H | $C(O)CH(CH_3)_2$ | $CH_3$ | $CH_3$ | CH | |
| H | $CH_3$ | H | $C(O)CH(CH_3)_2$ | $CH_3$ | $OCH_3$ | CH | |
| H | $CH_3$ | H | $C(O)CH(CH_3)_2$ | $OCH_3$ | $OCH_3$ | CH | |
| H | $CH_3$ | H | $C(O)CH(CH_3)_2$ | $CH_3$ | $CH_3$ | N | |
| H | $CH_3$ | H | $C(O)CH(CH_3)_2$ | $OCH_3$ | $OCH_3$ | N | |
| H | $CH_3$ | H | $C(O)CH(CH_3)_2$ | $OCH_3$ | Cl | CH | |
| H | $CH_3$ | H | $C(O)CHF_2$ | $CH_3$ | $CH_3$ | CH | |
| H | $CH_3$ | H | $C(O)CHF_2$ | $CH_3$ | $OCH_3$ | CH | |
| H | $CH_3$ | H | $C(O)CHF_2$ | $OCH_3$ | $OCH_3$ | CH | |
| H | $CH_3$ | H | $C(O)CF_3$ | $CH_3$ | $CH_3$ | N | |
| H | $CH_3$ | H | $C(O)CF_3$ | $CH_3$ | $OCH_3$ | N | |
| H | $CH_3$ | H | $C(O)CF_3$ | $OCH_3$ | $OCH_3$ | N | |
| H | $CH_3$ | H | $C(O)CF_2$ | $OCH_3$ | Cl | CH | |
| H | $CH_3$ | H | $C(O)CH_2CH_2CH_3$ | $CH_3$ | $CH_3$ | CH | |
| H | $CH_3$ | H | $C(O)CH_2CH_2CH_3$ | $CH_3$ | $OCH_3$ | CH | |
| H | $CH_3$ | H | $C(O)CH_2CH_2CH_3$ | $OCH_3$ | $OCH_3$ | CH | |
| H | $CH_3$ | H | $C(O)CH_2CH_2CH_3$ | $CH_3$ | $CH_3$ | N | |
| H | $CH_3$ | H | $C(O)CH_2CH_2CH_3$ | $CH_3$ | $OCH_3$ | N | |
| H | $CH_3$ | $CH_3$ | $C(O)CH_2CH_2CH_3$ | $OCH_3$ | $OCH_3$ | N | |
| H | $CH_3$ | H | $C(O)CH_2CH_2CH_3$ | $OCH_3$ | Cl | CH | |
| H | $CH_3$ | H | $C(O)CH_2OCH_3$ | $CH_3$ | $CH_3$ | CH | |
| H | $CH_3$ | H | $C(O)CH_2OCH_3$ | $CH_3$ | $OCH_3$ | CH | |
| H | $CH_3$ | H | $C(O)CH_2OCH_3$ | $OCH_3$ | $OCH_3$ | CH | |

TABLE Ia-continued

General Structure Ia

| R | $R_1$ | $R_2$ | $R_3$ | X | Y | Z | m.p. (°C.) |
|---|---|---|---|---|---|---|---|
| H | $CH_3$ | H | $C(O)CH_2OCH_3$ | $CH_3$ | $CH_3$ | N | |
| H | $CH_3$ | H | $C(O)CH_2Cl$ | $CH_3$ | $OCH_3$ | N | |
| H | $CH_3$ | H | $C(O)CH_2Cl$ | $OCH_3$ | $OCH_3$ | N | |
| H | $CH_3$ | H | $C(O)CH_2Cl$ | $OCH_3$ | Cl | CH | |
| H | $CH_3$ | H | $C(O)CH_2CH(CH_3)CN$ | $CH_3$ | $CH_3$ | CH | |
| $CH_3$ | $CH_3$ | H | $C(O)CH_2CH(CH_3)CN$ | $CH_3$ | $OCH_3$ | CH | |
| H | $CH_3$ | H | $C(O)CH_2N(CH_3)_2$ | $OCH_3$ | $OCH_3$ | CH | |
| H | $CH_3$ | H | $C(O)CH_2N(CH_3)_2$ | $CH_3$ | $CH_3$ | N | |
| H | $CH_3$ | H | $C(O)CH_2CH=CH_2$ | $CH_3$ | $OCH_3$ | N | |
| H | $CH_3$ | H | $C(O)CH_2CH=CH_2$ | $OCH_3$ | $OCH_3$ | N | |
| H | $CH_3$ | H | $C(O)CH_2C\equiv CH$ | $OCH_3$ | Cl | CH | |
| H | $CH_3$ | H | $CO_2CH_3$ | $CH_3$ | $CH_3$ | CH | |
| H | $CH_3$ | H | $CO_2CH_3$ | $CH_3$ | $OCH_3$ | CH | |
| H | $CH_3$ | H | $CO_2CH_3$ | $OCH_3$ | $OCH_3$ | CH | |
| H | $CH_3$ | H | $CO_2CH_3$ | $CH_3$ | $CH_3$ | N | |
| H | $CH_3$ | H | $CO_2CH_3$ | $CH_3$ | $OCH_3$ | N | |
| H | $CH_3$ | H | $CO_2CH_3$ | $OCH_3$ | $OCH_3$ | N | |
| H | $CH_3$ | H | $CO_2CH_3$ | $OCH_3$ | Cl | CH | |
| H | $CH_3$ | H | $CO_2CH_2CH_3$ | $CH_3$ | $CH_3$ | CH | |
| H | $CH_3$ | H | $CO_2CH_2CH_3$ | $CH_3$ | $OCH_3$ | CH | |
| H | $CH_3$ | H | $CO_2CH_2CH_3$ | $OCH_3$ | $OCH_3$ | CH | |
| H | $CH_3$ | H | $CO_2CH_2CH_3$ | $CH_3$ | $CH_3$ | N | |
| H | $CH_3$ | H | $CO_2CH_2CH_3$ | $CH_3$ | $OCH_3$ | N | |
| H | $CH_3$ | H | $CO_2CH_2CH_3$ | $OCH_3$ | $OCH_3$ | N | |
| H | $CH_3$ | H | $CO_2CH_2CH_3$ | $OCH_3$ | Cl | CH | |
| H | $CH_3$ | H | $CO_2CH_2CF_3$ | $CH_3$ | $CH_3$ | CH | |
| H | $CH_3$ | H | $CO_2CH_2CF_3$ | $CH_3$ | $OCH_3$ | CH | |
| H | $CH_3$ | H | $CO_2CH_2CF_3$ | $OCH_3$ | $OCH_3$ | CH | |
| H | $CH_3$ | H | $CO_2CH_2CF_3$ | $CH_3$ | $CH_3$ | N | |
| H | $CH_3$ | H | $CO_2CF_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CH_2C\equiv CH$ | $CH_3$ | $OCH_3$ | CH | |
| H | $CH_3$ | H | $CO_2CH_2C\equiv CH$ | $OCH_3$ | $OCH_3$ | CH | |
| H | $CH_3$ | H | $CO_2CH_2C\equiv CH$ | $CH_3$ | $CH_3$ | N | |
| H | $CH_3$ | H | $CO_2CH_2C\equiv CH$ | $CH_3$ | $OCH_3$ | N | |
| H | $CH_3$ | H | $CO_2CH_2C\equiv CH$ | $OCH_3$ | $OCH_3$ | N | |
| H | $CH_3$ | H | $CO_2CH_2CH=CH_2$ | $OCH_3$ | Cl | CH | |
| H | $CH_3$ | H | $CO_2CH_2CH=CH_2$ | $CH_3$ | $CH_3$ | CH | |
| H | $CH_3$ | H | $CO_2CH_2CH=CH_2$ | $CH_3$ | $OCH_3$ | CH | |
| H | $CH_3$ | H | $CO_2CH_2CH=CH_2$ | $OCH_3$ | $OCH_3$ | CH | |
| H | $CH_3$ | H | $CO_2CH_2CH=CH_2$ | $CH_3$ | $CH_3$ | N | |
| H | $CH_3$ | H | $CO_2CH_2CH=CH_2$ | $CH_3$ | $OCH_3$ | N | |
| H | $CH_3$ | $CH_3$ | $CO_2CH_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CF_3$ | $CH_3$ | $OCH_3$ | CH | |
| H | $CH_3$ | H | $CO_2CF_3$ | $OCH_3$ | $OCH_3$ | CH | |
| H | $CH_3$ | H | $CO_2CH_2CH_2Cl$ | $CH_3$ | $CH_3$ | N | |
| H | $CH_3$ | H | $CO_2CH_2CH_2Cl$ | $CH_3$ | $OCH_3$ | N | |
| H | $CH_3$ | H | $CO_2CH_2CH_2Cl$ | $OCH_3$ | $OCH_3$ | N | |
| H | $CH_3$ | H | $CO_2CH_2CH_2P(O)(CH_3)_2$ | $OCH_3$ | Cl | CH | |
| H | $CH_3$ | H | $CO_2CH_2CH_2P(O)(CH_3)_2$ | $CH_3$ | $CH_3$ | CH | |
| $CH_3$ | $CH_3$ | H | $CO_2C(CH_3)_3$ | $CH_3$ | $OCH_3$ | CH | |
| H | $CH_3$ | H | $CO_2C(CH_3)_3$ | $OCH_3$ | $OCH_3$ | CH | |
| H | $CH_3$ | H | $CO_2CH_2(CH_2)_4CH_3$ | $CH_3$ | $CH_3$ | N | |
| H | $CH_3$ | H | $CO_2CH_2(CH_2)_4CH_3$ | $CH_3$ | $OCH_3$ | N | |
| H | $CH_3$ | H | $CO_2CH_2OCH_3$ | $OCH_3$ | $OCH_3$ | N | |
| H | $CH_3$ | H | $CO_2CH_2OCH_3$ | $OCH_3$ | Cl | CH | |
| H | $CH_3$ | H | $(C(O))_2OCH_3$ | $CH_3$ | $CH_3$ | CH | |
| H | $CH_3$ | H | $(C(O))_2OCH_3$ | $CH_3$ | $OCH_3$ | CH | |
| H | $CH_3$ | H | $(C(O))_2OCH_3$ | $OCH_3$ | $OCH_3$ | CH | |
| H | $CH_3$ | H | $(C(O))_2OCH_3$ | $CH_3$ | $CH_3$ | N | |
| H | $CH_3$ | H | $(C(O))_2OCH_3$ | $CH_3$ | $OCH_3$ | N | |
| H | $CH_3$ | H | $(C(O))_2OCH_3$ | $OCH_3$ | $OCH_3$ | N | |
| H | $CH_3$ | H | $(C(O))_2OCH_3$ | $OCH_3$ | Cl | CH | |
| H | $CH_3$ | H | $(CO)_2CH_3$ | $CH_3$ | $CH_3$ | CH | |
| H | $CH_3$ | H | $(CO)_2CH_3$ | $CH_3$ | $OCH_3$ | CH | |
| H | $CH_3$ | H | $(CO)_2CH_3$ | $OCH_3$ | $OCH_3$ | CH | |
| H | $CH_3$ | H | $(CO)_2CH_3$ | $CH_3$ | $CH_3$ | N | |
| H | $CH_3$ | H | $(CO)_2CH_3$ | $CH_3$ | $OCH_3$ | N | |
| H | $CH_3$ | H | $(CO)_2CH_3$ | $OCH_3$ | $OCH_3$ | N | |
| H | $CH_3$ | H | $(CO)_2CH_3$ | $OCH_3$ | Cl | CH | |
| H | $CH_3$ | H | $C(O)N(CH_3)_2$ | $CH_3$ | $CH_3$ | CH | |
| H | $CH_3$ | H | $C(O)N(CH_3)_2$ | $CH_3$ | $OCH_3$ | CH | |
| H | $CH_3$ | H | $C(O)N(CH_3)_2$ | $OCH_3$ | $OCH_3$ | CH | |
| H | $CH_3$ | H | $C(O)N(CH_3)_2$ | $CH_3$ | $CH_3$ | N | |
| H | $CH_3$ | H | $C(O)N(CH_3)_2$ | $CH_3$ | $OCH_3$ | N | |
| H | $CH_3$ | H | $C(O)N(CH_3)_2$ | $OCH_3$ | Cl | CH | |
| H | $CH_3$ | H | $C(O)N(CH_2CH_3)_2$ | $CH_3$ | $CH_3$ | CH | |

TABLE Ia-continued

General Structure Ia

| R | R₁ | R₂ | R₃ | X | Y | Z | m.p. (°C.) |
|---|---|---|---|---|---|---|---|
| H | CH₃ | H | C(O)N(CH₂CH₃)₂ | CH₃ | OCH₃ | CH | |
| H | CH₃ | H | C(O)N(CH₂CH₃)₂ | OCH₃ | OCH₃ | CH | |
| H | CH₃ | H | C(O)N(CH₂CH₃)₂ | CH₃ | CH₃ | N | |
| H | CH₃ | H | C(O)N(CH₂CH₃)₂ | CH₃ | OCH₃ | N | |
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(CH₃)₂ | OCH₃ | OCH₃ | N | |
| H | CH₃ | H | C(O)N(CH₃)₂ | OCH₃ | Cl | CH | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |

TABLE Ia-continued

General Structure Ia

| R | R$_1$ | R$_2$ | R$_3$ | X | Y | Z | m.p. (°C.) |
|---|---|---|---|---|---|---|---|
| H | CH$_3$ | H | CN | CH$_3$ | CH$_3$ | N | |
| H | CH$_3$ | H | CN | CH$_3$ | OCH$_3$ | N | |
| H | CH$_3$ | H | CN | OCH$_3$ | OCH$_3$ | N | |
| H | CH$_3$ | H | CN | OCH$_3$ | Cl | CH | |
| H | CH$_3$ | H | P(O)(CH$_3$)$_2$ | CH$_3$ | CH$_3$ | CH | |
| H | CH$_3$ | H | P(O)(CH$_3$)$_2$ | CH$_3$ | OCH$_3$ | CH | |
| H | CH$_3$ | H | P(O)(CH$_3$)$_2$ | OCH$_3$ | OCH$_3$ | CH | |
| H | CH$_3$ | H | P(O)(CH$_3$)$_2$ | CH$_3$ | CH$_3$ | N | |
| H | CH$_3$ | H | P(O)(CH$_3$)$_2$ | OCH$_3$ | OCH$_3$ | N | |
| H | CH$_3$ | H | P(O)(OCH$_3$)$_2$ | OCH$_3$ | Cl | CH | |
| H | CH$_3$ | H | P(O)(OCH$_3$)$_2$ | CH$_3$ | CH$_3$ | CH | |
| H | CH$_3$ | H | P(O)(OCH$_3$)$_2$ | CH$_3$ | OCH$_3$ | CH | |
| H | CH$_3$ | H | P(O)(OCH$_3$)$_2$ | OCH$_3$ | OCH$_3$ | CH | |
| H | CH$_3$ | H | P(O)(OCH$_3$)SCH$_3$ | CH$_3$ | CH$_3$ | N | |
| H | CH$_3$ | H | P(O)(OCH$_3$)SCH$_3$ | CH$_3$ | OCH$_3$ | N | |
| H | CH$_3$ | H | P(O)(OCH$_3$)SCH$_3$ | OCH$_3$ | OCH$_3$ | N | |
| H | CH$_3$ | H | P(O)(OCH$_3$)SCH$_3$ | OCH$_3$ | Cl | CH | |
| H | CH$_3$ | H | P(O)(OCH$_3$)SCH$_2$CH$_2$CH$_3$ | CH$_3$ | CH$_3$ | CH | |
| H | CH$_3$ | H | P(O)(OCH$_3$)SCH$_2$CH$_2$CH$_3$ | CH$_3$ | OCH$_3$ | CH | |
| H | CH$_3$ | H | P(O)(OCH$_3$)SCH$_2$CH$_2$CH$_3$ | OCH$_3$ | OCH$_3$ | CH | |
| H | CH$_3$ | H | P(O)(OCH$_3$)SCH$_2$CH$_2$CH$_3$ | CH$_3$ | CH$_3$ | N | |
| H | CH$_3$ | H | P(O)(OCH$_3$)SCH$_2$CH$_2$CH$_3$ | CH$_3$ | OCH$_3$ | N | |
| H | CH$_3$ | CH$_3$ | OH | OCH$_3$ | OCH$_3$ | N | |
| H | CH$_3$ | H | P(S)(CH$_3$)$_2$ | OCH$_3$ | Cl | CH | |
| H | CH$_3$ | H | P(S)(CH$_3$)$_2$ | CH$_3$ | CH$_3$ | CH | |
| H | CH$_3$ | H | P(S)(CH$_3$)$_2$ | CH$_3$ | OCH$_3$ | CH | |
| H | CH$_3$ | H | P(S)(CH$_3$)$_2$ | OCH$_3$ | OCH$_3$ | CH | |
| H | CH$_3$ | H | P(S)(CH$_3$)$_2$ | CH$_3$ | CH$_3$ | N | |
| H | CH$_3$ | H | P(S)(CH$_3$)$_2$ | CH$_3$ | OCH$_3$ | N | |
| H | CH$_3$ | H | P(S)(CH$_3$)$_2$ | OCH$_3$ | OCH$_3$ | N | |
| H | CH$_3$ | H | P(S)(OCH$_3$)$_2$ | OCH$_3$ | Cl | CH | |
| H | CH$_3$ | H | P(S)(OCH$_3$)$_2$ | CH$_3$ | CH$_3$ | CH | |
| CH$_3$ | CH$_3$ | H | P(S)(OCH$_3$)$_2$ | CH$_3$ | OCH$_3$ | CH | |
| H | CH$_3$ | H | P(S)(OCH$_3$)$_2$ | OCH$_3$ | OCH$_3$ | CH | |
| H | CH$_3$ | H | P(S)(OCH$_3$)$_2$ | CH$_3$ | CH$_3$ | N | |
| H | CH$_3$ | H | P(S)(OCH$_3$)$_2$ | CH$_3$ | OCH$_3$ | N | |
| H | CH$_3$ | H | P(S)(OCH$_3$)SCH$_3$ | OCH$_3$ | OCH$_3$ | N | |
| H | CH$_3$ | H | P(S)(OCH$_3$)SCH$_3$ | OCH$_3$ | Cl | CH | |
| H | CH$_3$ | H | NO$_2$ | CH$_3$ | CH$_3$ | CH | |
| H | CH$_3$ | H | NO$_2$ | CH$_3$ | OCH$_3$ | CH | |
| H | CH$_3$ | H | NO$_2$ | OCH$_3$ | OCH$_3$ | CH | |
| H | CH$_3$ | H | NO$_2$ | CH$_3$ | CH$_3$ | N | |
| H | CH$_3$ | H | NO$_2$ | CH$_3$ | OCH$_3$ | N | |
| H | CH$_3$ | H | NO$_2$ | OCH$_3$ | OCH$_3$ | N | |
| H | CH$_3$ | H | CH$_2$C(O)CH(CH$_2$)(CH$_2$) | CH$_3$ | CH$_3$ | N | |
| H | CH$_3$ | H | CH$_2$C(O)CH(CH$_2$)(CH$_2$) | CH$_3$ | OCH$_3$ | N | |
| H | CH$_3$ | H | CH$_2$C(O)CH(CH$_2$)(CH$_2$) | OCH$_3$ | OCH$_3$ | N | |
| H | CH$_3$ | H | CH$_2$C(O)CH(CH$_2$)(CH$_2$) | OCH$_3$ | Cl | CH | |
| H | CH$_3$ | H | CH$_2$C(O)CH(CH$_2$)(CH$_2$) | CH$_3$ | CH$_3$ | CH | |
| H | CH$_3$ | H | CH$_2$C(O)CH(CH$_2$)(CH$_2$) | CH$_3$ | OCH$_3$ | CH | |

TABLE Ia-continued

General Structure Ia

| R | R₁ | R₂ | R₃ | X | Y | Z | m.p. (°C.) |
|---|----|----|----|---|---|---|------------|
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |
| H | CH₃ | H | CH₂C(O)Ph | CH₃ | CH₃ | CH | |
| H | CH₃ | H | CH₂C(O)Ph | CH₃ | OCH₃ | CH | |
| H | CH₃ | H | CH(CH)₃C(O)CH₃ | OCH₃ | OCH₃ | CH | |
| H | CH₃ | H | CH(CH)₃C(O)CH₃ | CH₃ | CH₃ | N | |
| H | CH₃ | H | CH(CH)₃C(O)CH₃ | CH₃ | OCH₃ | N | |
| H | CH₃ | H | CH(CH)₃C(O)CH₃ | OCH₃ | OCH₃ | N | |
| H | CH₃ | H | CH₂CF₂—C(O)CH₃ | OCH₃ | Cl | CH | |
| H | CH₃ | H | CH₂CF₂—C(O)CH₃ | CH₃ | CH₃ | CH | |
| CH₃ | CH₃ | H | CH₂CF₂—C(O)CH₃ | CH₃ | OCH₃ | CH | |
| H | CH₃ | H | CH₂CF₂—C(O)CH₃ | OCH₃ | OCH₃ | CH | |
| H | CH₃ | H | CH₂C(O)CH₂OCH₃ | CH₃ | CH₃ | N | |
| H | CH₃ | H | CH₂C(O)CH₂OCH₃ | CH₃ | OCH₃ | N | |
| H | CH₃ | H | CH₂C(O)CH₂OCH₃ | OCH₃ | OCH₃ | N | |
| H | CH₃ | H | CH₂C(O)CH₂OCH₃ | OCH₃ | Cl | CH | |
| H | CH₃ | H | CH₂CO₂CH₃ | CH₃ | CH₃ | CH | |
| H | CH₃ | H | CH₂CO₂CH₃ | CH₃ | OCH₃ | CH | |
| H | CH₃ | H | CH₂CO₂CH₃ | OCH₃ | OCH₃ | CH | |
| H | CH₃ | H | CH₂CO₂CH₃ | CH₃ | CH₃ | N | |
| H | CH₃ | H | CH₂CO₂CH₃ | CH₃ | OCH₃ | N | |
| H | CH₃ | H | CH₂CO₂CH₃ | OCH₃ | OCH₃ | N | |
| H | CH₃ | H | CH₂CO₂CH₃ | OCH₃ | Cl | CH | |
| H | CH₃ | H | CH₂CO₂CH₂CH₃ | CH₃ | CH₃ | CH | |
| H | CH₃ | H | CH₂CO₂CH₂CH₃ | CH₃ | OCH₃ | CH | |
| H | CH₃ | H | CH₂CO₂CH₂CH₃ | OCH₃ | OCH₃ | CH | |
| H | CH₃ | H | CH₂CO₂CH₂CH₃ | CH₃ | CH₃ | N | |
| H | CH₃ | H | CH₂CO₂CH₂CH₃ | CH₃ | OCH₃ | N | |
| H | CH₃ | H | CH₂CO₂CH₂CH₃ | OCH₃ | OCH₃ | N | |
| H | CH₃ | H | CH₂CO₂CH₂CH₃ | OCH₃ | Cl | CH | |
| H | CH₃ | H | CH₂CH₂CO₂CH₃ | CH₃ | CH₃ | CH | |
| H | CH₃ | H | CH₂CH₂CO₂CH₃ | CH₃ | OCH₃ | CH | |
| H | CH₃ | H | CH₂CH₂CO₂CH₃ | OCH₃ | OCH₃ | CH | |
| H | CH₃ | H | CH₂CH₂CO₂CH₃ | CH₃ | CH₃ | N | |
| H | CH₃ | H | CH₂CH₂CO₂CH₃ | OCH₃ | OCH₃ | N | |
| H | CH₃ | H | CH₂CH₂CO₂CH₃ | OCH₃ | Cl | CH | |
| H | CH₃ | H | CH₂—CO₂CH₂CH=CH₂ | CH₃ | CH₃ | CH | |
| H | CH₃ | H | CH₂—CO₂CH₂CH=CH₂ | CH₃ | OCH₃ | CH | |
| H | CH₃ | H | CH₂—CO₂CH₂CH=CH₂ | OCH₃ | OCH₃ | CH | |
| H | CH₃ | H | CH₂—CO₂CH₂CH=CH₂ | CH₃ | CH₃ | N | |
| H | CH₃ | H | CH₂—CO₂CH₂CH=CH₂ | CH₃ | OCH₃ | N | |
| H | CH₃ | H | CH₂—CO₂CH₂CH=CH₂ | OCH₃ | OCH₃ | N | |
| H | CH₃ | H | CH₂—CO₂CH₂CH=CH₂ | OCH₃ | Cl | CH | |
| H | CH₃ | H | CH₂(CH₂)₄CO₂CH₃ | CH₃ | CH₃ | CH | |
| H | CH₃ | H | CH₂(CH₂)₄CO₂CH₃ | CH₃ | OCH₃ | CH | |
| H | CH₃ | H | CH₂(CH₂)₄CO₂CH₃ | OCH₃ | OCH₃ | CH | |
| H | CH₃ | H | CH₂(CH₂)₄CO₂CH₃ | CH₃ | CH₃ | N | |
| H | CH₃ | H | CH₂(CH₂)₄CO₂CH₃ | CH₃ | OCH₃ | N | |
| H | CH₃ | CH₃ | CH₂(CH₂)₄CO₂CH₃ | OCH₃ | OCH₃ | N | |
| H | CH₃ | H | CH₂(CH₂)₄CO₂CH₃ | OCH₃ | Cl | CH | |
| H | CH₃ | H | CH₂CO₂CH₂C≡CH | CH₃ | CH₃ | CH | |
| H | CH₃ | H | CH₂CO₂CH₂C≡CH | CH₃ | OCH₃ | CH | |
| H | CH₃ | H | CH₂CO₂CH₂C≡CH | OCH₃ | OCH₃ | CH | |
| H | CH₃ | H | CH₂CO₂CH₂C≡CH | CH₃ | CH₃ | N | |
| H | CH₃ | H | CH₂CO₂CH₂C≡CH | CH₃ | OCH₃ | N | |
| H | CH₃ | H | CH₂CO₂CH₂C≡CH | OCH₃ | OCH₃ | N | |
| H | CH₃ | H | CH₂CO₂CH₂C≡CH | OCH₃ | Cl | CH | |
| H | CH₃ | H | CH₂CO₂CF₃ | CH₃ | CH₃ | CH | |
| CH₃ | CH₃ | H | CH₂CO₂CF₃ | CH₃ | OCH₃ | CH | |
| H | CH₃ | H | CH₂CO₂CF₃ | OCH₃ | OCH₃ | CH | |
| H | CH₃ | H | CH₂CO₂CF₃ | CH₃ | CH₃ | N | |
| H | CH₃ | H | CH₂CO₂CF₃ | CH₃ | OCH₃ | N | |
| H | CH₃ | H | CH₂CO₂CF₃ | OCH₃ | OCH₃ | N | |
| H | CH₃ | H | CH₂CO₂CF₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | SeCH₃ | CH₃ | CH₃ | CH | |
| H | CH₃ | H | SeCH₃ | CH₃ | OCH₃ | CH | |
| H | CH₃ | H | SeCH₃ | OCH₃ | OCH₃ | CH | |
| H | CH₃ | H | SeCH₃ | CH₃ | CH₃ | N | |
| H | CH₃ | H | SeCH₃ | CH₃ | OCH₃ | N | |

TABLE Ia-continued

General Structure Ia

| R | R₁ | R₂ | R₃ | X | Y | Z | m.p. (°C.) |
|---|----|----|----|---|---|---|-----------|
| H | CH₃ | H | SeCH₃ | OCH₃ | OCH₃ | N | |
| H | CH₃ | H | SeCH₃ | OCH₃ | Cl | CH | |
| H | CH₃ | H | CH₂Ph | CH₃ | CH₃ | CH | |
| H | CH₃ | H | CH₂Ph | CH₃ | OCH₃ | CH | |
| H | CH₃ | H | CH₂Ph | OCH₃ | OCH₃ | CH | |
| H | CH₃ | H | CH₂Ph | CH₃ | CH₃ | N | |
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A—HET | CH₃ | CH₃ | CH | |
| H | CH₃ | H | A—HET | CH₃ | OCH₃ | CH | |
| H | CH₃ | H | A—HET | OCH₃ | OCH₃ | CH | |
| H | CH₃ | H | A—HET | CH₃ | CH₃ | N | |
| H | CH₃ | H | A—HET | CH₃ | OCH₃ | N | |
| H | CH₃ | H | A—HET | OCH₃ | OCH₃ | N | |
| H | CH₃ | H | A—HET | OCH₃ | Cl | CH | |
| H | CH₃ | H | B—HET | CH₃ | CH₃ | CH | |
| H | CH₃ | H | B—HET | CH₃ | OCH₃ | CH | |
| H | CH₃ | H | B—HET | OCH₃ | OCH₃ | CH | |
| H | CH₃ | H | B—HET | CH₃ | CH₃ | N | |
| H | CH₃ | H | B—HET | CH₃ | OCH₃ | N | |
| H | CH₃ | CH₃ | B—HET | OCH₃ | OCH₃ | N | |
| H | CH₃ | H | B—HET | OCH₃ | Cl | CH | |
| H | CH₃ | H | C—HET | CH₃ | CH₃ | CH | |
| H | CH₃ | H | C—HET | CH₃ | OCH₃ | CH | |
| H | CH₃ | H | C—HET | OCH₃ | OCH₃ | CH | |
| H | CH₃ | H | C—HET | CH₃ | CH₃ | N | |
| H | CH₃ | H | C—HET | CH₃ | OCH₃ | N | |
| H | CH₃ | H | C—HET | OCH₃ | OCH₃ | N | |
| H | CH₃ | H | C—HET | OCH₃ | Cl | CH | |
| H | CH₃ | H | D—HET | CH₃ | CH₃ | CH | |
| CH₃ | CH₃ | H | D—HET | CH₃ | OCH₃ | CH | |
| H | CH₃ | H | D—HET | OCH₃ | OCH₃ | CH | |
| H | CH₃ | H | D—HET | CH₃ | CH₃ | N | |
| H | CH₃ | H | D—HET | CH₃ | OCH₃ | N | |
| H | CH₃ | H | D—HET | OCH₃ | OCH₃ | N | |
| H | CH₃ | H | D—HET | OCH₃ | Cl | CH | |
| H | CH₃ | H | C(O)A—HET | CH₃ | CH₃ | CH | |
| H | CH₃ | H | C(O)A—HET | CH₃ | OCH₃ | CH | |
| H | CH₃ | H | C(O)A—HET | OCH₃ | OCH₃ | CH | |
| H | CH₃ | H | C(O)A—HET | CH₃ | CH₃ | N | |
| H | CH₃ | H | C(O)A—HET | CH₃ | OCH₃ | N | |
| H | CH₃ | H | C(O)A—HET | OCH₃ | OCH₃ | N | |
| H | CH₃ | H | C(O)A—HET | OCH₃ | Cl | CH | |
| H | CH₃ | H | C(O)B—HET | CH₃ | CH₃ | CH | |
| H | CH₃ | H | C(O)B—HET | CH₃ | OCH₃ | CH | |
| H | CH₃ | H | C(O)B—HET | OCH₃ | OCH₃ | CH | |
| H | CH₃ | H | C(O)B—HET | CH₃ | CH₃ | N | |

TABLE Ia-continued

General Structure Ia

| R | R₁ | R₂ | R₃ | X | Y | Z | m.p. (°C.) |
|---|---|---|---|---|---|---|---|
| H | CH₃ | H | C(O)B—HET | CH₃ | OCH₃ | N | |
| H | CH₃ | H | C(O)B—HET | OCH₃ | OCH₃ | N | |
| H | CH₃ | H | C(O)B—HET | OCH₃ | Cl | CH | |
| H | CH₃ | H | C(O)C—HET | CH₃ | CH₃ | CH | |
| H | CH₃ | H | C(O)C—HET | CH₃ | OCH₃ | CH | |
| H | CH₃ | H | C(O)C—HET | OCH₃ | OCH₃ | CH | |
| H | CH₃ | H | C(O)C—HET | CH₃ | CH₃ | N | |
| H | CH₃ | H | C(O)C—HET | OCH₃ | OCH₃ | N | |
| H | CH₃ | H | C(O)C—HET | OCH₃ | Cl | CH | |
| H | CH₃ | H | C(O)D—HET | CH₃ | CH₃ | CH | |
| H | CH₃ | H | C(O)D—HET | CH₃ | OCH₃ | CH | |
| H | CH₃ | H | C(O)D—HET | OCH₃ | OCH₃ | CH | |
| H | CH₃ | H | C(O)D—HET | CH₃ | CH₃ | N | |
| H | CH₃ | H | C(O)D—HET | CH₃ | OCH₃ | N | |
| H | CH₃ | H | C(O)D—HET | OCH₃ | OCH₃ | N | |
| H | CH₃ | H | C(O)D—HET | OCH₃ | Cl | CH | | wherein

A—HET is 

B—HET is 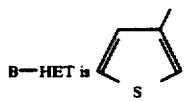

C—HET is 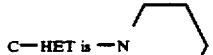

D—HET is 

TABLE II

General Structure II

| R | R₁ | R₂ | R₃ | X | Y | Z | m.p. (°C.) |
|---|---|---|---|---|---|---|---|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |
| H | CH₃ | H | CH₂CHF₂ | CH₃ | CH₃ | CH | |
| H | CH₃ | H | CH₂CHF₂ | CH₃ | OCH₃ | CH | |
| H | CH₃ | H | CH₂CHF₂ | OCH₃ | OCH₃ | CH | |
| H | CH₃ | H | CH₂CHF₂ | CH₃ | CH₃ | N | |
| H | CH₃ | H | CH₂CHF₂ | CH₃ | OCH₃ | N | |
| H | CH₃ | H | CH₂CHF₂ | OCH₃ | OCH₃ | N | |
| H | CH₃ | H | CH₂CHF₂ | OCH₃ | Cl | CH | |
| H | CH₃ | H | CH(CH₂F)₂ | CH₃ | CH₃ | CH | |
| H | CH₃ | H | CH(CH₂F)₂ | CH₃ | OCH₃ | CH | |
| H | CH₃ | H | CH(CH₂F)₂ | OCH₃ | OCH₃ | CH | |
| H | CH₃ | H | CH₂CH₂CH₂F | CH₃ | CH₃ | N | |
| H | CH₃ | H | CH₂CH₂CH₂F | CH₃ | OCH₃ | N | |
| H | CH₃ | CH₃ | CH₂CH₂CH₂F | OCH₃ | OCH₃ | N | |
| H | CH₃ | H | CH₂CH₂CH₂F | OCH₃ | Cl | N | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |

TABLE II-continued

General Structure II

| R | R₁ | R₂ | R₃ | X | Y | Z | m.p. (°C.) |
|---|----|----|----|---|---|---|------------|
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |
| H | CH₃ | H | CH₂(CH₂)₂CH₂F | OCH₃ | OCH₃ | CH | |
| H | CH₃ | H | CH(CH₃)₂CH₂F | CH₃ | CH₃ | N | |
| H | CH₃ | H | CH(CH₃)₂CH₂F | CH₃ | OCH₃ | N | |
| H | CH₃ | H | CH(CH₃)₂CH₂F | OCH₃ | OCH₃ | N | |
| H | CH₃ | H | CH(CH₃)₂CH₂F | OCH₃ | Cl | N | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBr—CH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBrCH₃ | CH₃ | OCH₃ | N | |
| H | CH₃ | CH₃ | CH₂CHBrCH₃ | OCH₃ | OCH₃ | N | |
| H | CH₃ | H | CH₂CHBrCH₃ | OCH₃ | Cl | CH | |
| H | CH₃ | H | CH₂CHBrCH₃ | CH₃ | CH₃ | CH | |
| H | CH₃ | H | CH₂CHBrCH₃ | CH₃ | OCH₃ | CH | |
| H | CH₃ | H | CH₂(CH₂)₂CH₂Br | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | N | |
| H | CH₃ | H | CH₂CCl₂CH₃ | CH₃ | CH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |
| H | CH₃ | H | CH₂CH₂CH₂Cl | CH₃ | OCH₃ | CH | |
| H | CH₃ | H | CH₂CH₂CH₂Cl | OCH₃ | OCH₃ | CH | |
| H | CH₃ | H | CH₂CH₂CH₂Cl | CH₃ | CH₃ | N | |
| H | CH₃ | H | CH₂CH₂CH₂Cl | CH₃ | OCH₃ | N | |
| H | CH₃ | CH₃ | CH₂CH₂CH₂Cl | OCH₃ | OCH₃ | N | |
| H | CH₃ | H | CH₂CH₂CH₂Cl | OCH₃ | Cl | CH | |
| H | CH₃ | H | CH₂CH₂CH₂Cl | CH₃ | CH₃ | CH | |
| H | CH₃ | H | CH₂(CH₂)₂CH₂Cl | CH₃ | OCH₃ | CH | |
| H | CH₃ | H | CH₂(CH₂)₂CH₂Cl | OCH₃ | OCH₃ | CH | |
| H | CH₃ | H | CH₂(CH₂)₂CH₂Cl | CH₃ | CH₃ | N | |
| H | CH₃ | H | CH₂(CH₂)₂CH₂Cl | CH₃ | OCH₃ | N | |
| H | CH₃ | H | CH₂(CH₂)₂CH₂Cl | OCH₃ | OCH₃ | N | |
| H | CH₃ | H | CH₂(CH₂)₂CH₂Cl | OCH₃ | Cl | CH | |
| H | CH₃ | H | CH₂(CH₂)₂CH₂Cl | CH₃ | CH₃ | CH | |
| CH₃ | CH₃ | H | CH(CH₃)CH₂Cl | CH₃ | OCH₃ | CH | |
| H | CH₃ | H | CH(CH₃)CH₂Cl | OCH₃ | OCH₃ | CH | |
| H | CH₃ | H | CH(CH₃)CH₂Cl | CH₃ | CH₃ | N | |
| H | CH₃ | H | CHClCHClCH₃ | CH₃ | OCH₃ | N | |
| H | CH₃ | H | CHClCHClCH₃ | OCH₃ | OCH₃ | N | |
| H | CH₃ | H | CHClCHClCH₃ | OCH₃ | Cl | CH | |
| H | CH₃ | H | CH₂I | CH₃ | CH₃ | CH | |
| H | CH₃ | H | CH₂I | CH₃ | OCH₃ | CH | |
| H | CH₃ | H | CH₂I | OCH₃ | OCH₃ | CH | |
| H | CH₃ | H | CH₂I | CH₃ | CH₃ | N | |
| H | CH₃ | H | CH₂I | CH₃ | OCH₃ | N | |
| H | CH₃ | H | CH₂I | OCH₃ | OCH₃ | N | |
| H | CH₃ | H | CH₂I | OCH₃ | Cl | CH | |
| H | CH₃ | H | CH₂CF₃ | CH₃ | CH₃ | CH | |
| H | CH₃ | H | CH₂CF₃ | CH₃ | OCH₃ | CH | |
| H | CH₃ | H | CH₂CF₃ | OCH₃ | OCH₃ | CH | |
| H | CH₃ | H | CH₂CF₃ | CH₃ | CH₃ | N | |
| H | CH₃ | H | CH₂CF₃ | CH₃ | OCH₃ | N | |
| H | CH₃ | H | CH₂CF₃ | OCH₃ | OCH₃ | N | |
| H | CH₃ | H | CH₂CF₃ | OCH₃ | Cl | CH | |
| H | CH₃ | H | CH₂CH₂CF₃ | CH₃ | CH₃ | CH | |
| H | CH₃ | H | CH₂CH₂CF₃ | CH₃ | OCH₃ | CH | |
| H | CH₃ | H | CH₂CH₂CF₃ | OCH₃ | OCH₃ | CH | |
| H | CH₃ | H | CH₂CH₂CF₃ | CH₃ | CH₃ | N | |
| H | CH₃ | H | CH₂CH₂CF₃ | OCH₃ | OCH₃ | N | |
| H | CH₃ | H | CH₂CH₂CF₃ | OCH₃ | Cl | CH | |
| H | CH₃ | H | CH₂(CH₂)₂CF₃ | CH₃ | CH₃ | CH | |
| H | CH₃ | H | CH₂(CH₂)₂CF₃ | CH₃ | OCH₃ | CH | |
| H | CH₃ | H | CH₂(CH₂)₂CF₃ | OCH₃ | OCH₃ | CH | |
| H | CH₃ | H | CH₂(CH₂)₂CF₃ | CH₃ | CH₃ | N | |
| H | CH₃ | H | CH₂(CH₂)₂CF₃ | CH₃ | OCH₃ | N | |
| H | CH₃ | H | CH₂(CH₂)₂CF₃ | OCH₃ | OCH₃ | N | |
| H | CH₃ | H | CH₂(CH₂)₃CF₃ | OCH₃ | Cl | CH | |
| H | CH₃ | H | CH₂(CH₂)₃CF₃ | CH₃ | CH₃ | CH | |
| H | CH₃ | H | CH₂(CH₂)₃CF₃ | CH₃ | OCH₃ | CH | |
| H | CH₃ | H | CH₂(CH₂)₃CF₃ | OCH₃ | OCH₃ | CH | |
| H | CH₃ | H | CH₂(CH₂)₃CF₃ | CH₃ | CH₃ | N | |
| H | CH₃ | H | CH₂(CH₂)₃CF₃ | CH₃ | OCH₃ | N | |
| H | CH₃ | CH₃ | CH₂(CH₂)₃CF₃ | OCH₃ | OCH₃ | N | |
| H | CH₃ | H | CH(CF₃)₂ | OCH₃ | Cl | CH | |
| H | CH₃ | H | CH(CF₃)₂ | CH₃ | CH₃ | CH | |
| H | CH₃ | H | CH(CF₃)₂ | CH₃ | OCH₃ | CH | |
| H | CH₃ | H | CH(CF₃)₂ | OCH₃ | OCH₃ | CH | |
| H | CH₃ | H | CH(CF₃)₂ | CH₃ | CH₃ | N | |
| H | CH₃ | H | CH(CF₃)₂ | CH₃ | OCH₃ | N | |
| H | CH₃ | H | CH(CF₃)₂ | OCH₃ | OCH₃ | N | |
| H | CH₃ | H | CH₂(CH₂)₄CF₃ | OCH₃ | Cl | CH | |
| H | CH₃ | H | CH₂(CH₂)₅CF₃ | CH₃ | CH₃ | CH | |
| CH₃ | CH₃ | H | CH₂(CH₂)₆CF₃ | CH₃ | OCH₃ | CH | |
| H | CH₃ | H | CH₂(CH₂)₇CF₃ | OCH₃ | OCH₃ | CH | |
| H | CH₃ | H | CH₂(CH₂)₈CF₃ | CH₃ | CH₃ | N | |
| H | CH₃ | H | CHF(CH₂)₈CF₃ | CH₃ | OCH₃ | N | |
| H | CH₃ | H | CH(CHF)₈CF₃ | OCH₃ | OCH₃ | N | |
| H | CH₃ | H | CH(CHF)₈CF₃ | OCH₃ | Cl | CH | |
| H | CH₃ | H | CH₂OCH₃ | CH₃ | CH₃ | CH | |
| H | CH₃ | H | CH₂OCH₃ | CH₃ | OCH₃ | CH | |
| H | CH₃ | H | CH₂OCH₃ | OCH₃ | OCH₃ | CH | |
| H | CH₃ | H | CH₂OCH₃ | CH₃ | CH₃ | N | |
| H | CH₃ | H | CH₂OCH₃ | CH₃ | OCH₃ | N | |

TABLE II-continued

General Structure II

| R | R$_1$ | R$_2$ | R$_3$ | X | Y | Z | m.p. (°C.) |
|---|---|---|---|---|---|---|---|
| H | CH$_3$ | H | CH$_2$OCH$_3$ | OCH$_3$ | OCH$_3$ | N | |
| H | CH$_3$ | H | CH$_2$OCH$_3$ | OCH$_3$ | Cl | CH | |
| H | CH$_3$ | H | CH$_2$OCH$_2$CH$_3$ | CH$_3$ | CH$_3$ | CH | |
| H | CH$_3$ | H | CH$_2$OCH$_2$CH$_3$ | CH$_3$ | OCH$_3$ | CH | |
| H | CH$_3$ | H | CH$_2$OCH$_2$CH$_3$ | OCH$_3$ | OCH$_3$ | CH | |
| H | CH$_3$ | H | CH$_2$—OCH$_2$F | CH$_3$ | CH$_3$ | N | |
| H | CH$_3$ | H | CH$_2$—OCH$_2$F | CH$_3$ | OCH$_3$ | N | |
| H | CH$_3$ | H | CH$_2$—OCH$_2$F | OCH$_3$ | OCH$_3$ | N | |
| H | CH$_3$ | H | CH$_2$—OCH$_2$F | OCH$_3$ | Cl | CH | |
| H | CH$_3$ | H | CH$_2$—CH$_2$OCH$_3$ | CH$_3$ | CH$_3$ | CH | |
| H | CH$_3$ | H | CH$_2$—CH$_2$OCH$_3$ | CH$_3$ | OCH$_3$ | CH | |
| H | CH$_3$ | H | CH$_2$—CH$_2$OCH$_3$ | OCH$_3$ | OCH$_3$ | CH | |
| H | CH$_3$ | H | CH$_2$—CH$_2$OCH$_3$ | CH$_3$ | CH$_3$ | N | |
| H | CH$_3$ | H | CH(OCH$_3$)$_2$ | OCH$_3$ | OCH$_3$ | N | |
| H | CH$_3$ | H | CH(OCH$_3$)$_2$ | OCH$_3$ | Cl | CH | |
| H | CH$_3$ | H | CH$_2$(CH$_2$)$_2$OCH$_3$ | CH$_3$ | CH$_3$ | CH | |
| H | CH$_3$ | H | CH$_2$(CH$_2$)$_2$OCH$_3$ | CH$_3$ | OCH$_3$ | CH | |
| H | CH$_3$ | H | CH$_2$(CH$_2$)$_2$OCH$_3$ | OCH$_3$ | OCH$_3$ | CH | |
| H | CH$_3$ | H | CH$_2$(CH$_2$)$_2$OCH$_3$ | CH$_3$ | CH$_3$ | N | |
| H | CH$_3$ | H | CH$_2$(CH$_2$)$_2$OCH$_3$ | CH$_3$ | OCH$_3$ | N | |
| H | CH$_3$ | H | CH$_2$(CH$_2$)$_2$OCH$_3$ | OCH$_3$ | OCH$_3$ | N | |
| H | CH$_3$ | H | CH$_2$(CH$_2$)$_3$OCH$_3$ | OCH$_3$ | Cl | CH | |
| H | CH$_3$ | H | CH$_2$(CH$_2$)$_3$OCH$_3$ | CH$_3$ | CH$_3$ | CH | |
| H | CH$_3$ | H | CH$_2$(CH$_2$)$_3$OCH$_3$ | CH$_3$ | OCH$_3$ | CH | |
| H | CH$_3$ | H | CH$_2$(CH$_2$)$_2$OCH$_3$ | OCH$_3$ | OCH$_3$ | CH | |
| H | CH$_3$ | H | CH(OCH$_3$)CH$_3$ | CH$_3$ | CH$_3$ | N | |
| H | CH$_3$ | H | CH(OCH$_3$)CH$_3$ | CH$_3$ | OCH$_3$ | N | |
| H | CH$_3$ | CH$_3$ | CH(OCH$_3$)CH$_3$ | OCH$_3$ | OCH$_3$ | N | |
| H | CH$_3$ | H | CH$_2$OCH$_2$C≡CH$_2$ | OCH$_3$ | Cl | CH | |
| H | CH$_3$ | H | CH$_2$OCH$_2$C≡CH$_2$ | CH$_3$ | CH$_3$ | CH | |
| H | CH$_3$ | H | CH$_2$OCH$_2$C≡CH$_2$ | CH$_3$ | OCH$_3$ | CH | |
| H | CH$_3$ | H | CH$_2$OCH$_2$C≡CH$_2$ | OCH$_3$ | OCH$_3$ | CH | |
| H | CH$_3$ | H | CH$_2$OCH$_2$C≡CH$_2$ | CH$_3$ | CH$_3$ | N | |
| H | CH$_3$ | H | CH$_2$OCH$_2$C≡CH$_2$ | CH$_3$ | OCH$_3$ | N | |
| H | CH$_3$ | H | CH$_2$CH(OCH$_3$)$_2$ | OCH$_3$ | OCH$_3$ | N | |
| H | CH$_3$ | H | CH$_2$CH(OCH$_3$)$_2$ | OCH$_3$ | Cl | CH | |
| H | CH$_3$ | H | CH$_2$CH(OCH$_3$)$_2$ | CH$_3$ | CH$_3$ | CH | |
| CH$_3$ | CH$_3$ | H | CH$_2$CH(OCH$_3$)$_2$ | CH$_3$ | OCH$_3$ | CH | |
| H | CH$_3$ | H | CH$_2$C(OCH$_3$)$_2$CH$_3$ | OCH$_3$ | OCH$_3$ | CH | |
| H | CH$_3$ | H | CH$_2$C(OCH$_3$)$_2$CH$_3$ | CH$_3$ | CH$_3$ | N | |
| H | CH$_3$ | H | CH$_2$C(OCH$_3$)$_2$CH$_3$ | CH$_3$ | OCH$_3$ | N | |
| H | CH$_3$ | H | CH$_2$(CH$_2$)$_6$OCH$_3$ | OCH$_3$ | OCH$_3$ | N | |
| H | CH$_3$ | H | CH$_2$(CH$_2$)$_6$OCH$_3$ | OCH$_3$ | Cl | CH | |
| H | CH$_3$ | H | CH$_2$OC(O)CH$_3$ | CH$_3$ | CH$_3$ | CH | |
| H | CH$_3$ | H | CH$_2$OC(O)CH$_3$ | CH$_3$ | OCH$_3$ | CH | |
| H | CH$_3$ | H | CH$_2$OC(O)CH$_3$ | OCH$_3$ | OCH$_3$ | CH | |
| H | CH$_3$ | H | CH$_2$OC(O)CH$_3$ | CH$_3$ | CH$_3$ | N | |
| H | CH$_3$ | H | CH$_2$OC(O)CH$_3$ | CH$_3$ | OCH$_3$ | N | |
| H | CH$_3$ | H | CH$_2$OC(O)CH$_3$ | OCH$_3$ | OCH$_3$ | N | |
| H | CH$_3$ | H | CH$_2$OC(O)CH$_3$ | OCH$_3$ | Cl | CH | |
| H | CH$_3$ | H | CH$_2$CH$_2$OC(O)CH$_3$ | CH$_3$ | CH$_3$ | CH | |
| H | CH$_3$ | H | CH$_2$CH$_2$OC(O)CH$_3$ | CH$_3$ | OCH$_3$ | CH | |
| H | CH$_3$ | H | CH$_2$CH$_2$OC(O)CH$_3$ | OCH$_3$ | OCH$_3$ | CH | |
| H | CH$_3$ | H | CH$_2$CH$_2$OC(O)CH$_3$ | CH$_3$ | CH$_3$ | N | |
| H | CH$_3$ | H | CH$_2$CH$_2$OC(O)CH$_3$ | CH$_3$ | OCH$_3$ | N | |
| H | CH$_3$ | H | CH$_2$CH$_2$OC(O)CH$_3$ | OCH$_3$ | OCH$_3$ | N | |
| H | CH$_3$ | H | CH$_2$CH$_2$OC(O)CH$_3$ | OCH$_3$ | Cl | CH | |
| H | CH$_3$ | H | CH$_2$(CH$_2$)$_2$OC(O)CH$_3$ | CH$_3$ | CH$_3$ | CH | |
| H | CH$_3$ | H | CH$_2$(CH$_2$)$_2$OC(O)CH$_3$ | CH$_3$ | OCH$_3$ | CH | |
| H | CH$_3$ | H | CH$_2$(CH$_2$)$_2$OC(O)CH$_3$ | OCH$_3$ | OCH$_3$ | CH | |
| H | CH$_3$ | H | CH$_2$(CH$_2$)$_3$OC(O)CH$_3$ | CH$_3$ | CH$_3$ | N | |
| H | CH$_3$ | H | CH$_2$(CH$_2$)$_3$OC(O)CH$_3$ | OCH$_3$ | OCH$_3$ | N | |
| H | CH$_3$ | H | CH$_2$(CH$_2$)$_3$OC(O)CH$_3$ | OCH$_3$ | Cl | CH | |
| H | CH$_3$ | H | CH$_2$(CH$_2$)$_2$OC(O)CH$_3$ | CH$_3$ | CH$_3$ | CH | |
| H | CH$_3$ | H | CH$_2$P(CH$_3$)(Br)(CH$_3$) | CH$_3$ | OCH$_3$ | CH | |
| H | CH$_3$ | H | CH$_2$P(C$_6$H$_5$)$_3$ | OCH$_3$ | OCH$_3$ | CH | |
| H | CH$_3$ | H | CH$_2$OC(O)N(CH$_3$)$_2$ | CH$_3$ | CH$_3$ | N | |
| H | CH$_3$ | H | CH$_2$OC(O)N(CH$_3$)$_2$ | CH$_3$ | OCH$_3$ | N | |
| H | CH$_3$ | H | CH$_2$OC(O)N(CH$_3$)$_2$ | OCH$_3$ | OCH$_3$ | N | |
| H | CH$_3$ | H | CH$_2$OC(O)N(CH$_3$)$_2$ | OCH$_3$ | Cl | CH | |
| H | CH$_3$ | H | CH$_2$OC(O)N(CH$_3$)$_2$ | CH$_3$ | CH$_3$ | CH | |
| H | CH$_3$ | H | CH$_2$OC(O)N(CH$_3$)$_2$ | CH$_3$ | OCH$_3$ | CH | |
| H | CH$_3$ | H | CH$_2$OC(O)N(CH$_3$)$_2$ | OCH$_3$ | OCH$_3$ | CH | |
| H | CH$_3$ | H | CH$_2$CH$_2$OC(O)N(CH$_3$)$_2$ | CH$_3$ | CH$_3$ | N | |
| H | CH$_3$ | H | CH$_2$CH$_2$OC(O)N(CH$_3$)$_2$ | CH$_3$ | OCH$_3$ | N | |
| H | CH$_3$ | CH$_3$ | CH$_2$CH$_2$OC(O)N(CH$_3$)$_2$ | OCH$_3$ | OCH$_3$ | N | |
| H | CH$_3$ | H | CH$_2$CH$_2$OC(O)N(CH$_3$)$_2$ | OCH$_3$ | Cl | CH | |
| H | CH$_3$ | H | CH$_2$CH$_2$OC(O)N(CH$_3$)$_2$ | CH$_3$ | CH$_3$ | CH | |
| H | CH$_3$ | H | CH$_2$CH$_2$OC(O)N(CH$_3$)$_2$ | CH$_3$ | OCH$_3$ | CH | |
| H | CH$_3$ | H | CH$_2$OSO$_2$CH$_3$ | OCH$_3$ | OCH$_3$ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂OSO₂CH₃ | CH₃ | CH₃ | N | |
| H | CH₃ | H | CH₂OSO₂CH₃ | CH₃ | OCH₃ | N | |
| H | CH₃ | H | CH₂OSO₂CH₃ | OCH₃ | OCH₃ | N | |
| H | CH₃ | H | CH₂OSO₂CH₂CH₃ | OCH₃ | Cl | CH | |
| H | CH₃ | H | CH₂OSO₂CH₂CH₃ | CH₃ | CH₃ | CH | |
| CH₃ | CH₃ | H | CH₂OSO₂CH₂CH₃ | CH₃ | OCH₃ | CH | |
| H | CH₃ | H | CH₂(CH₂)₂OSO₂CH₃ | OCH₃ | OCH₃ | CH | |
| H | CH₃ | H | CH₂(CH₂)₂OSO₂CH₃ | CH₃ | CH₃ | N | |
| H | CH₃ | H | CH₂(CH₂)₂OSO₂CH₃ | CH₃ | OCH₃ | N | |
| H | CH₃ | H | CH₂(CH₂)₂OSO₂CH₃ | OCH₃ | OCH₃ | N | |
| H | CH₃ | H | CH₂(CH₂)₂OSO₂CH₃ | OCH₃ | Cl | CH | |
| H | CH₃ | H | CH₂OP(O)(CH₃)₂ | CH₃ | CH₃ | CH | |
| H | CH₃ | H | CH₂OP(O)(CH₃)₂ | CH₃ | OCH₃ | CH | |
| H | CH₃ | H | CH₂OP(O)(CH₃)₂ | OCH₃ | OCH₃ | CH | |
| H | CH₃ | H | CH₂OP(O)(CH₃)₂ | CH₃ | CH₃ | N | |
| H | CH₃ | H | CH₂OP(O)(CH₃)₂ | CH₃ | OCH₃ | N | |
| H | CH₃ | H | CH₂OP(O)(CH₃)₂ | OCH₃ | OCH₃ | N | |
| H | CH₃ | H | CH₂OP(O)(CH₃)₂ | OCH₃ | Cl | CH | |
| H | CH₃ | H | CH₂OP(O)(CH₃)Ph | CH₃ | CH₃ | CH | |
| H | CH₃ | H | CH₂OP(O)(CH₃)Ph | CH₃ | OCH₃ | CH | |
| H | CH₃ | H | CH₂OP(O)(CH₃)Ph | OCH₃ | OCH₃ | CH | |
| H | CH₃ | H | CH₂OP(O)(CH₃)Ph | CH₃ | CH₃ | N | |
| H | CH₃ | H | CH₂OP(O)(Ph)₂ | CH₃ | OCH₃ | N | |
| H | CH₃ | H | CH₂OP(O)(Ph)₂ | OCH₃ | OCH₃ | N | |
| H | CH₃ | H | CH₂OP(O)(Ph)₂ | OCH₃ | Cl | CH | |
| H | CH₃ | H | CH₂OP(O)(Ph)₂ | CH₃ | CH₃ | CH | |
| H | CH₃ | H | CH₂OP(O)(Ph)₂ | CH₃ | OCH₃ | CH | |
| H | CH₃ | H | CH₂OP(O)(Ph)₂ | OCH₃ | OCH₃ | CH | |
| H | CH₃ | H | CH₂CH₂OP(O)(CH₃)₂ | CH₃ | CH₃ | N | |
| H | CH₃ | H | CH₂CH₂OP(O)(CH₃)₂ | OCH₃ | OCH₃ | N | |
| H | CH₃ | H | CH₂CH₂OP(O)(CH₃)₂ | OCH₃ | Cl | CH | |
| H | CH₃ | H | CH₂CH₂OP(O)(CH₃)₂ | CH₃ | CH₃ | CH | |
| H | CH₃ | H | CH₂CH₂OP(O)(CH₃)₂ | CH₃ | OCH₃ | CH | |
| H | CH₃ | H | CH₂(CH₂)₂OP(O)(CH₃)₂ | OCH₃ | OCH₃ | CH | |
| H | CH₃ | H | CH₂(CH₂)₂OP(O)(CH₃)₂ | CH₃ | CH₃ | N | |
| H | CH₃ | H | CH₂(CH₂)₂OP(O)(CH₃)₂ | CH₃ | OCH₃ | N | |
| H | CH₃ | H | CH₂(CH₂)₂OP(O)(CH₃)₂ | OCH₃ | OCH₃ | N | |
| H | CH₃ | H | CH₂(CH₂)₂OP(O)(CH₃)₂ | OCH₃ | Cl | CH | |
| H | CH₃ | H | CH₂(CH₂)₂OP(O)(CH₃)₂ | CH₃ | CH₃ | CH | |
| H | CH₃ | H | CH₂P(O)(CH₃)₂ | CH₃ | OCH₃ | CH | |
| H | CH₃ | H | CH₂P(O)(CH₃)₂ | OCH₃ | OCH₃ | CH | |
| H | CH₃ | H | CH₂P(O)(CH₃)₂ | CH₃ | CH₃ | N | |
| H | CH₃ | H | CH₂P(O)(CH₃)₂ | CH₃ | OCH₃ | N | |
| H | CH₃ | H | CH₂P(O)(CH₃)₂ | OCH₃ | OCH₃ | N | |
| H | CH₃ | H | CH₂P(O)(CH₃)₂ | OCH₃ | Cl | CH | |
| H | CH₃ | H | CH₂P(O)(CH₃)₂ | CH₃ | CH₃ | CH | |
| H | CH₃ | H | CH₂P(O)(OCH₃)₂ | CH₃ | OCH₃ | CH | |
| H | CH₃ | H | CH₂P(O)(OCH₃)₂ | OCH₃ | OCH₃ | CH | |
| H | CH₃ | H | CH₂P(O)(OCH₃)₂ | CH₃ | CH₃ | N | |
| H | CH₃ | H | CH₂P(O)(OCH₃)₂ | CH₃ | OCH₃ | N | |
| H | CH₃ | H | CH₂P(O)(OCH₃)₂ | OCH₃ | OCH₃ | N | |
| H | CH₃ | H | CH₂P(O)(OCH₃)₂ | OCH₃ | Cl | CH | |
| H | CH₃ | H | CH₂P(O)(OCH₃)₂ | CH₃ | CH₃ | CH | |
| CH₃ | CH₃ | H | CH₂CH₂P(O)(OCH₂CH₃)₂ | CH₃ | OCH₃ | CH | |
| H | CH₃ | H | CH₂CH₂P(O)(OCH₂CH₃)₂ | OCH₃ | OCH₃ | CH | |
| H | CH₃ | H | CH₂(CH₂)₃P(O)(OCH₃)₂ | CH₃ | CH₃ | N | |
| H | CH₃ | H | CH₂(CH₂)₃P(O)(OCH₃)₂ | CH₃ | OCH₃ | N | |
| H | CH₃ | H | CH₂(CH₂)₃P(O)(OCH₃)₂ | OCH₃ | OCH₃ | N | |
| H | CH₃ | H | CH₂(CH₂)₃P(O)(OCH₃)₂ | OCH₃ | Cl | CH | |
| H | CH₃ | H | CH₂OP(S)(CH₃)₂ | CH₃ | CH₃ | CH | |
| H | CH₃ | H | CH₂OP(S)(CH₃)₂ | CH₃ | OCH₃ | CH | |
| H | CH₃ | H | CH₂OP(S)(CH₃)₂ | OCH₃ | OCH₃ | CH | |
| H | CH₃ | H | CH₂OP(S)(CH₃)₂ | CH₃ | CH₃ | N | |
| H | CH₃ | H | CH₂OP(S)(CH₃)₂ | CH₃ | OCH₃ | N | |
| H | CH₃ | H | CH₂OP(S)(CH₃)₂ | OCH₃ | OCH₃ | N | |
| H | CH₃ | H | CH₂OP(S)(CH₃)₂ | OCH₃ | Cl | CH | |
| H | CH₃ | H | CH₂OP(S)(OCH₃)₂ | CH₃ | CH₃ | CH | |
| H | CH₃ | H | CH₂OP(S)(OCH₃)₂ | CH₃ | OCH₃ | CH | |
| H | CH₃ | H | CH₂OP(S)(OCH₃)₂ | OCH₃ | OCH₃ | CH | |
| H | CH₃ | H | CH₂OP(S)(OCH₃)₂ | CH₃ | CH₃ | N | |
| H | CH₃ | H | CH₂OP(S)(OCH₃)₂ | CH₃ | OCH₃ | N | |
| H | CH₃ | H | CH₂OP(S)(OCH₃)₂ | OCH₃ | OCH₃ | N | |
| H | CH₃ | H | CH₂OP(S)(OCH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂P(S)(CH₃)₂ | OCH₃ | OCH₃ | CH | |
| H | CH₃ | H | CH₂P(S)(CH₃)₂ | CH₃ | CH₃ | N | |
| H | CH₃ | H | CH₂P(S)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(OCH₃)₂ | CH₃ | CH₃ | CH | |

TABLE II-continued

General Structure II

| R | R₁ | R₂ | R₃ | X | Y | Z | m.p. (°C.) |
|---|----|----|----|---|---|---|------------|
| H | CH₃ | H | CH₂P(S)(OCH₃)₂ | CH₃ | OCH₃ | CH | |
| H | CH₃ | H | CH₂P(S)(OCH₃)₂ | OCH₃ | OCH₃ | CH | |
| H | CH₃ | H | CH₂P(S)(OCH₃)₂ | CH₃ | CH₃ | N | |
| H | CH₃ | H | CH₂P(S)(OCH₃)₂ | CH₃ | OCH₃ | N | |
| H | CH₃ | H | CH₂P(S)(OCH₃)₂ | OCH₃ | OCH₃ | N | |
| H | CH₃ | H | CH₂P(S)(OCH₃)₂ | OCH₃ | Cl | CH | |
| H | CH₃ | H | CH₂CH₂OP(S)(CH₃)₂ | CH₃ | CH₃ | CH | |
| H | CH₃ | H | CH₂CH₂OP(S)(CH₃)₂ | CH₃ | OCH₃ | CH | |
| H | CH₃ | H | CH₂CH₂OP(S)(CH₃)₂ | OCH₃ | OCH₃ | CH | |
| H | CH₃ | H | CH₂CH₂OP(S)(CH₃)₂ | CH₃ | CH₃ | N | |
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |

TABLE II-continued

General Structure II

| R | R₁ | R₂ | R₃ | X | Y | Z | m.p. (°C.) |
|---|----|----|----|---|---|---|---|
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | N | |
| H | CH₃ | H | CH₂CH₂SCH₃ | OCH₃ | Cl | CH | |
| H | CH₃ | H | CH₂CH₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₂SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |
| H | CH₃ | CH₃ | CH₂CH₂SO₂CH₃ | OCH₃ | OCH₃ | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | H | CH₂(CH₂)₃SO₂CH₃ | CH₃ | OCH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | CH₃ | OCH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | OCH₃ | CH | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CN | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |
| H | CH₃ | H | CH₂CH₂CN | OCH₃ | Cl | CH | |
| H | CH₃ | H | CH₂CH₂CN | CH₃ | CH₃ | CH | |
| CH₃ | CH₃ | H | CH₂CH₂CN | CH₃ | OCH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂—CH₂P(S)(CH₃)₂ | OCH₃ | OCH₃ | CH | |
| H | CH₃ | H | CH₂—CH₂P(S)(CH₃)₂ | CH₃ | CH₃ | N | |
| H | CH₃ | H | CH₂—CH₂P(S)(CH₃)₂ | OCH₃ | OCH₃ | N | |
| H | CH₃ | H | CH₂—CH₂P(S)(CH₃)₂ | OCH₃ | Cl | CH | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH_2-CH_2P(S)(CH_3)_2$ | $CH_3$ | $CH_3$ | CH | |
| H | $CH_3$ | H | $CH_2N(CH_3)_2$ | $CH_3$ | $OCH_3$ | CH | |
| H | $CH_3$ | H | $CH_2N(CH_3)_2$ | $OCH_3$ | $OCH_3$ | CH | |
| H | $CH_3$ | H | $CH_2N(CH_3)_2$ | $CH_3$ | $CH_3$ | N | |
| H | $CH_3$ | H | $CH_2N(CH_3)_2$ | $CH_3$ | $OCH_3$ | N | |
| H | $CH_3$ | H | $CH_2N(CH_3)_2$ | $OCH_3$ | $OCH_3$ | N | |
| H | $CH_3$ | H | $CH_2N(CH_3)_2$ | $OCH_3$ | Cl | CH | |
| H | $CH_3$ | H | $CH_2N(CH_3)_2$ | $CH_3$ | $CH_3$ | CH | |
| H | $CH_3$ | H | $CH_2(CH_2)_3N(CH_3)_2$ | $CH_3$ | $OCH_3$ | CH | |
| H | $CH_3$ | H | $CH_2(CH_2)_3N(CH_3)_2$ | $OCH_3$ | $OCH_3$ | CH | |
| H | $CH_3$ | H | $CH_2(CH_2)_3N(CH_3)_2$ | $CH_3$ | $CH_3$ | N | |
| H | $CH_3$ | H | $CH_2(CH_2)_3N(CH_3)_2$ | $CH_3$ | $OCH_3$ | N | |
| H | $CH_3$ | $CH_3$ | $CH_2(CH_2)_3N(CH_3)_2$ | $OCH_3$ | $OCH_3$ | N | |
| H | $CH_3$ | H | $CH_2(CH_2)_3N(CH_3)_2$ | $OCH_3$ | Cl | CH | |
| H | $CH_3$ | H | $CH_2(CH_2)_3N(CH_3)_2$ | $CH_3$ | $CH_3$ | CH | |
| H | $CH_3$ | H | $CH_2N(CH_3)_2Ph$ | $CH_3$ | $OCH_3$ | CH | |
| H | $CH_3$ | H | $CH_2N(CH_3)_2Ph$ | $OCH_3$ | $OCH_3$ | CH | |
| H | $CH_3$ | H | $CH_2N(CH_3)_2Ph$ | $CH_3$ | $CH_3$ | N | |
| H | $CH_3$ | H | $CH_2N(CH_3)_2Ph$ | $CH_3$ | $OCH_3$ | N | |
| H | $CH_3$ | H | $CH_2-CH(CH_3)N(CH_3)_2$ | $OCH_3$ | $OCH_3$ | N | |
| H | $CH_3$ | H | $CH_2-CH(CH_3)N(CH_3)_2$ | $OCH_3$ | Cl | CH | |
| H | $CH_3$ | H | $CH_2-CH(CH_3)N(CH_3)_2$ | $CH_3$ | $CH_3$ | CH | |
| $CH_3$ | $CH_3$ | H | $CH_2-CH(CH_3)N(CH_3)_2$ | $CH_3$ | $OCH_3$ | CH | |
| H | $CH_3$ | H | $CH_2-CH(CH_3)N(CH_3)_2$ | $OCH_3$ | $OCH_3$ | CH | |
| H | $CH_3$ | H | $CH_2CH_2CH(CH_3)_2$ | $CH_3$ | $CH_3$ | N | |
| H | $CH_3$ | H | $CH_2CH_2CH(CH_3)_2$ | $CH_3$ | $OCH_3$ | N | |
| H | $CH_3$ | H | $CH_2CH_2CH(CH_3)_2$ | $OCH_3$ | $OCH_3$ | N | |
| H | $CH_3$ | H | $CH_2CH_2CH(CH_3)_2$ | $OCH_3$ | Cl | CH | |
| H | $CH_3$ | H | $CH_2NHC(O)CH_3$ | $CH_3$ | $CH_3$ | CH | |
| H | $CH_3$ | H | $CH_2NHC(O)CH_3$ | $CH_3$ | $OCH_3$ | CH | |
| H | $CH_3$ | H | $CH_2NHC(O)CH_3$ | $OCH_3$ | $OCH_3$ | CH | |
| H | $CH_3$ | H | $CH_2NHC(O)CH_3$ | $CH_3$ | $CH_3$ | N | |
| H | $CH_3$ | H | $CH_2NHC(O)CH_3$ | $CH_3$ | $OCH_3$ | N | |
| H | $CH_3$ | H | $CH_2NHC(O)CH_3$ | $OCH_3$ | $OCH_3$ | N | |
| H | $CH_3$ | H | $CH_2NHC(O)CH_3$ | $OCH_3$ | Cl | CH | |
| H | $CH_3$ | H | $CH_2CH_2N(CH_3)C(O)CH_3$ | $CH_3$ | $CH_3$ | CH | |
| H | $CH_3$ | H | $CH_2CH_2N(CH_3)C(O)CH_3$ | $CH_3$ | $OCH_3$ | CH | |
| H | $CH_3$ | H | $CH_2CH_2N(CH_3)C(O)CH_3$ | $OCH_3$ | $OCH_3$ | CH | |
| H | $CH_3$ | H | $CH_2CH_2N(CH_3)C(O)CH_3$ | $CH_3$ | $CH_3$ | N | |
| H | $CH_3$ | H | $CH_2(CH_2)_3NHC(O)CH_3$ | $CH_3$ | $OCH_3$ | N | |
| H | $CH_3$ | H | $CH_2(CH_2)_3NHC(O)CH_3$ | $OCH_3$ | $OCH_3$ | N | |
| H | $CH_3$ | H | $CH_2N(CH_3)C(O)OCH_3$ | $OCH_3$ | Cl | CH | |
| H | $CH_3$ | H | $CH_2N(CH_3)C(O)OCH_3$ | $CH_3$ | $CH_3$ | CH | |
| H | $CH_3$ | H | $CH_2NHC(O)OCH_3$ | $CH_3$ | $OCH_3$ | CH | |
| H | $CH_3$ | H | $CH_2NHC(O)OCH_3$ | $OCH_3$ | $OCH_3$ | CH | |
| H | $CH_3$ | H | $CH_2NHC(O)OCH_3$ | $CH_3$ | $CH_3$ | N | |
| H | $CH_3$ | H | $CH_2NHC(O)OCH_3$ | $OCH_3$ | $OCH_3$ | N | |
| H | $CH_3$ | H | $CH_2NHC(O)OCH_3$ | $OCH_3$ | Cl | CH | |
| H | $CH_3$ | H | $CH_2NHC(O)OCH_3$ | $CH_3$ | $CH_3$ | CH | |
| H | $CH_3$ | H | $CH_2(CH_2)_3NHC(O)OCH_3$ | $CH_3$ | $OCH_3$ | CH | |
| H | $CH_3$ | H | $CH_2(CH_2)_3NHC(O)OCH_3$ | $OCH_3$ | $OCH_3$ | CH | |
| H | $CH_3$ | H | $CH_2(CH_2)_3NHC(O)OCH_3$ | $CH_3$ | $CH_3$ | N | |
| H | $CH_3$ | H | $CH_2N(CH_3)C(O)OCH_2CH_3$ | $CH_3$ | $OCH_3$ | N | |
| H | $CH_3$ | H | $CH(CH_3)NHC(O)OCH_3$ | $OCH_3$ | $OCH_3$ | N | |
| H | $CH_3$ | H | $CH(CH_3)NHC(O)OCH_3$ | $OCH_3$ | Cl | CH | |
| H | $CH_3$ | H | $CH(CH_3)NHC(O)OCH_3$ | $CH_3$ | $CH_3$ | CH | |
| H | $CH_3$ | H | $CH_2NHSO_2CH_3$ | $CH_3$ | $OCH_3$ | CH | |
| H | $CH_3$ | H | $CH_2NHSO_2CH_3$ | $OCH_3$ | $OCH_3$ | CH | |
| H | $CH_3$ | H | $CH_2NHSO_2CH_3$ | $CH_3$ | $CH_3$ | N | |
| H | $CH_3$ | H | $CH_2NHSO_2CH_3$ | $CH_3$ | $OCH_3$ | N | |
| H | $CH_3$ | $CH_3$ | $CH_2NHSO_2CH_3$ | $OCH_3$ | $OCH_3$ | N | |
| H | $CH_3$ | H | $CH_2CH_2NHSO_2CH_3$ | $OCH_3$ | Cl | CH | |
| H | $CH_3$ | H | $CH_2CH_2NHSO_2CH_3$ | $CH_3$ | $CH_3$ | CH | |
| H | $CH_3$ | H | $CH_2CH_2NHSO_2CH_3$ | $CH_3$ | $OCH_3$ | CH | |
| H | $CH_3$ | H | $CH_2CH_2NHSO_2CH_3$ | $OCH_3$ | $OCH_3$ | CH | |
| H | $CH_3$ | H | $CH_2CH_2NHSO_2CH_3$ | $CH_3$ | $CH_3$ | N | |
| H | $CH_3$ | H | $CH_2CH_2NHSO_2CH_3$ | $CH_3$ | $OCH_3$ | N | |
| H | $CH_3$ | H | $CH_2(CH_2)_3NHSO_2CH_3$ | $OCH_3$ | $OCH_3$ | N | |
| H | $CH_3$ | H | $CH_2(CH_2)_3NHSO_2CH_3$ | $OCH_3$ | Cl | CH | |
| H | $CH_3$ | H | $CH_2(CH_2)_3NHSO_2CH_3$ | $CH_3$ | $CH_3$ | CH | |
| $CH_3$ | $CH_3$ | H | $CH_2NHP(O)(CH_3)_2$ | $CH_3$ | $OCH_3$ | CH | |
| H | $CH_3$ | H | $CH_2NHP(O)(CH_3)_2$ | $OCH_3$ | $OCH_3$ | CH | |
| H | $CH_3$ | H | $CH_2NHP(O)(CH_3)_2$ | $CH_3$ | $CH_3$ | N | |
| H | $CH_3$ | H | $CH_2NHP(O)(OCH_3)_2$ | $CH_3$ | $OCH_3$ | N | |
| H | $CH_3$ | H | $CH_2NHP(O)(OCH_3)_2$ | $OCH_3$ | $OCH_3$ | N | |
| H | $CH_3$ | H | $CH_2NHP(O)(OCH_3)_2$ | $OCH_3$ | Cl | CH | |
| H | $CH_3$ | H | $CH=CH_2$ | $CH_3$ | $CH_3$ | CH | |
| H | $CH_3$ | H | $CH=CH_2$ | $CH_3$ | $OCH_3$ | CH | |
| H | $CH_3$ | H | $CH_2NO_2$ | $CH_3$ | $CH_3$ | CH | |
| H | $CH_3$ | H | $CH_2NO_2$ | $CH_3$ | $OCH_3$ | CH | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH_2NO_2$ | $OCH_3$ | $OCH_3$ | CH | |
| H | $CH_3$ | H | $CH_2NO_2$ | $CH_3$ | $CH_3$ | N | |
| H | $CH_3$ | H | $CH_2NO_2$ | $CH_3$ | $OCH_3$ | N | |
| H | $CH_3$ | H | $CH_2NO_2$ | $OCH_3$ | $OCH_3$ | N | |
| H | $CH_3$ | H | $CH_2NO_2$ | $OCH_3$ | Cl | CH | |
| H | $CH_3$ | H | $CH_2CH_2NO_2$ | $CH_3$ | $CH_3$ | CH | |
| H | $CH_3$ | H | $CH_2CH_2NO_2$ | $CH_3$ | $OCH_3$ | CH | |
| H | $CH_3$ | H | $CH_2CH_2NO_2$ | $OCH_3$ | $OCH_3$ | CH | |
| H | $CH_3$ | H | $CH_2CH_2NO_2$ | $CH_3$ | $CH_3$ | N | |
| H | $CH_3$ | H | $CH_2CH_2NO_2$ | $CH_3$ | $OCH_3$ | N | |
| H | $CH_3$ | H | $CH_2CH_2NO_2$ | $OCH_3$ | $OCH_3$ | N | |
| H | $CH_3$ | H | $CH_2CH_2NO_2$ | $OCH_3$ | Cl | CH | |
| H | $CH_3$ | H | $CH_2C(O)CH_3$ | $CH_3$ | $CH_3$ | CH | |
| H | $CH_3$ | H | $CH_2C(O)CH_3$ | $CH_3$ | $OCH_3$ | CH | |
| H | $CH_3$ | H | $CH_2C(O)CH_3$ | $OCH_3$ | $OCH_3$ | N | |
| H | $CH_3$ | H | $CH_2C(O)CH_3$ | $CH_3$ | $CH_3$ | N · | |
| H | $CH_3$ | H | $CH_2C(O)CH_3$ | $OCH_3$ | $OCH_3$ | N | |
| H | $CH_3$ | H | $CH_2C(O)CH_3$ | $OCH_3$ | Cl | CH | |
| H | $CH_3$ | H | $CH_2C(O)CH_2CH_3$ | $CH_3$ | $CH_3$ | CH | |
| H | $CH_3$ | H | $CH_2C(O)CH_2CH_3$ | $CH_3$ | $OCH_3$ | CH | |
| H | $CH_3$ | H | $CH_2C(O)CH_2CH_3$ | $OCH_3$ | $OCH_3$ | CH | |
| H | $CH_3$ | H | $CH_2C(O)CH_2CH_3$ | $CH_3$ | $CH_3$ | N | |
| H | $CH_3$ | H | $CH_2C(O)CH_2CH_3$ | $CH_3$ | $OCH_3$ | N | |
| H | $CH_3$ | H | $CH_2C(O)CH_2CH_3$ | $OCH_3$ | $OCH_3$ | N | |
| H | $CH_3$ | H | $CH_2C(O)CH_2CH_3$ | $OCH_3$ | Cl | CH | |
| H | $CH_3$ | H | $CH_2(CH_2)_3C(O)CH_3$ | $CH_3$ | $CH_3$ | CH | |
| H | $CH_3$ | H | $CH_2(CH_2)_3C(O)CH_3$ | $CH_3$ | $OCH_3$ | CH | |
| H | $CH_3$ | H | $CH_2(CH_2)_3C(O)CH_3$ | $OCH_3$ | $OCH_3$ | CH | |
| H | $CH_3$ | H | $CH_2(CH_2)_3C(O)CH_3$ | $CH_3$ | $CH_3$ | N | |
| H | $CH_3$ | H | $CH_2(CH_2)_3C(O)CH_3$ | $CH_3$ | $OCH_3$ | N | |
| H | $CH_3$ | $CH_3$ | $CH_2(CH_2)_3C(O)CH_3$ | $OCH_3$ | $OCH_3$ | N | |
| H | $CH_3$ | H | $CH_2(CH_2)_3C(O)CH_3$ | $OCH_3$ | Cl | CH | |
| H | $CH_3$ | H | $CH_2CH_2C(O)CH_3$ | $CH_3$ | $CH_3$ | CH | |
| H | $CH_3$ | H | $CH_2CH_2C(O)CH_3$ | $CH_3$ | $OCH_3$ | CH | |
| H | $CH_3$ | H | $CH_2CH_2C(O)CH_3$ | $OCH_3$ | $OCH_3$ | CH | |
| H | $CH_3$ | H | $CH_2CH_2C(O)CH_3$ | $CH_3$ | $CH_3$ | N | |
| H | $CH_3$ | H | $CH_2—CH(CH_3)C(O)CH_3$ | $CH_3$ | $OCH_3$ | N | |
| H | $CH_3$ | $CH_3$ | $CH_2—CH(CH_2)C(O)CH_3$ | $OCH_3$ | $OCH_3$ | N | |
| H | $CH_3$ | H | $CH_2—CH(CH_2)C(O)CH_3$ | $OCH_3$ | Cl | CH | |
| H | $CH_3$ | H | $CH_2—CH(CH_3)C(O)CH_3$ | $CH_3$ | $CH_3$ | CH | |
| $CH_3$ | $CH_3$ | $CH_3$ | $CH_2—CH(CH_2)C(O)CH_3$ | $CH_3$ | $OCH_3$ | CH | |
| H | $CH_3$ | H | $CH_2(CH_2)_6C(O)CH_2CH_3$ | $OCH_3$ | $OCH_3$ | CH | |
| H | $CH_3$ | H | $CH_2(CH_2)_6C(O)CH_2CH_3$ | $CH_3$ | $CH_3$ | N | |
| H | $CH_3$ | H | $CH_2(CH_2)_6C(O)CH_2CH_3$ | $CH_3$ | $OCH_3$ | N | |
| H | $CH_3$ | H | $CH_2(CH_2)_6C(O)CH_2CH_3$ | $OCH_3$ | $OCH_3$ | N | |
| H | $CH_3$ | H | $CH_2(CH_2)_6C(O)CH_2CH_3$ | $OCH_3$ | Cl | CH | |
| H | $CH_3$ | H | $CH_2C(O)OCH_3$ | $CH_3$ | $CH_3$ | CH | |
| H | $CH_3$ | H | $CH_2C(O)OCH_3$ | $CH_3$ | $OCH_3$ | CH | |
| H | $CH_3$ | H | $CH_2C(O)OCH_3$ | $OCH_3$ | $OCH_3$ | CH | |
| H | $CH_3$ | H | $CH_2C(O)OCH_3$ | $CH_3$ | $CH_3$ | N | |
| H | $CH_3$ | H | $CH_2C(O)OCH_3$ | $CH_3$ | $OCH_3$ | N | |
| H | $CH_3$ | H | $CH_2C(O)OCH_3$ | $OCH_3$ | $OCH_3$ | N | |
| H | $CH_3$ | H | $CH_2C(O)OCH_3$ | $OCH_3$ | Cl | CH | |
| H | $CH_3$ | H | $CH_2C(O)OCH_2CH_3$ | $CH_3$ | $CH_3$ | CH | |
| H | $CH_3$ | H | $CH_2C(O)OCH_2CH_3$ | $CH_3$ | $OCH_3$ | CH | |
| H | $CH_3$ | H | $CH_2C(O)OCH_2CH_3$ | $OCH_3$ | $OCH_3$ | CH | |
| H | $CH_3$ | H | $CH_2C(O)OCH_2CH_3$ | $CH_3$ | $CH_3$ | N | |
| H | $CH_3$ | H | $CH_2C(O)OCH_2CH_3$ | $CH_3$ | $OCH_3$ | N | |
| H | $CH_3$ | H | $CH_2C(O)OCH_2CH_3$ | $OCH_3$ | $OCH_3$ | N | |
| H | $CH_3$ | H | $CH_2C(O)OCH_2CH_3$ | $OCH_3$ | Cl | CH | |
| H | $CH_3$ | H | $CH_2CH_2C(O)CH_3$ | $CH_3$ | $CH_3$ | CH | |
| H | $CH_3$ | H | $CH_2CH_2C(O)CH_3$ | $CH_3$ | $OCH_3$ | CH | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $CH_3$ | $CH_3$ | N | |
| H | $CH_3$ | H | $CH_2CH_2C(O)CH_3$ | $OCH_3$ | $OCH_3$ | N | |
| H | $CH_3$ | H | $CH_2CH_2C(O)CH_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $CH_2CH_2C(O)N(CH_3)_2$ | $CH_3$ | $CH_3$ | CH | |
| H | $CH_3$ | H | $CH_2CH_2C(O)N(CH_3)_2$ | $CH_3$ | $OCH_3$ | CH | |
| H | $CH_3$ | H | $CH_2CH_2C(O)N(CH_3)_2$ | $OCH_3$ | $OCH_3$ | CH | |
| H | $CH_3$ | H | $CH_2CH_2C(O)N(CH_3)_2$ | $CH_3$ | $CH_3$ | N | |
| H | $CH_3$ | H | $CH_2CH_2C(O)N(CH_3)_2$ | $CH_3$ | $OCH_3$ | N | |
| H | $CH_3$ | $CH_3$ | $CH_2CH_2C(O)N(CH_3)_2$ | $OCH_3$ | $OCH_3$ | N | |
| H | $CH_3$ | H | $CH_2CH_2C(O)N(CH_3)_2$ | $OCH_3$ | Cl | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂C(O)N(CH₃)CH₂CH₃ | CH₃ | CH₃ | CH | |
| H | CH₃ | H | CH₂C(O)N(CH₃)CH₂CH₃ | CH₃ | OCH₃ | CH | |
| H | CH₃ | H | CH₂C(O)N(CH₃)CH₂CH₃ | OCH₃ | OCH₃ | CH | |
| H | CH₃ | H | CH₂C(O)N(CH₃)CH₂CH₃ | CH₃ | CH₃ | N | |
| H | CH₃ | H | CH₂C(O)N(CH₃)CH₂OCH₃ | CH₃ | OCH₃ | N | |
| H | CH₃ | H | CH₂C(O)N(CH₃)CH₂OCH₃ | OCH₃ | OCH₃ | N | |
| H | CH₃ | H | CH₂C(O)N(CH₃)CH₂OCH₃ | OCH₃ | Cl | CH | |
| H | CH₃ | H | CH₂SeCH₃ | CH₃ | CH₃ | CH | |
| CH₃ | CH₃ | H | CH₂SeCH₃ | CH₃ | OCH₃ | CH | |
| H | CH₃ | H | CH₂SeCH₃ | OCH₃ | OCH₃ | CH | |
| H | CH₃ | H | CH₂SePh | CH₃ | CH₃ | N | |
| H | CH₃ | H | CH₂SePh | CH₃ | OCH₃ | N | |
| H | CH₃ | H | CH₂—CH₂SeCH₃ | OCH₃ | OCH₃ | N | |
| H | CH₃ | H | CH₂—CH₂SeCH₃ | OCH₃ | Cl | CH | |
| H | CH₃ | H | CH=CH₂ | OCH₃ | OCH₃ | CH | |
| H | CH₃ | H | CH=CH₂ | CH₃ | CH₃ | N | |
| H | CH₃ | H | CH=CH₂ | CH₃ | OCH₃ | N | |
| H | CH₃ | H | CH=CH₂ | OCH₃ | OCH₃ | N | |
| H | CH₃ | H | CH=CH₂ | OCH₃ | Cl | CH | |
| H | CH₃ | H | CH=CH—CH₃ | CH₃ | CH₃ | CH | |
| H | CH₃ | H | CH=CH—CH₃ | CH₃ | OCH₃ | CH | |
| H | CH₃ | H | CH=CH—CH₃ | OCH₃ | OCH₃ | CH | |
| H | CH₃ | H | CH=CH—CH₃ | CH₃ | CH₃ | N | |
| H | CH₃ | H | CH=CH—CH₃ | CH₃ | OCH₃ | N | |
| H | CH₃ | H | CH=CH—CH₃ | OCH₃ | OCH₃ | N | |
| H | CH₃ | H | CH=CH—CH₃ | OCH₃ | Cl | CH | |
| H | CH₃ | H | CH=CH—CH₂—CH₃ | CH₃ | CH₃ | CH | |
| H | CH₃ | H | CH=CH—CH₂—CH₃ | CH₃ | OCH₃ | CH | |
| H | CH₃ | H | CH=CH—CH₂—CH₃ | OCH₃ | OCH₃ | CH | |
| H | CH₃ | H | CH=CH—CH₂—CH₃ | CH₃ | CH₃ | N | |
| H | CH₃ | H | CH=CH—CH₂—CH₃ | OCH₃ | OCH₃ | N | |
| H | CH₃ | H | CH=CH—CH₂—CH₃ | OCH₃ | Cl | CH | |
| H | CH₃ | H | CH=C(CH₃)₂ | CH₃ | CH₃ | CH | |
| H | CH₃ | H | CH=C(CH₃)₂ | CH₃ | OCH₃ | CH | |
| H | CH₃ | H | CH=C(CH₃)₂ | OCH₃ | OCH₃ | CH | |
| H | CH₃ | H | CH=C(CH₃)₂ | CH₃ | CH₃ | N | |
| H | CH₃ | H | CH=C(CH₃)₂ | CH₃ | OCH₃ | N | |
| H | CH₃ | H | CH=C(CH₃)₂ | OCH₃ | OCH₃ | N | |
| H | CH₃ | H | CH=C(CH₃)₂ | OCH₃ | Cl | CH | |
| H | CH₃ | H | CH=CH(CH₂)₃CH₃ | CH₃ | CH₃ | CH | |
| H | CH₃ | H | CH=CH(CH₂)₃CH₃ | CH₃ | OCH₃ | CH | |
| H | CH₃ | H | CH=CH(CH₂)₃CH₃ | OCH₃ | OCH₃ | CH | |
| H | CH₃ | H | CH=CH(CH₂)₃CH₃ | CH₃ | CH₃ | N | |
| H | CH₃ | H | CH=CH(CH₂)₃CH₃ | CH₃ | OCH₃ | N | |
| H | CH₃ | CH₃ | CH=CH(CH₂)₃CH₃ | OCH₃ | OCH₃ | N | |
| H | CH₃ | H | CH=CH(CH₂)₃CH₃ | OCH₃ | Cl | CH | |
| H | CH₃ | H | CH=C(CH₃)CH₂CH₃ | CH₃ | CH₃ | CH | |
| H | CH₃ | H | CH=C(CH₃)CH₂CH₃ | CH₃ | OCH₃ | CH | |
| H | CH₃ | H | CH=C(CH₃)CH₂CH₃ | OCH₃ | OCH₃ | CH | |
| H | CH₃ | H | CH=CH—CH(CH₃)₂ | CH₃ | CH₃ | N | |
| H | CH₃ | H | CH=CH—CH(CH₃)₂ | CH₃ | OCH₃ | N | |
| H | CH₃ | H | CH=CH—CH(CH₃)₂ | OCH₃ | OCH₃ | N | |
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | CH₃ | OCH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |

TABLE II-continued

General Structure II

| R | R₁ | R₂ | R₃ | X | Y | Z | m.p. (°C.) |
|---|----|----|----|---|---|---|---|
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | CH₂—CH——CH₂ (epoxide, O bridging CH—CH₂) | CH₃ | CH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂—CH(—O—)CH₂ (epoxide) | CH₃ | OCH₃ | CH | |
| H | CH₃ | H | CH₂—CH(—O—)CH₂ (epoxide) | OCH₃ | OCH₃ | CH | |
| H | CH₃ | H | CH₂—CH(—O—)CH₂ (epoxide) | CH₃ | CH₃ | N | |
| H | CH₃ | H | CH₂—CH(—O—)CH₂ (epoxide) | CH₃ | OCH₃ | N | |
| H | CH₃ | H | CH₂—CH(—O—)CH₂ (epoxide) | OCH₃ | OCH₃ | N | |
| H | CH₃ | H | CH₂—CH(—O—)CH₂ (epoxide) | OCH₃ | Cl | CH | |
| H | CH₃ | H | CH₂—CH(—O—)CH—CH₃ (epoxide) | CH₃ | CH₃ | CH | |
| H | CH₃ | H | CH₂—CH(—O—)CH—CH₃ (epoxide) | CH₃ | OCH₃ | CH | |
| H | CH₃ | H | CH₂—CH(—O—)CH—CH₃ (epoxide) | OCH₃ | OCH₃ | CH | |
| H | CH₃ | H | CH₂—CH(—O—)CH—CH₃ (epoxide) | CH₃ | CH₃ | N | |
| H | CH₃ | H | CH₂—CH(—O—)CH—CH₃ (epoxide) | CH₃ | OCH₃ | N | |
| H | CH₃ | H | CH₂—CH(—O—)CH—CH₃ (epoxide) | OCH₃ | OCH₃ | N | |
| H | CH₃ | H | CH₂—CH(—O—)CH—CH₃ (epoxide) | OCH₃ | Cl | CH | |
| H | CH₃ | H | CH₂—CH₂—CH(—O—)CH₂ (oxetane) | CH₃ | CH₃ | CH | |
| H | CH₃ | H | CH₂—CH₂—CH(—O—)CH₂ (oxetane) | CH₃ | OCH₃ | CH | |
| H | CH₃ | H | CH₂—CH₂—CH(—O—)CH₂ (oxetane) | OCH₃ | OCH₃ | CH | |
| H | CH₃ | H | CH₂—CH₂—CH(—O—)CH₂ (oxetane) | CH₃ | CH₃ | N | |
| H | CH₃ | H | CH₂—CH₂—CH(—O—)CH₂ (oxetane) | OCH₃ | OCH₃ | N | |
| H | CH₃ | H | CH₂—CH₂—CH(—O—)CH₂ (oxetane) | OCH₃ | Cl | CH | |
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | $CH_3$ | cyclopentyl | $OCH_3$ | $OCH_3$ | N | |
| H | $CH_3$ | H | cyclopentyl | $OCH_3$ | Cl | CH | |
| H | $CH_3$ | H | cyclohexyl | $CH_3$ | $CH_3$ | CH | |
| H | $CH_3$ | H | cyclohexyl | $CH_3$ | $OCH_3$ | CH | |
| H | $CH_3$ | H | cyclohexyl | $OCH_3$ | $OCH_3$ | CH | |
| H | $CH_3$ | H | cyclohexyl | $CH_3$ | $CH_3$ | N | |
| H | $CH_3$ | H | cyclohexyl | $CH_3$ | $OCH_3$ | N | |
| H | $CH_3$ | $CH_3$ | cyclohexyl | $OCH_3$ | $OCH_3$ | N | |
| H | $CH_3$ | H | cyclohexyl | $OCH_3$ | Cl | CH | |
| H | $CH_3$ | H | cyclopropyl | $CH_3$ | $CH_3$ | CH | |
| $CH_3$ | $CH_3$ | H | cyclopropyl | $CH_3$ | $OCH_3$ | CH | |
| H | $CH_3$ | H | cyclopropyl | $OCH_3$ | $OCH_3$ | CH | |
| H | $CH_3$ | H | cyclopropyl | $CH_3$ | $CH_3$ | N | |
| H | $CH_3$ | H | cyclopropyl | $CH_3$ | $OCH_3$ | N | |
| H | $CH_3$ | H | cyclopropyl | $OCH_3$ | $OCH_3$ | N | |
| H | $CH_3$ | H | cyclopropyl | $OCH_3$ | Cl | CH | |
| H | $CH_3$ | H | $CH_2$—cyclopropyl | $CH_3$ | $CH_3$ | CH | |
| H | $CH_3$ | H | $CH_2$—cyclopropyl | $CH_3$ | $OCH_3$ | CH | |
| H | $CH_3$ | H | $CH_2$—cyclopropyl | $OCH_3$ | $OCH_3$ | CH | |
| H | $CH_3$ | H | $CH_2$—cyclopropyl | $CH_3$ | $CH_3$ | N | |
| H | $CH_3$ | H | $CH_2$—cyclopropyl | $CH_3$ | $OCH_3$ | N | |
| H | $CH_3$ | H | $CH_2$—cyclopropyl | $OCH_3$ | $OCH_3$ | N | |
| H | $CH_3$ | H | $CH_2$—cyclopropyl | $OCH_3$ | Cl | CH | |
| H | $CH_3$ | H | $CH_2$—cyclopentyl | $CH_3$ | $CH_3$ | CH | |
| H | $CH_3$ | H | $CH_2$—cyclopentyl | $CH_3$ | $OCH_3$ | CH | |
| H | $CH_3$ | H | $CH_2$—cyclopentyl | $OCH_3$ | $OCH_3$ | CH | |
| H | $CH_3$ | H | $CH_2$—cyclopentyl | $CH_3$ | $CH_3$ | N | |
| H | $CH_3$ | H | $CH_2$—cyclopentyl | $CH_3$ | $OCH_3$ | N | |
| H | $CH_3$ | H | $CH_2$—cyclopentyl | $OCH_3$ | $OCH_3$ | N | |
| H | $CH_3$ | H | $CH_2$—cyclopentyl | $OCH_3$ | Cl | CH | |
| H | $CH_3$ | H | $C_6H_5$ | $CH_3$ | $CH_3$ | CH | |
| H | $CH_3$ | H | $C_6H_5$ | $CH_3$ | $OCH_3$ | CH | |
| H | $CH_3$ | H | $C_6H_5$ | $OCH_3$ | $OCH_3$ | CH | |
| H | $CH_3$ | H | $C_6H_5$ | $CH_3$ | $CH_3$ | N | |
| H | $CH_3$ | H | $C_6H_5$ | $OCH_3$ | $OCH_3$ | N | |
| H | $CH_3$ | H | $C_6H_5$ | $OCH_3$ | Cl | CH | |
| H | $CH_3$ | H | CH=CH—$CF_3$ | $CH_3$ | $CH_3$ | CH | |
| H | $CH_3$ | H | CH=CH—$CF_3$ | $CH_3$ | $OCH_3$ | CH | |
| H | $CH_3$ | H | CH=CH—$CF_3$ | $OCH_3$ | $OCH_3$ | CH | |
| H | $CH_3$ | H | CH=CH—$CF_3$ | $CH_3$ | $CH_3$ | N | |
| H | $CH_3$ | H | CH=CH—$CF_3$ | $CH_3$ | $OCH_3$ | N | |
| H | $CH_3$ | H | CH=CH—$CF_3$ | $OCH_3$ | $OCH_3$ | N | |
| H | $CH_3$ | H | CH=CH—$CF_3$ | $OCH_3$ | Cl | CH | |
| H | $CH_3$ | H | $CH_2$—C≡C—$CF_3$ | $CH_3$ | $CH_3$ | CH | |
| H | $CH_3$ | H | $CH_2$—C≡C—$CF_3$ | $CH_3$ | $OCH_3$ | CH | |
| H | $CH_3$ | H | $CH_2$—C≡C—$CF_3$ | $OCH_3$ | $OCH_3$ | CH | |
| H | $CH_3$ | H | $CH_2$—C≡C—$CF_3$ | $CH_3$ | $CH_3$ | N | |
| H | $CH_3$ | H | $CH_2$—C≡C—$CF_3$ | $CH_3$ | $OCH_3$ | N | |
| H | $CH_3$ | $CH_3$ | $CH_2$—C≡C—$CF_3$ | $OCH_3$ | $OCH_3$ | N | |
| H | $CH_3$ | H | $CH_2$—CH=$CF_2$ | $OCH_3$ | Cl | CH | |
| H | $CH_3$ | H | CH=CH—$CH_2Cl$ | $CH_3$ | $CH_3$ | CH | |
| H | $CH_3$ | H | CH=CH—$CH_2Cl$ | $CH_3$ | $OCH_3$ | CH | |
| H | $CH_3$ | H | CH=CH—$CH_2Cl$ | $OCH_3$ | $OCH_3$ | CH | |
| H | $CH_3$ | H | CH=CH—$CH_2Cl$ | $CH_3$ | $CH_3$ | N | |
| H | $CH_3$ | H | CH=CH—$CH_2Cl$ | $CH_3$ | $OCH_3$ | N | |
| H | $CH_3$ | H | CH=CH—$CH_2Cl$ | $OCH_3$ | $OCH_3$ | N | |
| H | $CH_3$ | H | $CH_2$—C(CHF)(CH_2)(CH_2) cyclopropyl | $OCH_3$ | Cl | CH | |
| H | $CH_3$ | H | $CH_2$—C(CHF)(CH_2)(CH_2) cyclopropyl | $CH_3$ | $CH_3$ | CH | |
| $CH_3$ | $CH_3$ | H | $CH_2$—C(CHF)(CH_2)(CH_2) cyclopropyl | $CH_3$ | $OCH_3$ | CH | |
| H | $CH_3$ | H | $CH_2$—C(CHF)(CH_2)(CH_2) cyclopropyl | $OCH_3$ | $OCH_3$ | CH | |

TABLE II-continued

General Structure II

| R | R₁ | R₂ | R₃ | X | Y | Z | m.p. (°C.) |
|---|---|---|---|---|---|---|---|
| H | CH₃ | H | CH₂—C(CH₂)(CH₂)CHF (cyclopropane w/ CHF) | CH₃ | CH₃ | N | |
| H | CH₃ | H | CH₂—C(CH₂)(CH₂)CHF (cyclopropane w/ CHF) | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡CHOCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(CH₃)₂ | CH₃ | CH₃ | N | |
| H | CH₃ | H | CH₂—CH=CHP(O)(CH₃)₂ | OCH₃ | OCH₃ | N | |
| H | CH₃ | H | CH₂—CH=CHP(O)(CH₃)₂ | OCH₃ | Cl | CH | |
| H | CH₃ | H | CH₂—CH=CHP(O)(CH₃)₂ | CH₃ | CH₃ | CH | |
| H | CH₃ | H | CH₂—CH=CHP(O)(CH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | CH₃ | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—C≡C—CH₂OCH₃ | OCH₃ | OCH₃ | CH | |
| H | CH₃ | H | CH₂—CH=CH—CH₂SCH₃ | CH₃ | CH₃ | N | |
| H | CH₃ | H | CH₂—CH=CH—CH₂SCH₃ | CH₃ | OCH₃ | N | |
| H | CH₃ | H | CH₂—CH=CH—CH₂SCH₃ | OCH₃ | OCH₃ | N | |
| H | CH₃ | H | CH₂—CH=CH—CH₂SCH₃ | OCH₃ | Cl | CH | |
| H | CH₃ | H | CH=CH—CH₂N(CH₃)₂ | CH₃ | CH₃ | CH | |
| CH₃ | CH₃ | H | CH=CH—CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | CH₃ | OCH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |
| H | CH₃ | H | SCH₃ | OCH₃ | OCH₃ | N | |
| H | CH₃ | H | SCH₃ | OCH₃ | Cl | CH | |
| H | CH₃ | H | SCH₂CF₃ | CH₃ | CH₃ | CH | |
| H | CH₃ | H | SCH₂CF₃ | CH₃ | OCH₃ | CH | |
| H | CH₃ | H | SCH₂CF₃ | OCH₃ | OCH₃ | CH | |
| H | CH₃ | H | SCH₂CF₃ | CH₃ | CH₃ | N | |
| H | CH₃ | H | SCH₂CF₃ | CH₃ | OCH₃ | N | |
| H | CH₃ | H | SCH₂CF₃ | OCH₃ | OCH₃ | N | |
| H | CH₃ | H | SCH₂CF₃ | OCH₃ | Cl | CH | |
| H | CH₃ | H | SO₂CH₃ | CH₃ | CH₃ | CH | |
| H | CH₃ | H | SO₂CH₃ | CH₃ | OCH₃ | CH | |
| H | CH₃ | H | SO₂CH₃ | OCH₃ | OCH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | SO₂CH₃ | CH₃ | CH₃ | N | |
| H | CH₃ | H | SO₂CH₃ | OCH₃ | OCH₃ | N | |
| H | CH₃ | H | SO₂CH₃ | OCH₃ | Cl | CH | |
| H | CH₃ | H | SO₂CH₂CH₃ | CH₃ | CH₃ | CH | |
| H | CH₃ | H | SO₂CH₂CH₃ | CH₃ | OCH₃ | CH | |
| H | CH₃ | H | SO₂CH₂CH₃ | OCH₃ | OCH₃ | CH | |
| H | CH₃ | H | SO₂CH₂CH₃ | CH₃ | CH₃ | N | |
| H | CH₃ | H | SO₂CH₂CH₃ | CH₃ | OCH₃ | N | |
| H | CH₃ | H | SO₂CH₂CH₃ | OCH₃ | OCH₃ | N | |
| H | CH₃ | H | SO₂CH₂CH₃ | OCH₃ | Cl | CH | |
| H | CH₃ | H | OCH₃ | CH₃ | CH₃ | CH | |
| H | CH₃ | H | OCH₃ | CH₃ | OCH₃ | CH | |
| H | CH₃ | H | OCH₃ | OCH₃ | OCH₃ | CH | |
| H | CH₃ | H | OCH₃ | CH₃ | CH₃ | N | |
| H | CH₃ | H | OCH₃ | CH₃ | OCH₃ | N | |
| H | CH₃ | CH₃ | OCH₃ | OCH₃ | OCH₃ | N | |
| H | CH₃ | H | OCH₃ | OCH₃ | Cl | CH | |
| H | CH₃ | H | OCH₂CH₃ | CH₃ | CH₃ | CH | |
| H | CH₃ | H | OCH₂CH₃ | CH₃ | OCH₃ | CH | |
| H | CH₃ | H | OCH₂CH₃ | OCH₃ | OCH₃ | CH | |
| H | CH₃ | H | OCH₂CH₃ | CH₃ | CH₃ | N | |
| H | CH₃ | H | OCH₂CH₃ | CH₃ | OCH₃ | N | |
| H | CH₃ | H | OCH₂CH₃ | OCH₃ | OCH₃ | N | |
| H | CH₃ | H | OCH₂CH₃ | OCH₃ | Cl | CH | |
| H | CH₃ | H | OCH(CH₃)₂ | CH₃ | CH₃ | CH | |
| CH₃ | CH₃ | H | OCH(CH₃)₂ | CH₃ | OCH₃ | CH | |
| H | CH₃ | H | OCH(CH₃)₂ | OCH₃ | OCH₃ | CH | |
| H | CH₃ | H | OCH(CH₃)₂ | CH₃ | CH₃ | N | |
| H | CH₃ | H | OCH(CH₃)₂ | CH₃ | OCH₃ | N | |
| H | CH₃ | H | OCH(CH₃)₂ | OCH₃ | OCH₃ | N | |
| H | CH₃ | H | OCH(CH₃)₂ | OCH₃ | Cl | CH | |
| H | CH₃ | H | C(O)CH₃ | CH₃ | CH₃ | CH | |
| H | CH₃ | H | C(O)CH₃ | CH₃ | OCH₃ | CH | |
| H | CH₃ | H | C(O)CH₃ | OCH₃ | OCH₃ | CH | |
| H | CH₃ | H | C(O)CH₃ | CH₃ | CH₃ | N | |
| H | CH₃ | H | C(O)CH₃ | CH₃ | OCH₃ | N | |
| H | CH₃ | H | C(O)CH₃ | OCH₃ | OCH₃ | N | |
| H | CH₃ | H | C(O)CH₃ | OCH₃ | Cl | CH | |
| H | CH₃ | H | C(O)CH₂CH₃ | CH₃ | CH₃ | CH | |
| H | CH₃ | H | C(O)CH₂CH₃ | CH₃ | OCH₃ | CH | |
| H | CH₃ | H | C(O)CH₂CH₃ | OCH₃ | OCH₃ | CH | |
| H | CH₃ | H | C(O)CH₂CH₃ | CH₃ | CH₃ | N | |
| H | CH₃ | H | C(O)CH₂CH₃ | CH₃ | OCH₃ | N | |
| H | CH₃ | H | C(O)CH₂CH₃ | OCH₃ | OCH₃ | N | |
| H | CH₃ | H | C(O)CH₂CH₃ | OCH₃ | Cl | CH | |
| H | CH₃ | H | C(O)CH(CH₃)₂ | CH₃ | CH₃ | CH | |
| H | CH₃ | H | C(O)CH(CH₃)₂ | CH₃ | OCH₃ | CH | |
| H | CH₃ | H | C(O)CH(CH₃)₂ | OCH₃ | OCH₃ | CH | |
| H | CH₃ | H | C(O)CH(CH₃)₂ | CH₃ | CH₃ | N | |
| H | CH₃ | H | C(O)CH(CH₃)₂ | OCH₃ | OCH₃ | N | |
| H | CH₃ | H | C(O)CH(CH₃)₂ | OCH₃ | Cl | CH | |
| H | CH₃ | H | C(O)CHF₂ | CH₃ | CH₃ | CH | |
| H | CH₃ | H | C(O)CHF₂ | CH₃ | OCH₃ | CH | |
| H | CH₃ | H | C(O)CHF₂ | OCH₃ | OCH₃ | CH | |
| H | CH₃ | H | C(O)CF₃ | CH₃ | CH₃ | N | |
| H | CH₃ | H | C(O)CF₃ | CH₃ | OCH₃ | N | |
| H | CH₃ | H | C(O)CF₃ | OCH₃ | OCH₃ | N | |
| H | CH₃ | H | C(O)CF₃ | OCH₃ | Cl | CH | |
| H | CH₃ | H | C(O)CH₂CH₂CH₃ | CH₃ | CH₃ | CH | |
| H | CH₃ | H | C(O)CH₂CH₂CH₃ | CH₃ | OCH₃ | CH | |
| H | CH₃ | H | C(O)CH₂CH₂CH₃ | OCH₃ | OCH₃ | CH | |
| H | CH₃ | H | C(O)CH₂CH₂CH₃ | CH₃ | CH₃ | N | |
| H | CH₃ | H | C(O)CH₂CH₂CH₃ | CH₃ | OCH₃ | N | |
| H | CH₃ | CH₃ | C(O)CH₂CH₂CH₃ | OCH₃ | OCH₃ | N | |
| H | CH₃ | H | C(O)CH₂CH₂CH₃ | OCH₃ | Cl | CH | |
| H | CH₃ | H | C(O)CH₂OCH₃ | CH₃ | CH₃ | CH | |
| H | CH₃ | H | C(O)CH₂OCH₃ | CH₃ | OCH₃ | CH | |
| H | CH₃ | H | C(O)CH₂OCH₃ | OCH₃ | OCH₃ | CH | |
| H | CH₃ | H | C(O)CH₂OCH₃ | CH₃ | CH₃ | N | |
| H | CH₃ | H | C(O)CH₂Cl | CH₃ | OCH₃ | N | |
| H | CH₃ | H | C(O)CH₂Cl | OCH₃ | OCH₃ | N | |
| H | CH₃ | H | C(O)CH₂Cl | OCH₃ | Cl | CH | |
| H | CH₃ | H | C(O)CH₂CH(CH₃)CN | CH₃ | CH₃ | CH | |
| CH₃ | CH₃ | H | C(O)CH₂CH(CH₃)CN | CH₃ | OCH₃ | CH | |
| H | CH₃ | H | C(O)CH₂N(CH₃)₂ | OCH₃ | OCH₃ | CH | |
| H | CH₃ | H | C(O)CH₂N(CH₃)₂ | CH₃ | CH₃ | N | |
| H | CH₃ | H | C(O)CH₂CH=CH₂ | CH₃ | OCH₃ | N | |
| H | CH₃ | H | C(O)CH₂CH=CH₂ | OCH₃ | OCH₃ | N | |
| H | CH₃ | H | C(O)CH₂C≡CH | OCH₃ | Cl | CH | |
| H | CH₃ | H | CO₂CH₃ | CH₃ | CH₃ | CH | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CO_2CH_3$ | $CH_3$ | $OCH_3$ | CH | |
| H | $CH_3$ | H | $CO_2CH_3$ | $OCH_3$ | $OCH_3$ | CH | |
| H | $CH_3$ | H | $CO_2CH_3$ | $CH_3$ | $CH_3$ | N | |
| H | $CH_3$ | H | $CO_2CH_3$ | $CH_3$ | $OCH_3$ | N | |
| H | $CH_3$ | H | $CO_2CH_3$ | $OCH_3$ | $OCH_3$ | N | |
| H | $CH_3$ | H | $CO_2CH_3$ | $OCH_3$ | Cl | CH | |
| H | $CH_3$ | H | $CO_2CH_2CH_3$ | $CH_3$ | $CH_3$ | CH | |
| H | $CH_3$ | H | $CO_2CH_2CH_3$ | $CH_3$ | $OCH_3$ | CH | |
| H | $CH_3$ | H | $CO_2CH_2CH_3$ | $OCH_3$ | $OCH_3$ | CH | |
| H | $CH_3$ | H | $CO_2CH_2CH_3$ | $CH_3$ | $CH_3$ | N | |
| H | $CH_3$ | H | $CO_2CH_2CH_3$ | $CH_3$ | $OCH_3$ | N | |
| H | $CH_3$ | H | $CO_2CH_2CH_3$ | $OCH_3$ | $OCH_3$ | N | |
| H | $CH_3$ | H | $CO_2CH_2CH_3$ | $OCH_3$ | Cl | CH | |
| H | $CH_3$ | H | $CO_2CH_2CF_3$ | $CH_3$ | $CH_3$ | CH | |
| H | $CH_3$ | H | $CO_2CH_2CF_3$ | $CH_3$ | $OCH_3$ | CH | |
| H | $CH_3$ | H | $CO_2CH_2CF_3$ | $OCH_3$ | $OCH_3$ | CH | |
| H | $CH_3$ | H | $CO_2CH_2CF_3$ | $CH_3$ | $CH_3$ | N | |
| H | $CH_3$ | H | $CO_2CF_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CH_2C\equiv CH$ | $CH_3$ | $OCH_3$ | CH | |
| H | $CH_3$ | H | $CO_2CH_2C\equiv CH$ | $OCH_3$ | $OCH_3$ | CH | |
| H | $CH_3$ | H | $CO_2CH_2C\equiv CH$ | $CH_3$ | $CH_3$ | N | |
| H | $CH_3$ | H | $CO_2CH_2C\equiv CH$ | $CH_3$ | $OCH_3$ | N | |
| H | $CH_3$ | H | $CO_2CH_2C\equiv CH$ | $OCH_3$ | $OCH_3$ | N | |
| H | $CH_3$ | H | $CO_2CH_2CH=CH_2$ | $OCH_3$ | Cl | CH | |
| H | $CH_3$ | H | $CO_2CH_2CH=CH_2$ | $CH_3$ | $CH_3$ | CH | |
| H | $CH_3$ | H | $CO_2CH_2CH=CH_2$ | $CH_3$ | $OCH_3$ | CH | |
| H | $CH_3$ | H | $CO_2CH_2CH=CH_2$ | $OCH_3$ | $OCH_3$ | CH | |
| H | $CH_3$ | H | $CO_2CH_2CH=CH_2$ | $CH_3$ | $CH_3$ | N | |
| H | $CH_3$ | H | $CO_2CH_2CH=CH_2$ | $CH_3$ | $OCH_3$ | N | |
| H | $CH_3$ | $CH_3$ | $CO_2CH_3$ | $OCH_3$ | $OCH_3$ | N | |
| H | $CH_3$ | H | $CO_2CF_3$ | $OCH_3$ | Cl | CH | |
| H | $CH_3$ | H | $CO_2CF_3$ | $CH_3$ | $CH_3$ | CH | |
| H | $CH_3$ | H | $CO_2CF_3$ | $CH_3$ | $OCH_3$ | CH | |
| H | $CH_3$ | H | $CO_2CF_3$ | $OCH_3$ | $OCH_3$ | CH | |
| H | $CH_3$ | H | $CO_2CH_2CH_2Cl$ | $CH_3$ | $CH_3$ | N | |
| H | $CH_3$ | H | $CO_2CH_2CH_2Cl$ | $CH_3$ | $OCH_3$ | N | |
| H | $CH_3$ | H | $CO_2CH_2CH_2Cl$ | $OCH_3$ | $OCH_3$ | N | |
| H | $CH_3$ | H | $CO_2CH_2CH_2P(O)(CH_3)_2$ | $OCH_3$ | Cl | CH | |
| H | $CH_3$ | H | $CO_2CH_2CH_2P(O)(CH_3)_2$ | $CH_3$ | $CH_3$ | CH | |
| $CH_3$ | $CH_3$ | H | $CO_2C(CH_3)_3$ | $CH_3$ | $OCH_3$ | CH | |
| H | $CH_3$ | H | $CO_2C(CH_3)_3$ | $OCH_3$ | $OCH_3$ | CH | |
| H | $CH_3$ | H | $CO_2CH_2(CH_2)_4CH_3$ | $CH_3$ | $CH_3$ | N | |
| H | $CH_3$ | H | $CO_2CH_2(CH_2)_4CH_3$ | $CH_3$ | $OCH_3$ | N | |
| H | $CH_3$ | H | $CO_2CH_2OCH_3$ | $OCH_3$ | $OCH_3$ | N | |
| H | $CH_3$ | H | $CO_2CH_2OCH_3$ | $OCH_3$ | Cl | CH | |
| H | $CH_3$ | H | $(C(O))_2OCH_3$ | $CH_3$ | $CH_3$ | CH | |
| H | $CH_3$ | H | $(C(O))_2OCH_3$ | $CH_3$ | $OCH_3$ | CH | |
| H | $CH_3$ | H | $(C(O))_2OCH_3$ | $OCH_3$ | $OCH_3$ | CH | |
| H | $CH_3$ | H | $(C(O))_2OCH_3$ | $CH_3$ | $CH_3$ | N | |
| H | $CH_3$ | H | $(C(O))_2OCH_3$ | $CH_3$ | $OCH_3$ | N | |
| H | $CH_3$ | H | $(C(O))_2OCH_3$ | $OCH_3$ | $OCH_3$ | N | |
| H | $CH_3$ | H | $(C(O))_2OCH_3$ | $OCH_3$ | Cl | CH | |
| H | $CH_3$ | H | $(CO)_2CH_3$ | $CH_3$ | $CH_3$ | CH | |
| H | $CH_3$ | H | $(CO)_2CH_3$ | $CH_3$ | $OCH_3$ | CH | |
| H | $CH_3$ | H | $(CO)_2CH_3$ | $OCH_3$ | $OCH_3$ | CH | |
| H | $CH_3$ | H | $(CO)_2CH_3$ | $CH_3$ | $CH_3$ | N | |
| H | $CH_3$ | H | $(CO)_2CH_3$ | $CH_3$ | $OCH_3$ | N | |
| H | $CH_3$ | H | $(CO)_2CH_3$ | $OCH_3$ | $OCH_3$ | N | |
| H | $CH_3$ | H | $(CO)_2CH_3$ | $OCH_3$ | Cl | CH | |
| H | $CH_3$ | H | $C(O)N(CH_3)_2$ | $CH_3$ | $CH_3$ | CH | |
| H | $CH_3$ | H | $C(O)N(CH_3)_2$ | $CH_3$ | $OCH_3$ | CH | |
| H | $CH_3$ | H | $C(O)N(CH_3)_2$ | $OCH_3$ | $OCH_3$ | CH | |
| H | $CH_3$ | H | $C(O)N(CH_3)_2$ | $CH_3$ | $CH_3$ | N | |
| H | $CH_3$ | H | $C(O)N(CH_3)_2$ | $OCH_3$ | $OCH_3$ | N | |
| H | $CH_3$ | H | $C(O)N(CH_3)_2$ | $OCH_3$ | Cl | CH | |
| H | $CH_3$ | H | $C(O)N(CH_2CH_3)_2$ | $CH_3$ | $CH_3$ | CH | |
| H | $CH_3$ | H | $C(O)N(CH_2CH_3)_2$ | $CH_3$ | $OCH_3$ | CH | |
| H | $CH_3$ | H | $C(O)N(CH_2CH_3)_2$ | $OCH_3$ | $OCH_3$ | CH | |
| H | $CH_3$ | H | $C(O)N(CH_2CH_3)_2$ | $CH_3$ | $CH_3$ | N | |
| H | $CH_3$ | H | $C(O)N(CH_2CH_3)_2$ | $CH_3$ | $OCH_3$ | N | |
| H | $CH_3$ | H | $C(O)N(CH_2CH_3)_2$ | $OCH_3$ | $OCH_3$ | N | |
| H | $CH_3$ | H | $C(O)N(CH_3)CH_2CH_3$ | $OCH_3$ | Cl | CH | |
| H | $CH_3$ | H | $C(O)N(CH_3)CH_2CH_3$ | $CH_3$ | $CH_3$ | CH | |
| H | $CH_3$ | H | $C(O)N(CH_3)CH_2CH_3$ | $CH_3$ | $OCH_3$ | CH | |
| H | $CH_3$ | H | $C(O)N(CH_3)CH_2CH_3$ | $OCH_3$ | $OCH_3$ | CH | |
| H | $CH_3$ | H | $C(O)N(CH_3)CH_2CH_3$ | $CH_3$ | $CH_3$ | N | |
| H | $CH_3$ | H | $C(O)N(CF_3)CH_3$ | $CH_3$ | $OCH_3$ | N | |
| H | $CH_3$ | $CH_3$ | $C(O)N(CF_3)CH_3$ | $OCH_3$ | $OCH_3$ | N | |

TABLE II-continued

General Structure II

| R | R₁ | R₂ | R₃ | X | Y | Z | m.p. (°C.) |
|---|---|---|---|---|---|---|---|
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | N | |
| H | CH₃ | H | CS₂CH₃ | CH₃ | CH₃ | CH | |
| H | CH₃ | H | CS₂CH₃ | CH₃ | OCH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂CH₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | CH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | CH₃ | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |
| H | CH₃ | H | CN | CH₃ | CH₃ | N | |
| H | CH₃ | H | CN | CH₃ | OCH₃ | N | |
| H | CH₃ | H | CN | OCH₃ | OCH₃ | N | |
| H | CH₃ | H | CN | OCH₃ | Cl | CH | |
| H | CH₃ | H | P(O)(CH₃)₂ | CH₃ | CH₃ | CH | |
| H | CH₃ | H | P(O)(CH₃)₂ | CH₃ | OCH₃ | CH | |
| H | CH₃ | H | P(O)(CH₃)₂ | OCH₃ | OCH₃ | CH | |
| H | CH₃ | H | P(O)(CH₃)₂ | CH₃ | CH₃ | N | |
| H | CH₃ | H | P(O)(CH₃)₂ | OCH₃ | OCH₃ | N | |
| H | CH₃ | H | P(O)(OCH₃)₂ | OCH₃ | Cl | CH | |
| H | CH₃ | H | P(O)(OCH₃)₂ | CH₃ | CH₃ | CH | |
| H | CH₃ | H | P(O)(OCH₃)₂ | CH₃ | OCH₃ | CH | |

TABLE II-continued

General Structure II

| R | R₁ | R₂ | R₃ | X | Y | Z | m.p. (°C.) |
|---|---|---|---|---|---|---|---|
| H | CH₃ | H | P(O)(OCH₃)₂ | OCH₃ | OCH₃ | CH | |
| H | CH₃ | H | P(O)(OCH₃)SCH₃ | CH₃ | CH₃ | N | |
| H | CH₃ | H | P(O)(OCH₃)SCH₃ | CH₃ | OCH₃ | N | |
| H | CH₃ | H | P(O)(OCH₃)SCH₃ | OCH₃ | OCH₃ | N | |
| H | CH₃ | H | P(O)(OCH₃)SCH₃ | OCH₃ | Cl | CH | |
| H | CH₃ | H | P(O)(OCH₃)SCH₂CH₂CH₃ | CH₃ | CH₃ | CH | |
| H | CH₃ | H | P(O)(OCH₃)SCH₂CH₂CH₃ | CH₃ | OCH₃ | CH | |
| H | CH₃ | H | P(O)(OCH₃)SCH₂CH₂CH₃ | OCH₃ | OCH₃ | CH | |
| H | CH₃ | H | P(O)(OCH₃)SCH₂CH₂CH₃ | CH₃ | CH₃ | N | |
| H | CH₃ | H | P(O)(OCH₃)SCH₂CH₂CH₃ | CH₃ | OCH₃ | N | |
| H | CH₃ | CH₃ | OH | OCH₃ | OCH₃ | N | |
| H | CH₃ | H | P(S)(CH₃)₂ | OCH₃ | Cl | CH | |
| H | CH₃ | H | P(S)(CH₃)₂ | CH₃ | CH₃ | CH | |
| H | CH₃ | H | P(S)(CH₃)₂ | CH₃ | OCH₃ | CH | |
| H | CH₃ | H | P(S)(CH₃)₂ | OCH₃ | OCH₃ | CH | |
| H | CH₃ | H | P(S)(CH₃)₂ | CH₃ | CH₃ | N | |
| H | CH₃ | H | P(S)(CH₃)₂ | CH₃ | OCH₃ | N | |
| H | CH₃ | H | P(S)(CH₃)₂ | OCH₃ | OCH₃ | N | |
| H | CH₃ | H | P(S)(OCH₃)₂ | OCH₃ | Cl | CH | |
| H | CH₃ | H | P(S)(OCH₃)₂ | CH₃ | CH₃ | CH | |
| CH₃ | CH₃ | H | P(S)(OCH₃)₂ | CH₃ | OCH₃ | CH | |
| H | CH₃ | H | P(S)(OCH₃)₂ | OCH₃ | OCH₃ | CH | |
| H | CH₃ | H | P(S)(OCH₃)₂ | CH₃ | CH₃ | N | |
| H | CH₃ | H | P(S)(OCH₃)₂ | CH₃ | OCH₃ | N | |
| H | CH₃ | H | P(S)(OCH₃)SCH₃ | OCH₃ | OCH₃ | N | |
| H | CH₃ | H | P(S)(OCH₃)SCH₃ | OCH₃ | Cl | CH | |
| H | CH₃ | H | NO₂ | CH₃ | CH₃ | CH | |
| H | CH₃ | H | NO₂ | CH₃ | OCH₃ | CH | |
| H | CH₃ | H | NO₂ | OCH₃ | OCH₃ | CH | |
| H | CH₃ | H | NO₂ | CH₃ | CH₃ | N | |
| H | CH₃ | H | NO₂ | CH₃ | OCH₃ | N | |
| H | CH₃ | H | NO₂ | OCH₃ | OCH₃ | N | |
| H | CH₃ | H | CH₂C(O)CH₂CH₃ | CH₃ | CH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH(CH₂)(CH₂) (cyclopropyl) | CH₃ | CH₃ | N | |
| H | CH₃ | H | CH₂C(O)CH(CH₂)(CH₂) (cyclopropyl) | CH₃ | OCH₃ | N | |
| H | CH₃ | H | CH₂C(O)CH(CH₂)(CH₂) (cyclopropyl) | OCH₃ | OCH₃ | N | |
| H | CH₃ | H | CH₂C(O)CH(CH₂)(CH₂) (cyclopropyl) | OCH₃ | Cl | CH | |
| H | CH₃ | H | CH₂C(O)CH(CH₂)(CH₂) (cyclopropyl) | CH₃ | CH₃ | CH | |
| H | CH₃ | H | CH₂C(O)CH(CH₂)(CH₂) (cyclopropyl) | CH₃ | CH₃ | CH | |
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |

TABLE II-continued

General Structure II

| R | $R_1$ | $R_2$ | $R_3$ | X | Y | Z | m.p. (°C.) |
|---|---|---|---|---|---|---|---|
| H | $CH_3$ | H | $CH_2C(O)Ph$ | $CH_3$ | $CH_3$ | CH | |
| H | $CH_3$ | H | $CH_2C(O)Ph$ | $CH_3$ | $OCH_3$ | CH | |
| H | $CH_3$ | H | $CH(CH)_3C(O)CH_3$ | $OCH_3$ | $OCH_3$ | CH | |
| H | $CH_3$ | H | $CH(CH)_3C(O)CH_3$ | $CH_3$ | $CH_3$ | N | |
| H | $CH_3$ | H | $CH(CH)_3C(O)CH_3$ | $CH_3$ | $OCH_3$ | N | |
| H | $CH_3$ | H | $CH(CH)_3C(O)CH_3$ | $OCH_3$ | $OCH_3$ | N | |
| H | $CH_3$ | H | $CH_2CF_2-C(O)CH_3$ | $OCH_3$ | Cl | CH | |
| H | $CH_3$ | H | $CH_2CF_2-C(O)CH_3$ | $CH_3$ | $CH_3$ | CH | |
| $CH_3$ | $CH_3$ | H | $CH_2CF_2-C(O)CH_3$ | $CH_3$ | $OCH_3$ | CH | |
| H | $CH_3$ | H | $CH_2CF_2-C(O)CH_3$ | $OCH_3$ | $OCH_3$ | CH | |
| H | $CH_3$ | H | $CH_2C(O)CH_2OCH_3$ | $CH_3$ | $CH_3$ | N | |
| H | $CH_3$ | H | $CH_2C(O)CH_2OCH_3$ | $CH_3$ | $OCH_3$ | N | |
| H | $CH_3$ | H | $CH_2C(O)CH_2OCH_3$ | $OCH_3$ | $OCH_3$ | N | |
| H | $CH_3$ | H | $CH_2C(O)CH_2OCH_3$ | $OCH_3$ | Cl | CH | |
| H | $CH_3$ | H | $CH_2CO_2CH_3$ | $CH_3$ | $CH_3$ | CH | |
| H | $CH_3$ | H | $CH_2CO_2CH_3$ | $CH_3$ | $OCH_3$ | CH | |
| H | $CH_3$ | H | $CH_2CO_2CH_3$ | $OCH_3$ | $OCH_3$ | CH | |
| H | $CH_3$ | H | $CH_2CO_2CH_3$ | $CH_3$ | $CH_3$ | N | |
| H | $CH_3$ | H | $CH_2CO_2CH_3$ | $CH_3$ | $OCH_3$ | N | |
| H | $CH_3$ | H | $CH_2CO_2CH_3$ | $OCH_3$ | $OCH_3$ | N | |
| H | $CH_3$ | H | $CH_2CO_2CH_3$ | $OCH_3$ | Cl | CH | |
| H | $CH_3$ | H | $CH_2CO_2CH_2CH_3$ | $CH_3$ | $CH_3$ | CH | |
| H | $CH_3$ | H | $CH_2CO_2CH_2CH_3$ | $CH_3$ | $OCH_3$ | CH | |
| H | $CH_3$ | H | $CH_2CO_2CH_2CH_3$ | $OCH_3$ | $OCH_3$ | CH | |
| H | $CH_3$ | H | $CH_2CO_2CH_2CH_3$ | $CH_3$ | $CH_3$ | N | |
| H | $CH_3$ | H | $CH_2CO_2CH_2CH_3$ | $CH_3$ | $OCH_3$ | N | |
| H | $CH_3$ | H | $CH_2CO_2CH_2CH_3$ | $OCH_3$ | $OCH_3$ | N | |
| H | $CH_3$ | H | $CH_2CO_2CH_2CH_3$ | $OCH_3$ | Cl | CH | |
| H | $CH_3$ | H | $CH_2CH_2CO_2CH_3$ | $CH_3$ | $CH_3$ | CH | |
| H | $CH_3$ | H | $CH_2CH_2CO_2CH_3$ | $CH_3$ | $OCH_3$ | CH | |
| H | $CH_3$ | H | $CH_2CH_2CO_2CH_3$ | $OCH_3$ | $OCH_3$ | CH | |
| H | $CH_3$ | H | $CH_2CH_2CO_2CH_3$ | $CH_3$ | $CH_3$ | N | |
| H | $CH_3$ | H | $CH_2CH_2CO_2CH_3$ | $OCH_3$ | $OCH_3$ | N | |
| H | $CH_3$ | H | $CH_2CH_2CO_2CH_3$ | $OCH_3$ | Cl | CH | |
| H | $CH_3$ | H | $CH_2-CO_2CH_2CH=CH_2$ | $CH_3$ | $CH_3$ | CH | |
| H | $CH_3$ | H | $CH_2-CO_2CH_2CH=CH_2$ | $CH_3$ | $OCH_3$ | CH | |
| H | $CH_3$ | H | $CH_2-CO_2CH_2CH=CH_2$ | $OCH_3$ | $OCH_3$ | CH | |
| H | $CH_3$ | H | $CH_2-CO_2CH_2CH=CH_2$ | $CH_3$ | $CH_3$ | N | |
| H | $CH_3$ | H | $CH_2-CO_2CH_2CH=CH_2$ | $CH_3$ | $OCH_3$ | N | |
| H | $CH_3$ | H | $CH_2-CO_2CH_2CH=CH_2$ | $OCH_3$ | $OCH_3$ | N | |
| H | $CH_3$ | H | $CH_2-CO_2CH_2CH=CH_2$ | $OCH_3$ | Cl | CH | |
| H | $CH_3$ | H | $CH_2(CH_2)_4CO_2CH_3$ | $CH_3$ | $CH_3$ | CH | |
| H | $CH_3$ | H | $CH_2(CH_2)_4CO_2CH_3$ | $CH_3$ | $OCH_3$ | CH | |
| H | $CH_3$ | H | $CH_2(CH_2)_4CO_2CH_3$ | $OCH_3$ | $OCH_3$ | CH | |
| H | $CH_3$ | H | $CH_2(CH_2)_4CO_2CH_3$ | $CH_3$ | $CH_3$ | N | |
| H | $CH_3$ | H | $CH_2(CH_2)_4CO_2CH_3$ | $CH_3$ | $OCH_3$ | N | |
| H | $CH_3$ | $CH_3$ | $CH_2(CH_2)_4CO_2CH_3$ | $OCH_3$ | $OCH_3$ | N | |
| H | $CH_3$ | H | $CH_2(CH_2)_4CO_2CH_3$ | $OCH_3$ | Cl | CH | |
| H | $CH_3$ | H | $CH_2CO_2CH_2C\equiv CH$ | $CH_3$ | $CH_3$ | CH | |
| H | $CH_3$ | H | $CH_2CO_2CH_2C\equiv CH$ | $CH_3$ | $OCH_3$ | CH | |
| H | $CH_3$ | H | $CH_2CO_2CH_2C\equiv CH$ | $OCH_3$ | $OCH_3$ | CH | |
| H | $CH_3$ | H | $CH_2CO_2CH_2C\equiv CH$ | $CH_3$ | $CH_3$ | N | |
| H | $CH_3$ | H | $CH_2CO_2CH_2C\equiv CH$ | $CH_3$ | $OCH_3$ | N | |
| H | $CH_3$ | H | $CH_2CO_2CH_2C\equiv CH$ | $OCH_3$ | $OCH_3$ | N | |
| H | $CH_3$ | H | $CH_2CO_2CH_2C\equiv CH$ | $OCH_3$ | Cl | CH | |
| H | $CH_3$ | H | $CH_2CO_2CF_2$ | $CH_3$ | $CH_3$ | CH | |
| $CH_3$ | $CH_3$ | H | $CH_2CO_2CF_3$ | $CH_3$ | $OCH_3$ | CH | |
| H | $CH_3$ | H | $CH_2CO_2CF_3$ | $OCH_3$ | $OCH_3$ | CH | |
| H | $CH_3$ | H | $CH_2CO_2CF_3$ | $CH_3$ | $CH_3$ | N | |
| H | $CH_3$ | H | $CH_2CO_2CF_3$ | $CH_3$ | $OCH_3$ | N | |
| H | $CH_3$ | H | $CH_2CO_2CF_3$ | $OCH_3$ | $OCH_3$ | N | |
| H | $CH_3$ | H | $CH_2CO_2CF_3$ | $OCH_3$ | Cl | CH | |
| H | $CH_3$ | H | $CH_2C(O)N(CH_3)_2$ | $CH_3$ | $CH_3$ | CH | |
| H | $CH_3$ | H | $CH_2C(O)N(CH_3)_2$ | $CH_3$ | $OCH_3$ | CH | |
| H | $CH_3$ | H | $CH_2C(O)N(CH_3)_2$ | $OCH_3$ | $OCH_3$ | CH | |
| H | $CH_3$ | H | $CH_2C(O)N(CH_3)_2$ | $CH_3$ | $CH_3$ | N | |
| H | $CH_3$ | H | $CH_2C(O)N(CH_3)_2$ | $CH_3$ | $OCH_3$ | N | |
| H | $CH_3$ | H | $CH_2C(O)N(CH_3)_2$ | $OCH_3$ | $OCH_3$ | N | |
| H | $CH_3$ | H | $CH_2C(O)N(CH_3)_2$ | $OCH_3$ | Cl | CH | |
| H | $CH_3$ | H | $SeCH_3$ | $CH_3$ | $CH_3$ | CH | |
| H | $CH_3$ | H | $SeCH_3$ | $CH_3$ | $OCH_3$ | CH | |
| H | $CH_3$ | H | $SeCH_3$ | $OCH_3$ | $OCH_3$ | CH | |
| H | $CH_3$ | H | $SeCH_3$ | $CH_3$ | $CH_3$ | N | |
| H | $CH_3$ | H | $SeCH_3$ | $CH_3$ | $OCH_3$ | N | |
| H | $CH_3$ | H | $SeCH_3$ | $OCH_3$ | $OCH_3$ | N | |
| H | $CH_3$ | H | $SeCH_3$ | $OCH_3$ | Cl | CH | |
| H | $CH_3$ | H | $CH_2Ph$ | $CH_3$ | $CH_3$ | CH | |
| H | $CH_3$ | H | $CH_2Ph$ | $CH_3$ | $OCH_3$ | CH | |
| H | $CH_3$ | H | $CH_2Ph$ | $OCH_3$ | $OCH_3$ | CH | |
| H | $CH_3$ | H | $CH_2Ph$ | $CH_3$ | $CH_3$ | N | |

TABLE II-continued

General Structure II

| R | R₁ | R₂ | R₃ | X | Y | Z | m.p. (°C.) |
|---|---|---|---|---|---|---|---|
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | Si(CH₃)₂CH₂CH₃ | OCH₃ | Cl | CH | |
| H | CH₃ | H | A-HET | CH₃ | CH₃ | CH | |
| H | CH₃ | H | A-HET | CH₃ | OCH₃ | CH | |
| H | CH₃ | H | A-HET | OCH₃ | OCH₃ | CH | |
| H | CH₃ | H | A-HET | CH₃ | CH₃ | N | |
| H | CH₃ | H | A-HET | CH₃ | OCH₃ | N | |
| H | CH₃ | H | A-HET | OCH₃ | OCH₃ | N | |
| H | CH₃ | H | A-HET | OCH₃ | Cl | CH | |
| H | CH₃ | H | B-HET | CH₃ | CH₃ | CH | |
| H | CH₃ | H | B-HET | CH₃ | OCH₃ | CH | |
| H | CH₃ | H | B-HET | OCH₃ | OCH₃ | CH | |
| H | CH₃ | H | B-HET | CH₃ | CH₃ | N | |
| H | CH₃ | H | B-HET | CH₃ | OCH₃ | N | |
| H | CH₃ | CH₃ | B-HET | OCH₃ | OCH₃ | N | |
| H | CH₃ | H | B-HET | OCH₃ | Cl | CH | |
| H | CH₃ | H | C-HET | CH₃ | CH₃ | CH | |
| H | CH₃ | H | C-HET | CH₃ | OCH₃ | CH | |
| H | CH₃ | H | C-HET | OCH₃ | OCH₃ | CH | |
| H | CH₃ | H | C-HET | CH₃ | CH₃ | N | |
| H | CH₃ | H | C-HET | CH₃ | OCH₃ | N | |
| H | CH₃ | H | C-HET | OCH₃ | OCH₃ | N | |
| H | CH₃ | H | C-HET | OCH₃ | Cl | CH | |
| H | CH₃ | H | D-HET | CH₃ | CH₃ | CH | |
| CH₃ | CH₃ | H | D-HET | CH₃ | OCH₃ | CH | |
| H | CH₃ | H | D-HET | OCH₃ | OCH₃ | CH | |
| H | CH₃ | H | D-HET | CH₃ | CH₃ | N | |
| H | CH₃ | H | D-HET | CH₃ | OCH₃ | N | |
| H | CH₃ | H | D-HET | OCH₃ | OCH₃ | N | |
| H | CH₃ | H | D-HET | OCH₃ | Cl | CH | |
| H | CH₃ | H | C(O)A-HET | CH₃ | CH₃ | CH | |
| H | CH₃ | H | C(O)A-HET | CH₃ | OCH₃ | CH | |
| H | CH₃ | H | C(O)A-HET | OCH₃ | OCH₃ | CH | |
| H | CH₃ | H | C(O)A-HET | CH₃ | CH₃ | N | |
| H | CH₃ | H | C(O)A-HET | CH₃ | OCH₃ | N | |
| H | CH₃ | H | C(O)A-HET | OCH₃ | OCH₃ | N | |
| H | CH₃ | H | C(O)A-HET | OCH₃ | Cl | CH | |
| H | CH₃ | H | C(O)B-HET | CH₃ | CH₃ | CH | |
| H | CH₃ | H | C(O)B-HET | CH₃ | OCH₃ | CH | |
| H | CH₃ | H | C(O)B-HET | OCH₃ | OCH₃ | CH | |
| H | CH₃ | H | C(O)B-HET | CH₃ | CH₃ | N | |
| H | CH₃ | H | C(O)B-HET | CH₃ | OCH₃ | N | |
| H | CH₃ | H | C(O)B-HET | OCH₃ | OCH₃ | N | |
| H | CH₃ | H | C(O)B-HET | OCH₃ | Cl | CH | |
| H | CH₃ | H | C(O)C-HET | CH₃ | CH₃ | CH | |
| H | CH₃ | H | C(O)C-HET | CH₃ | OCH₃ | CH | |

TABLE II-continued

General Structure II

| R | R₁ | R₂ | R₃ | X | Y | Z | m.p. (°C.) |
|---|----|----|----|---|---|---|-----------|
| H | CH₃ | H | C(O)C-HET | OCH₃ | OCH₃ | CH | |
| H | CH₃ | H | C(O)C-HET | CH₃ | CH₃ | N | |
| H | CH₃ | H | C(O)C-HET | OCH₃ | OCH₃ | N | |
| H | CH₃ | H | C(O)C-HET | OCH₃ | Cl | CH | |
| H | CH₃ | H | C(O)D-HET | CH₃ | CH₃ | CH | |
| H | CH₃ | H | C(O)D-HET | CH₃ | OCH₃ | CH | |
| H | CH₃ | H | C(O)D-HET | OCH₃ | OCH₃ | CH | |
| H | CH₃ | H | C(O)D-HET | CH₃ | CH₃ | N | |
| H | CH₃ | H | C(O)D-HET | CH₃ | OCH₃ | N | |
| H | CH₃ | H | C(O)D-HET | OCH₃ | OCH₃ | N | |
| H | CH₃ | H | C(O)D-HET | OCH₃ | Cl | CH | | wherein

A-HET is 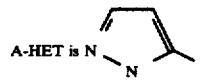

B-HET is 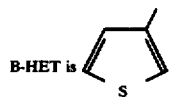

C-HET is 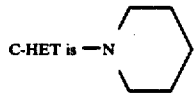

D-HET is 

TABLE IIa

| R | R₁ | R₂ | R₃ | X | Y | Z | m.p. (°C.) |
|---|----|----|----|---|---|---|-----------|
| H | CH₃ | H | CH₂F | CH₃ | CH₃ | CH | |
| H | CH₃ | H | CH₂F | CH₃ | OCH₃ | CH | |
| H | CH₃ | H | CH₂F | OCH₃ | OCH₃ | CH | |
| H | CH₃ | H | CH₂F | CH₃ | CH₃ | N | |
| H | CH₃ | H | CH₂F | CH₃ | OCH₃ | N | |
| H | CH₃ | H | CH₂F | OCH₃ | OCH₃ | N | |
| H | CH₃ | H | CH₂F | OCH₃ | Cl | CH | |
| H | CH₃ | H | CH₂CH₂F | CH₃ | CH₃ | CH | |
| H | CH₃ | H | CH₂CH₂F | CH₃ | OCH₃ | CH | |
| H | CH₃ | H | CH₂CH₂F | OCH₃ | OCH₃ | CH | |
| H | CH₃ | H | CH₂CH₂F | CH₃ | CH₃ | N | |
| H | CH₃ | H | CH₂CH₂F | CH₃ | OCH₃ | N | |
| H | CH₃ | H | CH₂CH₂F | OCH₃ | OCH₃ | N | |
| H | CH₃ | H | CH₂CH₂F | OCH₃ | Cl | CH | |
| H | CH₃ | H | CHFCH₂F | CH₃ | CH₃ | CH | |
| H | CH₃ | H | CHFCH₂F | CH₃ | OCH₃ | CH | |
| H | CH₃ | H | CHFCH₂F | OCH₃ | OCH₃ | CH | |
| H | CH₃ | H | CHFCH₂F | CH₃ | CH₃ | N | |
| H | CH₃ | H | CHFCH₂F | OCH₃ | OCH₃ | N | |
| H | CH₃ | H | CHFCH₂F | OCH₃ | Cl | CH | |
| H | CH₃ | H | CH₂CHF₂ | CH₃ | CH₃ | CH | |
| H | CH₃ | H | CH₂CHF₂ | CH₃ | OCH₃ | CH | |
| H | CH₃ | H | CH₂CHF₂ | OCH₃ | OCH₃ | CH | |
| H | CH₃ | H | CH₂CHF₂ | CH₃ | CH₃ | N | |
| H | CH₃ | H | CH₂CHF₂ | CH₃ | OCH₃ | N | |
| H | CH₃ | H | CH₂CHF₂ | OCH₃ | OCH₃ | N | |
| H | CH₃ | H | CH₂CHF₂ | OCH₃ | Cl | CH | |
| H | CH₃ | H | CH(CH₂F)₂ | CH₃ | CH₃ | CH | |
| H | CH₃ | H | CH(CH₂F)₂ | CH₃ | OCH₃ | CH | |
| H | CH₃ | H | CH(CH₂F)₂ | OCH₃ | OCH₃ | CH | |
| H | CH₃ | H | CH₂CH₂CH₂F | CH₃ | CH₃ | N | |
| H | CH₃ | H | CH₂CH₂CH₂F | CH₃ | OCH₃ | N | |
| H | CH₃ | CH₃ | CH₂CH₂CH₂F | OCH₃ | OCH₃ | N | |
| H | CH₃ | H | CH₂CH₂CH₂F | OCH₃ | Cl | CH | |
| H | CH₃ | H | CH₂CH₂CH₂F | CH₃ | CH₃ | CH | |
| H | CH₃ | H | CH₂CH₂CH₂F | CH₃ | OCH₃ | CH | |
| H | CH₃ | H | CH₂CH₂CH₂F | OCH₃ | OCH₃ | CH | |
| H | CH₃ | H | CH₂(CH₂)₂CH₂F | CH₃ | CH₃ | N | |
| H | CH₃ | H | CH₂(CH₂)₂CH₂F | CH₃ | OCH₃ | N | |
| H | CH₃ | H | CH₂(CH₂)₂CH₂F | OCH₃ | OCH₃ | N | |
| H | CH₃ | H | CH₂(CH₂)₂CH₂F | OCH₃ | Cl | CH | |
| H | CH₃ | H | CH₂(CH₂)₂CH₂F | CH₃ | CH₃ | CH | |
| CH₃ | CH₃ | H | CH₂(CH₂)₂CH₂F | CH₃ | OCH₃ | CH | |

TABLE IIa-continued

| R | R₁ | R₂ | R₃ | X | Y | Z | m.p. (°C.) |
|---|---|---|---|---|---|---|---|
| H | CH₃ | H | CH₂(CH₂)₂CH₂F | OCH₃ | OCH₃ | CH | |
| H | CH₃ | H | CH(CH₃)CH₂F | CH₃ | CH₃ | N | |
| H | CH₃ | H | CH(CH₃)CH₂F | CH₃ | OCH₃ | N | |
| H | CH₃ | H | CH(CH₃)CH₂F | OCH₃ | OCH₃ | N | |
| H | CH₃ | H | CH(CH₃)CH₂F | OCH₃ | Cl | CH | |
| H | CH₃ | H | CH₂Br | CH₃ | CH₃ | CH | |
| H | CH₃ | H | CH₂Br | CH₃ | OCH₃ | CH | |
| H | CH₃ | H | CH₂Br | OCH₃ | OCH₃ | CH | |
| H | CH₃ | H | CH₂Br | CH₃ | CH₃ | N | |
| H | CH₃ | H | CH₂Br | CH₃ | OCH₃ | N | |
| H | CH₃ | H | CH₂Br | OCH₃ | OCH₃ | N | |
| H | CH₃ | H | CH₂Br | OCH₃ | Cl | CH | |
| H | CH₃ | H | CH₂CH₂Br | CH₃ | CH₃ | CH | |
| H | CH₃ | H | CH₂CH₂Br | CH₃ | OCH₃ | CH | |
| H | CH₃ | H | CH₂CH₂Br | OCH₃ | OCH₃ | CH | |
| H | CH₃ | H | CH₂CH₂Br | CH₃ | CH₃ | N | |
| H | CH₃ | H | CH₂CH₂Br | CH₃ | OCH₃ | N | |
| H | CH₃ | H | CH₂CH₂Br | OCH₃ | OCH₃ | N | |
| H | CH₃ | H | CH₂CH₂Br | OCH₃ | Cl | CH | |
| H | CH₃ | H | CHBrCH₃ | CH₃ | CH₃ | CH | |
| H | CH₃ | H | CHBrCH₃ | CH₃ | OCH₃ | CH | |
| H | CH₃ | H | CHBrCH₃ | OCH₃ | OCH₃ | CH | |
| H | CH₃ | H | CHBrCH₃ | CH₃ | CH₃ | N | |
| H | CH₃ | H | CHBrCH₃ | OCH₃ | OCH₃ | N | |
| H | CH₃ | H | CHBrCH₃ | OCH₃ | Cl | CH | |
| H | CH₃ | H | CH₂CHBr₂ | CH₃ | CH₃ | CH | |
| H | CH₃ | H | CH₂CHBr₂ | CH₃ | OCH₃ | CH | |
| H | CH₃ | H | CH₂CHBr₂ | OCH₃ | OCH₃ | CH | |
| H | CH₃ | H | CH₂CHBr₂ | CH₃ | CH₃ | N | |
| H | CH₃ | H | CH₂CHBr₂ | CH₃ | OCH₃ | N | |
| H | CH₃ | H | CH₂CHBr₂ | OCH₃ | OCH₃ | N | |
| H | CH₃ | H | CH₂CHBr₂ | OCH₃ | Cl | CH | |
| H | CH₃ | H | CH(CH₂Br)₂ | CH₃ | CH₃ | CH | |
| H | CH₃ | H | CH(CH₂Br)₂ | CH₃ | OCH₃ | CH | |
| H | CH₃ | H | CH(CH₂Br)₂ | OCH₃ | OCH₃ | CH | |
| H | CH₃ | H | CH(CH₂Br)₂ | CH₃ | CH₃ | N | |
| H | CH₃ | H | CH₂CHBrCH₃ | CH₃ | OCH₃ | N | |
| H | CH₃ | CH₃ | CH₂CHBrCH₃ | OCH₃ | OCH₃ | N | |
| H | CH₃ | H | CH₂CHBrCH₃ | OCH₃ | Cl | CH | |
| H | CH₃ | H | CH₂CHBrCH₃ | CH₃ | CH₃ | CH | |
| H | CH₃ | H | CH₂CHBrCH₃ | CH₃ | OCH₃ | CH | |
| H | CH₃ | H | CH₂(CH₂)₂CH₂Br | OCH₃ | OCH₃ | CH | |
| H | CH₃ | H | CH₂(CH₂)₂CH₂Br | CH₃ | CH₃ | N | |
| H | CH₃ | H | CH₂(CH₂)₂CH₂Br | CH₃ | OCH₃ | N | |
| H | CH₃ | H | CH₂(CH₂)₂CH₂Br | OCH₃ | OCH₃ | N | |
| H | CH₃ | H | CH₂(CH₂)₂CH₂Br | OCH₃ | Cl | CH | |
| H | CH₃ | H | CH₂(CH₂)₂CH₂Br | CH₃ | CH₃ | CH | |
| CH₃ | CH₃ | H | CH₂(CH₂)₂CH₂Br | CH₃ | OCH₃ | CH | |
| H | CH₃ | H | C(CH₃)(CH₂Br)CH₃ | OCH₃ | OCH₃ | CH | |
| H | CH₃ | H | CH₂CHBrCH₂CH₃ | CH₃ | CH₃ | N | |
| H | CH₃ | H | CH₂CHBrCH₂CH₃ | CH₃ | OCH₃ | N | |
| H | CH₃ | H | CH₂CHBrCH₂CH₃ | OCH₃ | OCH₃ | N | |
| H | CH₃ | H | CH₂CHBrCH₂CH₃ | OCH₃ | Cl | CH | |
| H | CH₃ | H | CH₂Cl | CH₃ | CH₃ | CH | |
| H | CH₃ | H | CH₂Cl | CH₃ | OCH₃ | CH | |
| H | CH₃ | H | CH₂Cl | OCH₃ | OCH₃ | CH | |
| H | CH₃ | H | CH₂Cl | CH₃ | CH₃ | N | |
| H | CH₃ | H | CH₂Cl | CH₃ | OCH₃ | N | |
| H | CH₃ | H | CH₂Cl | OCH₃ | OCH₃ | N | |
| H | CH₃ | H | CH₂Cl | OCH₃ | Cl | CH | |
| H | CH₃ | H | CH₂CH₂Cl | CH₃ | CH₃ | CH | |
| H | CH₃ | H | CH₂CH₂Cl | CH₃ | OCH₃ | CH | |
| H | CH₃ | H | CH₂CH₂Cl | OCH₃ | OCH₃ | CH | |
| H | CH₃ | H | CH₂CH₂Cl | CH₃ | CH₃ | N | |
| H | CH₃ | H | CH₂CH₂Cl | CH₃ | OCH₃ | N | |
| H | CH₃ | H | CH₂CH₂Cl | OCH₃ | OCH₃ | N | |
| H | CH₃ | H | CH₂CH₂Cl | OCH₃ | Cl | CH | |
| H | CH₃ | H | CHClCH₂Cl | CH₃ | CH₃ | CH | |
| H | CH₃ | H | CHClCH₂Cl | CH₃ | OCH₃ | CH | |
| H | CH₃ | H | CHClCH₂Cl | OCH₃ | OCH₃ | CH | |
| H | CH₃ | H | CHClCH₂Cl | CH₃ | CH₃ | N | |
| H | CH₃ | H | CHClCH₂Cl | OCH₃ | OCH₃ | N | |
| H | CH₃ | H | CHClCH₂Cl | OCH₃ | Cl | CH | |
| H | CH₃ | H | CH₂CCl₂CH₃ | CH₃ | CH₃ | CH | |
| H | CH₃ | H | CH₂CCl₂CH₃ | CH₃ | OCH₃ | CH | |
| H | CH₃ | H | CH₂CCl₂CH₃ | OCH₃ | OCH₃ | CH | |
| H | CH₃ | H | CH(CH₂Cl)₂ | CH₃ | CH₃ | N | |
| H | CH₃ | H | CH(CH₂Cl)₂ | CH₃ | OCH₃ | N | |
| H | CH₃ | H | CH(CH₂Cl)₂ | OCH₃ | OCH₃ | N | |
| H | CH₃ | H | CH(CH₂Cl)₂ | OCH₃ | Cl | CH | |
| H | CH₃ | H | CH(CH₂Cl)₂ | CH₃ | CH₃ | CH | |

TABLE IIa-continued

| R | $R_1$ | $R_2$ | $R_3$ | X | Y | Z | m.p. (°C.) |
|---|---|---|---|---|---|---|---|
| H | $CH_3$ | H | $CH_2CH_2CH_2Cl$ | $CH_3$ | $OCH_3$ | CH | |
| H | $CH_3$ | H | $CH_2CH_2CH_2Cl$ | $OCH_3$ | $OCH_3$ | CH | |
| H | $CH_3$ | H | $CH_2CH_2CH_2Cl$ | $CH_3$ | $CH_3$ | N | |
| H | $CH_3$ | H | $CH_2CH_2CH_2Cl$ | $CH_3$ | $OCH_3$ | N | |
| H | $CH_3$ | $CH_3$ | $CH_2CH_2CH_2Cl$ | $OCH_3$ | $OCH_3$ | N | |
| H | $CH_3$ | H | $CH_2CH_2CH_2Cl$ | $OCH_3$ | Cl | CH | |
| H | $CH_3$ | H | $CH_2CH_2CH_2Cl$ | $CH_3$ | $CH_3$ | CH | |
| H | $CH_3$ | H | $CH_2(CH_2)CH_2Cl$ | $CH_3$ | $OCH_3$ | CH | |
| H | $CH_3$ | H | $CH_2(CH_2)CH_2Cl$ | $OCH_3$ | $OCH_3$ | CH | |
| H | $CH_3$ | H | $CH_2(CH_2)CH_2Cl$ | $CH_3$ | $CH_3$ | N | |
| H | $CH_3$ | H | $CH_2(CH_2)CH_2Cl$ | $CH_3$ | $OCH_3$ | N | |
| H | $CH_3$ | H | $CH_2(CH_2)CH_2Cl$ | $OCH_3$ | $OCH_3$ | N | |
| H | $CH_3$ | H | $CH_2(CH_2)CH_2Cl$ | $OCH_3$ | Cl | CH | |
| H | $CH_3$ | H | $CH_2(CH_2)CH_2Cl$ | $CH_3$ | $CH_3$ | CH | |
| $CH_3$ | $CH_3$ | H | $CH(CH_3)CH_2Cl$ | $CH_3$ | $OCH_3$ | CH | |
| H | $CH_3$ | H | $CH(CH_3)CH_2Cl$ | $OCH_3$ | $OCH_3$ | CH | |
| H | $CH_3$ | H | $CH(CH_3)CH_2Cl$ | $CH_3$ | $CH_3$ | N | |
| H | $CH_3$ | H | $CHClCHClCH_3$ | $CH_3$ | $OCH_3$ | N | |
| H | $CH_3$ | H | $CHClCHClCH_3$ | $OCH_3$ | $OCH_3$ | N | |
| H | $CH_3$ | H | $CHClCHClCH_3$ | $OCH_3$ | Cl | CH | |
| H | $CH_3$ | H | $CH_2I$ | $CH_3$ | $CH_3$ | CH | |
| H | $CH_3$ | H | $CH_2I$ | $CH_3$ | $OCH_3$ | CH | |
| H | $CH_3$ | H | $CH_2I$ | $OCH_3$ | $OCH_3$ | CH | |
| H | $CH_3$ | H | $CH_2I$ | $CH_3$ | $CH_3$ | N | |
| H | $CH_3$ | H | $CH_2I$ | $CH_3$ | $OCH_3$ | N | |
| H | $CH_3$ | H | $CH_2I$ | $OCH_3$ | $OCH_3$ | N | |
| H | $CH_3$ | H | $CH_2I$ | $OCH_3$ | Cl | CH | |
| H | $CH_3$ | H | $CH_2CF_3$ | $CH_3$ | $CH_3$ | CH | |
| H | $CH_3$ | H | $CH_2CF_3$ | $CH_3$ | $OCH_3$ | CH | |
| H | $CH_3$ | H | $CH_2CF_3$ | $OCH_3$ | $OCH_3$ | CH | |
| H | $CH_3$ | H | $CH_2CF_3$ | $CH_3$ | $CH_3$ | N | |
| H | $CH_3$ | H | $CH_2CF_3$ | $CH_3$ | $OCH_3$ | N | |
| H | $CH_3$ | H | $CH_2CF_3$ | $OCH_3$ | $OCH_3$ | N | |
| H | $CH_3$ | H | $CH_2CF_3$ | $OCH_3$ | Cl | CH | |
| H | $CH_3$ | H | $CH_2CH_2CF_3$ | $CH_3$ | $CH_3$ | CH | |
| H | $CH_3$ | H | $CH_2CH_2CF_3$ | $CH_3$ | $OCH_3$ | CH | |
| H | $CH_3$ | H | $CH_2CH_2CF_3$ | $OCH_3$ | $OCH_3$ | CH | |
| H | $CH_3$ | H | $CH_2CH_2CF_3$ | $CH_3$ | $CH_3$ | N | |
| H | $CH_3$ | H | $CH_2CH_2CF_3$ | $OCH_3$ | $OCH_3$ | N | |
| H | $CH_3$ | H | $CH_2CH_2CF_3$ | $OCH_3$ | Cl | CH | |
| H | $CH_3$ | H | $CH_2(CH_2)_2CF_3$ | $CH_3$ | $CH_3$ | CH | |
| H | $CH_3$ | H | $CH_2(CH_2)_2CF_3$ | $OCH_3$ | $OCH_3$ | CH | |
| H | $CH_3$ | H | $CH_2(CH_2)_2CF_3$ | $CH_3$ | $CH_3$ | N | |
| H | $CH_3$ | H | $CH_2(CH_2)_2CF_3$ | $CH_3$ | $OCH_3$ | N | |
| H | $CH_3$ | H | $CH_2(CH_2)_2CF_3$ | $OCH_3$ | $OCH_3$ | N | |
| H | $CH_3$ | H | $CH_2(CH_2)_3CF_3$ | $OCH_3$ | Cl | CH | |
| H | $CH_3$ | H | $CH_2(CH_2)_3CF_3$ | $CH_3$ | $CH_3$ | CH | |
| H | $CH_3$ | H | $CH_2(CH_2)_3CF_3$ | $CH_3$ | $OCH_3$ | CH | |
| H | $CH_3$ | H | $CH_2(CH_2)_3CF_3$ | $OCH_3$ | $OCH_3$ | CH | |
| H | $CH_3$ | H | $CH_2(CH_2)_3CF_3$ | $CH_3$ | $CH_3$ | N | |
| H | $CH_3$ | H | $CH_2(CH_2)_3CF_3$ | $CH_3$ | $OCH_3$ | N | |
| H | $CH_3$ | $CH_3$ | $CH_2(CH_2)_3CF_3$ | $OCH_3$ | $OCH_3$ | N | |
| H | $CH_3$ | H | $CH(CF_3)_2$ | $OCH_3$ | Cl | CH | |
| H | $CH_3$ | H | $CH(CF_3)_2$ | $CH_3$ | $CH_3$ | CH | |
| H | $CH_3$ | H | $CH(CF_3)_2$ | $CH_3$ | $OCH_3$ | CH | |
| H | $CH_3$ | H | $CH(CF_3)_2$ | $OCH_3$ | $OCH_3$ | CH | |
| H | $CH_3$ | H | $CH(CF_3)_2$ | $CH_3$ | $CH_3$ | N | |
| H | $CH_3$ | H | $CH(CF_3)_2$ | $CH_3$ | $OCH_3$ | N | |
| H | $CH_3$ | H | $CH(CF_3)_2$ | $OCH_3$ | $OCH_3$ | N | |
| H | $CH_3$ | H | $CH_2(CH_2)_4CF_3$ | $OCH_3$ | Cl | CH | |
| H | $CH_3$ | H | $CH_2(CH_2)_5CF_3$ | $CH_3$ | $CH_3$ | CH | |
| $CH_3$ | $CH_3$ | H | $CH_2(CH_2)_6CF_3$ | $CH_3$ | $OCH_3$ | CH | |
| H | $CH_3$ | H | $CH_2(CH_2)_7CF_3$ | $OCH_3$ | $OCH_3$ | CH | |
| H | $CH_3$ | H | $CH_2(CH_2)_8CF_3$ | $CH_3$ | $CH_3$ | N | |
| H | $CH_3$ | H | $CHF(CH_2)_8CF_3$ | $CH_3$ | $OCH_3$ | N | |
| H | $CH_3$ | H | $CH(CHF)_8CF_3$ | $OCH_3$ | $OCH_3$ | N | |
| H | $CH_3$ | H | $CH(CHF)_8CF_3$ | $OCH_3$ | Cl | CH | |
| H | $CH_3$ | H | $CH_2OCH_3$ | $CH_3$ | $CH_3$ | CH | |
| H | $CH_3$ | H | $CH_2OCH_3$ | $CH_3$ | $OCH_3$ | CH | |
| H | $CH_3$ | H | $CH_2OCH_3$ | $OCH_3$ | $OCH_3$ | CH | |
| H | $CH_3$ | H | $CH_2OCH_3$ | $CH_3$ | $CH_3$ | N | |
| H | $CH_3$ | H | $CH_2OCH_3$ | $CH_3$ | $OCH_3$ | N | |
| H | $CH_3$ | H | $CH_2OCH_3$ | $OCH_3$ | $OCH_3$ | N | |
| H | $CH_3$ | H | $CH_2OCH_3$ | $OCH_3$ | Cl | CH | |
| H | $CH_3$ | H | $CH_2OCH_2CH_3$ | $CH_3$ | $CH_3$ | CH | |
| H | $CH_3$ | H | $CH_2OCH_2CH_3$ | $CH_3$ | $OCH_3$ | CH | |
| H | $CH_3$ | H | $CH_2OCH_2CH_3$ | $OCH_3$ | $OCH_3$ | CH | |
| H | $CH_3$ | H | $CH_2—OCH_2F$ | $CH_3$ | $CH_3$ | N | |
| H | $CH_3$ | H | $CH_2—OCH_2F$ | $CH_3$ | $OCH_3$ | N | |
| H | $CH_3$ | H | $CH_2—OCH_2F$ | $OCH_3$ | $OCH_3$ | N | |

TABLE IIa-continued

| R | $R_1$ | $R_2$ | $R_3$ | X | Y | Z | m.p. (°C.) |
|---|---|---|---|---|---|---|---|
| H | $CH_3$ | H | $CH_2$—$OCH_2F$ | $OCH_3$ | Cl | CH | |
| H | $CH_3$ | H | $CH_2$—$CH_2OCH_3$ | $CH_3$ | $CH_3$ | CH | |
| H | $CH_3$ | H | $CH_2$—$CH_2OCH_3$ | $CH_3$ | $OCH_3$ | CH | |
| H | $CH_3$ | H | $CH_2$—$CH_2OCH_3$ | $OCH_3$ | $OCH_3$ | CH | |
| H | $CH_3$ | H | $CH_2$—$CH_2OCH_3$ | $CH_3$ | $CH_3$ | N | |
| H | $CH_3$ | H | $CH(OCH_3)_2$ | $OCH_3$ | $OCH_3$ | N | |
| H | $CH_3$ | H | $CH(OCH_3)_2$ | $OCH_3$ | Cl | CH | |
| H | $CH_3$ | H | $CH_2(CH_2)_2OCH_3$ | $CH_3$ | $CH_3$ | CH | |
| H | $CH_3$ | H | $CH_2(CH_2)_2OCH_3$ | $CH_3$ | $OCH_3$ | CH | |
| H | $CH_3$ | H | $CH_2(CH_2)_2OCH_3$ | $OCH_3$ | $OCH_3$ | CH | |
| H | $CH_3$ | H | $CH_2(CH_2)_2OCH_3$ | $CH_3$ | $CH_3$ | N | |
| H | $CH_3$ | H | $CH_2(CH_2)_2OCH_3$ | $CH_3$ | $OCH_3$ | N | |
| H | $CH_3$ | H | $CH_2(CH_2)_3OCH_3$ | $OCH_3$ | $OCH_3$ | N | |
| H | $CH_3$ | H | $CH_2(CH_2)_3OCH_3$ | $OCH_3$ | Cl | CH | |
| H | $CH_3$ | H | $CH_2(CH_2)_3OCH_3$ | $CH_3$ | $CH_3$ | CH | |
| H | $CH_3$ | H | $CH_2(CH_2)_3OCH_3$ | $CH_3$ | $OCH_3$ | CH | |
| H | $CH_3$ | H | $CH_2(CH_2)_3OCH_3$ | $OCH_3$ | $OCH_3$ | CH | |
| H | $CH_3$ | H | $CH(OCH_3)CH_3$ | $CH_3$ | $CH_3$ | N | |
| H | $CH_3$ | H | $CH(OCH_3)CH_3$ | $CH_3$ | $OCH_3$ | N | |
| H | $CH_3$ | $CH_3$ | $CH(OCH_3)CH_3$ | $OCH_3$ | $OCH_3$ | N | |
| H | $CH_3$ | H | $CH_2OCH_2C\equiv CH_2$ | $OCH_3$ | Cl | CH | |
| H | $CH_3$ | H | $CH_2OCH_2C\equiv CH_2$ | $CH_3$ | $CH_3$ | CH | |
| H | $CH_3$ | H | $CH_2OCH_2C\equiv CH_2$ | $CH_3$ | $OCH_3$ | CH | |
| H | $CH_3$ | H | $CH_2OCH_2C\equiv CH_2$ | $OCH_3$ | $OCH_3$ | CH | |
| H | $CH_3$ | H | $CH_2OCH_2C\equiv CH_2$ | $CH_3$ | $CH_3$ | N | |
| H | $CH_3$ | H | $CH_2OCH_2C\equiv CH_2$ | $CH_3$ | $OCH_3$ | N | |
| H | $CH_3$ | H | $CH_2CH(OCH_3)_2$ | $OCH_3$ | $OCH_3$ | N | |
| H | $CH_3$ | H | $CH_2CH(OCH_3)_2$ | $OCH_3$ | Cl | CH | |
| H | $CH_3$ | H | $CH_2CH(OCH_3)_2$ | $CH_3$ | $CH_3$ | CH | |
| $CH_3$ | $CH_3$ | H | $CH_2CH(OCH_3)_2$ | $CH_3$ | $OCH_3$ | CH | |
| H | $CH_3$ | H | $CH_2C(OCH_3)_2CH_3$ | $OCH_3$ | $OCH_3$ | CH | |
| H | $CH_3$ | H | $CH_2C(OCH_3)_2CH_3$ | $CH_3$ | $CH_3$ | N | |
| H | $CH_3$ | H | $CH_2C(OCH_3)_2CH_3$ | $CH_3$ | $OCH_3$ | N | |
| H | $CH_3$ | H | $CH_2(CH_2)_6OCH_3$ | $OCH_3$ | $OCH_3$ | N | |
| H | $CH_3$ | H | $CH_2(CH_2)_6OCH_3$ | $OCH_3$ | Cl | CH | |
| H | $CH_3$ | H | $CH_2OC(O)CH_3$ | $CH_3$ | $CH_3$ | CH | |
| H | $CH_3$ | H | $CH_2OC(O)CH_3$ | $CH_3$ | $OCH_3$ | CH | |
| H | $CH_3$ | H | $CH_2OC(O)CH_3$ | $OCH_3$ | $OCH_3$ | CH | |
| H | $CH_3$ | H | $CH_2OC(O)CH_3$ | $CH_3$ | $CH_3$ | N | |
| H | $CH_3$ | H | $CH_2OC(O)CH_3$ | $CH_3$ | $OCH_3$ | N | |
| H | $CH_3$ | H | $CH_2OC(O)CH_3$ | $OCH_3$ | $OCH_3$ | N | |
| H | $CH_3$ | H | $CH_2OC(O)CH_3$ | $OCH_3$ | Cl | CH | |
| H | $CH_3$ | H | $CH_2CH_2OC(O)CH_3$ | $CH_3$ | $CH_3$ | CH | |
| H | $CH_3$ | H | $CH_2CH_2OC(O)CH_3$ | $CH_3$ | $OCH_3$ | CH | |
| H | $CH_3$ | H | $CH_2CH_2OC(O)CH_3$ | $OCH_3$ | $OCH_3$ | CH | |
| H | $CH_3$ | H | $CH_2CH_2OC(O)CH_3$ | $CH_3$ | $CH_3$ | N | |
| H | $CH_3$ | H | $CH_2CH_2OC(O)CH_3$ | $CH_3$ | $OCH_3$ | N | |
| H | $CH_3$ | H | $CH_2CH_2OC(O)CH_3$ | $OCH_3$ | $OCH_3$ | N | |
| H | $CH_3$ | H | $CH_2CH_2OC(O)CH_3$ | $OCH_3$ | Cl | CH | |
| H | $CH_3$ | H | $CH_2(CH_2)_2OC(O)CH_3$ | $CH_3$ | $CH_3$ | CH | |
| H | $CH_3$ | H | $CH_2(CH_2)_2OC(O)CH_3$ | $CH_3$ | $OCH_3$ | CH | |
| H | $CH_3$ | H | $CH_2(CH_2)_2OC(O)CH_3$ | $OCH_3$ | $OCH_3$ | CH | |
| H | $CH_3$ | H | $CH_2(CH_2)_3OC(O)CH_3$ | $CH_3$ | $CH_3$ | N | |
| H | $CH_3$ | H | $CH_2(CH_2)_3OC(O)CH_3$ | $OCH_3$ | $OCH_3$ | N | |
| H | $CH_3$ | H | $CH_2(CH_2)_3OC(O)CH_3$ | $OCH_3$ | Cl | CH | |
| H | $CH_3$ | H | $CH_2(CH_2)_3OC(O)CH_3$ | $CH_3$ | $CH_3$ | CH | |
| H | $CH_3$ | H | $CH_2P(CH_3)(Br)(CH_3)$ | $CH_3$ | $OCH_3$ | CH | |
| H | $CH_3$ | H | $CH_2P(C_6H_5)_3$ | $OCH_3$ | $OCH_3$ | CH | |
| H | $CH_3$ | H | $CH_2OC(O)N(CH_3)_2$ | $CH_3$ | $CH_3$ | N | |
| H | $CH_3$ | H | $CH_2OC(O)N(CH_3)_2$ | $CH_3$ | $OCH_3$ | N | |
| H | $CH_3$ | H | $CH_2OC(O)N(CH_3)_2$ | $OCH_3$ | $OCH_3$ | N | |
| H | $CH_3$ | H | $CH_2OC(O)N(CH_3)_2$ | $OCH_3$ | Cl | CH | |
| H | $CH_3$ | H | $CH_2OC(O)N(CH_3)_2$ | $CH_3$ | $CH_3$ | CH | |
| H | $CH_3$ | H | $CH_2OC(O)N(CH_3)_2$ | $CH_3$ | $OCH_3$ | CH | |
| H | $CH_3$ | H | $CH_2OC(O)N(CH_3)_2$ | $OCH_3$ | $OCH_3$ | CH | |
| H | $CH_3$ | H | $CH_2CH_2OC(O)N(CH_3)_2$ | $CH_3$ | $CH_3$ | N | |
| H | $CH_3$ | H | $CH_2CH_2OC(O)N(CH_3)_2$ | $CH_3$ | $OCH_3$ | N | |
| H | $CH_3$ | $CH_3$ | $CH_2CH_2OC(O)N(CH_3)_2$ | $OCH_3$ | $OCH_3$ | N | |
| H | $CH_3$ | H | $CH_2CH_2OC(O)N(CH_3)_2$ | $OCH_3$ | Cl | CH | |
| H | $CH_3$ | H | $CH_2CH_2OC(O)N(CH_3)_2$ | $CH_3$ | $CH_3$ | CH | |
| H | $CH_3$ | H | $CH_2CH_2OC(O)N(CH_3)_2$ | $CH_3$ | $OCH_3$ | CH | |
| H | $CH_3$ | H | $CH_2OSO_2CH_3$ | $OCH_3$ | $OCH_3$ | CH | |
| H | $CH_3$ | H | $CH_2OSO_2CH_3$ | $CH_3$ | $CH_3$ | N | |
| H | $CH_3$ | H | $CH_2OSO_2CH_3$ | $CH_3$ | $OCH_3$ | N | |
| H | $CH_3$ | H | $CH_2OSO_2CH_3$ | $OCH_3$ | $OCH_3$ | N | |
| H | $CH_3$ | H | $CH_2OSO_2CH_2CH_3$ | $OCH_3$ | Cl | CH | |
| H | $CH_3$ | H | $CH_2OSO_2CH_2CH_3$ | $CH_3$ | $CH_3$ | CH | |
| $CH_3$ | $CH_3$ | H | $CH_2OSO_2CH_2CH_3$ | $CH_3$ | $OCH_3$ | CH | |
| H | $CH_3$ | H | $CH_2(CH_2)_2OSO_2CH_3$ | $OCH_3$ | $OCH_3$ | CH | |
| H | $CH_3$ | H | $CH_2(CH_2)_2OSO_2CH_3$ | $CH_3$ | $CH_3$ | N | |
| H | $CH_3$ | H | $CH_2(CH_2)_2OSO_2CH_3$ | $CH_3$ | $OCH_3$ | N | |

TABLE IIa-continued

| R | $R_1$ | $R_2$ | $R_3$ | X | Y | Z | m.p. (°C.) |
|---|---|---|---|---|---|---|---|
| H | $CH_3$ | H | $CH_2(CH_2)_2OSO_2CH_3$ | $OCH_3$ | $OCH_3$ | N | |
| H | $CH_3$ | H | $CH_2(CH_2)_2OSO_2CH_3$ | $OCH_3$ | Cl | CH | |
| H | $CH_3$ | H | $CH_2OP(O)(CH_3)_2$ | $CH_3$ | $CH_3$ | CH | |
| H | $CH_3$ | H | $CH_2OP(O)(CH_3)_2$ | $CH_3$ | $OCH_3$ | CH | |
| H | $CH_3$ | H | $CH_2OP(O)(CH_3)_2$ | $OCH_3$ | $OCH_3$ | CH | |
| H | $CH_3$ | H | $CH_2OP(O)(CH_3)_2$ | $CH_3$ | $CH_3$ | N | |
| H | $CH_3$ | H | $CH_2OP(O)(CH_3)_2$ | $CH_3$ | $OCH_3$ | N | |
| H | $CH_3$ | H | $CH_2OP(O)(CH_3)_2$ | $OCH_3$ | $OCH_3$ | N | |
| H | $CH_3$ | H | $CH_2OP(O)(CH_3)_2$ | $OCH_3$ | Cl | CH | |
| H | $CH_3$ | H | $CH_2OP(O)(CH_3)Ph$ | $CH_3$ | $CH_3$ | CH | |
| H | $CH_3$ | H | $CH_2OP(O)(CH_3)Ph$ | $CH_3$ | $OCH_3$ | CH | |
| H | $CH_3$ | H | $CH_2OP(O)(CH_3)Ph$ | $OCH_3$ | $OCH_3$ | CH | |
| H | $CH_3$ | H | $CH_2OP(O)(CH_3)Ph$ | $CH_3$ | $CH_3$ | N | |
| H | $CH_3$ | H | $CH_2OP(O)(Ph)_2$ | $CH_3$ | $OCH_3$ | N | |
| H | $CH_3$ | H | $CH_2OP(O)(Ph)_2$ | $OCH_3$ | $OCH_3$ | N | |
| H | $CH_3$ | H | $CH_2OP(O)(Ph)_2$ | $OCH_3$ | Cl | CH | |
| H | $CH_3$ | H | $CH_2OP(O)(Ph)_2$ | $CH_3$ | $CH_3$ | CH | |
| H | $CH_3$ | H | $CH_2OP(O)(Ph)_2$ | $CH_3$ | $OCH_3$ | CH | |
| H | $CH_3$ | H | $CH_2OP(O)(Ph)_2$ | $OCH_3$ | $OCH_3$ | CH | |
| H | $CH_3$ | H | $CH_2CH_2OP(O)(CH_3)_2$ | $CH_3$ | $CH_3$ | N | |
| H | $CH_3$ | H | $CH_2CH_2OP(O)(CH_3)_2$ | $OCH_3$ | $OCH_3$ | N | |
| H | $CH_3$ | H | $CH_2CH_2OP(O)(CH_3)_2$ | $OCH_3$ | Cl | CH | |
| H | $CH_3$ | H | $CH_2CH_2OP(O)(CH_3)_2$ | $CH_3$ | $CH_3$ | CH | |
| H | $CH_3$ | H | $CH_2CH_2OP(O)(CH_3)_2$ | $CH_3$ | $OCH_3$ | CH | |
| H | $CH_3$ | H | $CH_2(CH_2)_2OP(O)(CH_3)_2$ | $OCH_3$ | $OCH_3$ | CH | |
| H | $CH_3$ | H | $CH_2(CH_2)_2OP(O)(CH_3)_2$ | $CH_3$ | $CH_3$ | N | |
| H | $CH_3$ | H | $CH_2(CH_2)_2OP(O)(CH_3)_2$ | $CH_3$ | $OCH_3$ | N | |
| H | $CH_3$ | H | $CH_2(CH_2)_2OP(O)(CH_3)_2$ | $OCH_3$ | $OCH_3$ | N | |
| H | $CH_3$ | H | $CH_2(CH_2)_2OP(O)(CH_3)_2$ | $OCH_3$ | Cl | CH | |
| H | $CH_3$ | H | $CH_2P(O)(CH_3)_2$ | $CH_3$ | $OCH_3$ | CH | |
| H | $CH_3$ | H | $CH_2P(O)(CH_3)_2$ | $OCH_3$ | $OCH_3$ | CH | |
| H | $CH_3$ | H | $CH_2P(O)(CH_3)_2$ | $CH_3$ | $CH_3$ | N | |
| H | $CH_3$ | H | $CH_2P(O)(CH_3)_2$ | $CH_3$ | $OCH_3$ | N | |
| H | $CH_3$ | $CH_3$ | $CH_2P(O)(CH_3)_2$ | $OCH_3$ | $OCH_3$ | N | |
| H | $CH_3$ | H | $CH_2P(O)(CH_3)_2$ | $OCH_3$ | Cl | CH | |
| H | $CH_3$ | H | $CH_2P(O)(CH_3)_2$ | $CH_3$ | $CH_3$ | CH | |
| H | $CH_3$ | H | $CH_2P(O)(OCH_3)_2$ | $CH_3$ | $OCH_3$ | CH | |
| H | $CH_3$ | H | $CH_2P(O)(OCH_3)_2$ | $OCH_3$ | $OCH_3$ | CH | |
| H | $CH_3$ | H | $CH_2P(O)(OCH_3)_2$ | $CH_3$ | $CH_3$ | N | |
| H | $CH_3$ | H | $CH_2P(O)(OCH_3)_2$ | $CH_3$ | $OCH_3$ | N | |
| H | $CH_3$ | H | $CH_2P(O)(OCH_3)_2$ | $OCH_3$ | $OCH_3$ | N | |
| H | $CH_3$ | H | $CH_2P(O)(OCH_3)_2$ | $OCH_3$ | Cl | CH | |
| H | $CH_3$ | H | $CH_2P(O)(OCH_3)_2$ | $CH_3$ | $CH_3$ | CH | |
| $CH_3$ | $CH_3$ | H | $CH_2CH_2P(O)(OCH_2CH_3)_2$ | $CH_3$ | $OCH_3$ | CH | |
| H | $CH_3$ | H | $CH_2CH_2P(O)(OCH_2CH_3)_2$ | $OCH_3$ | $OCH_3$ | CH | |
| H | $CH_3$ | H | $CH_2(CH_2)_3P(O)(OCH_3)_2$ | $CH_3$ | $CH_3$ | N | |
| H | $CH_3$ | H | $CH_2(CH_2)_3P(O)(OCH_3)_2$ | $CH_3$ | $OCH_3$ | N | |
| H | $CH_3$ | H | $CH_2(CH_2)_3P(O)(OCH_3)_2$ | $OCH_3$ | $OCH_3$ | N | |
| H | $CH_3$ | H | $CH_2(CH_2)_3P(O)(OCH_3)_2$ | $OCH_3$ | Cl | CH | |
| H | $CH_3$ | H | $CH_2OP(S)(CH_3)_2$ | $CH_3$ | $CH_3$ | CH | |
| H | $CH_3$ | H | $CH_2OP(S)(CH_3)_2$ | $CH_3$ | $OCH_3$ | CH | |
| H | $CH_3$ | H | $CH_2OP(S)(CH_3)_2$ | $OCH_3$ | $OCH_3$ | CH | |
| H | $CH_3$ | H | $CH_2OP(S)(CH_3)_2$ | $CH_3$ | $CH_3$ | N | |
| H | $CH_3$ | H | $CH_2OP(S)(CH_3)_2$ | $CH_3$ | $OCH_3$ | N | |
| H | $CH_3$ | H | $CH_2OP(S)(CH_3)_2$ | $OCH_3$ | $OCH_3$ | N | |
| H | $CH_3$ | H | $CH_2OP(S)(CH_3)_2$ | $OCH_3$ | Cl | CH | |
| H | $CH_3$ | H | $CH_2OP(S)(OCH_3)_2$ | $CH_3$ | $CH_3$ | CH | |
| H | $CH_3$ | H | $CH_2OP(S)(OCH_3)_2$ | $CH_3$ | $OCH_3$ | CH | |
| H | $CH_3$ | H | $CH_2OP(S)(OCH_3)_2$ | $OCH_3$ | $OCH_3$ | CH | |
| H | $CH_3$ | H | $CH_2OP(S)(OCH_3)_2$ | $CH_3$ | $CH_3$ | N | |
| H | $CH_3$ | H | $CH_2OP(S)(OCH_3)_2$ | $CH_3$ | $OCH_3$ | N | |
| H | $CH_3$ | H | $CH_2OP(S)(OCH_3)_2$ | $OCH_3$ | $OCH_3$ | N | |
| H | $CH_3$ | H | $CH_2OP(S)(OCH_3)_2$ | $OCH_3$ | Cl | CH | |
| H | $CH_3$ | H | $CH_2P(S)(CH_3)_2$ | $CH_3$ | $CH_3$ | CH | |
| H | $CH_3$ | H | $CH_2P(S)(CH_3)_2$ | $CH_3$ | $OCH_3$ | CH | |
| H | $CH_3$ | H | $CH_2P(S)(CH_3)_2$ | $OCH_3$ | $OCH_3$ | CH | |
| H | $CH_3$ | H | $CH_2P(S)(CH_3)_2$ | $CH_3$ | $CH_3$ | N | |
| H | $CH_3$ | H | $CH_2P(S)(CH_3)_2$ | $OCH_3$ | $OCH_3$ | N | |
| H | $CH_3$ | H | $CH_2P(S)(CH_3)_2$ | $OCH_3$ | Cl | CH | |
| H | $CH_3$ | H | $CH_2P(S)(OCH_3)_2$ | $CH_3$ | $CH_3$ | CH | |
| H | $CH_3$ | H | $CH_2P(S)(OCH_3)_2$ | $OCH_3$ | $OCH_3$ | CH | |
| H | $CH_3$ | H | $CH_2P(S)(OCH_3)_2$ | $CH_3$ | $CH_3$ | N | |
| H | $CH_3$ | H | $CH_2P(S)(OCH_3)_2$ | $CH_3$ | $OCH_3$ | N | |
| H | $CH_3$ | H | $CH_2P(S)(OCH_3)_2$ | $OCH_3$ | $OCH_3$ | N | |
| H | $CH_3$ | H | $CH_2P(S)(OCH_3)_2$ | $OCH_3$ | Cl | CH | |
| H | $CH_3$ | H | $CH_2CH_2OP(S)(CH_3)_2$ | $CH_3$ | $CH_3$ | CH | |
| H | $CH_3$ | H | $CH_2CH_2OP(S)(CH_3)_2$ | $CH_3$ | $OCH_3$ | CH | |
| H | $CH_3$ | H | $CH_2CH_2OP(S)(CH_3)_2$ | $OCH_3$ | $OCH_3$ | CH | |
| H | $CH_3$ | H | $CH_2CH_2OP(S)(CH_3)_2$ | $CH_3$ | $CH_3$ | N | |

TABLE IIa-continued

| R | R₁ | R₂ | R₃ | X | Y | Z | m.p. (°C.) |
|---|---|---|---|---|---|---|---|
| H | CH₃ | H | CH₂CH₂OP(S)(CH₃)₂ | CH₃ | OCH₃ | N | |
| H | CH₃ | CH₃ | CH₂CH₂OP(S)(CH₃)₂ | OCH₃ | OCH₃ | N | |
| H | CH₃ | H | CH₂CH₂OP(S)(CH₃)₂ | OCH₃ | Cl | CH | |
| H | CH₃ | H | CH₂CH₂P(S)(OCH₃)₂ | CH₃ | CH₃ | CH | |
| H | CH₃ | H | CH₂CH₂P(S)(OCH₃)₂ | CH₃ | OCH₃ | CH | |
| H | CH₃ | H | CH₂CH₂P(S)(OCH₃)₂ | OCH₃ | OCH₃ | CH | |
| H | CH₃ | H | CH₂CH₂P(S)(OCH₃)₂ | CH₃ | CH₃ | N | |
| H | CH₃ | H | CH₂CH₂P(S)(OCH₃)₂ | CH₃ | OCH₃ | N | |
| H | CH₃ | H | CH₂CH₂P(S)(OCH₃)₂ | OCH₃ | OCH₃ | N | |
| H | CH₃ | H | CH₂CH₂P(S)(OCH₃)₂ | OCH₃ | Cl | CH | |
| H | CH₃ | H | CH₂(CH₂)₃OP(S)(CH₃)₂ | CH₃ | CH₃ | CH | |
| CH₃ | CH₃ | H | CH₂(CH₂)₃OP(S)(CH₃)₂ | CH₃ | OCH₃ | CH | |
| H | CH₃ | H | CH₂(CH₂)₃OP(S)(CH₃)₂ | OCH₃ | OCH₃ | CH | |
| H | CH₃ | H | CH₂(CH₂)₃OP(S)(CH₃)₂ | CH₃ | CH₃ | N | |
| H | CH₃ | H | CH₂(CH₂)₃OP(S)(CH₃)₂ | CH₃ | OCH₃ | N | |
| H | CH₃ | H | CH₂(CH₂)₃OP(S)(CH₃)₂ | OCH₃ | OCH₃ | N | |
| H | CH₃ | H | CH₂(CH₂)₃OP(S)(CH₃)₂ | OCH₃ | Cl | CH | |
| H | CH₃ | H | CH₂OSi(CH₃)₃ | CH₃ | CH₃ | CH | |
| H | CH₃ | H | CH₂OSi(CH₃)₃ | CH₃ | OCH₃ | CH | |
| H | CH₃ | H | CH₂OSi(CH₃)₃ | OCH₃ | OCH₃ | CH | |
| H | CH₃ | H | CH₂OSi(CH₃)₃ | CH₃ | CH₃ | N | |
| H | CH₃ | H | CH₂OSi(CH₃)₃ | CH₃ | OCH₃ | N | |
| H | CH₃ | H | CH₂OSi(CH₃)₃ | OCH₃ | OCH₃ | N | |
| H | CH₃ | H | CH₂OSi(CH₃)₃ | OCH₃ | Cl | CH | |
| H | CH₃ | H | CH₂CH₂OSi(CH₃)₃ | CH₃ | CH₃ | CH | |
| H | CH₃ | H | CH₂CH₂OSi(CH₃)₃ | CH₃ | OCH₃ | CH | |
| H | CH₃ | H | CH₂CH₂OSi(CH₃)₃ | OCH₃ | OCH₃ | CH | |
| H | CH₃ | H | CH₂CH₂OSi(CH₃)₃ | CH₃ | CH₃ | N | |
| H | CH₃ | H | CH₂CH₂OSi(CH₃)₃ | CH₃ | OCH₃ | N | |
| H | CH₃ | H | CH₂CH₂OSi(CH₃)₃ | OCH₃ | OCH₃ | N | |
| H | CH₃ | H | CH₂CH₂OSi(CH₃)₃ | OCH₃ | Cl | CH | |
| H | CH₃ | H | CH₂(CH₂)₂OSi(CH₃)₃ | CH₃ | CH₃ | CH | |
| H | CH₃ | H | CH₂(CH₂)₂OSi(CH₃)₃ | CH₃ | OCH₃ | CH | |
| H | CH₃ | H | CH₂(CH₂)₂OSi(CH₃)₃ | OCH₃ | OCH₃ | CH | |
| H | CH₃ | H | CH₂(CH₂)₂OSi(CH₃)₃ | CH₃ | CH₃ | N | |
| H | CH₃ | H | CH₂(CH₂)₂OSi(CH₃)₃ | OCH₃ | OCH₃ | N | |
| H | CH₃ | H | CH₂(CH₂)₂OSi(CH₃)₃ | OCH₃ | Cl | CH | |
| H | CH₃ | H | CH₂(CH₂)₃OSi(CH₃)₃ | CH₃ | CH₃ | CH | |
| H | CH₃ | H | CH₂(CH₂)₃OSi(CH₃)₃ | CH₃ | OCH₃ | CH | |
| H | CH₃ | H | CH₂(CH₂)₃OSi(CH₃)₃ | OCH₃ | OCH₃ | CH | |
| H | CH₃ | H | CH₂(CH₂)₃OSi(CH₃)₃ | CH₃ | CH₃ | N | |
| H | CH₃ | H | CH₂(CH₂)₃OSi(CH₃)₃ | CH₃ | OCH₃ | N | |
| H | CH₃ | H | CH₂(CH₂)₃OSi(CH₃)₃ | OCH₃ | OCH₃ | N | |
| H | CH₃ | H | CH₂(CH₂)₃OSi(CH₃)₃ | OCH₃ | Cl | CH | |
| H | CH₃ | H | CH₂(CH₂)₄OSi(CH₃)₃ | CH₃ | CH₃ | CH | |
| H | CH₃ | H | CH₂(CH₂)₅OSi(CH₃)₃ | CH₃ | OCH₃ | CH | |
| H | CH₃ | H | CH₂(CH₂)₆OSi(CH₃)₃ | OCH₃ | OCH₃ | CH | |
| H | CH₃ | H | CH₂(CH₂)₇OSi(CH₃)₃ | CH₃ | CH₃ | N | |
| H | CH₃ | H | CH₂OSi(CH₂CH₃)₃ | CH₃ | OCH₃ | N | |
| H | CH₃ | CH₃ | CH₂OSi(CH₃)₂(Ph) | OCH₃ | OCH₃ | N | |
| H | CH₃ | H | CH(CH₃)OSi(CH₃)₃ | OCH₃ | Cl | CH | |
| H | CH₃ | H | CH(CH₃)OSi(CH₃)₃ | CH₃ | CH₃ | CH | |
| H | CH₃ | H | CH(CH₃)OSi(CH₃)₃ | CH₃ | OCH₃ | CH | |
| H | CH₃ | H | CH(CH₃)OSi(CH₃)₃ | OCH₃ | OCH₃ | CH | |
| H | CH₃ | H | CH(CH₃)OSi(CH₃)₃ | CH₃ | CH₃ | N | |
| H | CH₃ | H | CH₂Si(CH₃)₃ | CH₃ | OCH₃ | N | |
| H | CH₃ | H | CH₂Si(CH₃)₃ | OCH₃ | OCH₃ | N | |
| H | CH₃ | H | CH₂Si(CH₃)₃ | OCH₃ | Cl | CH | |
| H | CH₃ | H | CH₂Si(CH₃)₃ | CH₃ | CH₃ | CH | |
| CH₃ | CH₃ | H | CH₂Si(CH₃)₃ | CH₃ | OCH₃ | CH | |
| H | CH₃ | H | CH₂Si(CH₃)₃ | OCH₃ | OCH₃ | CH | |
| H | CH₃ | H | CH₂Si(CH₃)₃ | CH₃ | CH₃ | N | |
| H | CH₃ | H | CH₂CH₂Si(CH₃)₃ | CH₃ | OCH₃ | N | |
| H | CH₃ | H | CH₂CH₂Si(CH₃)₃ | OCH₃ | OCH₃ | N | |
| H | CH₃ | H | CH₂CH₂Si(CH₃)₃ | OCH₃ | Cl | CH | |
| H | CH₃ | H | CH₂(CH₂)₂Si(CH₃)₃ | CH₃ | CH₃ | CH | |
| H | CH₃ | H | CH₂(CH₂)₂Si(CH₃)₃ | CH₃ | OCH₃ | CH | |
| H | CH₃ | H | CH₂(CH₂)₂Si(CH₃)₃ | OCH₃ | OCH₃ | CH | |
| H | CH₃ | H | CH₂(CH₂)₂Si(CH₃)₃ | CH₃ | CH₃ | N | |
| H | CH₃ | H | CH₂(CH₂)₂Si(CH₃)₃ | CH₃ | OCH₃ | N | |
| H | CH₃ | H | CH₂(CH₂)₂Si(CH₃)₃ | OCH₃ | OCH₃ | N | |
| H | CH₃ | H | CH₂(CH₂)₂Si(CH₃)₃ | OCH₃ | Cl | CH | |
| H | CH₃ | H | C(Si(CH₃)₃)(CH₃)₂ | CH₃ | CH₃ | CH | |
| H | CH₃ | H | C(Si(CH₃)₃)(CH₃)₂ | CH₃ | OCH₃ | CH | |
| H | CH₃ | H | C(Si(CH₃)₃)(CH₃)₂ | OCH₃ | OCH₃ | CH | |
| H | CH₃ | H | C(Si(CH₃)₃)(CH₃)₂ | CH₃ | CH₃ | N | |
| H | CH₃ | H | C(Si(CH₃)₃)(CH₃)₂ | CH₃ | OCH₃ | N | |
| H | CH₃ | H | C(Si(CH₃)₃)(CH₃)₂ | OCH₃ | OCH₃ | N | |
| H | CH₃ | H | C(Si(CH₃)₃)(CH₃)₂ | OCH₃ | Cl | CH | |
| H | CH₃ | H | CH₂SCH₃ | CH₃ | CH₃ | CH | |
| H | CH₃ | H | CH₂SCH₃ | CH₃ | OCH₃ | CH | |

TABLE IIa-continued

| R | R₁ | R₂ | R₃ | X | Y | Z | m.p. (°C.) |
|---|---|---|---|---|---|---|---|
| H | CH₃ | H | CH₂SCH₃ | OCH₃ | OCH₃ | CH | |
| H | CH₃ | H | CH₂SCH₃ | CH₃ | CH₃ | N | |
| H | CH₃ | H | CH₂SCH₃ | OCH₃ | OCH₃ | N | |
| H | CH₃ | H | CH₂SCH₃ | OCH₃ | Cl | CH | |
| H | CH₃ | H | CH₂SCH₂CH₃ | CH₃ | CH₃ | CH | |
| H | CH₃ | H | CH₂CH₂SCH₃ | CH₃ | OCH₃ | CH | |
| H | CH₃ | H | CH₂CH₂SCH₃ | OCH₃ | OCH₃ | CH | |
| H | CH₃ | H | CH₂CH₂SCH₃ | CH₃ | CH₃ | N | |
| H | CH₃ | H | CH₂CH₂SCH₃ | CH₃ | OCH₃ | N | |
| H | CH₃ | H | CH₂CH₂SCH₃ | OCH₃ | OCH₃ | CH | |
| H | CH₃ | H | CH₂CH₂SCH₃ | OCH₃ | Cl | CH | |
| H | CH₃ | H | CH₂CH₂SCH₃ | CH₃ | CH₃ | CH | |
| H | CH₃ | H | CH₂(CH₂)₂SCH₃ | CH₃ | OCH₃ | CH | |
| H | CH₃ | H | CH₂(CH₂)₂SCH₃ | OCH₃ | OCH₃ | CH | |
| H | CH₃ | H | CH₂(CH₂)₂SCH₃ | CH₃ | CH₃ | N | |
| H | CH₃ | H | CH₂(CH₂)₂SCH₃ | CH₃ | OCH₃ | N | |
| H | CH₃ | CH₃ | CH₂(CH₂)₂SCH₃ | OCH₃ | OCH₃ | N | |
| H | CH₃ | H | CH₂(CH₂)₂SCH₃ | OCH₃ | Cl | CH | |
| H | CH₃ | H | CH₂(CH₂)₃SCH₃ | CH₃ | CH₃ | CH | |
| H | CH₃ | H | CH₂(CH₂)₃SCH₃ | CH₃ | OCH₃ | CH | |
| H | CH₃ | H | CH₂(CH₂)₃SCH₃ | OCH₃ | OCH₃ | CH | |
| H | CH₃ | H | CH₂(CH₂)₃SCH₃ | CH₃ | CH₃ | N | |
| H | CH₃ | H | CH₂(CH₂)₃SCH₃ | CH₃ | OCH₃ | N | |
| H | CH₃ | H | CH₂(CH₂)₃SCH₃ | OCH₃ | OCH₃ | N | |
| H | CH₃ | H | CH(CH₃)SCH₃ | OCH₃ | Cl | CH | |
| H | CH₃ | H | CH(CH₃)SCH₃ | CH₃ | CH₃ | CH | |
| CH₃ | CH₃ | H | CH(CH₃)SCH₃ | CH₃ | OCH₃ | CH | |
| H | CH₃ | H | CH(SCH₃)₂ | OCH₃ | OCH₃ | CH | |
| H | CH₃ | H | CH₂CH(CH₃)SCH₃ | CH₃ | CH₃ | N | |
| H | CH₃ | H | CH₂CH(CH₃)SCH₃ | CH₃ | OCH₃ | N | |
| H | CH₃ | H | CH₂(CH₂)₈SCH₃ | OCH₃ | OCH₃ | N | |
| H | CH₃ | H | CH₂(CH₂)₈SCH₃ | OCH₃ | Cl | CH | |
| H | CH₃ | H | CH₂SOCH₃ | CH₃ | CH₃ | CH | |
| H | CH₃ | H | CH₂SOCH₃ | CH₃ | OCH₃ | CH | |
| H | CH₃ | H | CH₂SOCH₃ | OCH₃ | OCH₃ | CH | |
| H | CH₃ | H | CH₂SOCH₃ | CH₃ | CH₃ | N | |
| H | CH₃ | H | CH₂SOCH₃ | CH₃ | OCH₃ | N | |
| H | CH₃ | H | CH₂SOCH₃ | OCH₃ | OCH₃ | N | |
| H | CH₃ | H | CH₂SOCH₃ | OCH₃ | Cl | CH | |
| H | CH₃ | H | CH₂CH₂SOCH₃ | CH₃ | CH₃ | CH | |
| H | CH₃ | H | CH₂CH₂SOCH₃ | CH₃ | OCH₃ | CH | |
| H | CH₃ | H | CH₂CH₂SOCH₃ | OCH₃ | OCH₃ | CH | |
| H | CH₃ | H | CH₂CH₂SOCH₃ | CH₃ | CH₃ | N | |
| H | CH₃ | H | CH₂CH₂SOCH₃ | CH₃ | OCH₃ | N | |
| H | CH₃ | H | CH₂CH₂SOCH₃ | OCH₃ | OCH₃ | N | |
| H | CH₃ | H | CH₂CH₂SOCH₃ | OCH₃ | Cl | CH | |
| H | CH₃ | H | CH₂(CH₂)₃SOCH₃ | CH₃ | CH₃ | CH | |
| H | CH₃ | H | CH₂(CH₂)₃SOCH₃ | CH₃ | OCH₃ | CH | |
| H | CH₃ | H | CH₂(CH₂)₃SOCH₃ | OCH₃ | OCH₃ | CH | |
| H | CH₃ | H | CH₂(CH₂)₃SOCH₃ | CH₃ | CH₃ | N | |
| H | CH₃ | H | CH₂(CH₂)₃SOCH₃ | OCH₃ | OCH₃ | N | |
| H | CH₃ | H | CH₂(CH₂)₃SOCH₃ | OCH₃ | Cl | CH | |
| H | CH₃ | H | CH₂SO₂CH₃ | CH₃ | CH₃ | CH | |
| H | CH₃ | H | CH₂SO₂CH₃ | CH₃ | OCH₃ | CH | |
| H | CH₃ | H | CH₂SO₂CH₃ | OCH₃ | OCH₃ | CH | |
| H | CH₃ | H | CH₂SO₂CH₃ | CH₃ | CH₃ | N | |
| H | CH₃ | H | CH₂SO₂CH₃ | CH₃ | OCH₃ | N | |
| H | CH₃ | H | CH₂SO₂CH₃ | OCH₃ | OCH₃ | N | |
| H | CH₃ | H | CH₂SO₂CH₃ | OCH₃ | Cl | CH | |
| H | CH₃ | H | CH₂CH₂SO₂CH₃ | CH₃ | CH₃ | CH | |
| H | CH₃ | H | CH₂CH₂SO₂CH₃ | CH₃ | OCH₃ | CH | |
| H | CH₃ | H | CH₂CH₂SO₂CH₃ | OCH₃ | OCH₃ | CH | |
| H | CH₃ | H | CH₂CH₂SO₂CH₃ | CH₃ | CH₃ | N | |
| H | CH₃ | H | CH₂CH₂SO₂CH₃ | CH₃ | OCH₃ | N | |
| H | CH₃ | CH₃ | CH₂CH₂SO₂CH₃ | OCH₃ | OCH | N | |
| H | CH₃ | H | CH₂CH₂SO₂CH₃ | OCH₃ | Cl | CH | |
| H | CH₃ | H | CH₂(CH₂)₃SO₂CH₃ | CH₃ | CH₃ | CH | |
| H | CH₃ | H | CH₂(CH₂)₃SO₂CH₃ | CH₃ | OCH₃ | CH | |
| H | CH₃ | H | CH₂(CH₂)₃SO₂CH₃ | OCH₃ | OCH₃ | CH | |
| H | CH₃ | H | CH₂(CH₂)₃SO₂CH₃ | CH₃ | CH₃ | N | |
| H | CH₃ | H | CH₂(CH₂)₃SO₂CH₃ | CH₃ | OCH₃ | N | |
| H | CH₃ | CH₃ | CH₂(CH₂)₃SO₂CH₃ | OCH₃ | OCH₃ | N | |
| H | CH₃ | H | CH₂(CH₂)₃SO₂CH₃ | OCH₃ | Cl | CH | |
| H | CH₃ | H | CH₂SOCH₂CH₃ | CH₃ | CH₃ | CH | |
| CH₃ | CH₃ | H | CH₂SOCH₂CH₃ | CH₃ | OCH₃ | CH | |
| H | CH₃ | H | CH₂SO₂CH₂CH₃ | OCH₃ | OCH₃ | CH | |
| H | CH₃ | H | CH₂(CH₂)₆SOCH₃ | CH₃ | CH₃ | N | |
| H | CH₃ | H | CH₂(CH₂)₆SOCH₃ | CH₃ | OCH₃ | N | |
| H | CH₃ | H | CH₂(CH₂)₄SO₂CH₃ | OCH₃ | OCH₃ | N | |
| H | CH₃ | H | CH₂(CH₂)₄SO₂CH₃ | OCH₃ | Cl | CH | |
| H | CH₃ | H | CH₂SCN | CH₃ | CH₃ | CH | |

TABLE IIa-continued

| R | R₁ | R₂ | R₃ | X | Y | Z | m.p. (°C.) |
|---|---|---|---|---|---|---|---|
| H | CH₃ | H | CH₂SCN | CH₃ | OCH₃ | CH | |
| H | CH₃ | H | CH₂SCN | OCH₃ | OCH₃ | CH | |
| H | CH₃ | H | CH₂SCN | CH₃ | CH₃ | N | |
| H | CH₃ | H | CH₂SCN | CH₃ | OCH₃ | N | |
| H | CH₃ | H | CH₂SCN | OCH₃ | OCH₃ | N | |
| H | CH₃ | H | CH₂SCN | OCH₃ | Cl | CH | |
| H | CH₃ | H | CH₂CH₂SCN | CH₃ | CH₃ | CH | |
| H | CH₃ | H | CH₂CH₂SCN | CH₃ | OCH₃ | CH | |
| H | CH₃ | H | CH₂CH₂SCN | OCH₃ | OCH₃ | CH | |
| H | CH₃ | H | CH₂CH₂SCN | CH₃ | CH₃ | N | |
| H | CH₃ | H | CH₂CH₂SCN | CH₃ | OCH₃ | N | |
| H | CH₃ | H | CH₂CH₂SCN | OCH₃ | OCH₃ | N | |
| H | CH₃ | H | CH₂CH₂SCN | OCH₃ | Cl | CH | |
| H | CH₃ | H | CH₂(CH₂)₂SCN | CH₃ | CH₃ | CH | |
| H | CH₃ | H | CH₂(CH₂)₂SCN | CH₃ | OCH₃ | CH | |
| H | CH₃ | H | CH₂(CH₂)₂SCN | OCH₃ | OCH₃ | CH | |
| H | CH₃ | H | CH₂(CH₂)₂SCN | CH₃ | CH₃ | N | |
| H | CH₃ | H | CH₂(CH₂)₂SCN | OCH₃ | OCH₃ | N | |
| H | CH₃ | H | CH₂(CH₂)₂SCN | OCH₃ | Cl | CH | |
| H | CH₃ | H | CH₂(CH₂)₃SCN | CH₃ | CH₃ | CH | |
| H | CH₃ | H | CH₂(CH₂)₃SCN | CH₃ | OCH₃ | CH | |
| H | CH₃ | H | CH₂(CH₂)₃SCN | OCH₃ | OCH₃ | CH | |
| H | CH₃ | H | CH₂(CH₂)₃SCN | CH₃ | CH₃ | N | |
| H | CH₃ | H | CH₂(CH₂)₃SCN | CH₃ | OCH₃ | N | |
| H | CH₃ | H | CH₂(CH₂)₃SCN | OCH₃ | OCH₃ | N | |
| H | CH₃ | H | CH₂(CH₂)₃SCN | OCH₃ | Cl | CH | |
| H | CH₃ | H | CH₂CHFSCN | CH₃ | CH₃ | CH | |
| H | CH₃ | H | CH(CF₃)SCN | CH₃ | OCH₃ | CH | |
| H | CH₃ | H | CH₂(CH₂)₅SCN | OCH₃ | OCH₃ | CH | |
| H | CH₃ | H | CH₂CN | CH₃ | CH₃ | N | |
| H | CH₃ | H | CH₂CN | CH₃ | OCH₃ | N | |
| H | CH₃ | CH₃ | CH₂CN | OCH₃ | OCH₃ | N | |
| H | CH₃ | H | CH₂CN | OCH₃ | Cl | CH | |
| H | CH₃ | H | CH₂CN | CH₃ | CH₃ | CH | |
| H | CH₃ | H | CH₂CN | CH₃ | OCH₃ | CH | |
| H | CH₃ | H | CH₂CH₂CN | OCH₃ | OCH₃ | CH | |
| H | CH₃ | H | CH₂CH₂CN | CH₃ | CH₃ | N | |
| H | CH₃ | H | CH₂CH₂CN | CH₃ | OCH₃ | N | |
| H | CH₃ | H | CH₂CH₂CN | OCH₃ | OCH₃ | N | |
| H | CH₃ | H | CH₂CH₂CN | OCH₃ | Cl | CH | |
| H | CH₃ | H | CH₂CH₂CN | CH₃ | CH₃ | CH | |
| CH₃ | CH₃ | H | CH₂CH₂CN | CH₃ | OCH₃ | CH | |
| H | CH₃ | H | CH₂CH₂CN | OCH₃ | OCH₃ | CH | |
| H | CH₃ | H | CH₂(CH₂)₃CN | CH₃ | CH₃ | N | |
| H | CH₃ | H | CH₂(CH₂)₃CN | CH₃ | OCH₃ | N | |
| H | CH₃ | H | CH₂(CH₂)₃CN | OCH₃ | OCH₃ | N | |
| H | CH₃ | H | CH₂(CH₂)₃CN | OCH₃ | Cl | CH | |
| H | CH₃ | H | CH₂(CH₂)₄CN | CH₃ | CH₃ | CH | |
| H | CH₃ | H | CH₂(CH₂)₂CH(CN)₂ | CH₃ | OCH₃ | CH | |
| H | CH₃ | H | CH(CH₃)CH₂CN | OCH₃ | OCH₃ | CH | |
| H | CH₃ | H | CH(CH₃)CH₂CN | CH₃ | CH₃ | N | |
| H | CH₃ | H | CH(CH₃)CH₂CN | CH₃ | OCH₃ | N | |
| H | CH₃ | H | CH(CH₃)CH₂CN | OCH₃ | OCH₃ | N | |
| H | CH₃ | H | CH(CH₃)CH₂CN | OCH₃ | Cl | CH | |
| H | CH₃ | H | CH₂SP(O)(CH₃)₂ | CH₃ | CH₃ | CH | |
| H | CH₃ | H | CH₂SP(O)(CH₃)₂ | CH₃ | OCH₃ | CH | |
| H | CH₃ | H | CH₂SP(O)(CH₃)₂ | OCH₃ | OCH₃ | CH | |
| H | CH₃ | H | CH₂CH₂SP(O)(CH₃)₂ | CH₃ | CH₃ | N | |
| H | CH₃ | H | CH₂CH₂SP(O)(CH₃)₂ | CH₃ | OCH₃ | N | |
| H | CH₃ | H | CH₂CH₂SP(O)(CH₃)₂ | OCH₃ | OCH₃ | N | |
| H | CH₃ | H | CH₂P(S)(CH₃)₂ | OCH₃ | Cl | CH | |
| H | CH₃ | H | CH₂P(S)(CH₃)₂ | CH₃ | CH₃ | CH | |
| H | CH₃ | H | CH₂P(S)(CH₃)₂ | CH₃ | OCH₃ | CH | |
| H | CH₃ | H | CH₂—P(S)(CH₃)₂ | OCH₃ | OCH₃ | CH | |
| H | CH₃ | H | CH₂—P(S)(CH₃)₂ | CH₃ | CH₃ | N | |
| H | CH₃ | H | CH₂—P(S)(CH₃)₂ | OCH₃ | OCH₃ | N | |
| H | CH₃ | H | CH₂—P(S)(CH₃)₂ | OCH₃ | Cl | CH | |
| H | CH₃ | H | CH₂—P(S)(CH₃)₂ | CH₃ | CH₃ | CH | |
| H | CH₃ | H | CH₂N(CH₃)₂ | CH₃ | OCH₃ | CH | |
| H | CH₃ | H | CH₂N(CH₃)₂ | OCH₃ | OCH₃ | CH | |
| H | CH₃ | H | CH₂N(CH₃)₂ | CH₃ | CH₃ | N | |
| H | CH₃ | H | CH₂N(CH₃)₂ | CH₃ | OCH₃ | N | |
| H | CH₃ | H | CH₂N(CH₃)₂ | OCH₃ | OCH₃ | N | |
| H | CH₃ | H | CH₂N(CH₃)₂ | OCH₃ | Cl | CH | |
| H | CH₃ | H | CH₂N(CH₃)₂ | CH₃ | CH₃ | CH | |
| H | CH₃ | H | CH₂(CH₂)₃N(CH₃)₂ | CH₃ | OCH₃ | CH | |
| H | CH₃ | H | CH₂(CH₂)₃N(CH₃)₂ | OCH₃ | OCH₃ | CH | |
| H | CH₃ | H | CH₂(CH₂)₃N(CH₃)₂ | CH₃ | CH₃ | N | |
| H | CH₃ | H | CH₂(CH₂)₃N(CH₃)₂ | CH₃ | OCH₃ | N | |
| H | CH₃ | CH₃ | CH₂(CH₂)₃N(CH₃)₂ | OCH₃ | OCH₃ | N | |
| H | CH₃ | H | CH₂(CH₂)₃N(CH₃)₂ | OCH₃ | Cl | CH | |

TABLE IIa-continued

| R | R₁ | R₂ | R₃ | X | Y | Z | m.p. (°C.) |
|---|---|---|---|---|---|---|---|
| H | CH₃ | H | CH₂(CH₂)₃N(CH₃)₂ | CH₃ | CH₃ | CH | |
| H | CH₃ | H | CH₂N(CH₃)₂Ph | CH₃ | OCH₃ | CH | |
| H | CH₃ | H | CH₂N(CH₃)₂Ph | OCH₃ | OCH₃ | CH | |
| H | CH₃ | H | CH₂N(CH₃)₂Ph | CH₃ | CH₃ | N | |
| H | CH₃ | H | CH₂N(CH₃)₂Ph | CH₃ | OCH₃ | N | |
| H | CH₃ | H | CH₂—CH(CH₃)N(CH₃)₂ | OCH₃ | OCH₃ | N | |
| H | CH₃ | H | CH₂—CH(CH₃)N(CH₃)₂ | OCH₃ | Cl | CH | |
| H | CH₃ | H | CH₂—CH(CH₃)N(CH₃)₂ | CH₃ | CH₃ | CH | |
| CH₃ | CH₃ | H | CH₂—CH(CH₃)N(CH₃)₂ | CH₃ | OCH₃ | CH | |
| H | CH₃ | H | CH₂—CH(CH₃)N(CH₃)₂ | OCH₃ | OCH₃ | CH | |
| H | CH₃ | H | CH₂CH₂CH(CH₃)₂ | CH₃ | CH₃ | N | |
| H | CH₃ | H | CH₂CH₂CH(CH₃)₂ | CH₃ | OCH₃ | N | |
| H | CH₃ | H | CH₂CH₂CH(CH₃)₂ | OCH₃ | OCH₃ | N | |
| H | CH₃ | H | CH₂CH₂CH(CH₃)₂ | OCH₃ | Cl | CH | |
| H | CH₃ | H | CH₂NHC(O)CH₃ | CH₃ | CH₃ | CH | |
| H | CH₃ | H | CH₂NHC(O)CH₃ | CH₃ | OCH₃ | CH | |
| H | CH₃ | H | CH₂NHC(O)CH₃ | OCH₃ | OCH₃ | CH | |
| H | CH₃ | H | CH₂NHC(O)CH₃ | CH₃ | CH₃ | N | |
| H | CH₃ | H | CH₂NHC(O)CH₃ | CH₃ | OCH₃ | N | |
| H | CH₃ | H | CH₂NHC(O)CH₃ | OCH₃ | OCH₃ | N | |
| H | CH₃ | H | CH₂NHC(O)CH₃ | OCH₃ | Cl | CH | |
| H | CH₃ | H | CH₂CH₂N(CH₃)C(O)CH₃ | CH₃ | CH₃ | CH | |
| H | CH₃ | H | CH₂CH₂N(CH₃)C(O)CH₃ | CH₃ | OCH₃ | CH | |
| H | CH₃ | H | CH₂CH₂N(CH₃)C(O)CH₃ | OCH₃ | OCH₃ | CH | |
| H | CH₃ | H | CH₂CH₂N(CH₃)C(O)CH₃ | CH₃ | CH₃ | N | |
| H | CH₃ | H | CH₂(CH₂)₃NHC(O)CH₃ | CH₃ | OCH₃ | N | |
| H | CH₃ | H | CH₂(CH₂)₃NHC(O)CH₃ | OCH₃ | OCH₃ | N | |
| H | CH₃ | H | CH₂N(CH₃)C(O)OCH₃ | OCH₃ | Cl | CH | |
| H | CH₃ | H | CH₂N(CH₃)C(O)OCH₃ | CH₃ | CH₃ | CH | |
| H | CH₃ | H | CH₂NHC(O)OCH₃ | CH₃ | OCH₃ | CH | |
| H | CH₃ | H | CH₂NHC(O)OCH₃ | OCH₃ | OCH₃ | CH | |
| H | CH₃ | H | CH₂NHC(O)OCH₃ | CH₃ | CH₃ | N | |
| H | CH₃ | H | CH₂NHC(O)OCH₃ | OCH₃ | OCH₃ | N | |
| H | CH₃ | H | CH₂NHC(O)OCH₃ | OCH₃ | Cl | CH | |
| H | CH₃ | H | CH₂NHC(O)OCH₃ | CH₃ | CH₃ | CH | |
| H | CH₃ | H | CH₂(CH₂)₃NHC(O)OCH₃ | CH₃ | OCH₃ | CH | |
| H | CH₃ | H | CH₂(CH₂)₃NHC(O)OCH₃ | OCH₃ | OCH₃ | CH | |
| H | CH₃ | H | CH₂(CH₂)₃NHC(O)OCH₃ | CH₃ | CH₃ | N | |
| H | CH₃ | H | CH₂N(CH₃)C(O)OCH₂CH₃ | CH₃ | OCH₃ | N | |
| H | CH₃ | H | CH(CH₃)NHC(O)OCH₃ | OCH₃ | OCH₃ | N | |
| H | CH₃ | H | CH(CH₃)NHC(O)OCH₃ | OCH₃ | Cl | CH | |
| H | CH₃ | H | CH(CH₃)NHC(O)OCH₃ | CH₃ | CH₃ | CH | |
| H | CH₃ | H | CH₂NHSO₂CH₃ | CH₃ | OCH₃ | CH | |
| H | CH₃ | H | CH₂NHSO₂CH₃ | OCH₃ | OCH₃ | CH | |
| H | CH₃ | H | CH₂NHSO₂CH₃ | CH₃ | CH₃ | N | |
| H | CH₃ | H | CH₂NHSO₂CH₃ | CH₃ | OCH₃ | N | |
| H | CH₃ | CH₃ | CH₂NHSO₂CH₃ | OCH₃ | OCH₃ | N | |
| H | CH₃ | H | CH₂CH₂NHSO₂CH₃ | OCH₃ | Cl | CH | |
| H | CH₃ | H | CH₂CH₂NHSO₂CH₃ | CH₃ | CH₃ | CH | |
| H | CH₃ | H | CH₂CH₂NHSO₂CH₃ | CH₃ | OCH₃ | CH | |
| H | CH₃ | H | CH₂CH₂NHSO₂CH₃ | OCH₃ | OCH₃ | CH | |
| H | CH₃ | H | CH₂CH₂NHSO₂CH₃ | CH₃ | CH₃ | N | |
| H | CH₃ | H | CH₂CH₂NHSO₂CH₃ | CH₃ | OCH₃ | N | |
| H | CH₃ | H | CH₂(CH₂)₃NHSO₂CH₃ | OCH₃ | OCH₃ | N | |
| H | CH₃ | H | CH₂(CH₂)₃NHSO₂CH₃ | OCH₃ | Cl | CH | |
| H | CH₃ | H | CH₂(CH₂)₃NHSO₂CH₃ | CH₃ | CH₃ | CH | |
| CH₃ | CH₃ | H | CH₂NHP(O)(CH₃)₂ | CH₃ | OCH₃ | CH | |
| H | CH₃ | H | CH₂NHP(O)(CH₃)₂ | OCH₃ | OCH₃ | CH | |
| H | CH₃ | H | CH₂NHP(O)(CH₃)₂ | CH₃ | CH₃ | N | |
| H | CH₃ | H | CH₂NHP(O)(OCH₃)₂ | CH₃ | OCH₃ | N | |
| H | CH₃ | H | CH₂NHP(O)(OCH₃)₂ | OCH₃ | OCH₃ | N | |
| H | CH₃ | H | CH₂NHP(O)(OCH₃)₂ | OCH₃ | Cl | CH | |
| H | CH₃ | H | CH=CH₂ | CH₃ | CH₃ | CH | |
| H | CH₃ | H | CH=CH₂ | CH₃ | OCH₃ | CH | |
| H | CH₃ | H | CH₂NO₂ | CH₃ | CH₃ | CH | |
| H | CH₃ | H | CH₂NO₂ | CH₃ | OCH₃ | CH | |
| H | CH₃ | H | CH₂NO₂ | OCH₃ | OCH₃ | CH | |
| H | CH₃ | H | CH₂NO₂ | CH₃ | CH₃ | N | |
| H | CH₃ | H | CH₂NO₂ | CH₃ | OCH₃ | N | |
| H | CH₃ | H | CH₂NO₂ | OCH₃ | OCH₃ | N | |
| H | CH₃ | H | CH₂NO₂ | OCH₃ | Cl | CH | |
| H | CH₃ | H | CH₂CH₂NO₂ | CH₃ | CH₃ | CH | |
| H | CH₃ | H | CH₂CH₂NO₂ | CH₃ | OCH₃ | CH | |
| H | CH₃ | H | CH₂CH₂NO₂ | OCH₃ | OCH₃ | CH | |
| H | CH₃ | H | CH₂CH₂NO₂ | CH₃ | CH₃ | N | |
| H | CH₃ | H | CH₂CH₂NO₂ | CH₃ | OCH₃ | N | |
| H | CH₃ | H | CH₂CH₂NO₂ | OCH₃ | OCH₃ | N | |
| H | CH₃ | H | CH₂CH₂NO₂ | OCH₃ | Cl | CH | |
| H | CH₃ | H | CH₂C(O)CH₃ | CH₃ | CH₃ | CH | |
| H | CH₃ | H | CH₂C(O)CH₃ | CH₃ | OCH₃ | CH | |
| H | CH₃ | H | CH₂C(O)CH₃ | OCH₃ | OCH₃ | N | |

TABLE IIa-continued

| R | R₁ | R₂ | R₃ | X | Y | Z | m.p. (°C.) |
|---|---|---|---|---|---|---|---|
| H | CH₃ | H | CH₂C(O)CH₃ | CH₃ | CH₃ | N | |
| H | CH₃ | H | CH₂C(O)CH₃ | OCH₃ | OCH₃ | N | |
| H | CH₃ | H | CH₂C(O)CH₃ | OCH₃ | Cl | CH | |
| H | CH₃ | H | CH₂C(O)CH₂CH₃ | CH₃ | CH₃ | CH | |
| H | CH₃ | H | CH₂C(O)CH₂CH₃ | CH₃ | OCH₃ | CH | |
| H | CH₃ | H | CH₂C(O)CH₂CH₃ | OCH₃ | OCH₃ | CH | |
| H | CH₃ | H | CH₂C(O)CH₂CH₃ | CH₃ | CH₃ | N | |
| H | CH₃ | H | CH₂C(O)CH₂CH₃ | CH₃ | OCH₃ | N | |
| H | CH₃ | H | CH₂C(O)CH₂CH₃ | OCH₃ | OCH₃ | N | |
| H | CH₃ | H | CH₂C(O)CH₂CH₃ | OCH₃ | Cl | CH | |
| H | CH₃ | H | CH₂(CH₂)₃C(O)CH₃ | CH₃ | CH₃ | CH | |
| H | CH₃ | H | CH₂(CH₂)₃C(O)CH₃ | CH₃ | OCH₃ | CH | |
| H | CH₃ | H | CH₂(CH₂)₃C(O)CH₃ | OCH₃ | OCH₃ | CH | |
| H | CH₃ | H | CH₂(CH₂)₃C(O)CH₃ | CH₃ | CH₃ | N | |
| H | CH₃ | H | CH₂(CH₂)₃C(O)CH₃ | CH₃ | OCH₃ | N | |
| H | CH₃ | CH₃ | CH₂(CH₂)₃C(O)CH₃ | OCH₃ | OCH₃ | N | |
| H | CH₃ | H | CH₂(CH₂)₃C(O)CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | CH | |
| H | CH₃ | H | CH₂CH₂C(O)CH₃ | CH₃ | CH₃ | N | |
| H | CH₃ | H | CH₂—CH(CH₃)C(O)CH₃ | CH₃ | OCH₃ | N | |
| H | CH₃ | CH₃ | CH₂—CH(CH₂)C(O)CH₃ | OCH₃ | OCH₃ | N | |
| H | CH₃ | H | CH₂—CH(CH₂)C(O)CH₃ | OCH₃ | Cl | CH | |
| H | CH₃ | H | CH₂—CH(CH₃)C(O)CH₃ | CH₃ | CH₃ | CH | |
| CH₃ | CH₃ | CH₃ | CH₂—CH(CH₂)C(O)CH₃ | CH₃ | OCH₃ | CH | |
| H | CH₃ | H | CH₂(CH₂)₆C(O)CH₂CH₃ | OCH₃ | OCH₃ | CH | |
| H | CH₃ | H | CH₂(CH₂)₆C(O)CH₂CH₃ | CH₃ | CH₃ | N | |
| H | CH₃ | H | CH₂(CH₂)₆C(O)CH₂CH₃ | CH₃ | OCH₃ | N | |
| H | CH₃ | H | CH₂(CH₂)₆C(O)CH₂CH₃ | OCH₃ | OCH₃ | N | |
| H | CH₃ | H | CH₂(CH₂)₆C(O)CH₂CH₃ | OCH₃ | Cl | CH | |
| H | CH₃ | H | CH₂C(O)OCH₃ | CH₃ | CH₃ | CH | |
| H | CH₃ | H | CH₂C(O)OCH₃ | CH₃ | OCH₃ | CH | |
| H | CH₃ | H | CH₂C(O)OCH₃ | OCH₃ | OCH₃ | CH | |
| H | CH₃ | H | CH₂C(O)OCH₃ | CH₃ | CH₃ | N | |
| H | CH₃ | H | CH₂C(O)OCH₃ | CH₃ | OCH₃ | N | |
| H | CH₃ | H | CH₂C(O)OCH₃ | OCH₃ | OCH₃ | N | |
| H | CH₃ | H | CH₂C(O)OCH₃ | OCH₃ | Cl | CH | |
| H | CH₃ | H | CH₂C(O)OCH₂CH₃ | CH₃ | CH₃ | CH | |
| H | CH₃ | H | CH₂C(O)OCH₂CH₃ | CH₃ | OCH₃ | H | |
| H | CH₃ | H | CH₂C(O)OCH₂CH₃ | OCH₃ | OCH₃ | CH | |
| H | CH₃ | H | CH₂C(O)OCH₂CH₃ | CH₃ | CH₃ | N | |
| H | CH₃ | H | CH₂C(O)OCH₂CH₃ | CH₃ | OCH₃ | N | |
| H | CH₃ | H | CH₂C(O)OCH₂CH₃ | OCH₃ | OCH₃ | N | |
| H | CH₃ | H | CH₂C(O)OCH₂CH₃ | OCH₃ | Cl | CH | |
| H | CH₃ | H | CH₂CH₂C(O)CH₃ | CH₃ | CH₃ | CH | |
| H | CH₃ | H | CH₂CH₂C(O)CH₃ | CH₃ | OCH₃ | CH | |
| H | CH₃ | H | CH₂CH₂C(O)CH₃ | OCH₃ | OCH₃ | N | |
| H | CH₃ | H | CH₂CH₂C(O)CH₃ | CH₃ | CH₃ | N | |
| H | CH₃ | H | CH₂CH₂C(O)CH₃ | OCH₃ | OCH₃ | N | |
| H | CH₃ | H | CH₂CH₂C(O)CH₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | CH₂CH₂C(O)N(CH₃)₂ | CH₃ | CH₃ | CH | |
| H | CH₃ | H | CH₂CH₂C(O)N(CH₃)₂ | CH₃ | OCH₃ | CH | |
| H | CH₃ | H | CH₂CH₂C(O)N(CH₃)₂ | OCH₃ | OCH₃ | CH | |
| H | CH₃ | H | CH₂CH₂C(O)N(CH₃)₂ | CH₃ | CH₃ | N | |
| H | CH₃ | H | CH₂CH₂C(O)N(CH₃)₂ | CH₃ | OCH₃ | N | |
| H | CH₃ | CH₃ | CH₂CH₂C(O)N(CH₃)₂ | OCH₃ | OCH₃ | N | |
| H | CH₃ | H | CH₂CH₂C(O)N(CH₃)₂ | OCH₃ | Cl | CH | |
| H | CH₃ | H | CH₂C(O)N(CH₃)CH₂CH₃ | CH₃ | CH₃ | CH | |
| H | CH₃ | H | CH₂C(O)N(CH₃)CH₂CH₃ | CH₃ | OCH₃ | CH | |
| H | CH₃ | H | CH₂C(O)N(CH₃)CH₂CH₃ | OCH₃ | OCH₃ | CH | |
| H | CH₃ | H | CH₂C(O)N(CH₃)CH₂CH₃ | CH₃ | CH₃ | N | |
| H | CH₃ | H | CH₂C(O)N(CH₃)CH₂OCH₃ | CH₃ | OCH₃ | N | |
| H | CH₃ | H | CH₂C(O)N(CH₃)CH₂OCH₃ | OCH₃ | OCH₃ | N | |
| H | CH₃ | H | CH₂C(O)N(CH₃)CH₂OCH₃ | OCH₃ | Cl | CH | |
| H | CH₃ | H | CH₂SeCH₃ | CH₃ | CH₃ | CH | |
| CH₃ | CH₃ | H | CH₂SeCH₃ | CH₃ | OCH₃ | CH | |
| H | CH₃ | H | CH₂SeCH₃ | OCH₃ | OCH₃ | CH | |
| H | CH₃ | H | CH₂SePh | CH₃ | CH₃ | N | |
| H | CH₃ | H | CH₂SePh | CH₃ | OCH₃ | N | |
| H | CH₃ | H | CH₂—CH₂SeCH₃ | OCH₃ | OCH₃ | N | |
| H | CH₃ | H | CH₂—CH₂SeCH₃ | OCH₃ | Cl | CH | |
| H | CH₃ | H | CH=CH₂ | OCH₃ | OCH₃ | CH | |
| H | CH₃ | H | CH=CH₂ | CH₃ | CH₃ | N | |

TABLE IIa-continued

| R | R₁ | R₂ | R₃ | X | Y | Z | m.p. (°C.) |
|---|---|---|---|---|---|---|---|
| H | CH₃ | H | CH=CH₂ | CH₃ | OCH₃ | N | |
| H | CH₃ | H | CH=CH₂ | OCH₃ | OCH₃ | N | |
| H | CH₃ | H | CH=CH₂ | OCH₃ | Cl | CH | |
| H | CH₃ | H | CH=CH—CH₃ | CH₃ | CH₃ | CH | |
| H | CH₃ | H | CH=CH—CH₃ | CH₃ | OCH₃ | CH | |
| H | CH₃ | H | CH=CH—CH₃ | OCH₃ | OCH₃ | CH | |
| H | CH₃ | H | CH=CH—CH₃ | CH₃ | CH₃ | N | |
| H | CH₃ | H | CH=CH—CH₃ | CH₃ | OCH₃ | N | |
| H | CH₃ | H | CH=CH—CH₃ | OCH₃ | OCH₃ | N | |
| H | CH₃ | H | CH=CH—CH₃ | OCH₃ | Cl | CH | |
| H | CH₃ | H | CH=CH—CH₂—CH₃ | CH₃ | CH₃ | CH | |
| H | CH₃ | H | CH=CH—CH₂—CH₃ | CH₃ | OCH₃ | CH | |
| H | CH₃ | H | CH=CH—CH₂—CH₃ | OCH₃ | OCH₃ | CH | |
| H | CH₃ | H | CH=CH—CH₂—CH₃ | CH₃ | CH₃ | N | |
| H | CH₃ | H | CH=CH—CH₂—CH₃ | OCH₃ | OCH₃ | N | |
| H | CH₃ | H | CH=CH—CH₂—CH₃ | OCH₃ | Cl | CH | |
| H | CH₃ | H | CH=C(CH₃)₂ | CH₃ | CH₃ | CH | |
| H | CH₃ | H | CH=C(CH₃)₂ | CH₃ | OCH₃ | CH | |
| H | CH₃ | H | CH=C(CH₃)₂ | OCH₃ | OCH₃ | CH | |
| H | CH₃ | H | CH=C(CH₃)₂ | CH₃ | CH₃ | N | |
| H | CH₃ | H | CH=C(CH₃)₂ | CH₃ | OCH₃ | N | |
| H | CH₃ | H | CH=C(CH₃)₂ | OCH₃ | OCH₃ | N | |
| H | CH₃ | H | CH=C(CH₃)₂ | OCH₃ | Cl | CH | |
| H | CH₃ | H | CH=CH(CH₂)₃CH₃ | CH₃ | CH₃ | CH | |
| H | CH₃ | H | CH=CH(CH₂)₃CH₃ | CH₃ | OCH₃ | CH | |
| H | CH₃ | H | CH=CH(CH₂)₃CH₃ | OCH₃ | OCH₃ | CH | |
| H | CH₃ | H | CH=CH(CH₂)₃CH₃ | CH₃ | CH₃ | N | |
| H | CH₃ | H | CH=CH(CH₂)₃CH₃ | CH₃ | OCH₃ | N | |
| H | CH₃ | CH₃ | CH=CH(CH₂)₃CH₃ | OCH₃ | OCH₃ | N | |
| H | CH₃ | H | CH=CH(CH₂)₃CH₃ | OCH₃ | Cl | CH | |
| H | CH₃ | H | CH=C(CH₃)CH₂CH₃ | CH₃ | CH₃ | CH | |
| H | CH₃ | H | CH=C(CH₃)CH₂CH₃ | CH₃ | OCH₃ | CH | |
| H | CH₃ | H | CH=C(CH₃)CH₂CH₃ | OCH₃ | OCH₃ | CH | |
| H | CH₃ | H | CH=CH—CH(CH₃)₂ | CH₃ | CH₃ | N | |
| H | CH₃ | H | CH=CH—CH(CH₃)₂ | CH₃ | OCH₃ | N | |
| H | CH₃ | H | CH=CH—CH(CH₃)₂ | OCH₃ | OCH₃ | N | |
| H | CH₃ | H | CH=CH—CH(CH₃)₂ | OCH₃ | Cl | CH | |
| H | CH₃ | H | CH=CH(CH₂)₄CH₃ | CH₃ | CH₃ | CH | |
| CH₃ | CH₃ | H | CH=CH(CH₂)₄CH₃ | CH₃ | OCH₃ | CH | |
| H | CH₃ | H | CH=CH(CH₂)₆CH₃ | OCH₃ | OCH₃ | CH | |
| H | CH₃ | H | CH=CH(CH₂)₆CH₃ | CH₃ | CH₃ | N | |
| H | CH₃ | H | CH=CH(CH₂)₆CH₃ | CH₃ | OCH₃ | N | |
| H | CH₃ | H | CH=C(CH₃)(CH₂)₃CH₃ | OCH₃ | OCH₃ | N | |
| H | CH₃ | H | CH=C(CH₃)(CH₂)₃CH₃ | OCH₃ | Cl | CH | |
| H | CH₃ | H | CH₂CH=CH₂ | CH₃ | CH₃ | CH | |
| H | CH₃ | H | CH₂CH=CH₂ | CH₃ | OCH₃ | CH | |
| H | CH₃ | H | CH₂CH=CH₂ | OCH₃ | OCH₃ | CH | |
| H | CH₃ | H | CH₂CH=CH₂ | CH₃ | CH₃ | N | |
| H | CH₃ | H | CH₂CH=CH₂ | CH₃ | OCH₃ | N | |
| H | CH₃ | H | CH₂CH=CH₂ | OCH₃ | OCH₃ | N | |
| H | CH₃ | H | CH₂CH=CH₂ | OCH₃ | Cl | CH | |
| H | CH₃ | H | CH₂CH₂CH=CH₂ | CH₃ | CH₃ | CH | |
| H | CH₃ | H | CH₂CH₂CH=CH₂ | OCH₃ | OCH₃ | CH | |
| H | CH₃ | H | CH₂CH₂CH=CH₂ | CH₃ | CH₃ | N | |
| H | CH₃ | H | CH₂CH₂CH=CH₂ | CH₃ | OCH₃ | N | |
| H | CH₃ | H | CH₂CH₂CH=CH₂ | OCH₃ | OCH₃ | N | |
| H | CH₃ | H | CH₂CH₂CH=CH₂ | OCH₃ | Cl | CH | |
| H | CH₃ | H | CH₂CH=CHCH₃ | CH₃ | CH₃ | CH | |
| H | CH₃ | H | CH₂CH=CHCH₃ | CH₃ | OCH₃ | CH | |
| H | CH₃ | H | CH₂CH=CHCH₃ | OCH₃ | OCH₃ | CH | |
| H | CH₃ | H | CH₂CH=CHCH₃ | CH₃ | CH₃ | N | |
| H | CH₃ | H | CH₂—CH=CH—CH₃ | OCH₃ | OCH₃ | N | |
| H | CH₃ | H | CH₂—CH=CH—CH₃ | OCH₃ | Cl | CH | |
| H | CH₃ | H | CH₂—CH=C(CH₃)₂ | CH₃ | CH₃ | CH | |
| H | CH₃ | H | CH₂—CH=C(CH₃)₂ | CH₃ | OCH₃ | CH | |
| H | CH₃ | H | CH₂—CH=C(CH₃)₂ | OCH₃ | OCH₃ | CH | |
| H | CH₃ | H | CH₂—CH=C(CH₃)₂ | CH₃ | CH₃ | N | |
| H | CH₃ | H | CH₂—CH=C(CH₃)₂ | CH₃ | OCH₃ | N | |
| H | CH₃ | H | CH₂—CH=C(CH₃)₂ | OCH₃ | OCH₃ | N | |
| H | CH₃ | H | CH₂—CH=CH(CH₂)₃CH₃ | OCH₃ | Cl | CH | |
| H | CH₃ | H | CH₂—CH=CH(CH₂)₃CH₃ | CH₃ | CH₃ | CH | |
| H | CH₃ | H | CH₂—CH=CH(CH₂)₃CH₃ | CH₃ | OCH₃ | CH | |
| H | CH₃ | H | CH₂—CH=CH(CH₂)₃CH₃ | OCH₃ | OCH₃ | CH | |
| H | CH₃ | H | CH₂—CH=CH(CH₂)₃CH₃ | CH₃ | CH₃ | N | |
| H | CH₃ | H | CH₂—CH=CH(CH₂)₃CH₃ | CH₃ | OCH₃ | N | |
| H | CH₃ | CH₃ | CH₂—CH=CH(CH₂)₃CH₃ | OCH₃ | OCH₃ | N | |
| H | CH₃ | H | CH₂—CH₂—CH=CH₂ | OCH₃ | Cl | CH | |
| H | CH₃ | H | CH₂—CH₂—CH=CH₂ | CH₃ | CH₃ | CH | |
| H | CH₃ | H | CH₂—CH₂—CH=CH₂ | CH₃ | OCH₃ | CH | |
| H | CH₃ | H | CH₂—CH₂—CH=CH₂ | OCH₃ | OCH₃ | CH | |

TABLE IIa-continued

| R | R₁ | R₂ | R₃ | X | Y | Z | m.p. (°C.) |
|---|---|---|---|---|---|---|---|
| H | CH₃ | H | CH₂—CH₂—CH=CH₂ | CH₃ | CH₃ | N | |
| H | CH₃ | H | CH₂—(CH₂)₄CH=CH₂ | CH₃ | OCH₃ | N | |
| H | CH₃ | H | CH₂—CH=CH—CH(CH₃)₂ | OCH₃ | OCH₃ | N | |
| H | CH₃ | H | CH₂—CH=CH—CH(CH₃)₂ | OCH₃ | Cl | CH | |
| H | CH₃ | H | CH₂—CH=CH—CH(CH₃)₂ | CH₃ | CH₃ | CH | |
| CH₃ | CH₃ | H | CH₂—CH=CH—CH(CH₃)₂ | CH₃ | OCH₃ | CH | |
| H | CH₃ | H | CH₂—CH=CH—CH(CH₃)₂ | OCH₃ | OCH₃ | CH | |
| H | CH₃ | H | CH₂—CH=CH—CH=CH₂ | CH₃ | CH₃ | N | |
| H | CH₃ | H | CH₂—CH=CH—CH=CH₂ | CH₃ | OCH₃ | N | |
| H | CH₃ | H | CH₂—CH=CH—CH=CH₂ | OCH₃ | OCH₃ | N | |
| H | CH₃ | H | CH₂—CH=CH—CH=CH₂ | OCH₃ | Cl | CH | |
| H | CH₃ | H | C≡CH | CH₃ | CH₃ | CH | |
| H | CH₃ | H | C≡CH | CH₃ | OCH₃ | CH | |
| H | CH₃ | H | C≡CH | OCH₃ | OCH₃ | CH | |
| H | CH₃ | H | C≡CH | CH₃ | CH₃ | N | |
| H | CH₃ | H | C≡CH | CH₃ | OCH₃ | N | |
| H | CH₃ | H | C≡CH | OCH₃ | OCH₃ | N | |
| H | CH₃ | H | C≡CH | OCH₃ | Cl | CH | |
| H | CH₃ | H | C≡C—CH₃ | CH₃ | CH₃ | CH | |
| H | CH₃ | H | C≡C—CH₃ | CH₃ | OCH₃ | CH | |
| H | CH₃ | H | C≡C—CH₃ | OCH₃ | OCH₃ | CH | |
| H | CH₃ | H | C≡C—CH₃ | CH₃ | CH₃ | N | |
| H | CH₃ | H | C≡C—CH₃ | CH₃ | OCH₃ | N | |
| H | CH₃ | H | C≡C—CH₃ | OCH₃ | OCH₃ | N | |
| H | CH₃ | H | C≡C—CH₃ | OCH₃ | Cl | CH | |
| H | CH₃ | H | C≡C(CH₂)₂CH₃ | CH₃ | CH₃ | CH | |
| H | CH₃ | H | C≡C(CH₂)₂CH₃ | CH₃ | OCH₃ | CH | |
| H | CH₃ | H | C≡C(CH₂)₂CH₃ | OCH₃ | OCH₃ | CH | |
| H | CH₃ | H | C≡C(CH₂)₂CH₃ | CH₃ | CH₃ | N | |
| H | CH₃ | H | C≡C(CH₂)₂CH₃ | OCH₃ | OCH₃ | N | |
| H | CH₃ | H | CH₂—C≡CH | OCH₃ | Cl | CH | |
| H | CH₃ | H | CH₂—C≡CH | CH₃ | CH₃ | CH | |
| H | CH₃ | H | CH₂—C≡CH | CH₃ | OCH₃ | CH | |
| H | CH₃ | H | CH₂—C≡CH | OCH₃ | OCH₃ | CH | |
| H | CH₃ | H | CH₂—C≡CH | CH₃ | CH₃ | N | |
| H | CH₃ | H | CH₂—C≡CH | CH₃ | OCH₃ | N | |
| H | CH₃ | H | CH₂—C≡CH | OCH₃ | OCH₃ | N | |
| H | CH₃ | H | CH₂—C≡C—CH₃ | OCH₃ | Cl | CH | |
| H | CH₃ | H | CH₂—C≡C—CH₃ | CH₃ | CH₃ | CH | |
| H | CH₃ | H | CH₂—C≡C—CH₃ | CH₃ | OCH₃ | CH | |
| H | CH₃ | H | CH₂—C≡C—CH₃ | OCH₃ | OCH₃ | CH | |
| H | CH₃ | H | CH₂—C≡C—CH₃ | CH₃ | CH₃ | N | |
| H | CH₃ | H | CH₂—C≡C—CH₃ | CH₃ | OCH₃ | N | |
| H | CH₃ | CH₃ | CH₂—C≡C—CH₃ | OCH₃ | OCH₃ | N | |
| H | CH₃ | H | CH₂—CH₂—C≡CH | OCH₃ | Cl | CH | |
| H | CH₃ | H | CH₂—CH₂—C≡CH | CH₃ | CH₃ | CH | |
| H | CH₃ | H | CH₂—CH₂—C≡CH | CH₃ | OCH₃ | CH | |
| H | CH₃ | H | CH₂—CH₂—C≡CH | OCH₃ | OCH₃ | CH | |
| H | CH₃ | H | CH₂—CH₂—C≡CH | CH₃ | CH₃ | N | |
| H | CH₃ | H | CH₂—CH₂—C≡CH | CH₃ | OCH₃ | N | |
| H | CH₃ | H | CH₂—CH₂—C≡CH | OCH₃ | OCH₃ | N | |
| H | CH₃ | H | CH₂—C≡C—CH(CH₃)₂ | OCH₃ | Cl | CH | |
| H | CH₃ | H | CH₂—C≡C—CH(CH₃)₂ | CH₃ | CH₃ | CH | |
| CH₃ | CH₃ | H | CH₂—C≡C—CH(CH₃)₂ | CH₃ | OCH₃ | CH | |
| H | CH₃ | H | C≡C—(CH₂)₆CH₃ | OCH₃ | OCH₃ | CH | |
| H | CH₃ | H | C≡C—(CH₂)₆CH₃ | CH₃ | CH₃ | N | |
| H | CH₃ | H | C≡C—(CH₂)₆CH₃ | CH₃ | OCH₃ | N | |
| H | CH₃ | H | CH₂(CH₂)₇C≡CH | OCH₃ | OCH₃ | N | |
| H | CH₃ | H | CH₂(CH₂)₇C≡CH | OCH₃ | Cl | CH | |
| H | CH₃ | H | 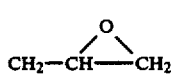 | CH₃ | CH₃ | CH | |
| H | CH₃ | H | 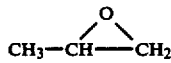 | CH₃ | OCH₃ | CH | |
| H | CH₃ | H | 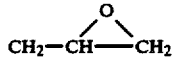 | OCH₃ | OCH₃ | CH | |
| H | CH₃ | H | 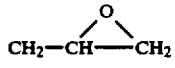 | CH₃ | CH₃ | N | |
| H | CH₃ | H | 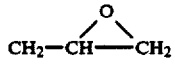 | CH₃ | OCH₃ | N | |

TABLE IIa-continued

| R | R₁ | R₂ | R₃ | X | Y | Z | m.p. (°C.) |
|---|---|---|---|---|---|---|---|
| H | CH₃ | H | 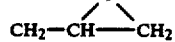 | OCH₃ | OCH₃ | N | |
| H | CH₃ | H | 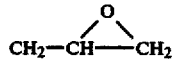 | OCH₃ | Cl | CH | |
| H | CH₃ | H | 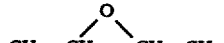 | CH₃ | CH₃ | CH | |
| H | CH₃ | H | 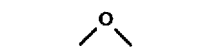 | CH₃ | OCH₃ | CH | |
| H | CH₃ | H | 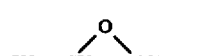 | OCH₃ | OCH₃ | CH | |
| H | CH₃ | H |  | CH | CH₃ | N | |
| H | CH₃ | H | 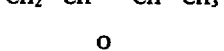 | CH₃ | OCH₃ | N | |
| H | CH₃ | H | 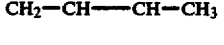 | OCH₃ | OCH₃ | N | |
| H | CH₃ | H | 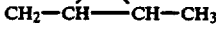 | OCH₃ | Cl | CH | |
| H | CH₃ | H | 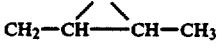 | CH₃ | CH₃ | CH | |
| H | CH₃ | H | 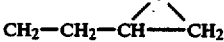 | CH₃ | OCH₃ | CH | |
| H | CH₃ | H | 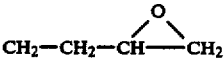 | OCH₃ | OCH₃ | CH | |
| H | CH₃ | H |  | CH₃ | CH₃ | N | |
| H | CH₃ | H |  | OCH₃ | OCH₃ | N | |
| H | CH₃ | H |  | OCH₃ | Cl | CH | |
| H | CH₃ | H | cyclobutyl | CH₃ | CH₃ | CH | |
| H | CH₃ | H | cyclobutyl | CH₃ | OCH₃ | CH | |
| H | CH₃ | H | cyclobutyl | OCH₃ | OCH₃ | CH | |
| H | CH₃ | H | cyclobutyl | CH₃ | CH₃ | N | |
| H | CH₃ | H | cyclobutyl | CH₃ | OCH₃ | N | |
| H | CH₃ | H | cyclobutyl | OCH₃ | OCH₃ | N | |
| H | CH₃ | H | cyclobutyl | OCH₃ | Cl | CH | |
| H | CH₃ | H | cyclopentyl | CH₃ | CH₃ | CH | |
| H | CH₃ | H | cyclopentyl | CH₃ | OCH₃ | CH | |
| H | CH₃ | H | cyclopentyl | OCH₃ | OCH₃ | CH | |
| H | CH₃ | H | cyclopentyl | CH₃ | CH₃ | N | |
| H | CH₃ | H | cyclopentyl | CH₃ | OCH₃ | N | |
| H | CH₃ | CH₃ | cyclopentyl | OCH₃ | OCH₃ | N | |
| H | CH₃ | H | cyclopentyl | OCH₃ | Cl | CH | |
| H | CH₃ | H | cyclohexyl | CH₃ | CH₃ | CH | |
| H | CH₃ | H | cyclohexyl | CH₃ | OCH₃ | CH | |
| H | CH₃ | H | cyclohexyl | OCH₃ | OCH₃ | CH | |
| H | CH₃ | H | cyclohexyl | CH₃ | CH₃ | N | |
| H | CH₃ | H | cyclohexyl | CH₃ | OCH₃ | N | |
| H | CH₃ | CH₃ | cyclohexyl | OCH₃ | OCH₃ | N | |
| H | CH₃ | H | cyclohexyl | OCH₃ | Cl | CH | |
| H | CH₃ | H | cyclopropyl | CH₃ | CH₃ | CH | |

TABLE IIa-continued

| R | R₁ | R₂ | R₃ | X | Y | Z | m.p. (°C.) |
|---|---|---|---|---|---|---|---|
| CH₃ | CH₃ | H | cyclopropyl | CH₃ | OCH₃ | CH | |
| H | CH | H | cyclopropyl | OCH₃ | OCH₃ | CH | |
| H | CH | H | cyclopropyl | CH₃ | CH₃ | N | |
| H | CH | H | cyclopropyl | CH₃ | OCH₃ | N | |
| H | CH₃ | H | cyclopropyl | OCH₃ | OCH₃ | N | |
| H | CH₃ | H | cyclopropyl | OCH₃ | Cl | CH | |
| H | CH₃ | H | CH₂—cyclopropyl | CH₃ | CH₃ | CH | |
| H | CH | H | CH₂—cyclopropyl | CH₃ | OCH₃ | CH | |
| H | CH₃ | H | CH₂—cyclopropyl | OCH₃ | OCH₃ | CH | |
| H | CH₃ | H | CH₂—cyclopropyl | CH₃ | CH₃ | N | |
| H | CH₃ | H | CH₂—cyclopropyl | CH₃ | OCH₃ | N | |
| H | CH₃ | H | CH₂—cyclopropyl | OCH₃ | OCH₃ | N | |
| H | CH₃ | H | CH₂—cyclopropyl | OCH₃ | Cl | CH | |
| H | CH₃ | H | CH₂—cyclopentyl | CH₃ | CH₃ | CH | |
| H | CH₃ | H | CH₂—cyclopentyl | CH₃ | OCH₃ | CH | |
| H | CH₃ | H | CH₂—cyclopentyl | OCH₃ | OCH₃ | CH | |
| H | CH₃ | H | CH₂—cyclopentyl | CH₃ | CH₃ | N | |
| H | CH₃ | H | CH₂—cyclopentyl | CH₃ | OCH₃ | N | |
| H | CH₃ | H | CH₂—cyclopentyl | OCH₃ | OCH₃ | N | |
| H | CH₃ | H | CH₂—cyclopentyl | OCH₃ | Cl | CH | |
| H | CH₃ | H | C₆H₅ | CH₃ | CH₃ | CH | |
| H | CH₃ | H | C₆H₅ | CH₃ | OCH₃ | CH | |
| H | CH₃ | H | C₆H₅ | OCH₃ | OCH₃ | CH | |
| H | CH₃ | H | C₆H₅ | CH₃ | CH₃ | N | |
| H | CH₃ | H | C₆H₅ | OCH₃ | OCH₃ | N | |
| H | CH₃ | H | C₆H₅ | OCH₃ | Cl | CH | |
| H | CH₃ | H | CH=CH—CF₃ | CH₃ | CH₃ | CH | |
| H | CH₃ | H | CH=CH—CF₃ | CH₃ | OCH₃ | CH | |
| H | CH₃ | H | CH=CH—CF₃ | OCH₃ | OCH₃ | CH | |
| H | CH₃ | H | CH=CH—CF₃ | CH₃ | CH₃ | N | |
| H | CH₃ | H | CH=CH—CF₃ | CH₃ | OCH₃ | N | |
| H | CH₃ | H | CH=CH—CF₃ | OCH₃ | OCH₃ | N | |
| H | CH₃ | H | CH=CH—CF₃ | OCH₃ | Cl | CH | |
| H | CH₃ | H | CH₂—C≡C—CF₃ | CH₃ | CH₃ | CH | |
| H | CH₃ | H | CH₂—C≡C—CF₃ | CH₃ | OCH₃ | CH | |
| H | CH₃ | H | CH₂—C≡C—CF₃ | OCH₃ | OCH₃ | CH | |
| H | CH₃ | H | CH₂—C≡C—CF₃ | CH₃ | CH₃ | N | |
| H | CH₃ | H | CH₂—C≡C—CF₃ | CH₃ | OCH₃ | N | |
| H | CH₃ | CH₃ | CH₂—C≡C—CF₃ | OCH₃ | OCH₃ | N | |
| H | CH₃ | H | CH₂—CH=CF₂ | OCH₃ | Cl | CH | |
| H | CH₃ | H | CH=CH—CH₂Cl | CH₃ | CH₃ | CH | |
| H | CH₃ | H | CH=CH—CH₂Cl | CH₃ | OCH₃ | CH | |
| H | CH₃ | H | CH=CH—CH₂Cl | OCH₃ | OCH₃ | CH | |
| H | CH₃ | H | CH=CH—CH₂Cl | CH₃ | CH₃ | N | |
| H | CH₃ | H | CH=CH—CH₂Cl | CH₃ | OCH₃ | N | |
| H | CH₃ | H | CH=CH—CH₂Cl | OCH₃ | OCH₃ | N | |
| H | CH₃ | H | CH₂—C(CHF)(CH₂)(CH₂) (cyclopropyl with CHF) | OCH₃ | Cl | CH | |
| H | CH₃ | H | CH₂—C(CHF)(CH₂)(CH₂) | CH₃ | CH₃ | CH | |
| CH₃ | CH₃ | H | CH₂—C(CHF)(CH₂)(CH₂) | CH₃ | OCH₃ | CH | |
| H | CH₃ | H | CH₂—C(CHF)(CH₂)(CH₂) | OCH₃ | OCH₃ | CH | |
| H | CH₃ | H | CH₂—C(CHF)(CH₂)(CH₂) | CH₃ | CH₃ | N | |

TABLE IIa-continued

| R | R₁ | R₂ | R₃ | X | Y | Z | m.p. (°C.) |
|---|---|---|---|---|---|---|---|
| H | CH₃ | H | CH₂—C(CHF)(CH₂) (cyclopropane with CHF) | CH₃ | OCH₃ | N | |
| H | CH₃ | H | CH₂—C≡C—CH₂Br | OCH₃ | OCH₃ | N | |
| H | CH₃ | H | CH₂—C≡C—CH₂Br | OCH₃ | Cl | CH | |
| H | CH₃ | H | CH₂—CH=CHOCH₃ | CH₃ | CH₃ | CH | |
| H | CH₃ | H | CH₂—CH=CHOCH₃ | CH₃ | OCH₃ | CH | |
| H | CH₃ | H | CH₂—CH=CHOCH₃ | OCH₃ | OCH₃ | CH | |
| H | CH₃ | H | CH₂—CH=CHOCH₃ | CH₃ | CH₃ | N | |
| H | CH₃ | H | CH₂—C≡C—OCH₃ | CH₃ | OCH₃ | N | |
| H | CH₃ | H | CH₂—C≡C—OCH₃ | OCH₃ | OCH₃ | N | |
| H | CH₃ | H | CH₂—CH₂—CH=CHCN | OCH₃ | Cl | CH | |
| H | CH₃ | H | CH₂—CH₂—CH=CHCN | CH₃ | CH₃ | CH | |
| H | CH₃ | H | CH₂—CH₂—CH=CHCN | CH₃ | OCH₃ | CH | |
| H | CH₃ | H | CH(OSO₂CH₃)C≡CH | OCH₃ | OCH₃ | CH | |
| H | CH₃ | H | CH(OSO₂CH₃)C≡CH | CH₃ | CH₃ | N | |
| H | CH₃ | H | CH(OSO₂CH₃)C≡CH | CH₃ | OCH₃ | N | |
| H | CH₃ | H | CH(OSO₂CH₃)C≡CH | OCH₃ | OCH₃ | N | |
| H | CH₃ | H | CH(OSO₂CH₃)C≡CH | OCH₃ | Cl | CH | |
| H | CH₃ | H | C≡C—Si(CH₃)₃ | CH₃ | CH₃ | CH | |
| H | CH₃ | H | C≡C—Si(CH₃)₃ | CH₃ | OCH₃ | CH | |
| H | CH₃ | H | C≡C—Si(CH₃)₃ | OCH₃ | OCH₃ | CH | |
| H | CH₃ | H | CH₂—CH=CHP(O)(OCH₃)₂ | CH₃ | CH₃ | N | |
| H | CH₃ | H | CH₂—CH=CHP(O)(OCH₃)₂ | OCH₃ | OCH₃ | N | |
| H | CH₃ | H | CH₂—CH=CHP(O)(OCH₃)₂ | OCH₃ | Cl | CH | |
| H | CH₃ | H | CH₂—CH=CHP(O)(OCH₃)₂ | CH₃ | CH₃ | CH | |
| H | CH₃ | H | CH₂—CH=CHP(O)(OCH₃)₂ | CH₃ | OCH₃ | CH | |
| H | CH₃ | H | CH=CH—OSi(CH₃)₃ | OCH₃ | OCH₃ | CH | |
| H | CH₃ | H | CH=CH—OSi(CH₃)₃ | CH₃ | CH₃ | N | |
| H | CH₃ | H | CH=CH—OSi(CH₃)₃ | CH₃ | OCH₃ | N | |
| H | CH₃ | H | CH=CH—OSi(CH₃)₃ | OCH₃ | OCH₃ | N | |
| H | CH₃ | H | CH₂(CH₂)₅CH=CH—CN | OCH₃ | Cl | CH | |
| H | CH₃ | H | CH₂(CH₂)₅CH=CH—CN | CH₃ | CH₃ | CH | |
| H | CH₃ | H | CH₂(CH₂)₅CH=CH—CN | CH₃ | OCH₃ | CH | |
| H | CH₃ | H | CH₂(CH₂)₅CH=CH—CN | OCH₃ | OCH₃ | CH | |
| H | CH₃ | H | CH₂(CH₂)₅CH=CH—CN | CH₃ | CH₃ | N | |
| H | CH₃ | H | CH=CH—CH₂SCN | CH₃ | OCH₃ | N | |
| H | CH₃ | CH₃ | CH=CH—CH₂SCN | OCH₃ | OCH₃ | N | |
| H | CH₃ | H | CH=CH—CH₂SCN | OCH₃ | Cl | CH | |
| H | CH₃ | H | C≡C—C≡C—CH₂OCH₃ | CH₃ | CH₃ | CH | |
| H | CH₃ | H | C≡C—C≡C—CH₂OCH₃ | CH₃ | OCH₃ | CH | |
| H | CH₃ | H | C≡C—C≡C—CH₂OCH₃ | OCH₃ | OCH₃ | CH | |
| H | CH₃ | H | CH₂—CH=CH—CH₂SCH₃ | CH₃ | CH₃ | N | |
| H | CH₃ | H | CH₂—CH=CH—CH₂SCH₃ | CH₃ | OCH₃ | N | |
| H | CH₃ | H | CH₂—CH=CH—CH₂SCH₃ | OCH₃ | OCH₃ | N | |
| H | CH₃ | H | CH₂—CH=CH—CH₂SCH₃ | OCH₃ | Cl | CH | |
| H | CH₃ | H | CH=CH—CH₂N(CH₃)₂ | CH₃ | CH₃ | CH | |
| CH₃ | CH₃ | H | CH=CH—CH₂N(CH₃)₂ | CH₃ | OCH₃ | CH | |
| H | CH₃ | H | CH=CH—CH₂N(CH₃)₂ | OCH₃ | OCH₃ | CH | |
| H | CH₃ | H | CH₂—CH=CH—P(O)(OCH₃)₂ | CH₃ | CH₃ | N | |
| H | CH₃ | H | CH₂—CH=CH—P(O)(OCH₃)₂ | CH₃ | OCH₃ | N | |
| H | CH₃ | H | CH₂—CH=CH—P(O)(OCH₃)₂ | OCH₃ | OCH₃ | N | |
| H | CH₃ | H | CH₂—CH=CH—P(O)(OCH₃)₂ | OCH₃ | Cl | CH | |
| H | CH₃ | H | SCH₃ | CH₃ | CH₃ | CH | |
| H | CH₃ | H | SCH₃ | CH₃ | OCH₃ | CH | |
| H | CH₃ | H | SCH₃ | OCH₃ | OCH₃ | CH | |
| H | CH₃ | H | SCH₃ | CH₃ | CH₃ | N | |
| H | CH₃ | H | SCH₃ | CH₃ | OCH₃ | N | |
| H | CH₃ | H | SCH₃ | OCH₃ | OCH₃ | N | |
| H | CH₃ | H | SCH₃ | OCH₃ | Cl | CH | |
| H | CH₃ | H | SCH₂CF₃ | CH₃ | CH₃ | CH | |
| H | CH₃ | H | SCH₂CH₃ | CH₃ | OCH₃ | CH | |
| H | CH₃ | H | SCH₂CH₃ | OCH₃ | OCH₃ | CH | |
| H | CH₃ | H | SCH₂CH₃ | CH₃ | CH₃ | N | |
| H | CH₃ | H | SCH₂CH₃ | CH₃ | OCH₃ | N | |
| H | CH₃ | H | SCH₂CH₃ | OCH₃ | OCH₃ | N | |
| H | CH₃ | H | SCH₂CH₃ | OCH₃ | Cl | CH | |
| H | CH₃ | H | SO₂CH₃ | CH₃ | CH₃ | CH | |
| H | CH₃ | H | SO₂CH₃ | CH₃ | OCH₃ | CH | |
| H | CH₃ | H | SO₂CH₃ | OCH₃ | OCH₃ | CH | |
| H | CH₃ | H | SO₂CH₃ | CH₃ | CH₃ | N | |
| H | CH₃ | H | SO₂CH₃ | CH₃ | OCH₃ | N | |
| H | CH₃ | H | SO₂CH₃ | OCH₃ | Cl | CH | |
| H | CH₃ | H | SO₂CH₂CH₃ | CH₃ | CH₃ | CH | |
| H | CH₃ | H | SO₂CH₂CH₃ | CH₃ | OCH₃ | CH | |
| H | CH₃ | H | SO₂CH₂CH₃ | OCH₃ | OCH₃ | CH | |
| H | CH₃ | H | SO₂CH₂CH₃ | CH₃ | CH₃ | N | |
| H | CH₃ | H | SO₂CH₂CH₃ | CH₃ | OCH₃ | N | |

TABLE IIa-continued

| R | R₁ | R₂ | R₃ | X | Y | Z | m.p. (°C.) |
|---|---|---|---|---|---|---|---|
| H | CH₃ | H | SO₂CH₂CH₃ | OCH₃ | OCH₃ | N | |
| H | CH₃ | H | SO₂CH₂CH₃ | OCH₃ | Cl | CH | |
| H | CH₃ | H | OCH₃ | CH₃ | CH₃ | CH | |
| H | CH₃ | H | OCH₃ | CH₃ | OCH₃ | CH | |
| H | CH₃ | H | OCH₃ | OCH₃ | OCH₃ | CH | |
| H | CH₃ | H | OCH₃ | CH₃ | CH₃ | N | |
| H | CH₃ | H | OCH₃ | CH₃ | OCH₃ | N | |
| H | CH₃ | CH₃ | OCH₃ | OCH₃ | OCH₃ | N | |
| H | CH₃ | H | OCH₃ | OCH₃ | Cl | CH | |
| H | CH₃ | H | OCH₂CH₃ | CH₃ | CH₃ | CH | |
| H | CH₃ | H | OCH₂CH₃ | CH₃ | OCH₃ | CH | |
| H | CH₃ | H | OCH₂CH₃ | OCH₃ | OCH₃ | CH | |
| H | CH₃ | H | OCH₂CH₃ | CH₃ | CH₃ | N | |
| H | CH₃ | H | OCH₂CH₃ | CH₃ | OCH₃ | N | |
| H | CH₃ | H | OCH₂CH₃ | OCH₃ | OCH₃ | N | |
| H | CH₃ | H | OCH₂CH₃ | OCH₃ | Cl | CH | |
| H | CH₃ | H | OCH(CH₃)₂ | CH₃ | CH₃ | CH | |
| H | CH₃ | H | OCH(CH₃)₂ | CH₃ | OCH₃ | CH | |
| H | CH₃ | H | OCH(CH₃)₂ | OCH₃ | OCH₃ | CH | |
| H | CH₃ | H | OCH(CH₃)₂ | CH₃ | CH₃ | N | |
| H | CH₃ | H | OCH(CH₃)₂ | CH₃ | OCH₃ | N | |
| H | CH₃ | H | OCH(CH₃)₂ | OCH₃ | OCH₃ | N | |
| H | CH₃ | H | OCH(CH₃)₂ | OCH₃ | Cl | CH | |
| H | CH₃ | H | C(O)CH₃ | CH₃ | CH₃ | CH | |
| H | CH₃ | H | C(O)CH₃ | CH₃ | OCH₃ | CH | |
| H | CH₃ | H | C(O)CH₃ | OCH₃ | OCH₃ | CH | |
| H | CH₃ | H | C(O)CH₃ | CH₃ | CH₃ | N | |
| H | CH₃ | H | C(O)CH₃ | CH₃ | OCH₃ | N | |
| H | CH₃ | H | C(O)CH₃ | OCH₃ | OCH₃ | N | |
| H | CH₃ | H | C(O)CH₃ | OCH₃ | Cl | CH | |
| H | CH₃ | H | C(O)CH₂CH₃ | CH₃ | CH₃ | CH | |
| H | CH₃ | H | C(O)CH₂CH₃ | CH₃ | OCH₃ | CH | |
| H | CH₃ | H | C(O)CH₂CH₃ | OCH₃ | OCH₃ | CH | |
| H | CH₃ | H | C(O)CH₂CH₃ | CH₃ | CH₃ | N | |
| H | CH₃ | H | C(O)CH₂CH₃ | CH₃ | OCH₃ | N | |
| H | CH₃ | H | C(O)CH₂CH₃ | OCH₃ | OCH₃ | N | |
| H | CH₃ | H | C(O)CH₂CH₃ | OCH₃ | Cl | CH | |
| H | CH₃ | H | C(O)CH(CH₃)₂ | CH₃ | CH₃ | CH | |
| H | CH₃ | H | C(O)CH(CH₃)₂ | OCH₃ | OCH₃ | CH | |
| H | CH₃ | H | C(O)CH(CH₃)₂ | CH₃ | CH₃ | N | |
| H | CH₃ | H | C(O)CH(CH₃)₂ | OCH₃ | OCH₃ | N | |
| H | CH₃ | H | C(O)CH(CH₃)₂ | OCH₃ | Cl | CH | |
| H | CH₃ | H | C(O)CHF₂ | CH₃ | CH₃ | CH | |
| H | CH₃ | H | C(O)CHF₂ | CH₃ | OCH₃ | CH | |
| H | CH₃ | H | C(O)CHF₂ | OCH₃ | OCH₃ | CH | |
| H | CH₃ | H | C(O)CF₃ | CH₃ | CH₃ | N | |
| H | CH₃ | H | C(O)CF₃ | CH₃ | OCH₃ | N | |
| H | CH₃ | H | C(O)CF₃ | OCH₃ | OCH₃ | N | |
| H | CH₃ | H | C(O)CF₃ | OCH₃ | Cl | CH | |
| H | CH₃ | H | C(O)CH₂CH₂CH₃ | CH₃ | CH₃ | CH | |
| H | CH₃ | H | C(O)CH₂CH₂CH₃ | CH₃ | OCH₃ | CH | |
| H | CH₃ | H | C(O)CH₂CH₂CH₃ | OCH₃ | OCH₃ | CH | |
| H | CH₃ | H | C(O)CH₂CH₂CH₃ | CH₃ | CH₃ | N | |
| H | CH₃ | H | C(O)CH₂CH₂CH₃ | CH₃ | OCH₃ | N | |
| H | CH₃ | CH₃ | C(O)CH₂CH₂CH₃ | OCH₃ | OCH₃ | N | |
| H | CH₃ | H | C(O)CH₂CH₂CH₃ | OCH₃ | Cl | CH | |
| H | CH₃ | H | C(O)CH₂OCH₃ | CH₃ | CH₃ | CH | |
| H | CH₃ | H | C(O)CH₂OCH₃ | CH₃ | OCH₃ | CH | |
| H | CH₃ | H | C(O)CH₂OCH₃ | OCH₃ | OCH₃ | CH | |
| H | CH₃ | H | C(O)CH₂OCH₃ | CH₃ | CH₃ | N | |
| H | CH₃ | H | C(O)CH₂Cl | CH₃ | OCH₃ | N | |
| H | CH₃ | H | C(O)CH₂Cl | OCH₃ | OCH₃ | N | |
| H | CH₃ | H | C(O)CH₂Cl | OCH₃ | Cl | CH | |
| H | CH₃ | H | C(O)CH₂CH(CH₃)CN | CH₃ | CH₃ | CH | |
| CH₃ | CH₃ | H | C(O)CH₂CH(CH₃)CN | CH₃ | OCH₃ | CH | |
| H | CH₃ | H | C(O)CH₂N(CH₃)₂ | OCH₃ | OCH₃ | CH | |
| H | CH₃ | H | C(O)CH₂N(CH₃)₂ | CH₃ | CH₃ | N | |
| H | CH₃ | H | C(O)CH₂CH=CH₂ | CH₃ | OCH₃ | N | |
| H | CH₃ | H | C(O)CH₂CH=CH₂ | OCH₃ | OCH₃ | N | |
| H | CH₃ | H | C(O)CH₂C≡CH | OCH₃ | Cl | CH | |
| H | CH₃ | H | CO₂CH₃ | CH₃ | CH₃ | CH | |
| H | CH₃ | H | CO₂CH₃ | CH₃ | OCH₃ | CH | |
| H | CH₃ | H | CO₂CH₃ | OCH₃ | OCH₃ | CH | |
| H | CH₃ | H | CO₂CH₃ | CH₃ | CH₃ | N | |
| H | CH₃ | H | CO₂CH₃ | CH₃ | OCH₃ | N | |
| H | CH₃ | H | CO₂CH₃ | OCH₃ | OCH₃ | N | |
| H | CH₃ | H | CO₂CH₃ | OCH₃ | Cl | CH | |
| H | CH₃ | H | CO₂CH₂CH₃ | CH₃ | CH₃ | CH | |
| H | CH₃ | H | CO₂CH₂CH₃ | CH₃ | OCH₃ | CH | |
| H | CH₃ | H | CO₂CH₂CH₃ | OCH₃ | OCH₃ | CH | |

TABLE IIa-continued

| R | R₁ | R₂ | R₃ | X | Y | Z | m.p. (°C.) |
|---|---|---|---|---|---|---|---|
| H | CH₃ | H | CO₂CH₂CH₃ | CH₃ | CH₃ | N | |
| H | CH₃ | H | CO₂CH₂CH₃ | CH₃ | OCH₃ | N | |
| H | CH₃ | H | CO₂CH₂CH₃ | OCH₃ | OCH₃ | N | |
| H | CH₃ | H | CO₂CH₂CH₃ | OCH₃ | Cl | CH | |
| H | CH₃ | H | CO₂CH₂CF₃ | CH₃ | CH₃ | CH | |
| H | CH₃ | H | CO₂CH₂CF₃ | CH₃ | OCH₃ | CH | |
| H | CH₃ | H | CO₂CH₂CF₃ | OCH₃ | OCH₃ | CH | |
| H | CH₃ | H | CO₂CH₂CF₃ | CH₃ | CH₃ | N | |
| H | CH₃ | H | CO₂CF₃ | OCH₃ | OCH₃ | N | |
| H | CH₃ | H | CO₂CF₃ | OCH₃ | Cl | CH | |
| H | CH₃ | H | CO₂CF₃ | CH₃ | CH₃ | CH | |
| H | CH₃ | H | CO₂CH₂C≡CH | CH₃ | OCH₃ | CH | |
| H | CH₃ | H | CO₂CH₂C≡CH | OCH₃ | OCH₃ | CH | |
| H | CH₃ | H | CO₂CH₂C≡CH | CH₃ | CH₃ | N | |
| H | CH₃ | H | CO₂CH₂C≡CH | CH₃ | OCH₃ | N | |
| H | CH₃ | H | CO₂CH₂C≡CH | OCH₃ | OCH₃ | N | |
| H | CH₃ | H | CO₂CH₂CH=CH₂ | OCH₃ | Cl | CH | |
| H | CH₃ | H | CO₂CH₂CH=CH₂ | CH₃ | CH₃ | CH | |
| H | CH₃ | H | CO₂CH₂CH=CH₂ | CH₃ | OCH₃ | CH | |
| H | CH₃ | H | CO₂CH₂CH=CH₂ | OCH₃ | OCH₃ | CH | |
| H | CH₃ | H | CO₂CH₂CH=CH₂ | CH₃ | CH₃ | N | |
| H | CH₃ | H | CO₂CH₂CH=CH₂ | CH₃ | OCH₃ | N | |
| H | CH₃ | CH₃ | CO₂CH₃ | OCH₃ | OCH₃ | N | |
| H | CH₃ | H | CO₂CF₃ | OCH₃ | Cl | CH | |
| H | CH₃ | H | CO₂CF₃ | CH₃ | CH₃ | CH | |
| H | CH₃ | H | CO₂CF₃ | CH₃ | OCH₃ | CH | |
| H | CH₃ | H | CO₂CF₃ | OCH₃ | OCH₃ | CH | |
| H | CH₃ | H | CO₂CH₂CH₂Cl | CH₃ | CH₃ | N | |
| H | CH₃ | H | CO₂CH₂CH₂Cl | CH₃ | OCH₃ | N | |
| H | CH₃ | H | CO₂CH₂CH₂Cl | OCH₃ | OCH₃ | N | |
| H | CH₃ | H | CO₂CH₂CH₂P(O)(CH₃)₂ | OCH₃ | Cl | CH | |
| H | CH₃ | H | CO₂CH₂CH₂P(O)(CH₃)₂ | CH₃ | CH₃ | CH | |
| CH₃ | CH₃ | H | CO₂C(CH₃)₃ | CH₃ | OCH₃ | CH | |
| H | CH₃ | H | CO₂C(CH₃)₃ | OCH₃ | OCH₃ | CH | |
| H | CH₃ | H | CO₂CH₂(CH₂)₄CH₃ | CH₃ | CH₃ | N | |
| H | CH₃ | H | CO₂CH₂(CH₂)₄CH₃ | CH₃ | OCH₃ | N | |
| H | CH₃ | H | CO₂CH₂OCH₃ | OCH₃ | OCH₃ | N | |
| H | CH₃ | H | CO₂CH₂OCH₃ | OCH₃ | Cl | CH | |
| H | CH₃ | H | (C(O))₂OCH₃ | CH₃ | CH₃ | CH | |
| H | CH₃ | H | (C(O))₂OCH₃ | CH₃ | OCH₃ | CH | |
| H | CH₃ | H | (C(O))₂OCH₃ | OCH₃ | OCH₃ | CH | |
| H | CH₃ | H | (C(O))₂OCH₃ | CH₃ | CH₃ | N | |
| H | CH₃ | H | (C(O))₂OCH₃ | CH₃ | OCH₃ | N | |
| H | CH₃ | H | (C(O))₂OCH₃ | OCH₃ | OCH₃ | N | |
| H | CH₃ | H | (C(O))₂OCH₃ | OCH₃ | Cl | CH | |
| H | CH₃ | H | (CO)₂CH₃ | CH₃ | CH₃ | CH | |
| H | CH₃ | H | (CO)₂CH₃ | CH₃ | OCH₃ | CH | |
| H | CH₃ | H | (CO)₂CH₃ | OCH₃ | OCH₃ | CH | |
| H | CH₃ | H | (CO)₂CH₃ | CH₃ | CH₃ | N | |
| H | CH₃ | H | (CO)₂CH₃ | CH₃ | OCH₃ | N | |
| H | CH₃ | H | (CO)₂CH₃ | OCH₃ | OCH₃ | N | |
| H | CH₃ | H | (CO)₂CH₃ | OCH₃ | Cl | CH | |
| H | CH₃ | H | C(O)N(CH₃)₂ | CH₃ | CH₃ | CH | |
| H | CH₃ | H | C(O)N(CH₃)₂ | CH₃ | OCH₃ | CH | |
| H | CH₃ | H | C(O)N(CH₃)₂ | OCH₃ | OCH₃ | CH | |
| H | CH₃ | H | C(O)N(CH₃)₂ | CH₃ | CH₃ | N | |
| H | CH₃ | H | C(O)N(CH₃)₂ | OCH₃ | OCH₃ | N | |
| H | CH₃ | H | C(O)N(CH₃)₂ | OCH₃ | Cl | CH | |
| H | CH₃ | H | C(O)N(CH₂CH₃)₂ | CH₃ | CH₃ | CH | |
| H | CH₃ | H | C(O)N(CH₂CH₃)₂ | CH₃ | OCH₃ | CH | |
| H | CH₃ | H | C(O)N(CH₂CH₃)₂ | OCH₃ | OCH₃ | CH | |
| H | CH₃ | H | C(O)N(CH₂CH₃)₂ | CH₃ | CH₃ | N | |
| H | CH₃ | H | C(O)N(CH₂CH₃)₂ | CH₃ | OCH₃ | N | |
| H | CH₃ | H | C(O)N(CH₂CH₃)₂ | OCH₃ | OCH₃ | N | |
| H | CH₃ | H | C(O)N(CH₃)CH₂CH₃ | OCH₃ | Cl | CH | |
| H | CH₃ | H | C(O)N(CH₃)CH₂CH₃ | CH₃ | CH₃ | CH | |
| H | CH₃ | H | C(O)N(CH₃)CH₂CH₃ | CH₃ | OCH₃ | CH | |
| H | CH₃ | H | C(O)N(CH₃)CH₂CH₃ | OCH₃ | OCH₃ | CH | |
| H | CH₃ | H | C(O)N(CH₃)CH₂CH₃ | CH₃ | CH₃ | N | |
| H | CH₃ | H | C(O)N(CF₃)CH₃ | CH₃ | OCH₃ | N | |
| H | CH₃ | CH₃ | C(O)N(CF₃)CH₃ | OCH₃ | OCH₃ | N | |
| H | CH₃ | H | C(O)N(CF₃)CH₃ | OCH₃ | Cl | CH | |
| H | CH₃ | H | C(O)N(CH₃)OCH₃ | CH₃ | CH₃ | CH | |
| H | CH₃ | H | C(O)N(CH₃)OCH₃ | CH₃ | OCH₃ | CH | |
| H | CH₃ | H | C(O)N(CH₃)OCH₃ | OCH₃ | OCH₃ | CH | |
| H | CH₃ | H | C(O)N(CH₃)OCH₃ | CH₃ | CH₃ | N | |
| H | CH₃ | H | C(O)N(CH=CH₂)CH₃ | CH₃ | OCH₃ | N | |
| H | CH₃ | H | C(O)N(CH=CH₂)CH₃ | OCH₃ | OCH₃ | N | |
| H | CH₃ | H | C(O)N(CH=CH₂)CH₃ | OCH₃ | Cl | CH | |
| H | CH₃ | H | C(O)N(CH=CH₂)CH₃ | CH₃ | CH₃ | CH | |
| CH₃ | CH₃ | H | C(O)N(CH=CH₂)CH₃ | CH₃ | OCH₃ | CH | |

TABLE IIa-continued

| R | R₁ | R₂ | R₃ | X | Y | Z | m.p. (°C.) |
|---|---|---|---|---|---|---|---|
| H | CH₃ | H | C(O)N(CH₃)Ph | OCH₃ | OCH₃ | CH | |
| H | CH₃ | H | C(O)N(CH₃)Ph | CH₃ | CH₃ | N | |
| H | CH₃ | H | C(O)N(CH₃)Ph | CH₃ | OCH₃ | N | |
| H | CH₃ | H | C(O)N(OCH₃)₂ | OCH₃ | OCH₃ | N | |
| H | CH₃ | H | C(O)N(OCH₃)₂ | OCH₃ | Cl | CH | |
| H | CH₃ | H | CS₂CH₃ | CH₃ | CH₃ | CH | |
| H | CH₃ | H | CS₂CH₃ | OCH₃ | OCH₃ | CH | |
| H | CH₃ | H | CS₂CH₃ | CH₃ | CH₃ | N | |
| H | CH₃ | H | CS₂CH₃ | CH₃ | OCH₃ | N | |
| H | CH₃ | H | CS₂CH₃ | OCH₃ | OCH₃ | N | |
| H | CH₃ | H | CS₂CH₃ | OCH₃ | Cl | CH | |
| H | CH₃ | H | CS₂CH₂CH₃ | CH₃ | CH₃ | CH | |
| H | CH₃ | H | CS₂CH₂₃ | CH₃ | OCH₃ | CH | |
| H | CH₃ | H | CS₂CH₂CH₃ | OCH₃ | OCH₃ | CH | |
| H | CH₃ | H | CS₂CH₂CH₃ | CH₃ | CH₃ | N | |
| H | CH₃ | H | CS₂CH₂CH₃ | CH₃ | OCH₃ | N | |
| H | CH₃ | H | CS₂CH₂CH=CH₂ | OCH₃ | OCH₃ | N | |
| H | CH₃ | H | CS₂CH₂CH=CH₂ | OCH₃ | Cl | CH | |
| H | CH₃ | H | CS₂CH₂CH=CH₂ | OCH₃ | CH₃ | CH | |
| H | CH₃ | H | NH₂ | CH₃ | CH₃ | CH | |
| H | CH₃ | H | NH₂ | CH₃ | OCH₃ | CH | |
| H | CH₃ | H | NH₂ | OCH₃ | OCH₃ | CH | |
| H | CH₃ | H | NH₂ | CH₃ | CH₃ | N | |
| H | CH₃ | H | NH₂ | CH₃ | OCH₃ | N | |
| H | CH₃ | H | NH₂ | OCH₃ | OCH₃ | N | |
| H | CH₃ | H | NH₂ | OCH₃ | Cl | CH | |
| H | CH₃ | H | N(CH₃)₂ | CH₃ | CH₃ | CH | |
| H | CH₃ | H | N(CH₃)₂ | CH₃ | OCH₃ | CH | |
| H | CH₃ | H | N(CH₃)₂ | OCH₃ | OCH₃ | CH | |
| H | CH₃ | H | N(CH₃)₂ | CH₃ | CH₃ | N | |
| H | CH₃ | H | N(CH₃)₂ | CH₃ | OCH₃ | N | |
| H | CH₃ | H | N(CH₃)₂ | OCH₃ | OCH₃ | N | |
| H | CH₃ | H | N(CH₃)₂ | OCH₃ | Cl | CH | |
| H | CH₃ | H | N(CH₃)(CH₂CH₃) | CH₃ | CH₃ | CH | |
| H | CH₃ | H | N(CH₃)(CH₂CH₃) | CH₃ | OCH₃ | CH | |
| H | CH₃ | H | N(CH₃)(CH₂CH₃) | OCH₃ | OCH₃ | CH | |
| H | CH₃ | H | N(CH₃)OCH₃ | CH₃ | CH₃ | N | |
| H | CH₃ | H | N(CH₃)OCH₃ | CH₃ | OCH₃ | N | |
| H | CH₃ | H | N(CH₃)OCH₃ | OCH₃ | OCH₃ | N | |
| H | CH₃ | H | N(CH₃)CH=CH₂ | OCH₃ | Cl | CH | |
| H | CH₃ | H | N(CH₃)CH=CH₂ | CH₃ | CH₃ | CH | |
| CH₃ | CH₃ | H | N(CH₃)CH=CH₂ | CH₃ | OCH₃ | CH | |
| H | CH₃ | H | N(CH₃)CH=CH₂ | OCH₃ | OCH₃ | CH | |
| H | CH₃ | H | N(CH₂CH₃)₂ | CH₃ | CH₃ | N | |
| H | CH₃ | H | N(CH₂CH₃)₂ | CH₃ | OCH₃ | N | |
| H | CH₃ | H | N(CH₂CH₃)₂ | OCH₃ | OCH₃ | N | |
| H | CH₃ | H | N(CH₂CH₃)₂ | OCH₃ | Cl | CH | |
| H | CH₃ | H | OH | CH₃ | CH₃ | CH | |
| H | CH₃ | H | OH | CH₃ | OCH₃ | CH | |
| H | CH₃ | H | OH | OCH₃ | OCH₃ | CH | |
| H | CH₃ | H | OH | CH₃ | CH₃ | N | |
| H | CH₃ | H | OH | CH₃ | OCH₃ | N | |
| H | CH₃ | H | OH | OCH₃ | OCH₃ | N | |
| H | CH₃ | H | OH | OCH₃ | Cl | CH | |
| H | CH₃ | H | CN | CH₃ | CH₃ | CH | |
| H | CH₃ | H | CN | CH₃ | OCH₃ | CH | |
| H | CH₃ | H | CN | OCH₃ | OCH₃ | CH | |
| H | CH₃ | H | CN | CH₃ | CH₃ | N | |
| H | CH₃ | H | CN | CH₃ | OCH₃ | N | |
| H | CH₃ | H | CN | OCH₃ | OCH₃ | N | |
| H | CH₃ | H | CN | OCH₃ | Cl | CH | |
| H | CH₃ | H | P(O)(CH₃)₂ | CH₃ | CH₃ | CH | |
| H | CH₃ | H | P(O)(CH₃)₂ | CH₃ | OCH₃ | CH | |
| H | CH₃ | H | P(O)(CH₃)₂ | OCH₃ | OCH₃ | CH | |
| H | CH₃ | H | P(O)(CH₃)₂ | CH₃ | CH₃ | N | |
| H | CH₃ | H | P(O)(CH₃)₂ | OCH₃ | OCH₃ | N | |
| H | CH₃ | H | P(O)(OCH₃)₂ | OCH₃ | Cl | CH | |
| H | CH₃ | H | P(O)(OCH₃)₂ | CH₃ | CH₃ | CH | |
| H | CH₃ | H | P(O)(OCH₃)₂ | CH₃ | OCH₃ | CH | |
| H | CH₃ | H | P(O)(OCH₃)₂ | OCH₃ | OCH₃ | CH | |
| H | CH₃ | H | P(O)(OCH₃)SCH₃ | CH₃ | CH₃ | N | |
| H | CH₃ | H | P(O)(OCH₃)SCH₃ | CH₃ | OCH₃ | N | |
| H | CH₃ | H | P(O)(OCH₃)SCH₃ | OCH₃ | OCH₃ | N | |
| H | CH₃ | H | P(O)(OCH₃)SCH₃ | OCH₃ | Cl | CH | |
| H | CH₃ | H | P(O)(OCH₃)SCH₂CH₂CH₃ | CH₃ | CH₃ | CH | |
| H | CH₃ | H | P(O)(OCH₃)SCH₂CH₂CH₃ | CH₃ | OCH₃ | CH | |
| H | CH₃ | H | P(O)(OCH₃)SCH₂CH₂CH₃ | OCH₃ | OCH₃ | CH | |
| H | CH₃ | H | P(O)(OCH₃)SCH₂CH₂CH₃ | CH₃ | CH₃ | N | |
| H | CH₃ | H | P(O)(OCH₃)SCH₂CH₂CH₃ | CH₃ | OCH₃ | N | |
| H | CH₃ | CH₃ | OH | OCH₃ | OCH₃ | N | |

TABLE IIa-continued

| R | R₁ | R₂ | R₃ | X | Y | Z | m.p. (°C.) |
|---|---|---|---|---|---|---|---|
| H | CH₃ | H | P(S)(CH₃)₂ | OCH₃ | Cl | CH | |
| H | CH₃ | H | P(S)(CH₃)₂ | CH₃ | CH₃ | CH | |
| H | CH₃ | H | P(S)(CH₃)₂ | CH₃ | OCH₃ | CH | |
| H | CH₃ | H | P(S)(CH₃)₂ | OCH₃ | OCH₃ | CH | |
| H | CH₃ | H | P(S)(CH₃)₂ | CH₃ | CH₃ | N | |
| H | CH₃ | H | P(S)(CH₃)₂ | CH₃ | OCH₃ | N | |
| H | CH₃ | H | P(S)(CH₃)₂ | OCH₃ | OCH₃ | N | |
| H | CH₃ | H | P(S)(OCH₃)₂ | OCH₃ | Cl | CH | |
| H | CH₃ | H | P(S)(OCH₃)₂ | CH₃ | CH₃ | CH | |
| CH₃ | CH₃ | H | P(S)(OCH₃)₂ | CH₃ | OCH₃ | CH | |
| H | CH₃ | H | P(S)(OCH₃)₂ | OCH₃ | OCH₃ | CH | |
| H | CH₃ | H | P(S)(OCH₃)₂ | CH₃ | CH₃ | N | |
| H | CH₃ | H | P(S)(OCH₃)₂ | CH₃ | OCH₃ | N | |
| H | CH₃ | H | P(S)(OCH₃)SCH₃ | OCH₃ | OCH₃ | N | |
| H | CH₃ | H | P(S)(OCH₃)SCH₃ | OCH₃ | Cl | CH | |
| H | CH₃ | H | NO₂ | CH₃ | CH₃ | CH | |
| H | CH₃ | H | NO₂ | CH₃ | OCH₃ | CH | |
| H | CH₃ | H | NO₂ | OCH₃ | OCH₃ | CH | |
| H | CH₃ | H | NO₂ | CH₃ | CH₃ | N | |
| H | CH₃ | H | NO₂ | CH₃ | OCH₃ | N | |
| H | CH₃ | H | NO₂ | OCH₃ | OCH₃ | N | |
| H | CH₃ | H | CH₂C(O)CH(-CH₂-CH₂-) (cyclopropyl) | CH₃ | CH₃ | N | |
| H | CH₃ | H | CH₂C(O)CH(-CH₂-CH₂-) (cyclopropyl) | CH₃ | OCH₃ | N | |
| H | CH₃ | H | CH₂C(O)CH(-CH₂-CH₂-) (cyclopropyl) | OCH₃ | OCH₃ | N | |
| H | CH₃ | H | CH₂C(O)CH(-CH₂-CH₂-) (cyclopropyl) | OCH₃ | Cl | CH | |
| H | CH₃ | H | CH₂C(O)CH(-CH₂-CH₂-) (cyclopropyl) | CH₃ | CH₃ | CH | |
| H | CH₃ | H | CH₂C(O)CH(-CH₂-CH₂-) (cyclopropyl) | CH₃ | OCH₃ | CH | |
| H | CH₃ | H | CH₂C(O)Ph | OCH₃ | OCH₃ | CH | |
| H | CH₃ | H | CH₂C(O)Ph | CH₃ | CH₃ | N | |
| H | CH₃ | H | CH₂C(O)Ph | CH₃ | OCH₃ | N | |
| H | CH₃ | CH₃ | CH₂C(O)Ph | OCH₃ | OCH₃ | N | |
| H | CH₃ | H | CH₂C(O)Ph | OCH₃ | Cl | CH | |
| H | CH₃ | H | CH₂C(O)Ph | CH₃ | CH₃ | CH | |
| H | CH₃ | H | CH₂C(O)Ph | CH₃ | OCH₃ | CH | |
| H | CH₃ | H | CH(CH)₃C(O)CH₃ | OCH₃ | OCH₃ | CH | |
| H | CH₃ | H | CH(CH)₃C(O)CH₃ | CH₃ | CH₃ | N | |
| H | CH₃ | H | CH(CH)₃C(O)CH₃ | CH₃ | OCH₃ | N | |
| H | CH₃ | H | CH(CH)₃C(O)CH₃ | OCH₃ | OCH₃ | N | |
| H | CH₃ | H | CH₂CF₂—C(O)CH₃ | OCH₃ | Cl | CH | |
| H | CH₃ | H | CH₂CF₂—C(O)CH₃ | CH₃ | CH₃ | CH | |
| CH₃ | CH₃ | H | CH₂CF₂—C(O)CH₃ | CH₃ | OCH₃ | CH | |
| H | CH₃ | H | CH₂CF₂—C(O)CH₃ | OCH₃ | OCH₃ | CH | |
| H | CH₃ | H | CH₂C(O)CH₂OCH₃ | CH₃ | CH₃ | N | |
| H | CH₃ | H | CH₂C(O)CH₂OCH₃ | CH₃ | OCH₃ | N | |
| H | CH₃ | H | CH₂C(O)CH₂OCH₃ | OCH₃ | OCH₃ | N | |
| H | CH₃ | H | CH₂C(O)CH₂OCH₃ | OCH₃ | Cl | CH | |
| H | CH₃ | H | CH₂CO₂CH₃ | CH₃ | CH₃ | CH | |
| H | CH₃ | H | CH₂CO₂CH₃ | CH₃ | OCH₃ | CH | |
| H | CH₃ | H | CH₂CO₂CH₃ | OCH₃ | OCH₃ | CH | |
| H | CH₃ | H | CH₂CO₂CH₃ | CH₃ | CH₃ | N | |

TABLE IIa-continued

| R | R₁ | R₂ | R₃ | X | Y | Z | m.p. (°C.) |
|---|---|---|---|---|---|---|---|
| H | CH₃ | H | CH₂CO₂CH₃ | CH₃ | OCH₃ | N | |
| H | CH₃ | H | CH₂CO₂CH₃ | OCH₃ | OCH₃ | N | |
| H | CH₃ | H | CH₂CO₂CH₃ | OCH₃ | Cl | CH | |
| H | CH₃ | H | CH₂CO₂CH₂CH₃ | CH₃ | CH₃ | CH | |
| H | CH₃ | H | CH₂CO₂CH₂CH₃ | CH₃ | OCH₃ | CH | |
| H | CH₃ | H | CH₂CO₂CH₂CH₃ | OCH₃ | OCH₃ | CH | |
| H | CH₃ | H | CH₂CO₂CH₂CH₃ | CH₃ | CH₃ | N | |
| H | CH₃ | H | CH₂CO₂CH₂CH₃ | CH₃ | OCH₃ | N | |
| H | CH₃ | H | CH₂CO₂CH₂CH₃ | OCH₃ | OCH₃ | N | |
| H | CH₃ | H | CH₂CO₂CH₂CH₃ | OCH₃ | Cl | CH | |
| H | CH₃ | H | CH₂CH₂CO₂CH₃ | CH₃ | CH₃ | CH | |
| H | CH₃ | H | CH₂CH₂CO₂CH₃ | CH₃ | OCH₃ | CH | |
| H | CH₃ | H | CH₂CH₂CH₃ | OCH₃ | OCH₃ | CH | |
| H | CH₃ | H | CH₂CH₂CO₂CH₃ | CH₃ | CH₃ | N | |
| H | CH₃ | H | CH₂CH₂CO₂CH₃ | OCH₃ | OCH₃ | N | |
| H | CH₃ | H | CH₂CH₂CO₂CH₃ | OCH₃ | Cl | CH | |
| H | CH₃ | H | CH₂—CO₂CH₂CH=CH₂ | CH₃ | CH₃ | CH | |
| H | CH₃ | H | CH₂—CO₂CH₂CH=CH₂ | CH₃ | OCH₃ | CH | |
| H | CH₃ | H | CH₂—CO₂CH₂CH=CH₂ | OCH₃ | OCH₃ | CH | |
| H | CH₃ | H | CH₂—CO₂CH₂CH=CH₂ | CH₃ | CH₃ | N | |
| H | CH₃ | H | CH₂—CO₂CH₂CH=CH₂ | CH₃ | OCH₃ | N | |
| H | CH₃ | H | CH₂—CO₂CH₂CH=CH₂ | OCH₃ | OCH₃ | N | |
| H | CH₃ | H | CH₂—CO₂CH₂CH=CH₂ | OCH₃ | Cl | CH | |
| H | CH₃ | H | CH₂(CH₂)₄CO₂CH₃ | CH₃ | CH₃ | CH | |
| H | CH₃ | H | CH₂(CH₂)₄CO₂CH₃ | CH₃ | OCH₃ | CH | |
| H | CH₃ | H | CH₂(CH₂)₄CO₂CH₃ | OCH₃ | OCH₃ | CH | |
| H | CH₃ | H | CH₂(CH₂)₄CO₂CH₃ | CH₃ | CH₃ | N | |
| H | CH₃ | H | CH₂(CH₂)₄CO₂CH₃ | CH₃ | OCH₃ | N | |
| H | CH₃ | CH₃ | CH₂(CH₂)₄CO₂CH₃ | OCH₃ | OCH₃ | N | |
| H | CH₃ | H | CH₂(CH₂)₄CO₂CH₃ | OCH₃ | Cl | CH | |
| H | CH₃ | H | CH₂CO₂CH₂C≡CH | CH₃ | CH₃ | CH | |
| H | CH₃ | H | CH₂CO₂CH₂C≡CH | CH₃ | OCH₃ | CH | |
| H | CH₃ | H | CH₂CO₂CH₂C≡CH | OCH₃ | OCH₃ | CH | |
| H | CH₃ | H | CH₂CO₂CH₂C≡CH | CH₃ | CH₃ | N | |
| H | CH₃ | H | CH₂CO₂CH₂C≡CH | CH₃ | OCH₃ | N | |
| H | CH₃ | H | CH₂CO₂CH₂C≡CH | OCH₃ | OCH₃ | N | |
| H | CH₃ | H | CH₂CO₂CH₂C≡CH | OCH₃ | Cl | CH | |
| H | CH₃ | H | CH₂CO₂CF₃ | CH₃ | CH₃ | CH | |
| CH₃ | CH₃ | H | CH₂CO₂CF₃ | CH₃ | OCH₃ | CH | |
| H | CH₃ | H | CH₂CO₂CF₃ | OCH₃ | OCH₃ | CH | |
| H | CH₃ | H | CH₂CO₂CF₃ | CH₃ | CH₃ | N | |
| H | CH₃ | H | CH₂CO₂CF₃ | CH₃ | OCH₃ | N | |
| H | CH₃ | H | CH₂CO₂CF₃ | OCH₃ | OCH₃ | N | |
| H | CH₃ | H | CH₂CO₂CF₃ | OCH₃ | Cl | CH | |
| H | CH₃ | H | CH₂C(O)N(CH₃)₂ | CH₃ | CH₃ | CH | |
| H | CH₃ | H | CH₂C(O)N(CH₃)₂ | CH₃ | OCH₃ | CH | |
| H | CH₃ | H | CH₂C(O)N(CH₃)₂ | OCH₃ | OCH₃ | CH | |
| H | CH₃ | H | CH₂C(O)N(CH₃)₂ | CH₃ | CH₃ | N | |
| H | CH₃ | H | CH₂C(O)N(CH₃)₂ | CH₃ | OCH₃ | N | |
| H | CH₃ | H | CH₂C(O)N(CH₃)₂ | OCH₃ | OCH₃ | N | |
| H | CH₃ | H | CH₂C(O)N(CH₃)₂ | OCH₃ | Cl | CH | |
| H | CH₃ | H | SeCH₃ | CH₃ | CH₃ | CH | |
| H | CH₃ | H | SeCH₃ | CH₃ | OCH₃ | CH | |
| H | CH₃ | H | SeCH₃ | OCH₃ | OCH₃ | CH | |
| H | CH₃ | H | SeCH₃ | CH₃ | CH₃ | N | |
| H | CH₃ | H | SeCH₃ | CH₃ | OCH₃ | N | |
| H | CH₃ | H | SeCH₃ | OCH₃ | OCH₃ | N | |
| H | CH₃ | H | SeCH₃ | OCH₃ | Cl | CH | |
| H | CH₃ | H | CH₂Ph | CH₃ | CH₃ | CH | |
| H | CH₃ | H | CH₂Ph | CH₃ | OCH₃ | CH | |
| H | CH₃ | H | CH₂Ph | OCH₃ | OCH₃ | CH | |
| H | CH₃ | H | CH₂Ph | CH₃ | CH₃ | N | |
| H | CH₃ | H | CH₂Ph | OCH₃ | OCH₃ | N | |
| H | CH₃ | H | CH₂Ph | OCH₃ | Cl | CH | |
| H | CH₃ | H | CH₂—(1,3-dioxolan-2-yl) | CH₃ | CH₃ | CH | |
| H | CH₃ | H | CH₂—(1,3-dioxolan-2-yl) | CH₃ | OCH₃ | CH | |
| H | CH₃ | H | CH₂—(1,3-dioxolan-2-yl) | OCH₃ | OCH₃ | CH | |
| H | CH₃ | H | CH₂—(1,3-dioxolan-2-yl) | CH₃ | CH₃ | N | |
| H | CH₃ | H | CH₂—(1,3-dioxolan-2-yl) | CH₃ | OCH₃ | N | |
| H | CH₃ | H | CH₂—(1,3-dioxolan-2-yl) | OCH₃ | OCH₃ | N | |
| H | CH₃ | H | CH₂—OTHP | OCH₃ | Cl | CH | |
| H | CH₃ | H | CH₂—OTHP | CH₃ | CH₃ | CH | |
| H | CH₃ | H | CH₂—OTHP | CH₃ | OCH₃ | CH | |
| H | CH₃ | H | CH₂—OTHP | OCH₃ | OCH₃ | CH | |
| H | CH₃ | H | CH₂—OTHP | CH₃ | CH₃ | N | |
| H | CH₃ | H | CH₂—OTHP | CH₃ | OCH₃ | N | |
| H | CH₃ | CH₃ | CH₂—OTHP | OCH₃ | OCH₃ | N | |
| H | CH₃ | H | Si(CH₃)₃ | CH₃ | CH₃ | CH | |
| H | CH₃ | H | Si(CH₃)₃ | CH₃ | OCH₃ | CH | |
| H | CH₃ | H | Si(CH₃)₃ | OCH₃ | OCH₃ | CH | |
| H | CH₃ | H | Si(CH₃)₃ | CH₃ | CH₃ | N | |

TABLE IIa-continued

| R | R₁ | R₂ | R₃ | X | Y | Z | m.p. (°C.) |
|---|---|---|---|---|---|---|---|
| H | CH₃ | H | Si(CH₃)₃ | CH₃ | OCH₃ | N | |
| H | CH₃ | H | Si(CH₃)₃ | OCH₃ | OCH₃ | N | |
| H | CH₃ | H | Si(CH₃)₃ | OCH₃ | Cl | CH | |
| H | CH₃ | H | Si(CH₃)₂Ph | CH₃ | CH₃ | CH | |
| H | CH₃ | H | Si(CH₃)₂Ph | CH₃ | OCH₃ | CH | |
| H | CH₃ | H | Si(CH₃)₂Ph | OCH₃ | OCH₃ | CH | |
| H | CH₃ | H | Si(CH₃)₂Ph | CH₃ | CH₃ | N | |
| H | CH₃ | H | Si(CH₃)₂Ph | CH₃ | OCH₃ | N | |
| H | CH₃ | H | Si(CH₃)₂Ph | OCH₃ | OCH₃ | N | |
| H | CH₃ | H | Si(CH₃)₂Ph | OCH₃ | Cl | CH | |
| H | CH₃ | H | Si(CH₃)₂CH₂CH₃ | CH₃ | CH₃ | CH | |
| H | CH₃ | H | Si(CH₃)₂CH₂CH₃ | CH₃ | OCH₃ | CH | |
| H | CH₃ | H | Si(CH₃)₂CH₂CH₃ | OCH₃ | OCH₃ | CH | |
| H | CH₃ | H | Si(CH₃)₂CH₂CH₃ | CH₃ | CH₃ | N | |
| H | CH₃ | H | Si(CH₃)₂CH₂CH₃ | OCH₃ | OCH₃ | N | |
| H | CH₃ | H | Si(CH₃)₂CH₂CH₃ | OCH₃ | Cl | CH | |
| H | CH₃ | H | A—HET | CH₃ | CH₃ | CH | |
| H | CH₃ | H | A—HET | CH₃ | OCH₃ | CH | |
| H | CH₃ | H | A—HET | OCH₃ | OCH₃ | CH | |
| H | CH₃ | H | A—HET | CH₃ | CH₃ | N | |
| H | CH₃ | H | A—HET | CH₃ | OCH₃ | N | |
| H | CH₃ | H | A—HET | OCH₃ | OCH₃ | N | |
| H | CH₃ | H | A—HET | OCH₃ | Cl | CH | |
| H | CH₃ | H | B—HET | CH₃ | CH₃ | CH | |
| H | CH₃ | H | B—HET | CH₃ | OCH₃ | CH | |
| H | CH₃ | H | B—HET | OCH₃ | OCH₃ | CH | |
| H | CH₃ | H | B—HET | CH₃ | CH₃ | N | |
| H | CH₃ | H | B—HET | CH₃ | OCH₃ | N | |
| H | CH₃ | CH₃ | B—HET | OCH₃ | OCH₃ | N | |
| H | CH₃ | H | B—HET | OCH₃ | Cl | CH | |
| H | CH₃ | H | C—HET | CH₃ | CH₃ | CH | |
| H | CH₃ | H | C—HET | CH₃ | OCH₃ | CH | |
| H | CH₃ | H | C—HET | OCH₃ | OCH₃ | CH | |
| H | CH₃ | H | C—HET | CH₃ | CH₃ | N | |
| H | CH₃ | H | C—HET | CH₃ | OCH₃ | N | |
| H | CH₃ | H | C—HET | OCH₃ | OCH₃ | N | |
| H | CH₃ | H | C—HET | OCH₃ | Cl | CH | |
| H | CH₃ | H | D—HET | CH₃ | CH₃ | CH | |
| CH₃ | CH₃ | H | D—HET | CH₃ | OCH₃ | CH | |
| H | CH₃ | H | D—HET | OCH₃ | OCH₃ | CH | |
| H | CH₃ | H | D—HET | CH₃ | CH₃ | N | |
| H | CH₃ | H | D—HET | CH₃ | OCH₃ | N | |
| H | CH₃ | H | D—HET | OCH₃ | OCH₃ | N | |
| H | CH₃ | H | D—HET | OCH₃ | Cl | CH | |
| H | CH₃ | H | C(O)A—HET | CH₃ | CH₃ | CH | |
| H | CH₃ | H | C(O)A—HET | CH₃ | OCH₃ | CH | |
| H | CH₃ | H | C(O)A—HET | OCH₃ | OCH₃ | CH | |
| H | CH₃ | H | C(O)A—HET | CH₃ | CH₃ | N | |
| H | CH₃ | H | C(O)A—HET | CH₃ | OCH₃ | N | |
| H | CH₃ | H | C(O)A—HET | OCH₃ | OCH₃ | N | |
| H | CH₃ | H | C(O)A—HET | OCH₃ | Cl | CH | |
| H | CH₃ | H | C(O)B—HET | CH₃ | CH₃ | CH | |
| H | CH₃ | H | C(O)B—HET | CH₃ | OCH₃ | CH | |
| H | CH₃ | H | C(O)B—HET | OCH₃ | OCH₃ | CH | |
| H | CH₃ | H | C(O)B—HET | CH₃ | CH₃ | N | |
| H | CH₃ | H | C(O)B—HET | CH₃ | OCH₃ | N | |
| H | CH₃ | H | C(O)B—HET | OCH₃ | OCH₃ | N | |
| H | CH₃ | H | C(O)B—HET | OCH₃ | Cl | CH | |
| H | CH₃ | H | C(O)C—HET | CH₃ | CH₃ | CH | |
| H | CH₃ | H | C(O)C—HET | CH₃ | OCH₃ | CH | |
| H | CH₃ | H | C(O)C—HET | OCH₃ | OCH₃ | CH | |
| H | CH₃ | H | C(O)C—HET | CH₃ | CH₃ | N | |
| H | CH₃ | H | C(O)C—HET | OCH₃ | OCH₃ | N | |
| H | CH₃ | H | C(O)C—HET | OCH₃ | Cl | CH | |
| H | CH₃ | H | C(O)D—HET | CH₃ | CH₃ | CH | |
| H | CH₃ | H | C(O)D—HET | CH₃ | OCH₃ | CH | |
| H | CH₃ | H | C(O)D—HET | OCH₃ | OCH₃ | CH | |
| H | CH₃ | H | C(O)D—HET | CH₃ | CH₃ | N | |
| H | CH₃ | H | C(O)D—HET | CH₃ | OCH₃ | N | |
| H | CH₃ | H | C(O)D—HET | OCH₃ | OCH₃ | N | |

TABLE IIa-continued

| R | R₁ | R₂ | R₃ | X | Y | Z | m.p. (°C.) |
|---|----|----|-----|---|---|---|------------|
| H | CH₃ | H | C(O)D—HET | OCH₃ | Cl | CH | | wherein

A—HET is 

B—HET is 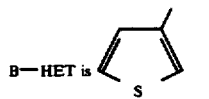

C—HET is 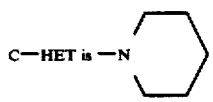

D—HET is 

TABLE III

General Structure III

| A | R | R₁ | R₂ | R₃ | X | Y | Z | m.p. (°C.) |
|---|---|----|----|-----|---|---|---|------------|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH | CH₃ | N | |
| A-1 | H | CH₃ | H | CH(CF₃)₂ | O—⊲ | OCH₃ | N | |
| A-1 | H | CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | SCF₂H | CH₃ | CH | |
| A-1 | H | CH₃ | H | Si(CH₃)₃ | OCH₃ | OCH₂CH=CH₂ | CH | |
| A-1 | H | CH₃ | H | CH₂F | OCH₃ | CN | CH | |
| A-1 | H | CH₃ | H | CH₂F | OCH₃ | CH(OCH₃)₂ | CH | |

| A | R | R₁ | R₂ | R₃ | X₁ | Y₁ | m.p. (°C.) |
|---|---|----|----|-----|-----|-----|------------|
| A-2 | H | CH₃ | H | CH₂—CH=CH₂ | CH₃ | CH₂ | |
| A-2 | H | CH₃ | H | CH₂—CH=CH₂ | CH₃ | O | |
| A-2 | H | CH₃ | H | CH₂—C≡CH | OCH₃ | CH₂ | |
| A-2 | H | CH₃ | H | CH₂F | OCF₂H | CH₂ | |
| A-3 | H | CH₃ | H | CH₂CH₂Cl | CH₃ | | |
| A-3 | H | CH₃ | H | CH₂P(O)(CH₃)₂ | OCH₃ | | |
| A-3 | H | CH₃ | H | CH₂(CH₂)₆CH₃ | OCH₂CH₃ | | |
| A-3 | H | CH₃ | H | CH₂CH=CF₂ | OCF₂H | | |

| A | R | R₁ | R₂ | R₃ | X₁ | Y₃ | m.p. (°C.) |
|---|---|----|----|-----|-----|-----|------------|
| A-4 | H | CH₃ | H | CH₂—CH(O)CH₂ | CH₃ | H | |
| A-4 | H | CH₃ | H | CH₂—CH(O)CH₂ | OCH₃ | H | |
| A-4 | H | CH₃ | H | CH₂SO₂CH₃ | OCF₂H | CH₃ | |
| A-4 | H | CH₃ | H | CH₂SO₂CH₃ | OCF₂H | H | |
| A-4 | H | CH₃ | H | SCH₃ | OCH₂CH₃ | H | |
| A-4 | H | CH₃ | H | CH₂Si(CH₃)₃ | CH₃ | H | |
| A-4 | H | CH₃ | H | CH₂C(O)CH₃ | OCH₃ | CH₃ | |

| A | R | R₁ | R₂ | R₃ | X₂ | Y₂ | m.p. (°C.) |
|---|---|----|----|-----|-----|-----|------------|
| A-5 | H | CH₃ | H | CH₂C(O)CH₃ | CH₃ | OCH₃ | |
| A-5 | H | CH₃ | H | CH₂C(O)CH₃ | CH₂CH₃ | OCH₃ | |
| A-5 | H | CH₃ | H | CH₂C(O)OCH₃ | CH₂CF₃ | SCH₃ | |
| A-5 | H | CH₃ | H | CH₂C(O)OCH₃ | CH₃ | CH₃ | |
| A-5 | H | CH₃ | H | CH₂C(O)OCH₃ | CH₃ | CH₂CH₃ | |
| A-5 | H | CH₃ | H | CH₂(CH₂)₂CF₃ | CH₃ | SCH₃ | |

TABLE III-continued

General Structure III

| A | R | R₁ | R₂ | R₃ | X₃ | m.p. (°C.) |
|---|---|---|---|---|---|---|
| A-6 | H | CH₃ | H | CH₂CHF₂ | CH₃ | |
| A-6 | H | CH₃ | H | C(O)N(CH₃)₂ | CH₃ | |
| A-6 | H | CH₃ | H | C(O)OCH₃ | OCH₃ | |
| A-6 | H | CH₃ | H | CH₂SCH₃ | OCH₃ | |
| A-6 | H | CH₃ | H | CH₂—CH(CH₂)(CH₂)(CH₂) (cyclopropyl-CH₂) | CH₃ | |

TABLE IIIa

General Structure IIIa

| A | R | R₁ | R₂ | R₃ | X | Y | Z | m.p. (°C.) |
|---|---|---|---|---|---|---|---|---|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O-cyclopropyl | OCH₃ | N | |
| A-1 | H | CH₂CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | SCF₂H | CH₃ | CH | |
| A-1 | H | CH₃ | H | Si(CH₃)₃ | OCH₃ | OCH₂CH=CH₂ | CH | |

| A | R | R₁ | R₂ | R₃ | X₁ | Y₁ | m.p. (°C.) |
|---|---|---|---|---|---|---|---|
| A-2 | H | CH₃ | H | CH₂—CH=CH₂ | CH₃ | CH₂ | |
| A-2 | H | CH₃ | H | CH₂—CH=CH₂ | CH₃ | O | |
| A-2 | H | CH₃ | H | CH₂—C≡CH | OCH₃ | CH₂ | |
| A-2 | H | CH₃ | H | CH₂F | OCF₂H | CH₂ | |
| A-3 | H | CH₃ | H | CH₂CH₂Cl | CH₃ | | |
| A-3 | H | CH₃ | H | CH₂P(O)(CH₃)₂ | OCH₃ | | |
| A-3 | H | CH₃ | H | CH₂(CH₂)₆CH₃ | OCH₂CH₃ | | |
| A-3 | H | CH₃ | H | CH₂CH=CF₂ | OCF₂H | | |

| A | R | R₁ | R₂ | R₃ | X₁ | Y₃ | m.p. (°C.) |
|---|---|---|---|---|---|---|---|
| A-4 | H | CH₃ | H | CH₂—CH(O)CH₂ (epoxide) | CH₃ | H | |
| A-4 | H | CH₃ | H | CH₂—CH(O)CH₂ (epoxide) | OCH₃ | H | |
| A-4 | H | CH₃ | H | CH₂SO₂CH₃ | OCF₂H | CH₃ | |
| A-4 | H | CH₃ | H | CH₂SO₂CH₃ | OCF₂H | H | |
| A-4 | H | CH₃ | H | SCH₃ | OCH₂CH₃ | H | |
| A-4 | H | CH₃ | H | CH₂Si(CH₃)₃ | CH₃ | H | |
| A-4 | H | CH₃ | H | CH₂C(O)CH₃ | OCH₃ | CH₃ | |

| A | R | R₁ | R₂ | R₃ | X₂ | Y₂ | m.p. (°C.) |
|---|---|---|---|---|---|---|---|
| A-5 | H | CH₃ | H | CH₂C(O)CH₃ | CH₃ | OCH₃ | |
| A-5 | H | CH₃ | H | CH₂C(O)CH₃ | CH₂CH₃ | OCH₃ | |
| A-5 | H | CH₃ | H | CH₂C(O)OCH₃ | CH₂CF₃ | SCH₃ | |
| A-5 | H | CH₃ | H | CH₂C(O)OCH₃ | CH₃ | CH₃ | |
| A-5 | H | CH₃ | H | CH₂C(O)OCH₃ | CH₃ | CH₂CH₃ | |
| A-5 | H | CH₃ | H | CH₂(CH₂)₂CF₃ | CH₃ | SCH₃ | |

| A | R | R₁ | R₂ | R₃ | X₃ | m.p. (°C.) |
|---|---|---|---|---|---|---|
| A-6 | H | CH₃ | H | CH₂CHF₂ | CH₃ | |
| A-6 | H | CH₃ | H | C(O)N(CH₃)₂ | CH₃ | |
| A-6 | H | CH₃ | H | C(O)OCH₃ | OCH₃ | |
| A-6 | H | CH₃ | H | CH₂SCH₃ | OCH₃ | |
| A-6 | H | CH₃ | H | CH₂—CH(CH₂)(CH₂)(CH₂) (cyclopropyl-CH₂) | CH₃ | |

TABLE IV

General Structure IV

| A | R | R₁ | R₂ | R₃ | X | Y | Z | m.p.(°C.) |
|---|---|---|---|---|---|---|---|---|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |
| A-1 | H | CH₃ | H | CH(CF₃)₂ | O–⊲ | OCH₃ | N | |
| A-1 | H | CH₃ | H | CH(CF₃)₂ | CH₂OCH₃ | CH₃ | CH | |
| A-1 | H | CH₃ | H | Si(CH₃)₃ | H | OCH₃ | CH | |
| A-1 | H | CH₃ | H | Si(CH₃)₃ | SCF₂H | CH₃ | CH | |
| A-1 | H | CH₃ | H | Si(CH₃)₃ | OCH₃ | OCH₂CH=CH₂ | CH | |
| A-1 | H | CH₃ | H | CH₂F | OCH₃ | CN | CH | |
| A-1 | H | CH₃ | H | CH₂F | OCH₃ | CH(OCH₃)₂ | CH | |

| A | R | R₁ | R₂ | R₃ | X₁ | Y₁ | m.p.(°C.) |
|---|---|---|---|---|---|---|---|
| A-2 | H | CH₃ | H | CH₂—CH=CH₂ | CH₃ | CH₂ | |
| A-2 | H | CH₃ | CH₃ | CH₂—CH=CH₂ | CH₃ | O | |
| A-2 | H | CH₃ | H | CH₂—C≡CH | OCH₃ | CH₂ | |
| A-2 | H | CH₃ | H | CH₂F | OCF₂H | CH₂ | |

| A | R | R₁ | R₂ | R₃ | X₁ | m.p.(°C.) |
|---|---|---|---|---|---|---|
| A-3 | H | CH₃ | H | CH₂CH₂Cl | CH₃ | |
| A-3 | H | CH₃ | H | CH₂P(O)(CH₃)₂ | OCH₃ | |
| A-3 | H | CH₃ | H | CH₂(CH₂)₆CH₃ | OCH₂CH₃ | |
| A-3 | H | CH₂CH₂CH₃ | H | CH₂CH=CF₂ | OCF₂H | |

| A | R | R₁ | R₂ | R₃ | X₁ | Y₃ | m.p.(°C.) |
|---|---|---|---|---|---|---|---|
| A-4 | H | CH₃ | H | CH₂—C(O)(CH₂) (epoxide) | CH₃ | H | |
| A-4 | H | CH₃ | H | CH₂—C(O)(CH₂) (epoxide) | OCH₃ | H | |
| A-4 | H | CH₃ | H | CH₂SO₂CH₃ | OCF₂H | CH₃ | |
| A-4 | H | CH₃ | H | CH₂SO₂CH₃ | OCF₂H | H | |
| A-4 | H | CH₃ | H | SCH₃ | OCH₂CH₃ | H | |
| A-4 | H | CH₃ | H | CH₂Si(CH₃)₃ | CH₃ | H | |
| A-4 | H | CH₃ | H | CH₂C(O)CH₃ | OCH₃ | CH₃ | |

| A | R | R₁ | R₂ | R₃ | X₂ | Y₂ | m.p.(°C.) |
|---|---|---|---|---|---|---|---|
| A-5 | H | CH₃ | H | CH₂C(O)CH₃ | CH₃ | OCH₃ | |
| A-5 | H | CH₃ | H | CH₂C(O)CH₃ | CH₂CH₃ | OCH₃ | |
| A-5 | H | CH₃ | H | CH₂C(O)OCH₃ | CH₂CF₃ | SCH₃ | |
| A-5 | H | CH₃ | H | CH₂C(O)OCH₃ | CH₃ | CH₃ | |
| A-5 | H | CH₃ | H | CH₂C(O)OCH₃ | CH₃ | CH₂CH₃ | |
| A-5 | H | CH₃ | H | CH₂(CH₂)₂CF₃ | CH₃ | SCH₃ | |

| A | R | R₁ | R₂ | R₃ | X₃ | m.p.(°C.) |
|---|---|---|---|---|---|---|
| A-6 | H | CH₃ | H | CH₂CHF₂ | CH₃ | |
| A-6 | H | CH₃ | H | C(O)N(CH₃)₂ | CH₃ | |
| A-6 | H | CH₃ | H | C(O)OCH₃ | OCH₃ | |
| A-6 | H | CH₃ | H | CH₂SCH₃ | OCH₃ | |
| A-6 | H | CH₃ | H | CH₂—CH(CH₂)(CH₂) (cyclopropyl) | CH₃ | |

TABLE IVa

General Structure IVa

| A | R | R₁ | R₂ | R₃ | X | Y | Z | m.p.(°C.) |
|---|---|---|---|---|---|---|---|---|
| A-1 | H | CH₃ | H | CH₂F | OCH₂CH₃ | OCH₃ | CH | |
| A-1 | H | CH₃ | H | CH₂F | OCH₂CH₃ | NHCH₃ | N | |
| A-1 | H | CH₃ | H | CH₂F | OCF₂H | CH₃ | CH | |
| A-1 | H | CH₃ | H | CH₂F | SCH₃ | CH₃ | N | |

TABLE IVa-continued

General Structure IVa

| A | R | R₁ | R₂ | R₃ | X₁ | Y₁ | |
|---|---|---|---|---|---|---|---|
| A-1 | H | CH₃ | H | CH(CF₃)₂ | O—△ | OCH₃ | N |
| A-1 | H | CH₃ | H | CH(CF₃)₂ | CH₂OCH₃ | CH₃ | CH |
| A-1 | H | CH₃ | H | Si(CH₃)₃ | H | OCH₃ | CH |
| A-1 | H | CH₃ | H | Si(CH₃)₃ | SCF₂H | CH₃ | CH |
| A-1 | H | CH₃ | H | Si(CH₃)₃ | OCH₃ | OCH₂CH=CH₂ | CH |
| A-1 | H | CH₃ | H | CH₂F | OCH₃ | CN | CH |
| A-1 | H | CH₃ | H | CH₂F | OCH₃ | CH(OCH₃)(OCH₃) | CH |

| A | R | R₁ | R₂ | R₃ | X₁ | Y₁ | m.p.(°C.) |
|---|---|---|---|---|---|---|---|
| A-2 | H | CH₃ | H | CH₂—CH=CH₂ | CH₃ | CH₂ | |
| A-2 | H | CH₃ | H | CH₂—CH=CH₂ | CH₃ | O | |
| A-2 | H | CH₃ | H | CH₂—C≡CH | OCH₃ | CH₂ | |
| A-2 | H | CH₃ | H | CH₂F | OCF₂H | CH₂ | |

| A | R | R₁ | R₂ | R₃ | X₁ | | m.p.(°C.) |
|---|---|---|---|---|---|---|---|
| A-3 | H | CH₃ | H | CH₂CH₂Cl | CH₃ | | |
| A-3 | H | CH₃ | H | CH₂P(O)(CH₃)₂ | OCH₃ | | |
| A-3 | H | CH₃ | H | CH₂(CH₂)₆CH₃ | OCH₂CH₃ | | |
| A-3 | H | CH₃ | H | CH₂CH=CF₂ | OCF₂H | | |

| A | R | R₁ | R₂ | R₃ | X₁ | Y₃ | m.p.(°C.) |
|---|---|---|---|---|---|---|---|
| A-4 | H | CH₃ | H | CH₂—C(O)—CH₂ (epoxide) | CH₃ | H | |
| A-4 | H | CH₃ | H | CH₂—C(O)—CH₂ (epoxide) | OCH₃ | H | |
| A-4 | H | CH₃ | H | CH₂SO₂CH₃ | OCF₂H | CH₃ | |
| A-4 | H | CH₃ | H | CH₂SO₂CH₃ | OCF₂H | H | |
| A-4 | H | CH₃ | H | SCH₃ | OCH₂CH₃ | H | |
| A-4 | H | CH₃ | H | CH₂Si(CH₃)₃ | CH₃ | H | |
| A-4 | H | CH₃ | H | CH₂C(O)CH₃ | OCH₃ | CH₃ | |

| A | R | R₁ | R₂ | R₃ | X₂ | Y₂ | m.p. °C.) |
|---|---|---|---|---|---|---|---|
| A-5 | H | CH₃ | H | CH₂C(O)CH₃ | CH₃ | OCH₃ | |
| A-5 | H | CH₃ | H | CH₂C(O)CH₃ | CH₂CH₃ | OCH₃ | |
| A-5 | H | CH₃ | H | CH₂C(O)OCH₃ | CH₂CF₃ | SCH₃ | |
| A-5 | H | CH₃ | H | CH₂C(O)OCH₃ | CH₃ | CH₃ | |
| A-5 | H | CH₃ | H | CH₂C(O)OCH₃ | CH₃ | CH₂CH₃ | |
| A-5 | H | CH₃ | H | CH₂(CH₂)₂CF₃ | CH₃ | SCH₃ | |

| A | R | R₁ | R₂ | R₃ | X₃ | | m.p.(°C.) |
|---|---|---|---|---|---|---|---|
| A-6 | H | CH₃ | H | CH₂CHF₂ | CH₃ | | |
| A-6 | H | CH₃ | H | C(O)N(CH₃)₂ | CH₃ | | |
| A-6 | H | CH₃ | H | C(O)OCH₃ | OCH₃ | | |
| A-6 | H | CH₃ | H | CH₂SCH₃ | OCH₃ | | |
| A-6 | H | CH₃ | H | CH₂—CH(CH₂)(CH₂) (cyclopropyl) | CH₃ | | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE V

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |

TABLE V-continued

| | Weight Percent* | | |
|---|---|---|---|
| | Active Ingredient | Diluent(s) | Surfactant(s) |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 3

Wettable Powder

| | |
|---|---|
| N—[(4,6-dimethoxypyrimidin-2-yl)aminocarbonyl]-5-(2-fluoroethyl)-2,5,6,7-tetrahydro-2-methylpyrazolo[3,4-e][1,2]thiazine-3-sulfonamide, 4,4-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 4

Wettable Powder

| | |
|---|---|
| 5-acetyl-2,5,6,7-tetrahydro-N—[(4-methoxy-6-methyl-1,3,5-triazin-2-yl)aminocarbonyl]-2-methylpyrazolo[3,4-e]thiazine-3-sulfonamide, 4,4-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 5

Granule

| | |
|---|---|
| Wettable Powder of Example 4 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 6

Extruded Pellet

| | |
|---|---|
| 5-butyl-N—[(4,6-dimethoxypyrimidin-2-yl)aminocarbonyl]-2,5,6,7-tetrahydro-2-methylpyrazolo[3,4-e]-[1,2]thiazine-3-sulfonamide, 4,4-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

| | |
|---|---|
| N—[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 8

Wettable Powder

| | |
|---|---|
| 5-acetyl-2,5,6,7-tetrahydro-N—[(4-methoxy-6-methyl-1,3,5-triazin-2-yl)aminocarbonyl]-2-methylpyrazolo[3,4-e]thiazine-3-sulfonamide, 4,4-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

Low Strength Granule

| | |
|---|---|
| 5-butyl-N—[(4,6-dimethoxypyrimidin-2-yl)aminocarbonyl]-2,5,6,7-tetrahydro-2-methylpyrazolo[3,4-e]-[1,2]thiazine-3-sulfonamide, 4,4-dioxide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

| | |
|---|---|
| 5-butyl-N—[(4,6-dimethoxypyrimidin-2-yl)aminocarbonyl]-2,5,6,7-tetrahydro-2-methylpyrazolo[3,4-e]-[1,2]thiazine-3-sulfonamide, 4,4-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 11

Solution

| | |
|---|---|
| N—[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide | 5% |
| water | 95% |

The salt is added directly to the water with stirring to produce the solution, which may then be packaged for use.

EXAMPLE 12

Low Strength Granule

| | |
|---|---|
| 5-acetyl-2,5,6,7-tetrahydro-N—[(4-methoxy-6-methyl-1,3,5-triazin-2-yl)aminocarbonyl]-2-methylpyrazolo[3,4-e]thiazine-3-sulfonamide, 4,4-dioxide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

| | |
|---|---|
| 5-acetyl-2,5,6,7-tetrahydro-N—[(4-methoxy-6-methyl-1,3,5-triazin-2-yl)aminocarbonyl]-2-methylpyrazolo[3,4-e]thiazine-3-sulfonamide, 4,4-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 14

High Strength Concentrate

| | |
|---|---|
| 5-butyl-N—[(4,6-dimethoxypyrimidin-2-yl)aminocarbonyl]-2,5,6,7-tetrahydro-2-methylpyrazolo[3,4-e]-[1,2]thiazine-3-sulfonamide, 4,4-dioxide | 99% |
| silica aerogel | 0.5% |
| synthetic amorphous silica | 0.5% |

The ingredients are blended and ground in a hammer-mill to produce a material essentially all passing a U.S.S.

EXAMPLE 15

Wettable Powder

| | |
|---|---|
| N—[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 16

Wettable Powder

| | |
|---|---|
| 5-acetyl-2,5,6,7-tetrahydro-N—[(4-methoxy-6-methyl-1,3,5-triazin-2-yl)aminocarbonyl]-2-methylpyrazolo[3,4-e]thiazine-3-sulfonamide, 4,4-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 17

Oil Suspension

| | |
|---|---|
| 5-butyl-N—[(4,6-dimethoxypyrimidin-2-yl)aminocarbonyl]-2,5,6,7-tetrahydro-2-methylpyrazolo[3,4-e]-[1,2]thiazine-3-sulfonamide, 4,4-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 18

Dust

| | |
|---|---|
| N—[(4,6-dimethoxypyrimidin-2-yl)aminocarbonyl]-5-(2-fluoroethyl)-2,5,6,7-tetrahydro-2-methyl-pyrazolo[3,4-e][1,2]thiazine-3-sulfonamide, 4,4-dioxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

What is claimed is:

1. A compound selected from

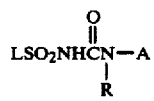

wherein
L is

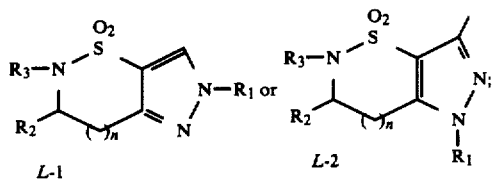

R is H or $CH_3$;
$R_1$ is H, $C_1$–$C_3$ alkyl, $CH_2CH=CH_2$, $CH_2C\equiv CH$, $CH_2CF_3$, $CHF_2$, $C(O)CH_3$, $SO_2CH_3$, $SO_2N(CH_3)_2$, $CO_2CH_3$, phenyl or phenyl substituted with $NO_2$, $CH_3$, $OCH_3$, Cl, Br or F;
n is 0 or 1;
$R_2$ is H or $CH_3$;
$R_3$ is $R_4$, $SR_4$, $SO_2R_4$, $OR_4$, $C(O)R_4$, $C(O)OR_4$, $(C(O))_2OR_4$, $(CO)_2R_4$, $C(O)NR_5R_6$, $C(O)NRA$, $C(S)SR_4$, $NR_5R_6$, OH, CN, $P(O)R_7R_8$, $P(S)R_7R_8$, $Si(CH_3)_2R_9$, J or C(O)J;
$R_4$ is $C_1$–$C_{10}$ alkyl, $C_2$–$C_{10}$ alkoxyalkyl, $C_2$–$C_{10}$ alkenyl, $C_2$–$C_{10}$ epoxyalkyl, $C_2$–$C_{10}$ alkynyl, $C_3$–$C_6$ cycloalkyl, $C_4$–$C_7$ cycloalkylalkyl or

when $R_4$ is $C_3$–$C_6$ cycloalkyl or $C_4$–$C_7$ cycloalkylalkyl it may optionally be substituted by $C_1$–$C_4$ alkyl, 1 to 3 atoms of Cl or F or 1 Br; when $R_4$ is $C_1$–$C_{10}$ alkyl, $C_2$–$C_{10}$ alkenyl or $C_2$–$C_{10}$ alkynyl it may optionally be substituted by one or more halogens and/or by $(R_{11})_p$, provided that when p is 2, the values of $R_{11}$ may be identical or different;

p is 1 or 2;

$R_5$ is H or $C_1$–$C_4$ alkyl;

$R_6$ is H, $C_1$–$C_{10}$ alkyl, $C_1$–$C_{10}$ haloalkyl, $C_2$–$C_{10}$ alkenyl, $C_2$–$C_{10}$ alkynyl, $C_3$–$C_6$ cycloalkyl or

[structure: phenyl with $R_{10}$ substituent];

$R_7$ and $R_8$ are independently $C_1$–$C_4$ alkyl, $C_1$–$C_4$ alkoxy or $C_1$–$C_4$ alkylthio;

$R_9$ is $C_1$–$C_{10}$ alkyl, benzyl or

[structure: phenyl with $R_{10}$ substituent];

$R_{10}$ is H, F, Cl, Br, $CH_3$, $OCH_3$, $NO_2$, CN, $SCH_3$, $SO_2CH_3$ or $CF_3$;

$R_{11}$ is $OR_6$, $OC(O)R_6$, $P^+R_9R_{13}R_{14}$, $P^+(C_6H_5)_3$, $OC(O)NR_5R_6$, $OSO_2R_6$, $OP(O)R_7R_8$, $P(O)R_7R_8$, $OP(S)R_7R_8$, $P(S)R_7R_8$, $OSi(CH_3)_2R_9$, $Si(CH_3)_2R_9$, $SR_6$, $SOR_6$, $SO_2R_6$, SCN, CN, $SP(O)R_7R_8$, $SP(S)R_7R_8$, $N^+R_5R_6R_9$, $NR_5R_6$, $NR_5C(O)R_6$, $NR_5C(O)OR_6$, $NR_5C(O)NR_5R_6$, $NR_5SO_2R_6$, $NR_5P(O)R_7R_8$, $NR_5P(S)R_7R_8$, $NO_2$, $C(O)R_6$, $C(O)OR_6$, $C(O)NR_5R_6$, $SeR_6$, naphthyl, J,

[structures]

$R_{12}$ is H, F, Cl, Br, $CH_3$,

[structures]

$R_{13}$ and $R_{14}$ are independently $C_1$–$C_3$ alkyl;

J is a 5- or 6-membered aromatic heterocycle, a 5- or 6-membered dihydroaromatic heterocycle or a 5- or 6-membered tetrahydroaromatic heterocycle which contains 1–4 heteroatoms selected from 0–1 oxygen atoms, 0–1 sulfur atoms and/or 0–4 nitrogen atoms and these heterocycles may optionally be substituted by 1–4 $CH_3$, 1–2 $OCH_3$, $SCH_3$, Cl, $N(CH_3)_2$ or CN groups or J is a 5- or 6-membered lactone, lactam or cycloalkanone which may optionally be substituted by 1–4 $CH_3$ groups;

A is

[structures A-1, A-2, A-3, A-4, A-5, A-6]

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino or $C_3$–$C_5$ cycloalkyl;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, azido, cyano,

[structures]

or $N(OCH_3)CH_3$;

m is 2 or 3;

$Q_1$ and $Q_2$ are independently O or S;

$R_a$ is H or $C_1$–$C_3$ alkyl;

$R_b$ and $R_c$ are independently $C_1$–$C_3$ alkyl;

Z is N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$; and $Y_3$ is H or $CH_3$;

provided that 1. when $R_3$ is $R_4$, then $R_4$ is other than $C_1$–$C_3$ alkyl or $CF_2H$;
2. the total number of carbon atoms in $R_3$ does not exceed 13;
3. when $R_6$ is H, then $R_{11}$ is other than $SOR_6$, $SO_2R_6$, $OSO_2R_6$ or $NR_5CO_2R_6$; and
4. X and/or Y are other than $OCF_2H$.

2. Compounds of claim 1 wherein

A is A-1;

X is $CH_3$, $OCH_3$, $OCH_2CH_3$, $CH_2F$, $CF_3$ or cyclopropyl;

Y is H, $C_1$–$C_3$ alkyl, $OCH_3$, $OC_2H_5$, $CH_2OCH_3$, $NH_2$, $NHCH_3$, $N(OCH_3)CH_3$, $N(CH_3)_2$, $C_2H_5$, $CF_3$, $SCH_3$, $OCH_2CH=CH_2$, $OCH_2C\equiv CH$, $OCH_2CF_3$, CN, $N_3$, $OCH_2CH_2OCH_3$, $CH_2SCH_3$,

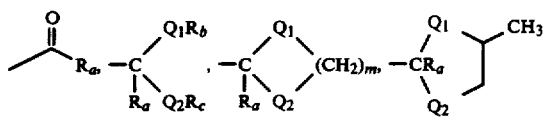

or $QCF_2T$;

Q is S; and

T is H, $CHClF$, $CHBrF$ or $CHFCF_3$.

3. Compounds of claim 2 wherein $R_3$ is $C_4$–$C_6$ alkyl, $C_1$–$C_6$ alkylcarbonyl, $C_1$–$C_6$ alkoxycarbonyl, $C_1$–$C_6$ alkyl substituted by 1–3 atoms of F, Cl or 1 Br, or by 1 or 2 groups selected from $C_1$–$C_2$ alkoxy, CN, $C_1$–$C_2$ alkoxycarbonyl, $C_1$–$C_2$ alkylcarbonyl, OH, $C_1$–$C_2$ alkylthio $C_1$–$C_2$ alkylsulfonyl, $C_1$–$C_2$ alkylsulfonyloxy or $C_1$–$C_2$ alkylcarbonyloxy, $C_3$–$C_4$ alkenyl, $C_3$–$C_4$ haloalkenyl, $C_3$–$C_4$ alkynyl, $C_4$ alkynyl substituted by 1 atom of F or Cl, phenyl or phenyl substituted with Cl, $CF_3$, $NO_2$, CN or $SO_2CH_3$.

4. Compounds of claim 3 wherein $R_1$ is H, $C_1$–$C_3$ alkyl, allyl, propargyl, $CH_2CF_3$ or $CHF_2$.

5. Compounds of claim 4 wherein R is H, Y is $CH_3$, $C_2H_5$, $OCH_3$, $CH_2OCH_3$, or $CH(OCH_3)_2$, and Z is N.

6. Compounds of claim 5 wherein $R_3$ is $C_4$ alkyl, $C_1$–$C_4$ alkyl substituted by 1–3 atoms of F or Cl or 1 Br, $C_1$–$C_3$ alkyl substituted with $C_1$–$C_2$ alkoxy, $C_1$–$C_2$ alkylthio, $C_1$–$C_2$ alkylsulfonyl or CN, $C_3$–$C_4$ alkenyl, $C_3$–$C_4$ haloalkenyl, $C_3$–$C_4$ alkynyl, $C_1$–$C_3$ alkoxycarbonyl or $C_1$–$C_3$ alkylcarbonyl.

7. Compounds of claim 5 wherein $R_3$ is $C_1$–$C_3$ alkoxycarbonyl or $C_1$–$C_3$ alkylcarbonyl.

8. The compound of claim 1 which is a 5-acetyl-2,5,6,7-tetrahydro-N-[(4-methoxy-6-methyl-1,3,5-triazim-2-yl)aminocarbonyl]-2-methylpyrazolo[3,4-e]thiazine-3-sulfonamide, 4,4-dioxide.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 3 and at least one of the following: surfactant, solid or liquid diluent.

12. A composition suitable for controlling the growth of undesired vegetation which comprises an effective amount of a compound of claim 4 and at least one of the following: surfactant, solid or liquid diluent.

13. A composition suitable for controlling the growth of undesired vegetation which comprises an effective amount of a compound of claim 5 and at least one of the following: surfactant, solid or liquid diluent.

14. A composition suitable for controlling the growth of undesired vegetation which comprises an effective amount of a compound of claim 6 and at least one of the following: surfactant, solid or liquid diluent.

15. A composition suitable for controlling the growth of undesired vegetation which comprises an effective amount of a compound of claim 7 and at least one of the following: surfactant, solid or liquid diluent.

16. A composition suitable for controlling the growth of undesired vegetation which comprises an effective amount of a compound of claim 8 and at least one of the following: surfactant, solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

23. A method for controlling the growth of undesired vegetation which comprises applying to the locus to be protected an effective amount of a compound of claim 7.

24. A method for controlling the growth of undesired vegetation which comprises applying to the locus to be protected an effective amount of a compound of claim 8.

* * * * *